(12) United States Patent
Collibee et al.

(10) Patent No.: US 7,572,814 B2
(45) Date of Patent: Aug. 11, 2009

(54) 3,5-DIBENZOYL-4-PHENYL-PIPERIDINE ANTI-CANCER COMPOUNDS

(75) Inventors: Scott Collibee, San Carlos, CA (US); Zhe Yang, Daly City, CA (US); Luke Ashcraft, San Francisco, CA (US); Gustave Bergnes, Pacifica, CA (US); Bradley P. Morgan, Moraga, CA (US); David J. Morgans, Jr., Los Altos, CA (US); Jianchao Wang, Foster City, CA (US)

(73) Assignee: Cytokinetics, Incorporated, South San Francisco, CA (US)

( * ) Notice: Subject to any disclaimer, the term of this patent is extended or adjusted under 35 U.S.C. 154(b) by 13 days.

(21) Appl. No.: 11/600,684

(22) Filed: Nov. 15, 2006

(65) Prior Publication Data

US 2007/0161674 A1  Jul. 12, 2007

Related U.S. Application Data

(60) Provisional application No. 60/737,226, filed on Nov. 15, 2005.

(51) Int. Cl.
*C07D 211/32* (2006.01)
*A61K 31/445* (2006.01)

(52) U.S. Cl. ........................... 514/330; 546/225
(58) Field of Classification Search ................ 514/304, 514/330; 546/225
See application file for complete search history.

(56) References Cited

U.S. PATENT DOCUMENTS

| | | | |
|---|---|---|---|
| 3,932,645 | A | 1/1976 | Meyer et al. |
| 4,492,703 | A | 1/1985 | Goldmann et al. |
| 4,495,192 | A | 1/1985 | Muto et al. |
| 4,766,213 | A | 8/1988 | Juraszyk et al. |
| 6,977,264 | B2 | 12/2005 | Fotsch et al. |
| 2007/0161683 | A1 | 7/2007 | Collibee et al. |

OTHER PUBLICATIONS

Hodgkinson, et. al. "Chemical synthesis and mode of action of the azinomycins" Tetrahedron 2001, 57, 4467-4488.*
Smith, A. B. et. al. "(D)-Discodermolide: total synthesis, construction of novel analogues, and biological evaluation." Tetrahedron 2008, 64, 261-298.*
Dorwald F. A. Side Reactions in Organic Synthesis, 2005, Wiley: VCH, Weinheim p. IX of Preface.*
International Search Report and Written Opinion mailed Oct. 2, 2007, for international application No. PCT/US2006/044753, filed Nov. 15, 2006.
M.V. Denisenko, G.V. Pavel and M.N. Tilichenko; *Synthesis of hydrogenated heterocyclic compounds from alpha-methylene-1,5-diketones. 5. Synthesis and stereochemistry of the products of addition of hydrazines to 2,4-dibenzoyl-3-phenyl-1,4-pentadiene*; Journal Khymiya Geterotsiklicheskikh Soedinenii, No. 6, pp. 789-791, Jun. 1981.
M.V. Denisenko, G.V. Pavel and M.N. Tilichenko; *Synthesis and stereochemistry of N-substituted 3,5-dibenzoyl-4-phenylpiperidines*; Journal Khymiya Geterotsiklicheskikh Soedinenii, No. 2, pp. 235-239, Feb. 1979.
Mi Jung Lee, Ka Young Lee, and Jae Nyoung Kim; *Synthesis of N-benzyl 3,5-disubstituted piperidines via double Michael addition strategy*; Bulletin Korean Chem. Soc. 2005, vol. 26, No. 3, pp. 477-480.
G.V. Pavel, N.P. Bagrina, and M.N. Tilichenko; *Synthesis of hydrogenated heterocyclic compounds from alpha-methylidene-1,5-diketones. 4. Hydropyridines based on the reaction of 1,3,5-triphenyl-2-aminomethyl-4-methylidene-1,5-pentadione with primary amines*; Journal Khymiya Geterotsiklicheskikh Soedinenii, No. 10, pp. 1374-1376, Oct. 1979.
G.V. Pavel, M.N. Tilichenko, and M.V. Denisenko; *Synthesis of a new form of 1,5-diketones of the piperidine series*, Journal Khymiya Geterotsiklicheskikh Soedinenii, No. 7, p. 999, Jul. 1976.
International Search Report and Written Opinion mailed Oct. 2, 2007, for international application No. PCT/US2006/044154, filed Nov. 14, 2006.
International Search Report and Written Opinion mailed Jul. 30, 2008, for international application No. PCT/US2008/006046, filed May 9, 2008.
Office Action mailed Aug. 19, 2008, for U.S. Appl. No. 11/600,014, filed Nov. 14, 2006.
Furdik et al. STN Accession No. 1964:476455; Document No. 61:76455 (1964).
STN Accession No. 1983:215488, Document No. 98:215488 (1983).
Katritzky et al. STN Accession No. 1987:438861, Document No. 107:38861 (1986).
Gunics et al. STN Accession No. 2001:294514, Document No. 135:220668 (2001).
Agamya et al., STN Accession No. 2001:854410, Document No. 136:263072 (2001).
Kawase et al., STN Accession No. 2002:106233, Document No. 137:41257 (2002).
Saponara et al., STN Accession No. 2004:187287, Document No. 140:368096 (2004).
Saponara et al., *British J. Pharmacology*, 141:415-422 (2004).

* cited by examiner

*Primary Examiner*—Rita J Desai
*Assistant Examiner*—David K O'Dell
(74) *Attorney, Agent, or Firm*—Finnegan, Henderson, Farabow, Garrett & Dunner, LLP

(57) ABSTRACT

Certain 3,5-dibenzoyl-4-phenyl-piperidine compounds and salts thereof are provided herein. The compounds and salts may be useful in causing mitotic arrest and cell death. Also provided herein are certain pharmaceutical compositions comprising 3,5-dibenzoyl-4-phenyl-piperidine compounds or salts thereof and certain methods of use thereof.

25 Claims, No Drawings

3,5-DIBENZOYL-4-PHENYL-PIPERIDINE ANTI-CANCER COMPOUNDS

This application claims the benefit of U.S. provisional patent application No. 60/737,226, filed 15 Nov. 2005, which is incorporated herein by reference.

Provided are certain chemical entities that cause mitotic arrest and cell death and are useful in the treatment of cellular proliferative diseases, for example cancer.

Improvements in the specificity of agents used to treat cancer is of considerable interest. Reducing the side effects associated with the administration of these agents would result in significant therapeutic benefits. Traditionally, dramatic improvements in the treatment of cancer have been associated with identification of therapeutic agents acting through novel mechanisms. Examples of such agents include not only the taxanes, but also the camptothecin class of topoisomerase I inhibitors.

Provided is at least one chemical entity chosen from compounds of Formula I:

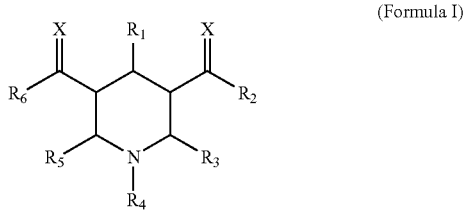

(Formula I)

and pharmaceutically acceptable salts, solvates, chelates, non-covalent complexes, prodrugs, and mixtures thereof, wherein =X is chosen from =O and =N—OR$_7$, where R$_7$ is selected from hydrogen and optionally substituted alkyl, provided that at least one =X is =O;

R$_1$ is chosen from hydrogen, optionally substituted alkyl, optionally substituted cycloalkyl, optionally substituted heterocycloalkyl, optionally substituted aryl and optionally substituted heteroaryl;

R$_2$ is chosen from optionally substituted aryl, optionally substituted heterocycloalkyl, optionally substituted alkyl, optionally substituted cycloalkyl, optionally substituted heteroaryl, optionally substituted alkoxy, hydroxy, and optionally substituted amino;

R$_3$ is chosen from hydrogen and optionally substituted alkyl;

R$_4$ is chosen from hydrogen, optionally substituted alkyl, optionally substituted heterocycloalkyl, optionally substituted acyl, optionally substituted aryl, optionally substituted heteroaryl, aminocarbonyl, sulfonyl, optionally substituted alkoxycarbonyl, and optionally substituted cycloalkyl;

R$_5$ is chosen from hydrogen and optionally substituted alkyl; and

R$_6$ is chosen from optionally substituted aryl, optionally substituted heterocycloalkyl, optionally substituted alkyl, optionally substituted cycloalkyl, optionally substituted heteroaryl, optionally substituted alkoxy, hydroxy, and optionally substituted amino provided that:
the compound of Formula I is not dimethyl 1-benzylpiperidine-3,5-dicarboxylate; methyl 5-acetyl-1-benzylpiperidine-3-carboxylate; dimethyl 1-benzyl-4-phenylpiperidine-3,5-dicarboxylate; (1-methyl-4-phenylpiperidine-3,5-diyl)bis(phenylmethanone); (1-benzyl-4-phenylpiperidine-3,5-diyl)bis(phenylmethanone); (1-(2-hydroxyethyl)-4-phenylpiperidine-3,5-diyl)bis(phenylmethanone); (1-cyclohexyl-4-phenylpiperidine-3,5-diyl)bis(phenylmethanone); (4-phenyl-1-(phenylamino)piperidine-3,5-diyl)bis(phenylmethanone); or (1-(dimethylamino)-4-phenylpiperidine-3,5-diyl)bis(phenylmethanone).

Also provided is pharmaceutical composition comprising a therapeutically effective amount of at least one chemical entity described herein together with at least one pharmaceutically acceptable vehicle chosen from carriers, adjuvants, and excipients.

Also provided is a packaged pharmaceutical composition, comprising
a pharmaceutical composition described herein; and
instructions for using the composition to treat a patient suffering from a cellular proliferative disease.

Also provided is a method for treating a patient having a cellular proliferative disease, comprising administering to the patient an effective amount of at least one chemical entity described herein.

As used herein, when any variable occurs more than one time in a chemical formula, its definition on each occurrence is independent of its definition at every other occurrence.

A dash ("-") that is not between two letters or symbols is used to indicate a point of attachment for a substituent. For example, —CONH$_2$ is attached through the carbon atom.

By "optional" or "optionally" is meant that the subsequently described event or circumstance may or may not occur, and that the description includes instances where the event or circumstance occurs and instances in which it does not. For example, "optionally substituted alkyl" encompasses both "alkyl" and "substituted alkyl" as defined below. It will be understood by those skilled in the art, with respect to any group containing one or more substituents, that such groups are not intended to introduce any substitution or substitution patterns that are sterically impractical, synthetically non-feasible and/or inherently unstable.

"Alkyl" encompasses straight chain and branched chain having the indicated number of carbon atoms, usually from 1 to 20 carbon atoms, for example 1 to 8 carbon atoms, such as 1 to 6 carbon atoms. For example C$_1$-C$_6$ alkyl encompasses both straight and branched chain alkyl of from 1 to 6 carbon atoms. Examples of alkyl groups include methyl, ethyl, propyl, isopropyl, n-butyl, sec-butyl, tert-butyl, pentyl, 2-pentyl, isopentyl, neopentyl, hexyl, 2-hexyl, 3-hexyl, 3-methylpentyl, and the like. Alkylene is another subset of alkyl, referring to the same residues as alkyl, but having two points of attachment. Alkylene groups will usually have from 2 to 20 carbon atoms, for example 2 to 8 carbon atoms, such as from 2 to 6 carbon atoms. For example, C$_0$ alkylene indicates a covalent bond and C$_1$ alkylene is a methylene group. When an alkyl residue having a specific number of carbons is named, all branched and straight chain versions having that number of carbons are intended to be encompassed; thus, for example, "butyl" is meant to include n-butyl, sec-butyl, isobutyl and t-butyl; "propyl" includes n-propyl and isopropyl. "Lower alkyl" refers to alkyl groups having one to four carbons.

"Alkenyl" refers to an unsaturated branched or straight-chain alkyl group having at least one carbon-carbon double bond derived by the removal of one hydrogen atom from a single carbon atom of a parent alkene. The group may be in either the cis or trans configuration about the double bond(s). Typical alkenyl groups include, but are not limited to, ethenyl;

propenyls such as prop-1-en-1-yl, prop-1-en-2-yl, prop-2-en-1-yl (allyl), prop-2-en-2-yl, cycloprop-1-en-1-yl; cycloprop-2-en-1-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl, cyclobut-1-en-1-yl, cyclobut-1-en-3-yl, cyclobuta-1,3-dien-1-yl; and the like. In certain embodiments, an alkenyl group has from 2 to 20 carbon atoms and in other embodiments, from 2 to 6 carbon atoms.

"Alkynyl" refers to an unsaturated branched or straight-chain alkyl group having at least one carbon-carbon triple bond derived by the removal of one hydrogen atom from a single carbon atom of a parent alkyne. Typical alkynyl groups include, but are not limited to, ethynyl; propynyls such as prop-1-yn-1-yl, prop-2-yn-1-yl; butynyls such as but-1-yn-1-yl, but-1-yn-3-yl, but-3-yn-1-yl; and the like. In certain embodiments, an alkynyl group has from 2 to 20 carbon atoms and in other embodiments, from 3 to 6 carbon atoms.

"Cycloalkyl" indicates a non-aromatic carbocyclic ring, usually having from 3 to 7 ring carbon atoms. The ring may be saturated or have one or more carbon-carbon double bonds. Examples of cycloalkyl groups include cyclopropyl, cyclobutyl, cyclopentyl, cyclopentenyl, cyclohexyl, and cyclohexenyl, as well as bridged and caged saturated ring groups such as norbornane.

By "alkoxy" is meant an alkyl group of the indicated number of carbon atoms attached through an oxygen bridge such as, for example, methoxy, ethoxy, propoxy, isopropoxy, n-butoxy, sec-butoxy, tert-butoxy, pentyloxy, 2-pentyloxy, isopentyloxy, neopentyloxy, hexyloxy, 2-hexyloxy, 3-hexyloxy, 3-methylpentyloxy, and the like. Alkoxy groups will usually have from 1 to 7 carbon atoms attached through the oxygen bridge. "Lower alkoxy" refers to alkoxy groups having one to four carbons.

"Mono- and di-alkylcarboxamide" encompasses a group of the formula —(C=O)NR$_a$R$_b$ where R$_a$ and R$_b$ are independently chosen from hydrogen and alkyl groups of the indicated number of carbon atoms, provided that R$_a$ and R$_b$ are not both hydrogen.

"Acyl" refers to the groups (alkyl)-C(O)—; (cycloalkyl)-C(O)—; (aryl)-C(O)—; (heteroaryl)-C(O)—; and (heterocycloalkyl)-C(O)—, wherein the group is attached to the parent structure through the carbonyl functionality and wherein alkyl, cycloalkyl, aryl, heteroaryl, and heterocycloalkyl are as described herein. Acyl groups have the indicated number of carbon atoms, with the carbon of the keto group being included in the numbered carbon atoms. For example a $C_2$ acyl group is an acetyl group having the formula $CH_3$(C=O)—.

By "alkoxycarbonyl" is meant a group of the formula (alkoxy)(C=O)— attached through the carbonyl carbon wherein the alkoxy group has the indicated number of carbon atoms. Thus a $C_1$-$C_6$ alkoxycarbonyl group is an alkoxy group having from 1 to 6 carbon atoms attached through its oxygen to a carbonyl linker.

By "amino" is meant the group —NH$_2$.

"Mono- and di-(alkyl)amino" encompasses secondary and tertiary alkyl amino groups, wherein the alkyl groups are as defined above and have the indicated number of carbon atoms. The point of attachment of the alkylamino group is on the nitrogen. Examples of mono- and di-alkylamino groups include ethylamino, dimethylamino, and methyl-propyl-amino.

The term "aminocarbonyl" refers to the group —CONR$^b$R$^c$, where $R^b$ is chosen from H, optionally substituted $C_1$-$C_6$ alkyl, optionally substituted cycloalkyl, optionally substituted heterocycloalkyl, optionally substituted aryl, and optionally substituted heteroaryl; and $R^c$ is independently chosen from hydrogen and optionally substituted $C_1$-$C_4$ alkyl; or $R^b$ and $R^c$ taken together with the nitrogen to which they are bound, form an optionally substituted 5- to 7-membered nitrogen-containing heterocycloalkyl which optionally includes 1 or 2 additional heteroatoms selected from O, N, and S in the heterocycloalkyl ring;

where each substituted group is independently substituted with one or more substituents independently selected from $C_1$-$C_4$ alkyl, aryl, heteroaryl, aryl-$C_1$-$C_4$ alkyl-, heteroaryl-$C_1$-$C_4$ alkyl-, $C_1$-$C_4$ haloalkyl, —O$C_1$-$C_4$ alkyl, —O$C_1$-$C_4$ alkylphenyl, —$C_1$-$C_4$ alkyl-OH, —O$C_1$-$C_4$ haloalkyl, halo, —OH, —NH$_2$, —$C_1$-$C_4$ alkyl-NH$_2$, —N($C_1$-$C_4$ alkyl)($C_1$-$C_4$ alkyl), —NH($C_1$-$C_4$ alkyl), —N($C_1$-$C_4$ alkyl)($C_1$-$C_4$ alkylphenyl), —NH($C_1$-$C_4$ alkylphenyl), cyano, nitro, oxo (as a substituent for cycloalkyl, heterocycloalkyl, or heteroaryl), —CO$_2$H, —C(O)O$C_1$-$C_4$ alkyl, —CON($C_1$-$C_4$ alkyl)($C_1$-$C_4$ alkyl), —CONH($C_1$-$C_4$ alkyl), —CONH$_2$, —NHC(O)($C_1$-$C_4$ alkyl), —NHC(O)(phenyl), —N($C_1$-$C_4$ alkyl)C(O)($C_1$-$C_4$ alkyl), —N($C_1$-$C_4$ alkyl)C(O)(phenyl), —C(O)$C_1$-$C_4$ alkyl, —C(O)$C_1$-$C_4$ alkylphenyl, —C(O)$C_1$-$C_4$ haloalkyl, —OC(O)$C_1$-$C_4$ alkyl, —SO$_2$($C_1$-$C_4$ alkyl), —SO$_2$(phenyl), —SO$_2$($C_1$-$C_4$ haloalkyl), —SO$_2$NH$_2$, —SO$_2$NH($C_1$-$C_4$ alkyl), —SO$_2$NH(phenyl), —NHSO$_2$($C_1$-$C_4$ alkyl), —NHSO$_2$(phenyl), and —NHSO$_2$($C_1$-$C_4$ haloalkyl).

"Aryl" encompasses:

6-membered carbocyclic aromatic rings, for example, benzene;

bicyclic ring systems wherein at least one ring is carbocyclic and aromatic, for example, naphthalene, indane, and tetralin; and tricyclic ring systems wherein at least one ring is carbocyclic and aromatic, for example, fluorene.

For example, aryl includes 6-membered carbocyclic aromatic rings fused to a 5- to 7-membered heterocycloalkyl ring containing 1 or more heteroatoms chosen from N, O, and S. For such fused, bicyclic ring systems wherein only one of the rings is a carbocyclic aromatic ring, the point of attachment may be at the carbocyclic aromatic ring or the heterocycloalkyl ring. Bivalent radicals formed from substituted benzene derivatives and having the free valences at ring atoms are named as substituted phenylene radicals. Bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene. Aryl, however, does not encompass or overlap in any way with heteroaryl, separately defined below. Hence, if one or more carbocyclic aromatic rings is fused with a heterocycloalkyl aromatic ring, the resulting ring system is heteroaryl, not aryl, as defined herein.

The term "aryloxy" refers to the group —O-aryl.

"Carbamimidoyl" refers to the group —C(=NH)—NH$_2$.

"Substituted carbamimidoyl" refers to the group —C(=NR$^e$)—NR$^f$R$^g$ where R$^e$, is chosen from: hydrogen, cyano, optionally substituted alkyl, optionally substituted cycloalkyl, optionally substituted aryl, optionally substituted heteroaryl, and optionally substituted heterocycloalkyl; and R$^f$ and R$^g$ are independently chosen from: hydrogen optionally substituted alkyl, optionally substituted cycloalkyl, optionally substituted aryl, optionally substituted heteroaryl, and optionally substituted heterocycloalkyl, provided that at least one of $R^e$, $R^f$, and $R^g$ is not hydrogen and wherein substituted alkyl, cycloalkyl, aryl, heterocycloalkyl, and heteroaryl refer respectively to alkyl, cycloalkyl, aryl, heterocycloalkyl, and heteroaryl wherein one or more (such as up to 5, for example, up to 3) hydrogen atoms are replaced by a substituent independently chosen from:

—$R^a$, —$OR^b$, optionally substituted amino (including —$NR^cCOR^b$, —$NR^cCO_2R^a$, —$NR^cCONR^bR^c$, —$NR^bC(NR^c)NR^bR^c$, —$NR^bC(NCN)NR^bR^c$, and —$NR^bSO_2R^a$), halo, cyano, nitro, oxo (as a substituent for cycloalkyl, heterocycloalkyl, and heteroaryl), optionally substituted acyl (such as —$COR^b$), optionally substituted alkoxycarbonyl (such as —$CO_2R^b$), aminocarbonyl (such as —$CONR^bR^c$), —$OCOR^b$, —$OCO_2R^a$, —$OCONR^bR^c$, sulfanyl (such as $SR^b$), sulfinyl (such as —$SOR^a$), and sulfonyl (such as —$SO_2R^a$ and —$SO_2NR^bR^c$), where $R^a$ is chosen from optionally substituted $C_1$-$C_6$ alkyl, optionally substituted aryl, and optionally substituted heteroaryl;

$R^b$ is chosen from H, optionally substituted $C_1$-$C_6$ alkyl, optionally substituted aryl, and optionally substituted heteroaryl; and $R^c$ is independently chosen from hydrogen and optionally substituted $C_1$-$C_4$ alkyl; or $R^b$ and $R^c$, and the nitrogen to which they are attached, form an optionally substituted heterocycloalkyl group; and where each optionally substituted group is unsubstituted or independently substituted with one or more, such as one, two, or three, substituents independently selected from $C_1$-$C_4$ alkyl, aryl, heteroaryl, aryl-$C_1$-$C_4$ alkyl-, heteroaryl-$C_1$-$C_4$ alkyl-, $C_1$-$C_4$ haloalkyl, —$OC_1$-$C_4$ alkyl, —$OC_1$-$C_4$ alkylphenyl, —$C_1$-$C_4$ alkyl-OH, —$OC_1$-$C_4$ haloalkyl, halo, —OH, —$NH_2$, —$C_1$-$C_4$ alkyl-$NH_2$, —$N(C_1$-$C_4$ alkyl)($C_1$-$C_4$ alkyl), —$NH(C_1$-$C_4$ alkyl), —$N(C_1$-$C_4$ alkyl)($C_1$-$C_4$ alkylphenyl), —$NH(C_1$-$C_4$ alkylphenyl), cyano, nitro, oxo (as a substituent for cycloalkyl, heterocycloalkyl, or heteroaryl), —$CO_2H$, —$C(O)OC_1$-$C_4$ alkyl, —$CON(C_1$-$C_4$ alkyl)($C_1$-$C_4$ alkyl), —$CONH(C_1$-$C_4$ alkyl), —$CONH_2$, —$NHC(O)(C_1$-$C_4$ alkyl), —$NHC(O)(phenyl)$, —$N(C_1$-$C_4$ alkyl)$C(O)(C_1$-$C_4$ alkyl), —$N(C_1$-$C_4$ alkyl)$C(O)(phenyl)$, —$C(O)C_1$-$C_4$ alkyl, —$C(O)C_1$-$C_4$ phenyl, —$C(O)C_1$-$C_4$ haloalkyl, —$OC(O)C_1$-$C_4$ alkyl, —$SO_2(C_1$-$C_4$ alkyl), —$SO_2(phenyl)$, —$SO_2(C_1$-$C_4$ haloalkyl), —$SO_2NH_2$, —$SO_2NH(C_1$-$C_4$ alkyl), —$SO_2NH(phenyl)$, —$NHSO_2(C_1$-$C_4$ alkyl), —$NHSO_2(phenyl)$, and —$NHSO_2(C_1$-$C_4$ haloalkyl).

The term "halo" includes fluoro, chloro, bromo, and iodo, and the term "halogen" includes fluorine, chlorine, bromine, and iodine.

"Haloalkyl" indicates alkyl as defined above having the specified number of carbon atoms, substituted with 1 or more halogen atoms, up to the maximum allowable number of halogen atoms. Examples of haloalkyl include, but are not limited to, trifluoromethyl, difluoromethyl, 2-fluoroethyl, and penta-fluoroethyl.

"Heteroaryl" encompasses:
5- to 7-membered aromatic, monocyclic rings containing one or more, for example, from 1 to 4, or in certain embodiments, from 1 to 3, heteroatoms chosen from N, O, and S, with the remaining ring atoms being carbon;
bicyclic heterocycloalkyl rings containing one or more, for example, from 1 to 4, or in certain embodiments, from 1 to 3, heteroatoms chosen from N, O, and S, with the remaining ring atoms being carbon and wherein at least one heteroatom is present in an aromatic ring; and
tricyclic heterocycloalkyl rings containing one or more, for example, from 1 to 5, or in certain embodiments, from 1 to 4, heteroatoms chosen from N, O, and S, with the remaining ring atoms being carbon and wherein at least one heteroatom is present in an aromatic ring.

For example, heteroaryl includes a 5- to 7-membered heterocycloalkyl, aromatic ring fused to a 5- to 7-membered cycloalkyl or heterocycloalkyl ring. For such fused, bicyclic heteroaryl ring systems wherein only one of the rings contains one or more heteroatoms, the point of attachment may be at either ring. When the total number of S and O atoms in the heteroaryl group exceeds 1, those heteroatoms are not adjacent to one another. In certain embodiments, the total number of S and O atoms in the heteroaryl group is not more than 2. In certain embodiments, the total number of S and O atoms in the aromatic heterocycle is not more than 1. Examples of heteroaryl groups include, but are not limited to, (as numbered from the linkage position assigned priority 1), 2-pyridyl, 3-pyridyl, 4-pyridyl, 2,3-pyrazinyl, 3,4-pyrazinyl, 2,4-pyrimidinyl, 3,5-pyrimidinyl, 2,3-pyrazolinyl, 2,4-imidazolinyl, isoxazolinyl, oxazolinyl, thiazolinyl, thiadiazolinyl, tetrazolyl, thienyl, benzothiophenyl, furanyl, benzofuranyl, benzoimidazolinyl, indolinyl, pyridazinyl, triazolyl, quinolinyl, pyrazolyl, and 5,6,7,8-tetrahydroisoquinolinyl. Bivalent radicals derived from univalent heteroaryl radicals whose names end in "-yl" by removal of one hydrogen atom from the atom with the free valence are named by adding "-idene" to the name of the corresponding univalent radical, e.g., a pyridyl group with two points of attachment is a pyridylidene. Heteroaryl does not encompass or overlap with aryl, cycloalkyl, or heterocycloalkyl, as defined herein Substituted heteroaryl also includes ring systems substituted with one or more oxide (—$O^-$) substituents, such as pyridinyl N-oxides.

By "heterocycloalkyl" is meant a single, non-aromatic ring, usually with 3 to 7 ring atoms, containing at least 2 carbon atoms in addition to 1-3 heteroatoms independently selected from oxygen, sulfur, and nitrogen, as well as combinations comprising at least one of the foregoing heteroatoms. The ring may be saturated or have one or more carbon-carbon double bonds. Suitable heterocycloalkyl groups include, for example (as numbered from the linkage position assigned priority 1), 2-pyrrolidinyl, 2,4-imidazolidinyl, 2,3-pyrazolidinyl, 2-piperidyl, 3-piperidyl, 4-piperidyl, and 2,5-piperizinyl. Morpholinyl groups are also contemplated, including 2-morpholinyl and 3-morpholinyl (numbered wherein the oxygen is assigned priority 1). Substituted heterocycloalkyl also includes ring systems substituted with one or more oxo (=O) or oxide (—$O^-$) substituents, such as piperidinyl N-oxide, morpholinyl-N-oxide, 1-oxo-1-thiomorpholinyl and 1,1-dioxo-1-thiomorpholinyl.

"Heterocycloalkyl" also includes bicyclic ring systems wherein one non-aromatic ring, usually with 3 to 7 ring atoms, contains at least 2 carbon atoms in addition to 1-3 heteroatoms independently selected from oxygen, sulfur, and nitrogen, as well as combinations comprising at least one of the foregoing heteroatoms; and the other ring, usually with 3 to 7 ring atoms, optionally contains 1-3 heteratoms independently selected from oxygen, sulfur, and nitrogen and is not aromatic.

As used herein, "modulation" refers to a change in activity as a direct or indirect response to the presence of compounds of Formula I relative to the activity in the absence of compounds of Formula I. The change may be an increase in activity or a decrease in activity, and may be due to the direct interaction of the compound with the kinesin, or due to the interaction of the compound with one or more other factors that in turn affect kinesin activity. For example, the presence of the compound may, for example, increase or decrease kinesin activity by directly binding to the kinesin, by causing (directly or indirectly) another factor to increase or decrease the kinesin activity, or by (directly or indirectly) increasing or decreasing the amount of kinesin present in the cell or organism.

The term "sulfanyl" includes the groups: —S-(optionally substituted ($C_1$-$C_6$)alkyl), —S-(optionally substituted aryl), —S-(optionally substituted heteroaryl), and —S-(optionally substituted heterocycloalkyl). Hence, sulfanyl includes the group $C_1$-$C_6$ alkylsulfanyl.

The term "sulfinyl" includes the groups: —S(O)-(optionally substituted ($C_1$-$C_6$)alkyl), —S(O)-optionally substituted aryl), —S(O)-optionally substituted heteroaryl), —S(O)-(optionally substituted heterocycloalkyl); and —S(O)-(optionally substituted amino).

The term "sulfonyl" includes the groups: —S($O_2$)-(optionally substituted ($C_1$-$C_6$)alkyl), —S($O_2$)-optionally substituted aryl), —S($O_2$)-(optionally substituted heteroaryl), —S($O_2$)-(optionally substituted heterocycloalkyl), and —S($O_2$)-(optionally substituted amino).

The term "substituted", as used herein, means that any one or more hydrogens on the designated atom or group is replaced with a selection from the indicated group, provided that the designated atom's normal valence is not exceeded. When a substituent is oxo (i.e., =O) then 2 hydrogens on the atom are replaced. Combinations of substituents and/or variables are permissible only if such combinations result in stable compounds or useful synthetic intermediates. A stable compound or stable structure is meant to imply a compound that is sufficiently robust to survive isolation from a reaction mixture, and subsequent formulation as an agent having at least practical utility. Unless otherwise specified, substituents are named into the core structure. For example, it is to be understood that when (cycloalkyl)alkyl is listed as a possible substituent, the point of attachment of this substituent to the core structure is in the alkyl portion.

The terms "substituted" alkyl, cycloalkyl, aryl, heterocycloalkyl, and heteroaryl, unless otherwise expressly defined, refer respectively to alkyl, cycloalkyl, aryl, heterocycloalkyl, and heteroaryl wherein one or more (such as up to 5, for example, up to 3) hydrogen atoms are replaced by a substituent independently chosen from:

—$R^a$, —$OR^b$, optionally substituted amino (including —$NR^cCOR^b$, —$NR^cCO_2R^a$, —$NR^cCONR^bR^c$, —$NR^bC(NRC)NR^bR^c$, —$NR^bC(NCN)NR^bR^c$, and —$NR^cSO_2R^a$), halo, cyano, nitro, oxo (as a substituent for cycloalkyl, heterocycloalkyl, and heteroaryl), optionally substituted acyl (such as —$COR^b$), optionally substituted alkoxycarbonyl (such as —$CO_2R^b$), aminocarbonyl (such as —$CONR^bR^c$), —$OCOR^b$, —$OCO_2R^a$, —$OCONR^bR^c$, sulfanyl (such as $SR^b$), sulfinyl (such as —$SOR^a$), and sulfonyl (such as —$SO_2R^a$ and —$SO_2NR^bR^c$), where $R^a$ is chosen from optionally substituted $C_1$-$C_6$ alkyl, optionally substituted cycloalkyl, optionally substituted heterocycloalkyl, optionally substituted alkenyl, optionally substituted alkynyl, optionally substituted aryl, and optionally substituted heteroaryl;

$R^b$ is chosen from hydrogen, optionally substituted $C_1$-$C_6$ alkyl, optionally substituted cycloalkyl, optionally substituted heterocycloalkyl, optionally substituted aryl, and optionally substituted heteroaryl; and $R^c$ is independently chosen from hydrogen and optionally substituted $C_1$-$C_4$ alkyl; or $R^b$ and $R^c$, and the nitrogen to which they are attached, form an optionally substituted heterocycloalkyl group; and where each optionally substituted group is unsubstituted or independently substituted with one or more, such as one, two, or three, substituents independently selected from $C_1$-$C_4$ alkyl, aryl, heteroaryl, aryl-$C_1$-$C_4$ alkyl-, heteroaryl-$C_1$-$C_4$ alkyl-, $C_1$-$C_4$ haloalkyl, —$OC_1$-$C_4$ alkyl, —$OC_1$-$C_4$ alkylphenyl, —$C_1$-$C_4$ alkyl-OH, —$OC_1$-$C_4$ haloalkyl, halo, —OH, —$NH_2$, —$C_1$-$C_4$ alkyl-$NH_2$, —N($C_1$-$C_4$ alkyl)($C_1$-$C_4$ alkyl), —NH($C_1$-$C_4$ alkyl), —N($C_1$-$C_4$ alkyl)($C_1$-$C_4$ alkylphenyl), —NH($C_1$-$C_4$ alkylphenyl), cyano, nitro, oxo (as a substituent for cycloalkyl, heterocycloalkyl, or heteroaryl), —$CO_2H$, —C(O)$OC_1$-$C_4$ alkyl, —CON($C_1$-$C_4$ alkyl)($C_1$-$C_4$ alkyl), —CONH($C_1$-$C_4$ alkyl), —$CONH_2$, —NHC(O)($C_1$-$C_4$ alkyl), —NHC(O)(phenyl), —N($C_1$-$C_4$ alkyl)C(O)($C_1$-$C_4$ alkyl), —N($C_1$-$C_4$ alkyl)C(O)(phenyl), —C(O)$C_1$-$C_4$ alkyl, —C(O)$C_1$-$C_4$ alkylphenyl, —C(O)$C_1$-$C_4$ haloalkyl, —OC(O)$C_1$-$C_4$ alkyl, —$SO_2$($C_1$-$C_4$ alkyl), —$SO_2$(phenyl), —$SO_2$($C_1$-$C_4$ haloalkyl), —$SO_2NH_2$, —$SO_2NH$($C_1$-$C_4$ alkyl), —$SO_2NH$(phenyl), —$NHSO_2$($C_1$-$C_4$ alkyl), —$NHSO_2$(phenyl), and —$NHSO_2$($C_1$-$C_4$ haloalkyl).

The term "substituted acyl" refers to the groups (substituted alkyl)-C(O)—; (substituted cycloalkyl)-C(O)—; (substituted aryl)-C(O)—; (substituted heteroaryl)-C(O)—; and (substituted heterocycloalkyl)-C(O)—, wherein the group is attached to the parent structure through the carbonyl functionality and wherein substituted alkyl, cycloalkyl, aryl, heteroaryl, and heterocycloalkyl, refer respectively to alkyl, cycloalkyl, aryl, heteroaryl, and heterocycloalkyl wherein one or more (such as up to 5, for example, up to 3) hydrogen atoms are replaced by a substituent independently chosen from:

—$R^a$, —$OR^b$, optionally substituted amino (including —$NR^cCOR^b$, —$NR^cCO_2R^a$, —$NR^cCONR^bR^c$, —$NR^bC(NR^c)NR^bR^c$, —$NR^bC(NCN)NR^bR^c$, and —$NR^cSO_2R^a$), halo, cyano, nitro, oxo (as a substituent for cycloalkyl, heterocycloalkyl, and heteroaryl), optionally substituted acyl (such as —$COR^b$), optionally substituted alkoxycarbonyl (such as —$CO_2R^b$), aminocarbonyl (such as —$CONR^bR^c$), —$OCOR^b$, —$OCO_2R^a$, —$OCONR^bR^c$, sulfanyl (such as $SR^b$), sulfinyl (such as —$SOR^a$), and sulfonyl (such as —$SO_2R^a$ and —$SO_2NR^bR^c$), where $R^a$ is chosen from optionally substituted $C_1$-$C_6$ alkyl, optionally substituted alkenyl, optionally substituted alkynyl, optionally substituted aryl, and optionally substituted heteroaryl;

$R^b$ is chosen from H, optionally substituted $C_1$-$C_6$ alkyl, optionally substituted cycloalkyl, optionally substituted heterocycloalkyl, optionally substituted aryl, and optionally substituted heteroaryl; and $R^c$ is independently chosen from hydrogen and optionally substituted $C_1$-$C_4$ alkyl; or $R^b$ and $R^c$, and the nitrogen to which they are attached, form an optionally substituted heterocycloalkyl group; and where each optionally substituted group is unsubstituted or independently substituted with one or more, such as one, two, or three, substituents independently selected from $C_1$-$C_4$ alkyl, aryl, heteroaryl, aryl-$C_1$-$C_4$ alkyl-, heteroaryl-$C_1$-$C_4$ alkyl-, $C_1$-$C_4$ haloalkyl, —$OC_1$-$C_4$ alkyl, —$OC_1$-$C_4$ alkylphenyl, —$C_1$-$C_4$ alkyl-OH, —$OC_1$-$C_4$ haloalkyl, halo, —OH, —$NH_2$, —$C_1$-$C_4$ alkyl-$NH_2$, —N($C_1$-$C_4$ alkyl)($C_1$-$C_4$ alkyl), —NH($C_1$-$C_4$ alkyl), —N($C_1$-$C_4$ alkyl)($C_1$-$C_4$ alkylphenyl), —NH($C_1$-$C_4$ alkylphenyl), cyano, nitro, oxo (as a substituent for cycloalkyl, heterocycloalkyl, or heteroaryl), —$CO_2H$, —C(O)$OC_1$-$C_4$ alkyl, —CON($C_1$-$C_4$ alkyl)($C_1$-$C_4$ alkyl), —CONH($C_1$-$C_4$ alkyl), —$CONH_2$, —NHC(O)($C_1$-

$C_4$ alkyl), —NHC(O)(phenyl), —N($C_1$-$C_4$ alkyl)C(O)($C_1$-$C_4$ alkyl), —N($C_1$-$C_4$ alkyl)C(O)(phenyl), —C(O)$C_1$-$C_4$ alkyl, —C(O)$C_1$-$C_4$ alkylphenyl, —C(O)$C_1$-$C_4$ haloalkyl, —OC(O)$C_1$-$C_4$ alkyl, —SO$_2$($C_1$-$C_4$ alkyl), —SO$_2$(phenyl), —SO$_2$($C_1$-$C_4$ haloalkyl), —SO$_2$NH$_2$, —SO$_2$NH($C_1$-$C_4$ alkyl), —SO$_2$NH(phenyl), —NHSO$_2$($C_1$-$C_4$ alkyl), —NHSO$_2$(phenyl), and —NHSO$_2$($C_1$-$C_4$ haloalkyl).

The term "substituted alkoxy" refers to alkoxy wherein the alkyl constituent is substituted (i.e., —O-(substituted alkyl)) wherein "substituted alkyl" refers to alkyl wherein one or more (such as up to 5, for example, up to 3) hydrogen atoms are replaced by a substituent independently chosen from:

—$R^a$, —$OR^b$, optionally substituted amino (including —NR$^c$COR$^b$, —NR$^c$CO$_2$R$^a$, —NR$^c$CONR$^b$R$^c$, —NR$^b$C(NR$^c$)NR$^b$R$^c$, —NR$^b$C(NCN)NR$^b$R$^c$, and —NRCSO$_2$R$^a$), halo, cyano, nitro, oxo (as a substituent for cycloalkyl, heterocycloalkyl, and heteroaryl), optionally substituted acyl (such as —COR$^b$), optionally substituted alkoxycarbonyl (such as —CO$_2$R$^b$), aminocarbonyl (such as —CONR$^b$R$^c$), —OCOR$^b$, —OCO$_2$R$^a$, —OCONR$^b$R$^c$, sulfanyl (such as SR$^b$), sulfinyl (such as —SOR$^a$), and sulfonyl (such as —SO$_2$R$^a$ and —SO$_2$NR$^b$R$^c$), where $R^a$ is chosen from optionally substituted $C_1$-$C_6$ alkyl, optionally substituted alkenyl, optionally substituted alkynyl, optionally substituted aryl, and optionally substituted heteroaryl;

$R^b$ is chosen from H, optionally substituted $C_1$-$C_6$ alkyl, optionally substituted cycloalkyl, optionally substituted heterocycloalkyl, optionally substituted aryl, and optionally substituted heteroaryl; and $R^c$ is independently chosen from hydrogen and optionally substituted $C_1$-$C_4$ alkyl; or $R^b$ and $R^c$, and the nitrogen to which they are attached, form an optionally substituted heterocycloalkyl group; and where each optionally substituted group is unsubstituted or independently substituted with one or more, such as one, two, or three, substituents independently selected from $C_1$-$C_4$ alkyl, aryl, heteroaryl, aryl-$C_1$-$C_4$ alkyl-, heteroaryl-$C_1$-$C_4$ alkyl-, $C_1$-$C_4$ haloalkyl, —O$C_1$-$C_4$ alkyl, —O$C_1$-$C_4$ alkylphenyl, —$C_1$-$C_4$ alkyl-OH, —O$C_1$-$C_4$ haloalkyl, halo, —OH, —NH$_2$, —$C_1$-$C_4$ alkyl-NH$_2$, —N($C_1$-$C_4$ alkyl)($C_1$-$C_4$ alkyl), —NH($C_1$-$C_4$ alkyl), —N($C_1$-$C_4$ alkyl)($C_1$-$C_4$ alkylphenyl), —NH($C_1$-$C_4$ alkylphenyl), cyano, nitro, oxo (as a substituent for cycloalkyl, heterocycloalkyl, or heteroaryl), —CO$_2$H, —C(O)O$C_1$-$C_4$ alkyl, —CON($C_1$-$C_4$ alkyl)($C_1$-$C_4$ alkyl), —CONH($C_1$-$C_4$ alkyl), —CONH$_2$, —NHC(O)($C_1$-$C_4$ alkyl), —NHC(O)(phenyl), —N($C_1$-$C_4$ alkyl)C(O)($C_1$-$C_4$ alkyl), —N($C_1$-$C_4$ alkyl)C(O)(phenyl), —C(O)$C_1$-$C_4$ alkyl, —C(O)$C_1$-$C_4$ alkylphenyl, —C(O)$C_1$-$C_4$ haloalkyl, —OC(O)$C_1$-$C_4$ alkyl, —SO$_2$($C_1$-$C_4$ alkyl), —SO$_2$(phenyl), —SO$_2$($C_1$-$C_4$ haloalkyl), —SO$_2$NH$_2$, —SO$_2$NH($C_1$-$C_4$ alkyl), —SO$_2$NH(phenyl), —NHSO$_2$($C_1$-$C_4$ alkyl), —NHSO$_2$(phenyl), and —NHSO$_2$($C_1$-$C_4$ haloalkyl). In some embodiments, a substituted alkoxy group is "polyalkoxy" or —O-(optionally substituted alkylene)-(optionally substituted alkoxy), and includes groups such as —OCH$_2$CH$_2$OCH$_3$, and residues of glycol ethers such as polyethyleneglycol, and —O(CH$_2$CH$_2$O)$_x$CH$_3$, where x is an integer of 2-20, such as 2-10, and for example, 2-5. Another substituted alkoxy group is hydroxyalkoxy or —OCH$_2$(CH$_2$)$_y$OH, where y is an integer of 1-10, such as 1-4.

The term "substituted alkoxycarbonyl" refers to the group (substituted alkyl)-O—C(O)— wherein the group is attached to the parent structure through the carbonyl functionality and wherein substituted refers to alkyl wherein one or more (such as up to 5, for example, up to 3) hydrogen atoms are replaced by a substituent independently chosen from:

—$R^a$, —$OR^b$, optionally substituted amino (including —NR$^c$COR$^b$, —NR$^c$CO$_2$R$^a$, —NR$^c$CONR$^b$R$^c$, —NR$^b$C(NR$^c$)NR$^b$R$^c$, —NR$^b$C(NCN)NR$^b$R$^c$, and —NR$^c$SO$_2$R$^a$), halo, cyano, nitro, oxo (as a substituent for cycloalkyl, heterocycloalkyl, and heteroaryl), optionally substituted acyl (such as —COR$^b$), optionally substituted alkoxycarbonyl (such as —CO$_2$R$^b$), aminocarbonyl (such as —CONR$^b$R$^c$), —OCOR$^b$, —OCO$_2$R$^a$, —OCONR$^b$R$^c$, sulfanyl (such as SR$^b$), sulfinyl (such as —SOR$^a$), and sulfonyl (such as —SO$_2$R$^a$ and —SO$_2$NR$^b$R$^c$), where $R^a$ is chosen from optionally substituted $C_1$-$C_6$ alkyl, optionally substituted alkenyl, optionally substituted alkynyl, optionally substituted aryl, and optionally substituted heteroaryl;

$R^b$ is chosen from H, optionally substituted $C_1$-$C_6$ alkyl, optionally substituted cycloalkyl, optionally substituted heterocycloalkyl, optionally substituted aryl, and optionally substituted heteroaryl; and $R^c$ is independently chosen from hydrogen and optionally substituted $C_1$-$C_4$ alkyl; or $R^b$ and $R^c$, and the nitrogen to which they are attached, form an optionally substituted heterocycloalkyl group; and where each optionally substituted group is unsubstituted or independently substituted with one or more, such as one, two, or three, substituents independently selected from $C_1$-$C_4$ alkyl, aryl, heteroaryl, aryl-$C_1$-$C_4$ alkyl-, heteroaryl-$C_1$-$C_4$ alkyl-, $C_1$-$C_4$ haloalkyl, —O$C_1$-$C_4$ alkyl, —O$C_1$-$C_4$ alkylphenyl, —$C_1$-$C_4$ alkyl-OH, —O$C_1$-$C_4$ haloalkyl, halo, —OH, —NH$_2$, —$C_1$-$C_4$ alkyl-NH$_2$, —N($C_1$-$C_4$ alkyl)($C_1$-$C_4$ alkyl), —NH($C_1$-$C_4$ alkyl), —N($C_1$-$C_4$ alkyl)($C_1$-$C_4$ alkylphenyl), —NH($C_1$-$C_4$ alkylphenyl), cyano, nitro, oxo (as a substituent for cycloalkyl, heterocycloalkyl, or heteroaryl), —CO$_2$H, —C(O)O$C_1$-$C_4$ alkyl, —CON($C_1$-$C_4$ alkyl)($C_1$-$C_4$ alkyl), —CONH($C_1$-$C_4$ alkyl), —CONH$_2$, —NHC(O)($C_1$-$C_4$ alkyl), —NHC(O)(phenyl), —N($C_1$-$C_4$ alkyl)C(O)($C_1$-$C_4$ alkyl), —N($C_1$-$C_4$ alkyl)C(O)(phenyl), —C(O)$C_1$-$C_4$ alkyl, —C(O)$C_1$-$C_4$ alkylphenyl, —C(O)$C_1$-$C_4$ haloalkyl, —OC(O)$C_1$-$C_4$ alkyl, —SO$_2$($C_1$-$C_4$ alkyl), —SO$_2$(phenyl), —SO$_2$($C_1$-$C_4$ haloalkyl), —SO$_2$NH$_2$, —SO$_2$NH($C_1$-$C_4$ alkyl), —SO$_2$NH(phenyl), —NHSO$_2$($C_1$-$C_4$ alkyl), —NHSO$_2$(phenyl), and —NHSO$_2$($C_1$-$C_4$ haloalkyl).

The term "substituted amino" refers to the group —NHR$^d$ or —NR$^d$R$^e$ wherein R$^d$ is chosen from: hydroxy, optionally substituted alkoxy, optionally substituted alkyl, optionally substituted cycloalkyl, optionally substituted acyl, optionally substituted carbamimidoyl, aminocarbonyl, optionally substituted aryl, optionally substituted heteroaryl, optionally substituted heterocycloalkyl, optionally substituted alkoxycarbonyl, sulfinyl and sulfonyl, and wherein R$^e$ is chosen from: optionally substituted alkyl, optionally substituted cycloalkyl, optionally substituted aryl, optionally substituted heteroaryl, and optionally substituted heterocycloalkyl, and wherein substituted alkyl, cycloalkyl, aryl, heterocycloalkyl, and heteroaryl refer respectively to alkyl, cycloalkyl, aryl, heterocycloalkyl, and heteroaryl wherein one or more (such as up to 5, for example, up to 3) hydrogen atoms are replaced by a substituent independently chosen from:

—$R^a$, —$OR^b$, optionally substituted amino (including —NR$^c$COR$^b$, —NR$^c$CO$_2$R$^a$, —NR$^c$CONR$^b$R$^c$, NR$^b$C(NR$^c$)NR$^b$R$^c$, —NR$^b$C(NCN)NR$^b$R$^c$, and —NR$^c$SO$_2$R$^a$), halo, cyano, nitro, oxo (as a substituent for cycloalkyl, heterocycloalkyl, and heteroaryl), optionally substituted acyl (such as —COR$^b$), optionally substituted alkoxycarbonyl (such as —CO$_2$R$^b$), aminocarbonyl (such as —CONR$^b$R$^c$), —OCOR$^b$, —OCO$_2$R$^a$, —OCONR$^b$R$^c$, sulfanyl (such as SR$^b$), sulfinyl (such as —SOR$^a$), and sulfonyl (such as —SO$_2$R$^a$ and —SO$_2$NR$^b$R$^c$), where $R^a$ is chosen from optionally substituted $C_1$-$C_6$ alkyl, optionally substituted alkenyl, optionally substituted alkynyl, optionally substituted aryl, and optionally substituted heteroaryl;

$R^b$ is chosen from H, optionally substituted $C_1$-$C_6$ alkyl, optionally substituted cycloalkyl, optionally substituted heterocycloalkyl, optionally substituted aryl, and optionally substituted heteroaryl; and $R^c$ is independently chosen from hydrogen and optionally substituted $C_1$-$C_4$ alkyl; or $R^b$ and $R^c$, and the nitrogen to which they are attached, form an optionally substituted heterocycloalkyl group; and where each optionally substituted group is unsubstituted or independently substituted with one or more, such as one, two, or three, substituents independently selected from $C_1$-$C_4$ alkyl, aryl, heteroaryl, aryl-$C_1$-$C_4$ alkyl-, heteroaryl-$C_1$-$C_4$ alkyl-, $C_1$-$C_4$ haloalkyl, —$OC_1$-$C_4$ alkyl, —$OC_1$-$C_4$ alkylphenyl, —$C_1$-$C_4$ alkyl-OH, —$OC_1$-$C_4$ haloalkyl, halo, —OH, —$NH_2$, —$C_1$-$C_4$ alkyl-$NH_2$, —N($C_1$-$C_4$ alkyl)($C_1$-$C_4$ alkyl), —NH($C_1$-$C_4$ alkyl), —N($C_1$-$C_4$ alkyl)($C_1$-$C_4$ alkylphenyl), —NH($C_1$-$C_4$ alkylphenyl), cyano, nitro, oxo (as a substituent for cycloalkyl, heterocycloalkyl, or heteroaryl), —$CO_2H$, —C(O)$OC_1$-$C_4$ alkyl, —CON($C_1$-$C_4$ alkyl)($C_1$-$C_4$ alkyl), —CONH($C_1$-$C_4$ alkyl), —$CONH_2$, —NHC(O)($C_1$-$C_4$ alkyl), —NHC(O)(phenyl), —N($C_1$-$C_4$ alkyl)C(O)($C_1$-$C_4$ alkyl), —N($C_1$-$C_4$ alkyl)C(O)(phenyl), —C(O)$C_1$-$C_4$ alkyl, —C(O)$C_1$-$C_4$ alkylphenyl, —C(O)$C_1$-$C_4$ haloalkyl, —OC(O)$C_1$-$C_4$ alkyl, —$SO_2$($C_1$-$C_4$ alkyl), —$SO_2$(phenyl), —$SO_2$($C_1$-$C_4$ haloalkyl), —$SO_2NH_2$, —$SO_2$NH($C_1$-$C_4$ alkyl), —$SO_2$NH(phenyl), —$NHSO_2$($C_1$-$C_4$ alkyl), —$NHSO_2$(phenyl), and —$NHSO_2$($C_1$-$C_4$ haloalkyl); and wherein optionally substituted acyl, optionally substituted alkoxycarbonyl, sulfinyl and sulfonyl are as defined herein.

The term "substituted amino" also refers to N-oxides of the groups —$NHR^d$, and $NR^dR^d$ each as described above. N-oxides can be prepared by treatment of the corresponding amino group with, for example, hydrogen peroxide or m-chloroperoxybenzoic acid. The person skilled in the art is familiar with reaction conditions for carrying out the N-oxidation.

Compounds of Formula I include, but are not limited to, optical isomers of compounds of Formula I, racemates, and other mixtures thereof. In those situations, the single enantiomers or diastereomers, i.e., optically active forms, can be obtained by asymmetric synthesis or by resolution of the racemates. Resolution of the racemates can be accomplished, for example, by conventional methods such as crystallization in the presence of a resolving agent, or chromatography, using, for example a chiral high-pressure liquid chromatography (HPLC) column. In addition, compounds of Formula I include Z- and E-forms (or cis- and trans-forms) of compounds with carbon-carbon double bonds. Where compounds of Formula I exists in various tautomeric forms, chemical entities of the present invention include all tautomeric forms of the compound.

Chemical entities of the present invention include, but are not limited to compounds of Formula I and all pharmaceutically acceptable forms thereof. Pharmaceutically acceptable forms of the compounds recited herein include pharmaceutically acceptable salts, solvates, crystal forms (including polymorphs and clathrates), chelates, non-covalent complexes, prodrugs, and mixtures thereof. In certain embodiments, the compounds described herein are in the form of pharmaceutically acceptable salts. Hence, the terms "chemical entity" and "chemical entities" also encompass pharmaceutically acceptable salts, solvates, chelates, non-covalent complexes, prodrugs, and mixtures.

"Pharmaceutically acceptable salts" include, but are not limited to salts with inorganic acids, such as hydrochloride, phosphate, diphosphate, hydrobromide, sulfate, sulfinate, nitrate, and like salts; as well as salts with an organic acid, such as malate, maleate, fumarate, tartrate, succinate, citrate, lactate, methanesulfonate, p-toluenesulfonate, 2-hydroxyethylsulfonate, benzoate, salicylate, stearate, and alkanoate such as acetate, HOOC—$(CH_2)_n$—COOH where n is 0-4, and like salts. Similarly, pharmaceutically acceptable cations include, but are not limited to sodium, potassium, calcium, aluminum, lithium, and ammonium.

In addition, if the compound of Formula I is obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare non-toxic pharmaceutically acceptable addition salts.

As noted above, prodrugs also fall within the scope of chemical entities, for example ester or amide derivatives of the compounds of Formula I. The term "prodrugs" includes any compounds that become compounds of Formula I when administered to a patient, e.g., upon metabolic processing of the prodrug. Examples of prodrugs include, but are not limited to, acetate, formate, phosphate, and benzoate and like derivatives of functional groups (such as alcohol or amine groups) in the compounds of Formula I.

The term "solvate" refers to the chemical entity formed by the interaction of a solvent and a compound. Suitable solvates are pharmaceutically acceptable solvates, such as hydrates, including monohydrates and hemi-hydrates.

The term "chelate" refers to the chemical entity formed by the coordination of a compound to a metal ion at two (or more) points.

The term "non-covalent complex" refers to the chemical entity formed by the interaction of a compound and another molecule wherein a covalent bond is not formed between the compound and the molecule. For example, complexation can occur through van der Waals interactions, hydrogen bonding, and electrostatic interactions (also called ionic bonding).

The term "active agent" is used to indicate a chemical entity which has biological activity. In certain embodiments, an "active agent" is a compound having pharmaceutical utility. For example an active agent may be an anti-cancer therapeutic.

By "significant" is meant any detectable change that is statistically significant in a standard parametric test of statistical significance such as Student's T-test, where $p<0.05$.

The term "antimitotic" refers to a drug for inhibiting or preventing mitosis, for example, by causing metaphase arrest. Some antitumour drugs block proliferation and are considered antimitotics.

The term "therapeutically effective amount" of a chemical entity of this invention means an amount effective, when administered to a human or non-human patient, to provide a therapeutic benefit such as amelioration of symptoms, slowing of disease progression, or prevention of disease e.g., a therapeutically effective amount may be an amount sufficient to decrease the symptoms of a disease. In some embodiments, a therapeutically effective amount is an amount sufficient to reduce cancer symptoms. In some embodiments a therapeutically effective amount is an amount sufficient to decrease the number of detectable cancerous cells in an organism, detectably slow, or stop the growth of a cancerous tumor. In some embodiments, a therapeutically effective amount is an amount sufficient to shrink a cancerous tumor.

The term "inhibition" indicates a significant decrease in the baseline activity of a biological activity or process.

"Treatment" or "treating" means any treatment of a disease in a patient, including:
a) preventing the disease, that is, causing the clinical symptoms of the disease not to develop;
b) inhibiting the disease;
c) slowing or arresting the development of clinical symptoms; and/or
d) relieving the disease, that is, causing the regression of clinical symptoms.

"Patient" refers to an animal, such as a mammal, that has been or will be the object of treatment, observation or experiment. The methods of the invention can be useful in both human therapy and veterinary applications. In some embodiments, the patient is a mammal; in some embodiments the patient is human; and in some embodiments the patient is chosen from cats and dogs.

The compounds of Formula I can be named and numbered in the manner described below. For example, using nomenclature software, such as Pipeline Pilot or Nomenclator™ available from ChemInnovation Software, Inc., the cis, cis-compound:

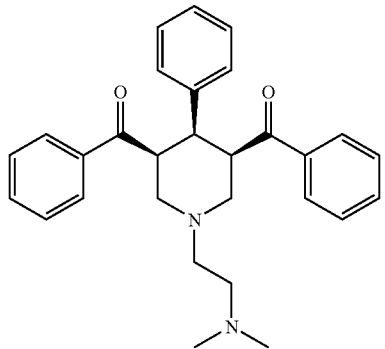

can be named ((5S,3R)-1-[2-(dimethylamino)ethyl]-4-phenyl-5-(phenylcarbonyl)(3-piperidyl)phenyl ketone. If that same compound is named with structure=name algorithm of ChemDraw Ultra 9.0, the name is ((3S,4R,5R)-1-(2-(dimethylamino)ethyl)-4-phenylpiperidine-3,5-diyl)bis(phenylmethanone).

The analogous trans, cis-compound

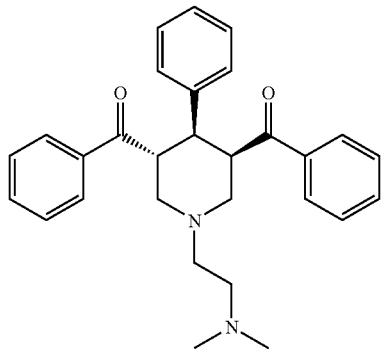

can be named, using Pipeline Pilot, (3R,5R)-1-[2-(dimethylamino)ethyl]-4-phenyl-5-(phenylcarbonyl)(3-piperidyl) phenyl ketone or, using ChemDraw, ((3R,5R)-1-(2-(dimethylamino)ethyl)-4-phenylpiperidine-3,5-diyl)bis (phenylmethanone).

Similarly, the analogous trans, trans-compound would have the structure:

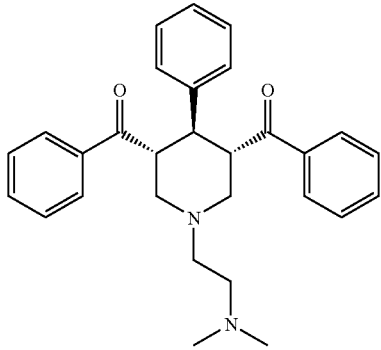

The present invention is directed to certain chemical entities that cause mitotic arrest and cell death. Accordingly, provided is at least one chemical entity chosen from compounds of Formula I:

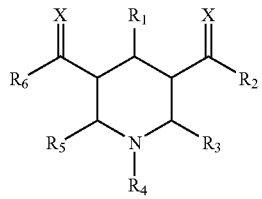

(Formula I)

and pharmaceutically acceptable salts, solvates, chelates, non-covalent complexes, prodrugs, and mixtures thereof, wherein $=X$ is chosen from $=O$ and $=N-OR_7$, where $R_7$ is selected from hydrogen and optionally substituted alkyl, provided that at least one $=X$ is $=O$ $R_1$ is chosen from hydrogen, optionally substituted alkyl, optionally substituted cycloalkyl, optionally substituted heterocycloalkyl, optionally substituted aryl and optionally substituted heteroaryl;

$R_2$ is chosen from optionally substituted aryl, optionally substituted heterocycloalkyl, optionally substituted alkyl, optionally substituted cycloalkyl, optionally substituted heteroaryl, optionally substituted alkoxy, hydroxy, and optionally substituted amino;

$R_3$ is chosen from hydrogen and optionally substituted alkyl;

$R_4$ is chosen from hydrogen, optionally substituted alkyl, optionally substituted heterocycloalkyl, optionally substituted acyl, optionally substituted aryl, optionally substituted heteroaryl, aminocarbonyl, sulfonyl, optionally substituted alkoxycarbonyl, and optionally substituted cycloalkyl;

$R_5$ is chosen from hydrogen and optionally substituted alkyl; and $R_6$ is chosen from optionally substituted aryl, optionally substituted heterocycloalkyl, optionally substituted alkyl, optionally substituted cycloalkyl, optionally substituted heteroaryl, optionally substituted alkoxy, hydroxy, and optionally substituted amino provided that:

the compound of Formula I is not dimethyl 1-benzylpiperidine-3,5-dicarboxylate; methyl 5-acetyl-1-benzylpiperidine-3-carboxylate; dimethyl 1-benzyl-4-phenylpiperidine-3,5-dicarboxylate; (1-methyl-4-phenylpiperidine-3,5-diyl)bis(phenylmethanone); (1-benzyl-4-phenylpiperidine-3,5-diyl)bis(phenylmethanone); (1-(2-hydroxyethyl)-4-phenylpiperidine-3,5-diyl)bis(phenylmethanone); (1-cyclohexyl-4-phenylpiperidine-3,5-diyl)bis(phenylmethanone); (4-phenyl-1-(phenylamino)piperidine-3,5-diyl)bis(phenylmethanone); or (1-(dimethylamino)-4-phenylpiperidine-3,5-diyl)bis(phenylmethanone).

In some embodiments, $R_1$ is chosen from hydrogen, optionally substituted lower alkyl, optionally substituted cycloalkyl, optionally substituted heterocycloalkyl, optionally substituted aryl, and optionally substituted heteroaryl. In some embodiments, $R_1$ is chosen from optionally substituted aryl and optionally substituted heteroaryl.

In some embodiments, $R_1$ is chosen from aryl and heteroaryl, either of which is optionally substituted with one, two, or three groups chosen from halo, optionally substituted lower alkyl, optionally substituted lower alkoxy, hydroxy, cyano, optionally substituted acyl, optionally substituted alkoxycarbonyl, carboxyl, optionally substituted aminocarbonyl, and sulfonyl. In some embodiments, $R_1$ is chosen from aryl and heteroaryl, either of which is optionally substituted with one, two, or three groups chosen from halo, optionally substituted lower alkyl, cyano, optionally substituted lower alkoxy, and hydroxy.

In some embodiments, $R_1$ is chosen from aryl and heteroaryl, either of which is optionally substituted with one, two, or three groups chosen from halo, methyl, trifluoromethyl, ethyl, methoxy, ethoxy, hydroxy, carboxyl, methoxycarbonyl, aminocarbonyl, N-methylaminocarbonyl, N,N-dimethylaminocarbonyl, cyano, hydroxymethyl, aminomethyl, acetamidomethyl, methylsulfonyl, acetyl, and isopropyl. In some embodiments, $R_1$ is chosen from aryl and heteroaryl, either of which is optionally substituted with one, two, or three groups chosen from halo, methyl, trifluoromethyl, ethyl, methoxy, ethoxy, cyano, and hydroxy.

In some embodiments, $R_1$ is chosen from optionally substituted phenyl and optionally substituted pyridinyl. In some embodiments, $R_1$ is chosen from phenyl and pyridinyl, either of which is optionally substituted with one, two, or three groups chosen from halo, optionally substituted lower alkyl, optionally substituted lower alkoxy, hydroxy, cyano, optionally substituted acyl, optionally substituted alkoxycarbonyl, carboxyl, optionally substituted aminocarbonyl, and sulfonyl. In some embodiments, $R_1$ is chosen from phenyl and pyridinyl, either of which is optionally substituted with one, two, or three groups chosen from halo, optionally substituted lower alkyl, cyano, optionally substituted lower alkoxy, and hydroxy.

In some embodiments, $R_1$ is chosen from phenyl and pyridinyl, either of which is optionally substituted with one, two, or three groups chosen halo, methyl, trifluoromethyl, ethyl, methoxy, ethoxy, hydroxy, carboxyl, methoxycarbonyl, aminocarbonyl, N-methylaminocarbonyl, N,N-dimethylaminocarbonyl, cyano, hydroxymethyl, aminomethyl, acetamidomethyl, methylsulfonyl, acetyl, and isopropyl. In some embodiments, $R_1$ is chosen from phenyl and pyridinyl, either of which is optionally substituted with one, two, or three groups chosen from halo, methyl, trifluoromethyl, ethyl, methoxy, ethoxy, cyano, and hydroxy.

In some embodiments, $R_1$ is chosen from hydrogen, phenyl, 2,3-dimethylphenyl, 3-halo-2-methylphenyl, 2,3-dihalophenyl, 2-methylphenyl, 3-methylpyridin-2-yl, 3-carbamoyl-2-methylphenyl, 3-(dimethylcarbamoyl)-2-methylphenyl, 3-methylphenyl, 2-chloro-3-fluorophenyl, 2-halo-3-methylphenyl, 3-carboxy-2-methylphenyl, 2-halophenyl, 3-halo-phenyl, 4-halo-phenyl, 2,6-dimethylphenyl, 3-(trifluoromethyl)phenyl, 2-cyanophenyl, 4-methylphenyl, 3,4-dimethylphenyl, 6-methylpyridin-2-yl, 3-(hydroxymethyl)-2-methylphenyl, 3-carboxyphenyl, 2-methoxyphenyl, 2-(trifluoromethyl)phenyl, 4-(trifluoromethyl)phenyl, 3,4-dichlorophenyl, 3-methoxyphenyl, 3,5-dichlorophenyl, 4-methoxyphenyl, 2,5-dichlorophenyl, 2,4-dichlorophenyl, 2,3-dihalophenyl, 3-(methoxycarbonyl)phenyl, 3-(methylcarbamoyl)phenyl, 4-hydroxyphenyl, 3-(dimethylcarbamoyl)phenyl, 3-(hydroxymethyl)phenyl, 2-hydroxyphenyl, 3-carbamoylphenyl, 3-hydroxyphenyl, 3-(aminomethyl)phenyl, 3-(acetamidomethyl)phenyl, 3-isopropylphenyl, and pyridinyl. In some embodiments, $R_1$ is chosen from phenyl, 2,3-dimethylphenyl, 3-halo-2-methylphenyl, 2,3-dihalophenyl, 2-methylphenyl, and pyridinyl.

In some embodiments, $R_2$ is chosen from optionally substituted amino, optionally substituted aryl and optionally substituted heteroaryl.

In some embodiments, $R_2$ is chosen from $—NR_8R_9$ wherein $R_8$ and $R_9$ together with the nitrogen to which they are bound form a 4- to 8-membered heterocycloalkyl ring which optionally includes an additional heteroatom chosen from O, S, and N, which 4- to 8-membered heterocycloalkyl ring optionally is fused to an aryl, heteroaryl, heterocyclyl, or cycloaliphatic ring and wherein the 4- to 8-membered heterocycloalkyl ring is optionally substituted with one, two, or three groups chosen from optionally substituted phenyl, aminocarbonyl, alkoxycarbonyl, halo, optionally substituted lower alkyl, optionally substituted lower alkoxy, and hydroxy. In some embodiments, $R_2$ is chosen from $—NR_8R_9$ wherein $R_8$ and $R_9$ together with the nitrogen to which they are bound form a 4- to 8-membered heterocycloalkyl ring which optionally includes an additional heteroatom chosen from O, S, and N, aryl, and heteroaryl, each of which is optionally substituted with one, two, or three groups chosen from aminocarbonyl, alkoxycarbonyl, lower alkoy, lower alkoxy, halo, trifluoromethyl, and hydroxy.

In some embodiments, $R_2$ is piperidinyl-1-yl or pyrrolidin-1-yl, each of which is optionally substituted with one or two groups chosen from aminocarbonyl, lower alkoxycarbonyl, methoxymethyl, halo, methyl, trifluoromethyl, ethyl, methoxy, ethoxy, and hydroxy. In some embodiments, $R_2$ is pyrrolidin-1-yl, optionally substituted with one or two groups chosen from aminocarbonyl, lower alkoxycarbonyl, methoxymethyl, halo, methyl, trifluoromethyl, ethyl, methoxy, ethoxy, and hydroxy. In some embodiments, $R_2$ is pyrrolidin-1-yl, optionally substituted with trifluoromethyl or methyl. In some embodiments, $R_2$ is (S)-2-(trifluoromethyl)pyrrolidin-1-yl or (R)-2-(trifluoromethyl)pyrrolidin-1-yl.

In some embodiments, $R_2$ is chosen from $—NR_{10}R_{11}$ wherein $R_{10}$ is chosen from hydrogen and optionally substituted alkyl, and $R_{11}$ is chosen from alkoxy, optionally substituted aryl, optionally substituted heteroaryl, optionally substituted alkyl, optionally substituted cycloalkyl, and optionally substituted heterocycloalkyl. In some embodiments, $R_{10}$ is chosen from hydrogen and optionally substituted lower alkyl. In some embodiments, $R_{10}$ is chosen from hydrogen and methyl. In some embodiments, $R_{11}$ is chosen from optionally substituted phenyl, optionally substituted lower alkyl, and optionally substituted cycloalkyl. In some embodiments, $R_{11}$ is chosen from phenyl, optionally substituted lower alkyl, and cycloalkyl.

In some embodiments, $R_2$ is chosen from optionally substituted aryl and optionally substituted heteroaryl. In some embodiments, $R_2$ is chosen from aryl and heteroaryl, each of which is optionally substituted with one, two, or three groups chosen from halo, optionally substituted lower alkyl, optionally substituted lower alkoxy, and hydroxy. In some embodiments, $R_2$ is chosen from aryl and heteroaryl, either of which is which is optionally substituted with one, two, or three groups chosen from halo, methyl, trifluoromethyl, ethyl, methoxy, ethoxy, and hydroxy.

In some embodiments, $R_2$ is chosen from optionally substituted phenyl and optionally substituted pyridinyl. In some embodiments, $R_2$ is chosen from phenyl and pyridinyl, either of which is optionally substituted with one, two, or three groups chosen from halo, optionally substituted lower alkyl, optionally substituted lower alkoxy, and hydroxy. In some embodiments, $R_2$ is chosen from phenyl and pyridinyl, either of which is which is optionally substituted with one, two, or three groups chosen from halo, methyl, trifluoromethyl, ethyl, methoxy, ethoxy, and hydroxy. In some embodiments, $R_2$ is chosen from phenyl, hydroxyphenyl, and pyridinyl.

In some embodiments, $R_2$ is optionally substituted alkoxy. In some embodiments, $R_2$ is optionally substituted lower alkoxy. In some embodiments, $R_2$ is ethoxy.

In some embodiments, $R_3$ is chosen from hydrogen and optionally substituted lower alkyl. In some embodiments, $R_3$ is chosen from hydrogen and lower alkyl. In some embodiments, $R_3$ is chosen from hydrogen and methyl. In some embodiments, $R_3$ is hydrogen.

In some embodiments, $R_4$ is chosen from hydrogen, optionally substituted lower alkyl, optionally substituted heterocycloalkyl, optionally substituted acyl, optionally substituted aryl, optionally substituted heteroaryl, aminocarbonyl, sulfonyl, optionally substituted alkoxycarbonyl, and optionally substituted cycloalkyl. In some embodiments, $R_4$ is chosen from hydrogen, optionally substituted acyl, optionally substituted aminocarbonyl, optionally substituted sulfonyl, optionally substituted alkoxycarbonyl optionally substituted lower alkyl, and optionally substituted cycloalkyl. In some embodiments, $R_4$ is chosen from hydrogen, allyl, acyl substituted with optionally substituted lower alkyl, aminocarbonyl substituted with optionally substituted lower alkyl, sulfonyl substituted with optionally substituted lower alkyl, alkoxycarbonyl substituted with optionally substituted lower alkyl, and lower alkyl optionally substituted with optionally substituted phenyl, hydroxy, lower alkoxy, alkoxycarbonyl, optionally substituted aminocarbonyl, heterocycloalkyl, acyloxy, optionally substituted amino, and carboxy. In some embodiments, $R_4$ is chosen from hydrogen, 2-hydroxyethyl, benzyl, 2-methoxyethyl, 2-hydroxycyclopentyl, 1,3-dihydroxypropan-2-yl, cyclopentyl, methyl, 2-morpholinoethyl, 2-methoxy-2-oxoethyl, 2-(methylamino)-2-oxoethyl, 2-acetoxyethyl, (R)-1-hydroxypropan-2-yl, (S)-1-hydroxypropan-2-yl, (R)-2-hydroxypropyl, (S)-2-hydroxypropyl, propyl, 2-(dimethylamino)ethyl, 2-(piperazin-1-yl)ethyl, 2-amino-2-oxoethyl, carboxymethyl, 3-hydroxypropyl, ethyl, 3-ethoxy-3-oxopropyl, 1,3-dihydroxypropan-2-yl, (tetrahydrofuran-2-yl)methyl, 2-ethoxy-2-oxoethyl, 3,3-dimethyl-1-(methylamino)-1-oxobutan-2-yl, 2-oxoazepan-3-yl, 1-hydroxy-3-methylbutan-2-yl, 2-(piperazin-1-yl)ethyl, 2-(4-acetylpiperazin-1-yl)ethyl, 1-propionyl, 2-(dimethylamino)-2-oxoethyl, 2-(4-(tert-butoxycarbonyl)piperazin-1-yl)-2-oxoethyl, 2-oxo-2-(piperidin-1-yl)ethyl, 2-oxo-2-(piperazin-1-yl)ethyl, 2-(4-methylpiperazin-1-yl)-2-oxoethyl, 3-(dimethylamino)propylsulfonyl, 2-(dimethylamino)ethoxycarbonyl, 2-(dimethylamino)ethylaminocarbonyl, N-[2-(dimethylamino)ethyl]-N-methylaminocarbonyl 4-(dimethylamino)-2,2-dimethylbutan-1-one and 2-(2-(dimethylamino)ethylamino)-2-oxoethyl.

In some embodiments, $R_5$ is chosen from hydrogen and optionally substituted lower alkyl. In some embodiments, $R_5$ is chosen from hydrogen and lower alkyl. In some embodiments, $R_5$ is chosen from hydrogen and methyl. In some embodiments, $R_5$ is hydrogen.

In some embodiments, $R_6$ is chosen from optionally substituted amino, optionally substituted aryl and optionally substituted heteroaryl.

In some embodiments, $R_6$ is chosen from —$NR_8R_9$ wherein $R_8$ and $R_9$ together with the nitrogen to which they are bound form a 4- to 8-membered heterocycloalkyl ring which optionally includes an additional heteroatom chosen from O, S, and N, which 4- to 8-membered heterocycloalkyl ring optionally is fused to an aryl, heteroaryl, heterocyclyl, or cycloaliphatic ring and wherein the 4- to 8-membered heterocycloalkyl ring is optionally substituted with one, two, or three groups chosen from optionally substituted phenyl, aminocarbonyl, alkoxycarbonyl, halo, optionally substituted lower alkyl, optionally substituted lower alkoxy, and hydroxy. In some embodiments, $R_6$ is chosen from —$NR_8R_9$ wherein $R_8$ and $R_9$ together with the nitrogen to which they are bound form a 4- to 8-membered heterocycloalkyl ring which optionally includes an additional heteroatom chosen from O, S, and N, aryl, and heteroaryl, each of which is optionally substituted with one, two, or three groups chosen from aminocarbonyl, alkoxycarbonyl, lower alkoy, lower alkoxy, halo, trifluoromethyl, and hydroxy.

In some embodiments, $R_6$ is piperidinyl-1-yl or pyrrolidin-1-yl, each of which is optionally substituted with one or two groups chosen from aminocarbonyl, lower alkoxycarbonyl, methoxymethyl, halo, methyl, trifluoromethyl, ethyl, methoxy, ethoxy, and hydroxy. In some embodiments, $R_6$ is pyrrolidin-1-yl, optionally substituted with one or two groups chosen from aminocarbonyl, lower alkoxycarbonyl, methoxymethyl, halo, methyl, trifluoromethyl, ethyl, methoxy, ethoxy, and hydroxy. In some embodiments, $R_6$ is pyrrolidin-1-yl, optionally substituted with trifluoromethyl or methyl. In some embodiments, $R_6$ is (S)-2-(trifluoromethyl)pyrrolidin-1-yl or (R)-2-(trifluoromethyl)pyrrolidin-1-yl.

In some embodiments, $R_6$ is chosen from —$NR_{10}R_{11}$ wherein $R_{10}$ is chosen from hydrogen and optionally substituted alkyl, and $R_{11}$ is chosen from alkoxy, optionally substituted aryl, optionally substituted heteroaryl, optionally substituted alkyl, optionally substituted cycloalkyl, and optionally substituted heterocycloalkyl. In some embodiments, $R_{10}$ is chosen from hydrogen and optionally substituted lower alkyl. In some embodiments, $R_{10}$ is chosen from hydrogen and methyl. In some embodiments, $R_{11}$ is chosen from optionally substituted phenyl, optionally substituted lower alkyl, and optionally substituted cycloalkyl. In some embodiments, $R_{11}$ is chosen from phenyl, optionally substituted lower alkyl, and cycloalkyl.

In some embodiments, $R_6$ is chosen from optionally substituted aryl and optionally substituted heteroaryl. In some embodiments, $R_6$ is chosen from aryl and heteroaryl, each of which is optionally substituted with one, two, or three groups chosen from halo, optionally substituted lower alkyl, optionally substituted lower alkoxy, and hydroxy. In some embodiments, $R_6$ is chosen from aryl and heteroaryl, either of which is which is optionally substituted with one, two, or three groups chosen from halo, methyl, trifluoromethyl, ethyl, methoxy, ethoxy, and hydroxy.

In some embodiments, $R_6$ is chosen from optionally substituted phenyl and optionally substituted pyridinyl. In some embodiments, $R_6$ is chosen from phenyl and pyridinyl, either of which is optionally substituted with one, two, or three groups chosen from halo, optionally substituted lower alkyl, optionally substituted lower alkoxy, and hydroxy. In some embodiments, R$_6$ is chosen from phenyl and pyridinyl, either of which is which is optionally substituted with one, two, or three groups chosen from halo, methyl, trifluoromethyl, ethyl, methoxy, ethoxy, and hydroxy. In some embodiments, R$_6$ is chosen from phenyl, hydroxyphenyl, and pyridinyl.

In some embodiments, R$_2$ is the same as R$_6$. In some embodiments, they are different. In some embodiments, if R$_2$ is optionally substituted alkoxy, hydroxy, or optionally substituted amino; then R$_6$ is optionally substituted aryl or optionally substituted heteroaryl.

In some embodiments, R$_7$ is chosen from hydrogen and optionally substituted lower alkyl. In some embodiments, R$_7$ is chosen from hydrogen and lower alkyl. In some embodiments, R$_7$ is hydrogen.

In some embodiments, each occurrence of =X is chosen from =O and =N—OH. In some embodiments, both =X are =O.

In some embodiments, the compounds of Formula I have cis,cis-stereochemistry. In some embodiments, the compounds of Formula I have cis,trans-stereochemistry. In some embodiments, the compounds of Formula I have trans,trans-stereochemistry.

Particular compounds of Formula I, each of which was synthesized using procedures similar to those described herein and each of which exhibited activity in one or more of the assays described herein, are chosen from:

(cis,trans)-1-(2-hydroxyethyl)-4-phenyl-5-(phenylcarbonyl)(3-piperidyl)phenyl ketone (cis,trans)-1-cyclopentyl-4-phenyl-5-(phenylcarbonyl)(3-piperidyl)phenyl ketone (cis,trans)-1-(3-hydroxypropyl)-4-phenyl-5-(phenylcarbonyl)(3-piperidyl)phenyl ketone (cis,trans)-4-phenyl-5-(phenylcarbonyl)-1-benzyl(3-piperidyl)phenyl ketone (cis,cis)-4-phenyl-5-(phenylcarbonyl)-1-propyl(3-piperidyl)phenyl ketone (cis,trans)-1-((1S)-2-hydroxy-isopropyl)-4-phenyl-5-(phenylcarbonyl)(3-piperidyl)phenyl ketone (cis,cis)-1-(2-methoxyethyl)-4-phenyl-5-(phenylcarbonyl)(3-piperidyl)phenyl ketone (cis,trans)-1-(2-methoxyethyl)-4-phenyl-5-(phenylcarbonyl)(3-piperidyl)phenyl ketone 1-((1R)-2-hydroxy-isopropyl)(cis,trans)-4-phenyl-5-(phenylcarbonyl)(3-piperidyl)phenyl ketone ethyl 3-[(cis,cis)-3,5-bis(phenylcarbonyl)-4-phenylpiperidyl]propanoate (cis,trans)-1-((2S)-2-hydroxypropyl)-4-phenyl-5-(phenylcarbonyl)(3-piperidyl)phenyl ketone (cis,cis)-1-(oxolan-2-ylmethyl)-4-phenyl-5-(phenylcarbonyl)(3-piperidyl)phenylketone (cis,trans)-1-(oxolan-2-ylmethyl)-4-phenyl-5-(phenylcarbonyl)(3-piperidyl)phenylketone (cis,cis)-1-[2-hydroxy-1-(hydroxymethyl)ethyl]-4-phenyl-5-(phenylcarbonyl)(3-piperidyl) phenyl ketone (cis,trans)-1-[2-hydroxy-1-(hydroxymethyl)ethyl]-4-phenyl-5-(phenylcarbonyl)(3-piperidyl) phenyl ketone (cis,cis)-1-(2-morpholin-4-ylethyl)-4-phenyl-5-(phenylcarbonyl)(3-piperidyl)phenyl ketone (cis,trans)-1-(2-morpholin-4-ylethyl)-4-phenyl-5-(phenylcarbonyl)(3-piperidyl)phenyl ketone (cis,cis)-1-[2-(dimethylamino)ethyl]-4-phenyl-5-(phenylcarbonyl)(3-piperidyl)phenyl ketone (cis,trans)-1-[2-(dimethylamino)ethyl]-4-phenyl-5-(phenylcarbonyl)(3-piperidyl)phenyl ketone (cis,cis)-1-cyclopentyl-4-phenyl-5-(phenylcarbonyl)(3-piperidyl)phenyl ketone ethyl 3-[(cis,trans)-3,5-bis(phenylcarbonyl)-4-phenylpiperidyl]propanoate 2-[(cis,trans)-3,5-bis(phenylcarbonyl)-4-phenylpiperidyl]-N-methylacetamide 1-((2S)-2-hydroxypropyl)(cis,cis)-4-phenyl-5-(phenylcarbonyl)(3-piperidyl)phenyl ketone 2-[3,5-bis(phenylcarbonyl)-4-phenylpiperidyl]-3,3-dimethyl-N-methylbutanamide 3-[(cis,cis)-3,5-bis(phenylcarbonyl)-4-phenylpiperidyl]azaperhydroepin-2-one (cis,cis)-1-[2-hydroxy-1-(methylethyl)ethyl]-4-phenyl-5-(phenylcarbonyl)(3-piperidyl)phenyl ketone (cis,trans)-4-(2,3-dimethylphenyl)-1-(2-hydroxyethyl)-5-(phenylcarbonyl)(3-piperidyl)phenyl ketone (cis,trans)-4-(2,3-dimethylphenyl)-1-(3-hydroxypropyl)-5-(phenylcarbonyl)(3-piperidyl)phenyl ketone (cis,trans)-4-(2,3-dimethylphenyl)-1-(2-morpholin-4-ylethyl)-5-(phenylcarbonyl)(3-piperidyl)phenyl ketone (cis,trans)-4-(2,3-dimethylphenyl)-5-(phenylcarbonyl)-1-(2-piperazinylethyl)(3-piperidyl)phenyl ketone 4-{2-[(cis,trans)-4-(2,3-dimethylphenyl)-3,5-bis(phenylcarbonyl)piperidyl]ethyl}-1-acetylpiperazine 2-[(cis,trans)-4-(2,3-dimethylphenyl)-3,5-bis(phenylcarbonyl)piperidyl]-N-methylacetamide (cis,trans)-4-(2,3-dimethylphenyl)-1-[2-hydroxy-1-(hydroxymethyl)ethyl]-5-(phenylcarbonyl)(3-piperidyl)phenyl ketone 1-[(cis,trans)-4-(2,3-dimethylphenyl)-3,5-bis(phenylcarbonyl)piperidyl]propan-1-one 2-[(trans,trans)-4-(2,3-dimethylphenyl)-3,5-bis(phenylcarbonyl)piperidyl]-N,N-dimethylacetamide 4-(2,3-dimethylphenyl)-5-(phenylcarbonyl)-1-prop-2-enyl(3-piperidyl)phenyl ketone (cis,trans)-4-(2,3-dimethylphenyl)-5-[(3-fluorophenyl)carbonyl]-1-(2-morpholin-4-ylethyl)(3-piperidyl) 3-fluorophenyl ketone (cis,trans)-4-(2,3-dimethylphenyl)-5-[(3-fluorophenyl)carbonyl]-1-(2-hydroxyethyl)(3-piperidyl)3-fluorophenyl ketone (cis,trans)-1-[2-(dimethylamino)ethyl]-4-(2,3-dimethylphenyl)-5-[(3-fluorophenyl)carbonyl](3-piperidyl)3-fluorophenyl ketone (cis,trans)-4-(2,3-dimethylphenyl)-5-[(3-fluorophenyl)carbonyl]-1-(3-morpholin-4-ylpropyl)(3-piperidyl)3-fluorophenyl ketone (cis,trans)-4-(2,3-dimethylphenyl)-5-[(3-fluorophenyl)carbonyl]-1-[3-(4-methylpiperazinyl)propyl](3-piperidyl)3-fluorophenyl ketone (cis,trans)-4-(2,3-dimethylphenyl)-5-[(3-fluorophenyl)carbonyl]-1-(2-piperazinylethyl)(3-piperidyl)3-fluorophenyl ketone 1-(3-{(cis,trans)-3,5-bis[(3-fluorophenyl)carbonyl]-4-(2,3-dimethylphenyl)piperidyl}propyl)pyrrolidin-2-one 1-(3-{(trans,trans)-3,5-bis[(3-fluorophenyl)carbonyl]-4-(2,3-dimethylphenyl)piperidyl}propyl)pyrrolidin-2-one (cis,trans)-4-(2,3-dimethylphenyl)-1-(3-morpholin-4-ylpropyl)-5-(phenylcarbonyl)(3-piperidyl)phenyl ketone (cis,trans)-4-(2,3-dimethylphenyl)-1-[3-(4-methylpiperazinyl)propyl]-5-(phenylcarbonyl)(3-piperidyl)phenyl ketone (cis,trans)-1-[2-(dimethylamino)ethyl]-4-(2,3-dimethylphenyl)-5-(phenylcarbonyl)(3-piperidyl)phenyl ketone 1-{3-[(cis,trans)-4-(2,3-dimethylphenyl)-3,5-bis(phenylcarbonyl)piperidyl]propyl}pyrrolidin-2-one (cis,trans)-4-(2,3-dimethylphenyl)-5-(phenylcarbonyl)-1-(2-(3-pyridyl)ethyl)(3-piperidyl)phenyl ketone (cis,trans)-1-[3-(dimethylamino)propyl]-4-(2,3-dimethylphenyl)-5-(phenylcarbonyl)(3-piperidyl)phenyl ketone (cis,trans)-4-(2,3-dimethylphenyl)-1-(3-imidazolylpropyl)-5-(phenylcarbonyl)(3-piperidyl)phenyl ketone (cis,trans)-4-(2,3-dimethylphenyl)-1-(2-imidazolylethyl)-5-(phenylcarbonyl)(3-piperidyl)phenyl ketone (cis,trans)-4-(2,3-dimethylphenyl)-5-(phenylcarbonyl)-1-(3-piperidylpropyl)(3-piperidyl)phenyl ketone (cis,trans)-4-(2,3-dimethylphenyl)-1-(4-hydroxybutyl)-5-(phenylcarbonyl)(3-piperidyl)phenyl ketone (cis,trans)-4-(2,3-dimethylphenyl)-5-(phenylcarbonyl)-1-(2-(2-piperidyl)ethyl)(3-piperidyl)phenyl ketone (cis,trans)-1-(3-aminopropyl)-4-(2,3-dimethylphenyl)-5-(phenylcarbonyl)(3-piperidyl)phenyl ketone (cis,trans)-1-(2-aminoethyl)-4-(2,3-dimethylphenyl)-5-(phenylcarbonyl)(3-piperidyl)phenyl ketone (cis,trans)-1-(2-aminoethyl)-4-(2,3-dimethylphenyl)-5-[(3-fluorophenyl)carbonyl](3-piperidyl)3-fluorophenyl ketone 2-[(cis,trans)-4-(2,3-dimethylphenyl)-3,5-bis(phenylcarbonyl)piperidyl]-N,N-dimethylacetamide 2-[(cis,trans)-3,5-bis(phenylcarbonyl)-4-phenylpiperidyl]-N,N-dimethylacetamide (cis,trans)-4-(2,3-dimethylphenyl)-5-(phenylcarbonyl)(3-piperidyl)phenyl ketone 1-[4-(2,3-dimethylphenyl)-3,5-bis(phenylcarbonyl)piperidyl]-3-hydroxypropan-1-one 1-acetyl-4-(2,3-dimethylphenyl)-3,5-bis(phenylcarbonyl)piperidine N-{2-[4-(2,3-dimethylphenyl)-3,5-bis(phenylcarbonyl)piperidyl]-2-oxoethyl}acetamide 2-(dimethylamino)-1-[4-(2,3-dimethylphenyl)-3,5-bis(phenylcarbonyl)piperidyl]ethan-1-one 1-[4-(2,3-dimethylphenyl)-3,5-bis(phenylcarbonyl)piperidyl]-2-hydroxyethan-1-one 2-[(cis,trans)-4-(2,3-dimethylphenyl)-3,5-bis(phenylcarbonyl)piperidyl]acetic acid 4-{2-[(cis,trans)-4-(2,3-dimethylphenyl)-3,5-bis(phenylcarbonyl)piperidyl]acetyl}-1-acetylpiperazine 2-[(cis,trans)-4-(2,3-dimethylphenyl)-3,5-bis(phenylcarbonyl)piperidyl]-N-[2-(dimethylamino)ethyl]-N-methylacetamide 2-[(trans,trans)-4-(2,3-dimethylphenyl)-3,5-bis(phenylcarbonyl)piperidyl]acetic acid 2-[(trans,trans)-4-(2,3-dimethylphenyl)-3,5-bis(phenylcarbonyl)piperidyl]-N-(2-hydroxyethyl)acetamide (cis,cis)-4-(2,3-dimethylphenyl)-1-(2-morpholin-4-ylethyl)-5-(phenylcarbonyl)(3-piperidyl)phenyl ketone (trans,trans)-4-(2,3-dimethylphenyl)-1-(2-morpholin-4-ylethyl)-5-(phenylcarbonyl)(3-piperidyl)phenyl ketone 2-{(trans,trans)-3,5-bis[(3-fluorophenyl)carbonyl]-4-(2,3-dimethylphenyl)piperidyl}-N,N-dimethylacetamide 2-[(trans,trans)-4-(2,3-dimethylphenyl)-3,5-bis(phenylcarbonyl)piperidyl]-N-(2-piperazinylethyl)acetamide 2-[(trans,trans)-4-(2,3-dimethylphenyl)-3,5-bis(phenylcarbonyl)piperidyl]-N-(2-morpholin-4-ylethyl)acetamide 2-[(trans,trans)-4-(2,3-dimethylphenyl)-3,5-bis(phenylcarbonyl)piperidyl]-1-piperazinylethan-1-one 4-{2-[(trans,trans)-4-(2,3-dimethylphenyl)-3,5-bis(phenylcarbonyl)piperidyl]acetyl}-1-acetylpiperazine 2-[(trans,trans)-4-(2,3-dimethylphenyl)-3,5-bis(phenylcarbonyl)piperidyl]-N-[2-(4-acetylpiperazinyl)ethyl]acetamide 2-[(trans,trans)-4-(2,3-dimethylphenyl)-3,5-bis(phenylcarbonyl)piperidyl]-N-[2-(dimethylamino)ethyl]-N-methylacetamide 2-[(trans,trans)-4-(2,3-dimethylphenyl)-3,5-bis(phenylcarbonyl)piperidyl]-N-methylacetamide 2-[(trans,trans)-4-(2,3-dimethylphenyl)-3,5-bis(phenylcarbonyl)piperidyl]-1-(4-methylpiperazinyl)ethan-1-one 2-[(trans,trans)-4-(2,3-dimethylphenyl)-3,5-bis(phenylcarbonyl)piperidyl]-1-morpholin-4-ylethan-1-one 2-{(trans,trans)-3,5-bis[(3-fluorophenyl)carbonyl]-4-(2,3-dimethylphenyl)piperidyl}-N-methylacetamide 2-[(trans,trans)-4-(2,3-dimethylphenyl)-3,5-bis(phenylcarbonyl)piperidyl]acetamide (trans,trans)-4-(2,3-dimethylphenyl)-1-(2-hydroxyethyl)-5-(phenylcarbonyl)(3-piperidyl)phenyl ketone (trans,trans)-4-(2,3-dimethylphenyl)-1-(3-hydroxypropyl)-5-(phenylcarbonyl)(3-piperidyl)phenyl ketone N-{2-[(trans,trans)-4-(2,3-dimethylphenyl)-3,5-bis(phenylcarbonyl)piperidyl]ethyl}(tert-butoxy)carboxamide (trans,trans)-1-[2-(dimethylamino)ethyl]-4-(2,3-dimethylphenyl)-5-(phenylcarbonyl)(3-piperidyl)phenyl ketone 3-[(trans,trans)-4-(2,3-dimethylphenyl)-3,5-bis(phenylcarbonyl)piperidyl]propanoic acid (trans,trans)-4-(2,3-dimethylphenyl)-1-[3-(4-methylpiperazinyl)propyl]-5-(phenylcarbonyl)(3-piperidyl)phenyl ketone (trans,trans)-1-(2-aminoethyl)-4-(2,3-dimethylphenyl)-5-(phenylcarbonyl)(3-piperidyl)phenyl ketone 2-[(trans,trans)-3,5-bis(phenylcarbonyl)-4-(3-fluoro-2-methylphenyl)piperidyl]-N,N-dimethylacetamide (trans,trans)-4-(2,3-dimethylphenyl)-1-[2-hydroxy-1-(hydroxymethyl)ethyl]-5-(phenylcarbonyl)(3-piperidyl)phenyl ketone (trans,trans)-4-(2,3-dimethylphenyl)-5-(phenylcarbonyl)-1-(3-piperidylpropyl)(3-piperidyl)phenyl ketone 3-[(trans,trans)-4-(2,3-dimethylphenyl)-3,5-bis(phenylcarbonyl)piperidyl]-N,N-dimethylpropanamide methyl (N-{2-[(trans,trans)-4-(2,3-dimethylphenyl)-3,5-bis(phenylcarbonyl)piperidyl]ethyl}methoxycarbonylamino)formate N-{2-[(trans,trans)-4-(2,3-dimethylphenyl)-3,5-bis(phenylcarbonyl)piperidyl]ethyl}acetamide 2-[(trans,trans)-3,5-bis(2-pyridylcarbonyl)-4-(3-fluoro-2-methylphenyl)piperidyl]-N,N-dimethylacetamide 2-[(trans,trans)-3,5-bis(2-pyridylcarbonyl)-4-(3-fluoro-2-methylphenyl)piperidyl]acetamide 2-[(trans,trans)-3,5-bis(2-pyridylcarbonyl)-4-(3-fluoro-2-methylphenyl)piperidyl]-N-methylacetamide N-{2-[(trans,trans)-4-(2,3-dimethylphenyl)-3,5-bis(phenylcarbonyl)piperidyl]ethyl}methoxycarboxamide 2-[(trans,trans)-3,5-bis(phenylcarbonyl)-4-(2-chlorophenyl)piperidyl]-N,N-dimethylacetamide N-{2-[(trans,trans)-4-(2,3-dimethylphenyl)-3,5-bis(phenylcarbonyl)piperidyl]ethyl}-2-[2-(2-methoxyethoxy)ethoxy]acetamide 2-[(trans,trans)-3,5-bis(phenylcarbonyl)-4-(2-methylphenyl)piperidyl]-N,N-dimethylacetamide 2-[(trans,trans)-3,5-bis(phenylcarbonyl)-4-(3-methyl(4-pyridyl))piperidyl]-N,N-dimethylacetamide 2-[(trans,trans)-3,5-bis(phenylcarbonyl)-4-(3-chloro-2-methylphenyl)piperidyl]-N,N-dimethylacetamide 2-[(trans,trans)-3,5-bis(phenylcarbonyl)-4-phenylpiperidyl]acetamide 2-[(trans,trans)-3,5-bis(phenylcarbonyl)-4-phenylpiperidyl]-N,N-dimethylacetamide tert-butyl 4-{2-[(trans,trans)-3,5-bis(phenylcarbonyl)-4-phenylpiperidyl]acetyl}piperazinecarboxylate 2-[(trans,trans)-3,5-bis(phenylcarbonyl)-4-cyclohexylpiperidyl]-N-(2-hydroxyethyl)acetamide 2-[(trans,trans)-3,5-bis(phenylcarbonyl)-4-cyclohexylpiperidyl]-1-(4-methylpiperazinyl)ethan-1-one 2-[(trans,trans)-3,5-bis(phenylcarbonyl)-4-cyclohexylpiperidyl]-1-piperazinylethan-1-one 2-[(trans,trans)-3,5-bis(phenylcarbonyl)-4-cyclohexylpiperidyl]-N,N-dimethylacetamide 2-[(trans,trans)-3,5-bis(phenylcarbonyl)-4-cyclohexylpiperidyl]-1-morpholin-4-ylethan-1-one 2-[(trans,trans)-3,5-bis(phenylcarbonyl)-4-(3-cyano-2-methylphenyl)piperidyl]-N,N-dimethylacetamide 2-{(trans,trans)-3,5-bis[(4-bromophenyl)carbonyl]-4-(3-fluoro-2-methylphenyl)piperidyl}-1-piperazinylethan-1-one 2-[(trans,trans)-4-(2,3-difluorophenyl)-3,5-bis(phenylcarbonyl)piperidyl]-N,N-dimethylacetamide 2-[(trans,trans)-3,5-bis(phenylcarbonyl)-4-(2-fluorophenyl)piperidyl]-N,N-dimethylacetamide 2-[(trans,trans)-3,5-bis(phenylcarbonyl)-4-(1-methylimidazol-2-yl)piperidyl]-1-piperazinylethan-1-one 2-[(trans,trans)-3,5-bis(phenylcarbonyl)-4-phenylpiperidyl]-1-piperazinylethan-1-one (trans,trans)-4-(2,3-dimethylphenyl)-1-methyl-5-(phenylcarbonyl)(3-piperidyl)phenyl ketone (trans,trans)-1-methyl-4-(3-methylphenyl)-5-(phenylcarbonyl)(3-piperidyl)phenyl ketone methyl 3-{(trans,trans)-1-[(N,N-dimethylcarbamoyl)methyl]-3,5-bis(phenylcarbonyl)(4-piperidyl)}-2-methylbenzoate 2-[(trans,trans)-3,5-bis(phenylcarbonyl)-4-(3-iodo-2-methylphenyl)piperidyl]-N,N-dimethylacetamide 2-[(trans,trans)-3,5-bis(phenylcarbonyl)-4-(3-chlorophenyl)piperidyl]-N,N-dimethylacetamide 2-[(trans,trans)-3,5-bis(phenylcarbonyl)-4-(1-methylimidazol-2-yl)piperidyl]-N,N-dimethylacetamide (trans,trans)-4-(3-chloro-2-methylphenyl)-1-methyl-5-(phenylcarbonyl)(3-piperidyl)phenyl ketone 2-[(trans,trans)-3,5-bis(phenylcarbonyl)-4-(1-methylpyrazol-5-yl)piperidyl]-N,N-dimethylacetamide 2-[(trans,trans)-4-(1,5-dimethylpyrazol-4-yl)-3,5-bis(phenylcarbonyl)piperidyl]-N,N-dimethylacetamide (trans,trans)-4-(3-fluoro-2-methylphenyl)-1-methyl-5-(1,3-thiazol-2-ylcarbonyl)(3-piperidyl)1,3-thiazol-2-yl ketone (trans,trans)-4-(3-fluoro-2-methylphenyl)-1-(2-hydroxyethyl)-5-(1,3-thiazol-2-ylcarbonyl)(3-piperidyl)1,3-thiazol-2-yl ketone 2-[(trans,trans)-3,5-bis(1,3-thiazol-2-ylcarbonyl)-4-(3-fluoro-2-methylphenyl)piperidyl]acetamide 2-[(trans,trans)-3,5-bis(1,3-thiazol-2-ylcarbonyl)-4-(3-fluoro-2-methylphenyl)piperidyl]-N-methylacetamide 2-[(trans,trans)-3,5-bis(1,3-thiazol-2-ylcarbonyl)-4-(3-fluoro-2-methylphenyl)piperidyl]-N,N-dimethylacetamide (trans,trans)-4-(2,3-dimethylphenyl)-1-ethyl-5-(phenylcarbonyl)(3-piperidyl)phenylketone (trans,trans)-4-(2,3-dimethylphenyl)-5-(phenylcarbonyl)-1-propyl(3-piperidyl)phenyl ketone 2-[(trans,trans)-3,5-bis(phenylcarbonyl)-4-(3-methylphenyl)piperidyl]-N,N-dimethylacetamide 4-{2-[(trans,trans)-3,5-bis(phenylcarbonyl)-4-phenylpiperidyl]acetyl}piperazin-2-one 2-[(trans,trans)-3,5-bis(phenylcarbonyl)-4-(2-chloro-3-methylphenyl)piperidyl]-N,N-dimethylacetamide 2-[(trans,trans)-3,5-bis(phenylcarbonyl)-4-(2-chloro-3-fluorophenyl)piperidyl]-N,N-dimethylacetamide (trans,trans)-4-(1,5-dimethylpyrazol-4-yl)-1-(2-hydroxyethyl)-5-(phenylcarbonyl)(3-piperidyl)phenyl ketone (trans,trans)-1-(2-hydroxyethyl)-4-(3-methyl(2-pyridyl))-5-(phenylcarbonyl)(3-piperidyl)phenyl ketone 2-{(trans,trans)-3,5-bis[(3-methoxyphenyl)carbonyl]-4-(3-fluoro-2-methylphenyl)piperidyl}-N,N-dimethylacetamide 2-{(trans,trans)-3,5-bis[(3-methoxyphenyl)carbonyl]-4-(3-fluoro-2-methylphenyl)piperidyl}-N-methylacetamide 2-{(trans,trans)-3,5-bis[(3-hydroxyphenyl)carbonyl]-4-(3-fluoro-2-methylphenyl)piperidyl}-N,N-dimethylacetamide 2-{(trans,trans)-3,5-bis[(3-hydroxyphenyl)carbonyl]-4-(3-fluoro-2-methylphenyl)piperidyl}-N-methylacetamide 2-{(trans,trans)-3,5-bis[(2-bromophenyl)carbonyl]-4-(3-fluoro-2-methylphenyl)piperidyl}-N,N-dimethylacetamide (trans,trans)-5-[(2-bromophenyl)carbonyl]-4-(3-fluoro-2-methylphenyl)-1-(2-hydroxyethyl)(3-piperidyl)2-bromophenyl ketone (trans,trans)-5-[(2-bromophenyl)carbonyl]-4-(3-fluoro-2-methylphenyl)-1-propyl(3-piperidyl)2-bromophenyl ketone 2-{(trans,trans)-5-[(2-bromophenyl)carbonyl]-3-[(2-cyanophenyl)carbonyl]-4-(3-fluoro-2-methylphenyl)piperidyl}-N,N-dimethylacetamide 3-{(trans,trans)-1-[(N,N-dimethylcarbamoyl)methyl]-3,5-bis(phenylcarbonyl)(4-piperidyl)}-2-methylbenzoic acid 2-[(trans,trans)-3,5-bis(phenylcarbonyl)-4-(2-iodophenyl)piperidyl]-N,N-dimethylacetamide 2-[(trans,trans)-3,5-bis(phenylcarbonyl)-4-(4-chlorophenyl)piperidyl]-N,N-dimethylacetamide 2-[(trans,trans)-3,5-bis(phenylcarbonyl)-4-(4-fluorophenyl)piperidyl]-N,N-dimethylacetamide 2-[(trans,trans)-3,5-bis(phenylcarbonyl)-4-(3-fluorophenyl)piperidyl]-N,N-dimethylacetamide (trans,trans)-4-(2,6-dimethylphenyl)-1-(2-hydroxyethyl)-5-(phenylcarbonyl)(3-piperidyl)phenyl ketone 2-{(trans,trans)-3,5-bis(phenylcarbonyl)-4-[3-(trifluoromethyl)phenyl]piperidyl}-N,N-dimethylacetamide 2-[(trans,trans)-3,5-bis(phenylcarbonyl)-4-(2-cyanophenyl)piperidyl]-N,N-dimethylacetamide 2-[(trans,trans)-3,5-bis(4-pyridylcarbonyl)-4-(3-fluoro-2-methylphenyl)piperidyl]-N,N-dimethylacetamide (trans,trans)-4-(3-fluoro-2-methylphenyl)-1-(2-hydroxyethyl)-5-[(3-methoxyphenyl)carbonyl](3-piperidyl)3-methoxyphenyl ketone (trans,trans)-4-(3-fluoro-2-methylphenyl)-1-(2-hydroxyethyl)-5-[(3-hydroxyphenyl)carbonyl](3-piperidyl)3-hydroxyphenyl ketone (trans,trans)-4-(3-fluoro-2-methylphenyl)-1-(2-hydroxyethyl)-5-[(2-methoxyphenyl)carbonyl](3-piperidyl)2-methoxyphenyl ketone (trans,trans)-4-(2,3-dimethylphenyl)-5-(phenylcarbonyl)-1-benzyl(3-piperidyl)phenyl ketone 2-[(trans,trans)-3,5-bis(phenylcarbonyl)-4-(4-methylphenyl)piperidyl]-N,N-dimethylacetamide 2-[(cis,trans)-3,5-bis(phenylcarbonyl)-4-(4-methylphenyl)piperidyl]-N,N-dimethylacetamide (trans,trans)-1-(2-hydroxyethyl)-4-(4-methylphenyl)-5-(phenylcarbonyl)(3-piperidyl)phenyl ketone (cis,trans)-1-(2-aminoethyl)-4-(4-methylphenyl)-5-(phenylcarbonyl)(3-piperidyl)phenyl ketone 2-{(trans,trans)-3,5-bis[(2-methoxyphenyl)carbonyl]-4-(3-fluoro-2-methylphenyl)piperidyl}-N,N-dimethylacetamide 2-{(trans,trans)-3,5-bis[(2-hydroxyphenyl)carbonyl]-4-(3-fluoro-2-methylphenyl)piperidyl}-N,N-dimethylacetamide (trans,trans)-4-(3-fluoro-2-methylphenyl)-1-(2-hydroxyethyl)-5-[(2-hydroxyphenyl)carbonyl](3-piperidyl)2-hydroxyphenyl ketone (trans,trans)-4-(3-fluoro-2-methylphenyl)-1-(2-hydroxyethyl)-5-[(4-methoxyphenyl)carbonyl](3-piperidyl)4-methoxyphenyl ketone 2-{(trans,trans)-3,5-bis[(4-methoxyphenyl)carbonyl]-4-(3-fluoro-2-methylphenyl)piperidyl}-N,N-dimethylacetamide (trans,trans)-4-(3-fluoro-2-methylphenyl)-1-(2-hydroxyethyl)-5-[(4-hydroxyphenyl)carbonyl](3-piperidyl)4-hydroxyphenyl ketone 2-{(trans,trans)-3,5-bis[(4-hydroxyphenyl)carbonyl]-4-(3-fluoro-2-methylphenyl)piperidyl}-N,N-dimethylacetamide methyl 3-({(trans,trans)-1-[(N,N-dimethylcarbamoyl)methyl]-5-[(3-carbamoylphenyl)carbonyl]-4-(3-fluoro-2-methylphenyl)-3-piperidyl}carbonyl)benzoate (trans,trans)-4-(3,4-dimethylphenyl)-1-(2-hydroxyethyl)-5-(phenylcarbonyl)(3-piperidyl)phenyl ketone 2-[(trans,trans)-4-(3,4-dimethylphenyl)-3,5-bis(phenylcarbonyl)piperidyl]-N,N-dimethylacetamide (trans,trans)-1-(2-aminoethyl)-4-cyclohexyl-5-(phenylcarbonyl)(3-piperidyl)phenyl ketone (trans,trans)-5-(cyclohexylcarbonyl)-4-(3-fluoro-2-methylphenyl)-1-(2-methoxyethyl)(3-piperidyl)cyclohexyl ketone (trans,trans)-1-(2-hydroxyethyl)-4-(6-methyl(2-pyridyl))-5-(phenylcarbonyl)(3-piperidyl)phenyl ketone 2-[(trans,trans)-3,5-bis(phenylcarbonyl)-4-(6-methyl(2-pyridyl))piperidyl]-N,N-dimethylacetamide N-{2-[(trans,trans)-3,5-bis(phenylcarbonyl)-4-cyclohexylpiperidyl]ethyl}acetamide N-{2-[(trans,trans)-4-(2,3-dimethylphenyl)-3-((hydroxyimino)phenylmethyl)-5-(phenylcarbonyl)piperidyl]ethyl}(tert-butoxy)carboxamide (trans,trans)-1-(2-aminoethyl)-4-(2,3-dimethylphenyl)-5-((hydroxyimino)phenylmethyl)(3-piperidyl)phenyl ketone methyl 3-[((trans,trans)-1-[(N,N-dimethylcarbamoyl)methyl]-4-(3-fluoro-2-methylphenyl)-5-{[3-(methoxycarbonyl)phenyl]carbonyl}-3-piperidyl)carbonyl]benzoate (trans,trans)-4-(3-fluoro-2-methylphenyl)-1-(2-hydroxyethyl)-5-(pyrazol-3-ylcarbonyl)(3-piperidyl)pyrazol-3-yl ketone (trans,trans)-4-(3-fluoro-2-methylphenyl)-1-(2-methoxyethyl)-5-(pyrazol-3-ylcarbonyl)(3-piperidyl)pyrazol-3-yl ketone 2-{(trans,trans)-3,5-bis(phenylcarbonyl)-4-[3-(hydroxymethyl)-2-methylphenyl]piperidyl}-N,N-dimethylacetamide 2-[(trans,trans)-3,5-bis(phenylcarbonyl)-4-(3-iodophenyl)piperidyl]-N,N-dimethylacetamide 2-[(trans,trans)-3,5-bis(phenylcarbonyl)-4-(2-methoxyphenyl)piperidyl]-N,N-dimethylacetamide 2-{(trans,trans)-3,5-bis(phenylcarbonyl)-4-[2-(trifluoromethyl)phenyl]piperidyl}-N,N-dimethylacetamide 2-[(trans,trans)-3,5-bis((hydroxyimino)phenylmethyl)-4-(2,3-dimethylphenyl)piperidyl]ethylamine 2-{(trans,trans)-3,5-bis(phenylcarbonyl)-4-[4-(trifluoromethyl)phenyl]piperidyl}-N,N-dimethylacetamide 2-[(trans,trans)-4-(3,4-dichlorophenyl)-3,5-bis(phenylcarbonyl)piperidyl]-N,N-dimethylacetamide 2-[(trans,trans)-3,5-bis(phenylcarbonyl)-4-(3-methoxyphenyl)piperidyl]-N,N-dimethylacetamide 2-[(trans,trans)-4-(3,5-dichlorophenyl)-3,5-bis(phenylcarbonyl)piperidyl]-N,N-dimethylacetamide 2-[(trans,trans)-3,5-bis(phenylcarbonyl)-4-(4-methoxyphenyl)piperidyl]-N,N-dimethylacetamide (trans,trans)-4-(3-fluoro-2-methylphenyl)-5-{[3-(hydroxymethyl)phenyl]carbonyl}-1-(2-methoxyethyl)(3-piperidyl)3-(hydroxymethyl)phenyl ketone 2-[(trans,trans)-4-(2,5-dichlorophenyl)-3,5-bis(phenylcarbonyl)piperidyl]-N,N-dimethylacetamide 2-[(trans,trans)-4-(2,4-dichlorophenyl)-3,5-bis(phenylcarbonyl)piperidyl]-N,N-dimethylacetamide 2-{(trans,trans)-3,5-bis(phenylcarbonyl)-4-[3-(hydroxymethyl)phenyl]piperidyl}-N,N-dimethylacetamide (trans,trans)-1-(2-aminoethyl)-4-(3-fluoro-2-methylphenyl)-5-[(3-hydroxyphenyl)carbonyl](3-piperidyl)3-hydroxyphenyl ketone (trans,trans)-1-(2-aminoethyl)-4-(3-fluoro-2-methylphenyl)-5-[(3-methoxyphenyl)carbonyl](3-piperidyl)3-hydroxyphenyl ketone 2-[(trans,trans)-3,5-bis(phenylcarbonyl)-4-(2-hydroxyphenyl)piperidyl]-N,N-dimethylacetamide 2-[(trans,trans)-3,5-bis(phenylcarbonyl)-4-(3-hydroxyphenyl)piperidyl]-N,N-dimethylacetamide (trans,trans)-4-(3-fluoro-2-methylphenyl)-1-(2-hydroxyethyl)-5-[(6-methoxy(2-pyridyl))carbonyl](3-piperidyl)6-methoxy(2-pyridyl)ketone 2-[(trans,trans)-3,5-bis(phenylcarbonyl)-4-(3-pyridyl)piperidyl]-N,N-dimethylacetamide 2-[(trans,trans)-3,5-bis(phenylcarbonyl)-4-(2-pyridyl)piperidyl]-N,N-dimethylacetamide 2-[(trans,trans)-3,5-bis(phenylcarbonyl)-4-(1,3-thiazol-4-yl)piperidyl]-N,N-dimethylacetamide 2-[(trans,trans)-3,5-bis(phenylcarbonyl)-4-(1,3-thiazol-2-yl)piperidyl]-N,N-dimethylacetamide 2-[(trans,trans)-3,5-bis(phenylcarbonyl)-4-(5-methylisoxazol-3-yl)piperidyl]-N,N-dimethylacetamide N-{2-[(trans,trans)-4-(2,3-dimethylphenyl)-3,5-bis(phenylcarbonyl)piperidyl]ethyl}-2-[(3,5,6-trimethyl-1,7-dioxo(3-pyrazolino[1,2-a]3-pyrazolin-2-yl))methylthio]acetamide N-{2-[(trans,trans)-4-(2,3-dimethylphenyl)-3,5-bis(phenylcarbonyl)piperidyl]ethyl}-6-[(7-nitrobenzo[2,3-c]1,2,5-oxadiazol-4-yl)amino]hexanamide N-{2-[(trans,trans)-4-(2,3-dimethylphenyl)-3,5-bis(phenylcarbonyl)piperidyl]ethyl}-6-({[5-(dimethylamino)naphthyl]sulfonyl}amino)hexanamide (trans,trans)-5-[(2-chlorophenyl)carbonyl]-4-(3-fluoro-2-methylphenyl)-1-(2-hydroxyethyl)(3-piperidyl)2-chlorophenyl ketone N-{2-[(trans,trans)-4-(2,3-dimethylphenyl)-3,5-bis(phenylcarbonyl)piperidyl]ethyl}(6,8-difluoro-7-hydroxy-2-oxochromen-3-yl)carboxamide N-{2-[(trans,trans)-4-(2,3-dimethylphenyl)-3,5-bis(phenylcarbonyl)piperidyl]ethyl}-2-[7-(dimethylamino)-2-oxochromen-4-yl]acetamide 1-((2S)-2-methoxypropyl)(trans,trans)-4-(3-fluoro-2-methylphenyl)-5-[(3-methoxyphenyl)carbonyl](3-piperidyl)3-methoxyphenyl ketone 1-((2S)-2-hydroxypropyl)(trans,trans)-4-(3-fluoro-2-methylphenyl)-5-[(3-hydroxyphenyl)carbonyl](3-piperidyl)3-hydroxyphenyl ketone 1-((2R)-2-hydroxypropyl)(trans,trans)-4-(3-fluoro-2-methylphenyl)-5-[(3-methoxyphenyl)carbonyl](3-piperidyl)3-methoxyphenyl ketone 1-((2R)-2-hydroxypropyl)(trans,trans)-4-(3-fluoro-2-methylphenyl)-5-[(3-hydroxyphenyl)carbonyl](3-piperidyl)3-hydroxyphenyl ketone (trans,trans)-1-(2,3-dihydroxypropyl)-4-(3-fluoro-2-methylphenyl)-5-[(3-methoxyphenyl)carbonyl](3-piperidyl)3-methoxyphenyl ketone (trans,trans)-1-(2,3-dihydroxypropyl)-4-(3-fluoro-2-methylphenyl)-5-[(3-methoxyphenyl)carbonyl](3-piperidyl)3-hydroxyphenyl ketone (trans,trans)-1-(3-amino-2-hydroxypropyl)-4-(3-fluoro-2-methylphenyl)-5-[(3-methoxyphenyl)carbonyl](3-piperidyl)3-methoxyphenyl ketone (trans,trans)-1-(3-amino-2-hydroxypropyl)-4-(3-fluoro-2-methylphenyl)-5-[(3-hydroxyphenyl)carbonyl](3-piperidyl)3-hydroxyphenyl ketone N-(2-{(trans,trans)-3,5-bis[(3-hydroxyphenyl)carbonyl]-4-(3-fluoro-2-methylphenyl)piperidyl}ethyl)-N-methylacetamide (trans,trans)-1-[2-(dimethylamino)ethyl]-4-(3-fluoro-2-methylphenyl)-5-[(3-methoxyphenyl)carbonyl](3-piperidyl)3-methoxyphenyl ketone (trans,trans)-1-[2-(dimethylamino)ethyl]-4-(3-fluoro-2-methylphenyl)-5-[(3-methoxyphenyl)carbonyl](3-piperidyl)3-hydroxyphenyl ketone (trans,trans)-4-(3-fluoro-2-methylphenyl)-5-[(3-methoxyphenyl)carbonyl]-1-(2-morpholin-4-ylethyl)(3-piperidyl)3-methoxyphenyl ketone (trans,trans)-4-(3-fluoro-2-methylphenyl)-5-[(3-methoxyphenyl)carbonyl]-1-(pyrazol-5-ylmethyl)(3-piperidyl)3-methoxyphenyl ketone (trans,trans)-4-(3-fluoro-2-methylphenyl)-5-[(3-hydroxyphenyl)carbonyl]-1-(pyrazol-5-ylmethyl)(3-piperidyl)3-hydroxyphenyl ketone 1-((1S)-2-hydroxy-isopropyl)(trans,trans)-4-(3-fluoro-2-methylphenyl)-5-[(3-methoxyphenyl)carbonyl](3-piperidyl)3-methoxyphenyl ketone 1-((1S)-2-hydroxy-isopropyl)(trans,trans)-4-(3-fluoro-2-methylphenyl)-5-[(3-hydroxyphenyl)carbonyl](3-piperidyl) 3-hydroxyphenyl ketone 1-((1R)-2-hydroxy-isopropyl)(trans,trans)-4-(3-fluoro-2-methylphenyl)-5-[(3-methoxyphenyl)carbonyl](3-piperidyl) 3-methoxyphenyl ketone 1-((1R)-2-hydroxy-isopropyl)(trans,trans)-4-(3-fluoro-2-methylphenyl)-5-[(3-hydroxyphenyl)carbonyl](3-piperidyl) 3-hydroxyphenyl ketone 2-[(trans,trans)-3,5-bis(phenylcarbonyl)-4-(2-methyl(1,3-thiazol-4-yl))piperidyl]-N,N-dimethylacetamide (trans,trans)-5-[(2-fluoro-5-methoxyphenyl)carbonyl]-4-(3-fluoro-2-methylphenyl)-1-(2-hydroxyethyl)(3-piperidyl)2-fluoro-5-methoxyphenyl ketone N-(2-{(trans,trans)-3,5-bis[(3-hydroxyphenyl)carbonyl]-4-(3-fluoro-2-methylphenyl)piperidyl}ethyl)acetamide (trans,trans)-4-(3-fluoro-2-methylphenyl)-5-[(3-hydroxyphenyl)carbonyl]-1-{2-[(methylsulfonyl)amino]ethyl}(3-piperidyl)3-hydroxyphenyl ketone N-(2-{(trans,trans)-3,5-bis[(3-hydroxyphenyl)carbonyl]-4-(3-fluoro-2-methylphenyl)piperidyl}ethyl)methoxycarboxamide 2-[(trans,trans)-3,5-bis(phenylcarbonyl)-4-(4-methyl(1,3-thiazol-2-yl))piperidyl]-N,N-dimethylacetamide (trans,trans)-4-(3-fluoro-2-methylphenyl)-5-[(2-fluorophenyl)carbonyl]-1-(2-hydroxyethyl)(3-piperidyl)2-fluorophenyl ketone (trans,trans)-4-(3-fluoro-2-methylphenyl)-5-[(3-hydroxyphenyl)carbonyl]-1-[2-(methylamino)ethyl](3-piperidyl)3-hydroxyphenyl ketone (trans,trans)-4-(3-fluoro-2-methylphenyl)-5-[(3-hydroxyphenyl)carbonyl]-1-{2-[methyl(methylsulfonyl)amino]ethyl}(3-piperidyl)3-hydroxyphenyl ketone N-(2-{(trans,trans)-3,5-bis[(3-hydroxyphenyl)carbonyl]-4-(3-fluoro-2-methylphenyl)piperidyl}ethyl)methoxy-N-methylcarboxamide 2-[(trans,trans)-3,5-bis(phenylcarbonyl)-4-(3-ethylphenyl)piperidyl]-N,N-dimethylacetamide (trans,trans)-4-(3-ethylphenyl)-1-(2-hydroxyethyl)-5-(phenylcarbonyl)(3-piperidyl)phenyl ketone 2-[(trans,trans)-3,5-bis(phenylcarbonyl)-4-(2-methylbutyl)piperidyl]-N,N-dimethylacetamide (trans,trans)-1-(2-hydroxyethyl)-4-(2-methylbutyl)-5-(phenylcarbonyl)(3-piperidyl)phenyl ketone (trans,trans)-5-[(2-fluoro-3-hydroxyphenyl)carbonyl]-4-(3-fluoro-2-methylphenyl)-1-(2-hydroxyethyl)(3-piperidyl)2-fluoro-3-hydroxyphenyl ketone (trans,trans)-5-[(2-fluoro-3-hydroxyphenyl)carbonyl]-4-(3-fluoro-2-methylphenyl)-1-(2-hydroxyethyl)(3-piperidyl)2-fluoro-3-methoxyphenyl ketone (trans,trans)-4-(3-fluoro-2-methylphenyl)-1-(2-hydroxy-2-methylpropyl)-5-[(3-methoxyphenyl)carbonyl](3-piperidyl) 3-methoxyphenyl ketone (trans,trans)-4-(3-fluoro-2-methylphenyl)-1-(2-hydroxy-2-methylpropyl)-5-[(3-hydroxyphenyl)carbonyl](3-piperidyl) 3-hydroxyphenyl ketone (trans,trans)-4-(3-fluoro-2-methylphenyl)-1-(2-methoxyethyl)-5-(phenylcarbonyl)(3-piperidyl)phenyl ketone (trans,trans)-4-(3-fluoro-2-methylphenyl)-5-[(3-hydroxyphenyl)carbonyl]-1-(2-methoxyethyl)(3-piperidyl)3-hydroxyphenyl ketone (trans,trans)-4-(3-fluoro-2-methylphenyl)-1-(2-hydroxyethyl)-5-[(3-methoxyphenyl)carbonyl](3-piperidyl)3-hydroxyphenyl ketone (trans,trans)-4-(3-fluoro-2-methylphenyl)-1-(2-methoxyethyl)-5-[(3-methoxyphenyl)carbonyl](3-piperidyl)3-hydroxyphenyl ketone (trans,trans)-4-(3-fluoro-2-methylphenyl)-1-(2-methoxyethyl)-5-[(3-methoxyphenyl)carbonyl](3-piperidyl)2-fluorophenyl ketone (trans,trans)-4-(3-fluoro-2-methylphenyl)-1-(2-hydroxyethyl)-5-[(3-hydroxyphenyl)carbonyl](3-piperidyl)2-fluorophenyl ketone (trans,trans)-1-(2,3-dihydroxypropyl)-4-(3-fluoro-2-methylphenyl)-5-[(3-hydroxyphenyl)carbonyl](3-piperidyl)3-hydroxyphenyl ketone 1-((1R)-2-hydroxy-isopropyl)(trans,trans)-4-(3-fluoro-2-methylphenyl)-5-[(3-hydroxyphenyl)carbonyl](3-piperidyl) 3-hydroxyphenyl ketone N-(2-{(trans,trans)-4-(3-fluoro-2-methylphenyl)-5-[(2-fluorophenyl)carbonyl]-3-[(3-methoxyphenyl)carbonyl] piperidyl}ethyl)methoxycarboxamide (trans,trans)-4-(3-fluoro-2-methylphenyl)-5-[(3-methoxyphenyl)carbonyl]-1-{2-[(methylsulfonyl)amino]ethyl}(3-piperidyl)2-fluorophenyl ketone (trans,trans)-4-(3-fluoro-2-methylphenyl)-5-[(3-methoxyphenyl)carbonyl]-1-{2-[methyl(methylsulfonyl)amino]ethyl}(3-piperidyl)2-fluorophenyl ketone (trans,trans)-4-(3-fluoro-2-methylphenyl)-5-[(3-methoxyphenyl)carbonyl]-1-[2-(methylamino)ethyl](3-piperidyl)2-fluorophenyl ketone 1-(2-{(trans,trans)-3,5-bis[(3-methoxyphenyl)carbonyl]-4-(3-fluoro-2-methylphenyl)piperidyl}ethyl)pyrrolidin-2-one 1-(2-{(trans,trans)-3,5-bis[(3-hydroxyphenyl)carbonyl]-4-(3-fluoro-2-methylphenyl)piperidyl}ethyl)pyrrolidin-2-one N-{2-[(trans,trans)-4-(2,3-dimethylphenyl)-3,5-bis(phenylcarbonyl)piperidyl]ethyl}-3-(2-{2-[2-(2-aminoethoxy)ethoxy]ethoxy}ethoxy)propanamide (trans,trans)-4-(2,3-dichlorophenyl)-5-[(3-methoxyphenyl)carbonyl]-1-[2-(methylamino)ethyl](3-piperidyl)3-methoxyphenyl ketone (trans,trans)-4-(3-chloro-2-fluorophenyl)-5-[(3-methoxyphenyl)carbonyl]-1-[2-(methylamino)ethyl](3-piperidyl)3-methoxyphenyl ketone (trans,trans)-4-(2,3-dichlorophenyl)-1-(2-hydroxyethyl)-5-[(3-hydroxyphenyl)carbonyl](3-piperidyl)3-hydroxyphenyl ketone (trans,trans)-4-(3-chloro-2-fluorophenyl)-1-(2-hydroxyethyl)-5-[(3-hydroxyphenyl)carbonyl](3-piperidyl)3-hydroxyphenyl ketone N-(2-{(trans,trans)-3,5-bis[(3-hydroxyphenyl)carbonyl]-4-(3-fluoro-2-methylphenyl)piperidyl}-isopropyl)methoxycarboxamide (trans,trans)-4-(3-fluoro-2-methylphenyl)-5-[(3-hydroxyphenyl)carbonyl]-1-{2-[(methylsulfonyl)amino]propyl}(3-piperidyl)3-hydroxyphenyl ketone N-((1S)-2-{(trans,trans)-3,5-bis[(3-hydroxyphenyl)carbonyl]-4-(3-fluoro-2-methylphenyl)piperidyl}-isopropyl)methoxycarboxamide N-(2-{(trans,trans)-3,5-bis[(3-hydroxyphenyl)carbonyl]-4-(3-fluoro-2-methylphenyl)piperidyl}-tert-butyl)methoxycarboxamide N-(2-{(trans,trans)-3,5-bis[(3-hydroxyphenyl)carbonyl]-4-(3-fluoro-2-methylphenyl)piperidyl}-isopropyl)methoxy-N-methylcarboxamide (trans,trans)-4-(3-fluoro-2-methylphenyl)-5-[(3-hydroxyphenyl)carbonyl]-1-{2-[methyl(methylsulfonyl)amino]propyl}(3-piperidyl)3-hydroxyphenyl ketone 1-{(2S)-2-[(methylsulfonyl)amino]propyl}(trans,trans)-4-(3-fluoro-2-methylphenyl)-5-[(3-hydroxyphenyl)carbonyl](3-piperidyl)3-hydroxyphenyl ketone 1-(2-{(trans,trans)-4-(3-fluoro-2-methylphenyl)-5-[(2-fluorophenyl)carbonyl]-3-[(3-hydroxyphenyl)carbonyl]piperidyl}ethyl)pyrrolidin-2-one (trans,trans)-4-(2,3-dichlorophenyl)-5-[(3-hydroxyphenyl)carbonyl]-1-{2-[methyl(methylsulfonyl)amino]ethyl}(3-piperidyl)3-hydroxyphenyl ketone (trans,trans)-4-(3-chloro-2-fluorophenyl)-5-[(3-hydroxyphenyl)carbonyl]-1-{2-[methyl(methylsulfonyl)amino]ethyl}(3-piperidyl)3-hydroxyphenyl ketone N-(2-{(trans,trans)-4-(2,3-dichlorophenyl)-3,5-bis[(3-hydroxyphenyl)carbonyl]piperidyl}ethyl)methoxy-N-methylcarboxamide N-(2-{(trans,trans)-3,5-bis[(3-hydroxyphenyl)carbonyl]-4-(3-chloro-2-fluorophenyl)piperidyl}ethyl)methoxy-N-methylcarboxamide (trans,trans)-4-(2-fluoro-3-methylphenyl)-5-[(3-hydroxyphenyl)carbonyl]-1-{2-[methyl(methylsulfonyl)amino]ethyl}(3-piperidyl)3-hydroxyphenyl ketone N-(2-{(trans,trans)-3,5-bis[(3-hydroxyphenyl)carbonyl]-4-(2-fluoro-3-methylphenyl)piperidyl}ethyl)methoxy-N-methylcarboxamide (trans,trans)-4-(2-fluoro-3-methylphenyl)-1-(2-hydroxyethyl)-5-[(3-hydroxyphenyl)carbonyl](3-piperidyl)3-hydroxyphenyl ketone N-(2-{(trans,trans)-3,5-bis[(3-hydroxyphenyl)carbonyl]-4-(3-fluoro-2-methylphenyl)piperidyl}ethyl)-N-methyl(methylamino)carboxamide 2-{(trans,trans)-3,5-bis[(3-hydroxyphenyl)carbonyl]-4-(3-fluoro-2-methylphenyl)piperidyl}acetamide 2-{(trans,trans)-3,5-bis[(3-hydroxyphenyl)carbonyl]-4-(3-fluoro-2-methylphenyl)piperidyl}methylpentanamide (trans,trans)-1-(benzimidazol-2-ylmethyl)-4-(3-fluoro-2-methylphenyl)-5-[(3-hydroxyphenyl)carbonyl](3-piperidyl)3-hydroxyphenyl ketone (trans,trans)-4-(2,6-difluoro-3-methylphenyl)-1-(2-hydroxyethyl)-5-[(3-hydroxyphenyl)carbonyl](3-piperidyl)3-hydroxyphenyl ketone N-(2-{(trans,trans)-3,5-bis[(3-hydroxyphenyl)carbonyl]-4-(3-fluoro-2-methylphenyl)piperidyl}ethyl)amino-N-methylamide (trans,trans)-1-(2-aminoethyl)-4-(3-fluoro-2-methylphenyl)-5-[(3-methoxyphenyl)carbonyl](3-piperidyl)3-methoxyphenyl ketone (trans,trans)-4-(3-fluoro-2-methylphenyl)-5-[(3-hydroxyphenyl)carbonyl]-1-(4-piperidyl)(3-piperidyl)3-hydroxyphenyl ketone (trans,trans)-4-(3-fluoro-2-methylphenyl)-5-[(3-hydroxyphenyl)carbonyl]1-[1-(methylsulfonyl)(4-piperidyl)](3-piperidyl)3-hydroxyphenyl ketone (trans,trans)-4-(2,6-difluoro-3-methylphenyl)-5-[(3-hydroxyphenyl)carbonyl]-1-{2-[methyl(methylsulfonyl)amino]ethyl}(3-piperidyl)3-hydroxyphenyl ketone N-(2-{(trans,trans)-4-(2,6-difluoro-3-methylphenyl)-3,5-bis[(3-hydroxyphenyl)carbonyl]piperidyl}ethyl)methoxy-N-methylcarboxamide (trans,trans)-5-[(2-fluoro-3-methoxyphenyl)carbonyl]-4-(3-fluoro-2-methylphenyl)-1-{2-[methyl(methylsulfonyl)amino]ethyl}(3-piperidyl)2-fluoro-3-methoxyphenyl ketone (trans,trans)-5-[(2-fluoro-3-hydroxyphenyl)carbonyl]-4-(3-fluoro-2-methylphenyl)-1-{2-[(methylsulfonyl)amino]ethyl}(3-piperidyl)2-fluoro-3-hydroxyphenyl ketone N-(2-{(trans,trans)-3,5-bis[(3-hydroxyphenyl)carbonyl]-4-(3-fluoro-2-methylphenyl)piperidyl}ethyl)aminoamide (trans,trans)-1-(2-{[(dimethylamino)sulfonyl]amino}ethyl)-4-(3-fluoro-2-methylphenyl)-5-[(3-hydroxyphenyl)carbonyl](3-piperidyl)3-hydroxyphenyl ketone (trans,trans)-1-(2-{[(dimethylamino)sulfonyl]methylamino}ethyl)-4-(3-fluoro-2-methylphenyl)-5-[(3-hydroxyphenyl)carbonyl](3-piperidyl)3-hydroxyphenyl ketone (trans,trans)-4-(3-fluoro-2-methylphenyl)-5-[(3-hydroxyphenyl)carbonyl]-1-(2,2,6,6-tetramethyl(4-piperidyl))(3-piperidyl)3-hydroxyphenyl ketone (trans,trans)-4-(3-fluoro-2-methylphenyl)-1-(2-methoxyethyl)-5-[(3-methoxyphenyl)carbonyl](3-piperidyl)2,3-difluorophenyl ketone (trans,trans)-5-[(2-fluoro-3-hydroxyphenyl)carbonyl]-4-(3-fluoro-2-methylphenyl)-1-[2-(methylamino)ethyl](3-piperidyl)2-fluoro-3-hydroxyphenyl ketone (trans,trans)-1-(2-aminoethyl)-5-[(6-fluoro-3-hydroxyphenyl)carbonyl]-4-(3-fluoro-2-methylphenyl)(3-piperidyl)6-fluoro-3-hydroxyphenyl ketone (trans,trans)-4-(3-fluoro-2-methylphenyl)-1-(2-hydroxyethyl)-5-[(3-hydroxyphenyl)carbonyl](3-piperidyl)2,3-difluorophenyl ketone (trans,trans)-4-(3-fluoro-2-methylphenyl)-5-[(3-methoxyphenyl)carbonyl]-1-(3,3,3-trifluoro-2-hydroxypropyl)(3-piperidyl)3-methoxyphenyl ketone (trans,trans)-4-(3-fluoro-2-methylphenyl)-5-[(3-hydroxyphenyl)carbonyl]-1-(3,3,3-trifluoro-2-hydroxypropyl)(3-piperidyl)3-hydroxyphenyl ketone 1-(2-{(trans,trans)-3,5-bis[(3-methoxyphenyl)carbonyl]-4-(3-fluoro-2-methylphenyl)piperidyl}ethyl)imidazolidin-2-one 1-(2-{(trans,trans)-3,5-bis[(3-hydroxyphenyl)carbonyl]-4-(3-fluoro-2-methylphenyl)piperidyl}ethyl)imidazolidin-2-one 1-((2R)-2-aminocyclohexyl)(trans,trans)-4-(3-fluoro-2-methylphenyl)-5-[(3-hydroxyphenyl)carbonyl](3-piperidyl)3-hydroxyphenyl ketone (trans,trans)-1-(2-aminocyclohexyl)-4-(3-fluoro-2-methylphenyl)-5-[(3-hydroxyphenyl)carbonyl](3-piperidyl)3-hydroxyphenyl ketone (trans,trans)-4-(3-fluoro-2-methylphenyl)-5-[(3-hydroxyphenyl)carbonyl]-1-{2-[(methylsulfonyl)amino]cyclohexyl}(3-piperidyl)3-hydroxyphenyl ketone (trans,trans)-5-[(2-fluoro-3-hydroxyphenyl)carbonyl]-4-(3-fluoro-2-methylphenyl)-1-{2-[methyl(methylsulfonyl)amino]ethyl}(3-piperidyl)2-fluoro-3-hydroxyphenyl ketone (trans,trans)-4-(3-fluoro-2-methylphenyl)-5-[(3-hydroxyphenyl)carbonyl]-1-benzyl(3-piperidyl)3-hydroxyphenyl ketone (trans,trans)-4-(3-fluoro-2-methylphenyl)-5-[(3-hydroxyphenyl)carbonyl]-1-pyrrolidin-3-yl(3-piperidyl)3-hydroxyphenyl ketone (trans,trans)-4-(3-fluoro-2-methylphenyl)-5-[(3-hydroxyphenyl)carbonyl]-1-[1-(methylsulfonyl)pyrrolidin-3-yl](3-piperidyl)3-hydroxyphenyl ketone methyl 3-{(trans,trans)-3,5-bis[(3-hydroxyphenyl)carbonyl]-4-(3-fluoro-2-methylphenyl)piperidyl}pyrrolidinecarboxylate 3-{(trans,trans)-3,5-bis[(3-hydroxyphenyl)carbonyl]-4-(3-fluoro-2-methylphenyl)piperidyl}-1-acetylpyrrolidine 3-{(trans,trans)-3,5-bis[(3-hydroxyphenyl)carbonyl]-4-(3-fluoro-2-methylphenyl)piperidyl}pyrrolidinecarboxamide (3-{(trans,trans)-3,5-bis[(3-hydroxyphenyl)carbonyl]-4-(3-fluoro-2-methylphenyl)piperidyl}pyrrolidinyl)-N-methylcarboxamide (trans,trans)-1-{1-[(dimethylamino)sulfonyl]pyrrolidin-3-yl}-4-(3-fluoro-2-methylphenyl)-5-[(3-hydroxyphenyl)carbonyl](3-piperidyl)3-hydroxyphenyl ketone (trans,trans)-4-(3-fluoro-2-methylphenyl)-5-[(3-methoxyphenyl)carbonyl]-1-[2-(methylamino)ethyl](3-piperidyl)2-fluoro-3-methoxyphenyl ketone (trans,trans)-4-(3-fluoro-2-methylphenyl)-1-(2-hydroxyethyl)-5-[(3-hydroxyphenyl)carbonyl](3-piperidyl)2-fluoro-3-hydroxyphenyl ketone (trans,trans)-4-(3-fluoro-2-methylphenyl)-5-[(3-hydroxyphenyl)carbonyl]-1-[2-(methylamino)ethyl](3-piperidyl)2-fluoro-3-hydroxyphenyl ketone 4-{(trans,trans)-3,5-bis[(3-hydroxyphenyl)carbonyl]-4-(3-fluoro-2-methylphenyl)piperidyl}-3-hydroxythiolane-1,1-dione (2-{(trans,trans)-3,5-bis[(3-hydroxyphenyl)carbonyl]-4-(3-fluoro-2-methylphenyl)piperidyl}ethyl)aminomethyl sulfonamide (trans,trans)-4-(3-fluoro-2-methylphenyl)-5-[(3-hydroxyphenyl)carbonyl]-1-(3-piperidylmethyl)(3-piperidyl)3-hydroxyphenyl ketone (trans,trans)-4-(3-fluoro-2-methylphenyl)-5-[(3-hydroxyphenyl)carbonyl]-1-(3-piperidyl)(3-piperidyl)3-hydroxyphenyl ketone (trans,trans)-4-(3-fluoro-2-methylphenyl)-5-[(3-hydroxyphenyl)carbonyl]-1-[2-(methylamino)ethyl](3-piperidyl)2-fluoro-3-(trifluoromethyl)phenyl ketone (trans,trans)-4-(3-fluoro-2-methylphenyl)-5-[(3-hydroxyphenyl)carbonyl]-1-[2-(methylamino)ethyl](3-piperidyl)2-fluoro-3-methylphenyl ketone (trans,trans)-4-(3-fluoro-2-methylphenyl)-1-(2-hydroxyethyl)-5-[(3-hydroxyphenyl)carbonyl](3-piperidyl)2-fluoro-3-methylphenyl ketone (trans,trans)-4-(3-fluoro-2-methylphenyl)-5-[(3-hydroxyphenyl)carbonyl]-1-thian-4-yl(3-piperidyl)3-hydroxyphenyl ketone (trans,trans)-4-(3-fluoro-2-methylphenyl)-1-(4-hydroxycyclohexyl)-5-[(3-hydroxyphenyl)carbonyl](3-piperidyl)3-hydroxyphenyl ketone (trans,trans)-4-(3-fluoro-2-methylphenyl)-5-[(3-hydroxyphenyl)carbonyl]-1-(pyrrolidin-2-ylmethyl)(3-piperidyl)3-hydroxyphenyl ketone (trans,trans)-1-(4-aminobutyl)-4-(3-fluoro-2-methylphenyl)-5-[(3-methoxyphenyl)carbonyl](3-piperidyl)3-methoxyphenyl ketone (trans,trans)-1-(4-aminobutyl)-4-(3-fluoro-2-methylphenyl)-5-[(3-hydroxyphenyl)carbonyl](3-piperidyl)3-hydroxyphenyl ketone 2-{(trans,trans)-3,5-bis[(3-hydroxyphenyl)carbonyl]-4-(3-fluoro-2-methylphenyl)piperidyl}-3-(dimethylamino)propanoic acid (trans,trans)-1-acetyl-3,5-bis[(3-methoxyphenyl)carbonyl]-4-(3-fluoro-2-methylphenyl)piperidine (trans,trans)-4-(3-fluoro-2-methylphenyl)-1-(2-methoxyethyl)-5-[(3-methoxyphenyl)carbonyl](3-piperidyl)3-chloro-2-[(2-methoxyethyl)amino]phenyl ketone (trans,trans)-4-(3-fluoro-2-methylphenyl)-5-[(3-methoxyphenyl)carbonyl]-1-[2-(methylamino)ethyl](3-piperidyl)3-chloro-2-{[2-(methylamino)ethyl]amino}phenyl ketone 2-{(trans,trans)-3,5-bis[(3-hydroxyphenyl)carbonyl]-4-(3-fluoro-2-methylphenyl)piperidyl}-3-(dimethylamino)propanamide 2-{(trans,trans)-3,5-bis[(3-hydroxyphenyl)carbonyl]-4-(3-fluoro-2-methylphenyl)piperidyl}-3-(dimethylamino)-N,N-dimethylpropanamide (trans,trans)-1-[4-(dimethylamino)butyl]-4-(3-fluoro-2-methylphenyl)-5-[(3-hydroxyphenyl)carbonyl](3-piperidyl)3-hydroxyphenyl ketone (trans,trans)-4-(3-fluoro-2-methylphenyl)-5-[(3-hydroxyphenyl)carbonyl]-1-[4-(methylamino)butyl](3-piperidyl)3-hydroxyphenyl ketone 2-{(trans,trans)-3,5-bis[(3-hydroxyphenyl)carbonyl]-4-(3-fluoro-2-methylphenyl)piperidyl}-N-[2-(methylamino)ethyl]acetamide 2-{(trans,trans)-3,5-bis[(3-hydroxyphenyl)carbonyl]-4-(3-fluoro-2-methylphenyl)piperidyl}-N-(2-aminoethyl)acetamide 1-{(trans,trans)-3,5-bis[(3-hydroxyphenyl)carbonyl]-4-(3-fluoro-2-methylphenyl)piperidyl}-N-(methylamino)propan-1-one (trans,trans)-4-(3-fluoro-2-methylphenyl)-5-[(3-hydroxyphenyl)carbonyl]-1-[2-(methylamino)ethyl](3-piperidyl)3-chloro-2-{[2-(methylamino)ethyl]amino}phenyl ketone (trans,trans)-1-acetyl-3,5-bis[(3-hydroxyphenyl)carbonyl]-4-(3-fluoro-2-methylphenyl)piperidine (trans,trans)-4-(3-fluoro-2-methylphenyl)-1-(2-hydroxyethyl)-5-[(3-hydroxyphenyl)carbonyl](3-piperidyl)3-chloro-2-fluorophenyl ketone N-(2-{(trans,trans)-3,5-bis[(3-methoxyphenyl)carbonyl]-4-(3-fluoro-2-methylphenyl)piperidyl}-2-oxoethyl)(tert-butoxy)-N-methylcarboxamide (trans,trans)-1-(5-aminopentyl)-4-(3-fluoro-2-methylphenyl)-5-[(3-methoxyphenyl)carbonyl](3-piperidyl)3-methoxyphenyl ketone (trans,trans)-1-(5-aminopentyl)-4-(3-fluoro-2-methylphenyl)-5-[(3-hydroxyphenyl)carbonyl](3-piperidyl)3-hydroxyphenyl ketone (trans,trans)-1-[5-(dimethylamino)pentyl]-4-(3-fluoro-2-methylphenyl)-5-[(3-hydroxyphenyl)carbonyl](3-piperidyl)3-hydroxyphenyl ketone 1-{(trans,trans)-3,5-bis[(3-hydroxyphenyl)carbonyl]-4-(3-fluoro-2-methylphenyl)piperidyl}-2-aminoethan-1-one 2-{(trans,trans)-3,5-bis[(3-hydroxyphenyl)carbonyl]-4-(3-fluoro-2-methylphenyl)piperidyl}-3-(dimethylamino)-N-methylpropanamide (trans,trans)-4-(3-fluoro-2-methylphenyl)-5-[(3-hydroxyphenyl)carbonyl]-1-(1,2,2,6,6-pentamethyl(4-piperidyl))(3-piperidyl)3-hydroxyphenyl ketone (trans,trans)-1-(2-amino-isopropyl)-4-(3-fluoro-2-methylphenyl)-5-[(3-hydroxyphenyl)carbonyl](3-piperidyl)3-hydroxyphenyl ketone 1-{(trans,trans)-3,5-bis[(3-hydroxyphenyl)carbonyl]-4-(3-fluoro-2-methylphenyl)piperidyl}-2-(methylamino)ethan-1-one 1-{(trans,trans)-3,5-bis[(3-methoxyphenyl)carbonyl]-4-(3-fluoro-2-methylphenyl)piperidyl}-2-(dimethylamino)ethan-1-one 1-{(trans,trans)-3,5-bis[(3-hydroxyphenyl)carbonyl]-4-(3-fluoro-2-methylphenyl)piperidyl}-2-(dimethylamino)ethan-1-one 2-{(trans,trans)-3,5-bis[(3-methoxyphenyl)carbonyl]-4-(3-fluoro-2-methylphenyl)piperidyl}-N-[3-(dimethylamino)propyl]-3-hydroxypropanamide 2-{(trans,trans)-3,5-bis[(3-hydroxyphenyl)carbonyl]-4-(3-fluoro-2-methylphenyl)piperidyl}-N-(2-aminoethyl)-3-hydroxypropanamide (trans,trans)-1-(azetidin-3-ylcarbonyl)-4-(3-fluoro-2-methylphenyl)-5-[(3-hydroxyphenyl)carbonyl](3-piperidyl)3-hydroxyphenyl ketone 2-{(trans,trans)-3,5-bis[(3-hydroxyphenyl)carbonyl]-4-(3-fluoro-2-methylphenyl)piperidyl}-N-[3-(dimethylamino)propyl]-3-hydroxypropanamide 2-{(trans,trans)-3,5-bis[(3-hydroxyphenyl)carbonyl]-4-(3-fluoro-2-methylphenyl)piperidyl}-N-[4-(dimethylamino)butyl]-3-hydroxypropanamide (trans,trans)-4-(3-fluoro-2-methylphenyl)-1-(2-hydroxyethyl)-5-[(3-hydroxyphenyl)carbonyl](3-piperidyl)2-chloro-6-fluorophenyl ketone (trans,trans)-4-(3-fluoro-2-methylphenyl)-5-[(3-hydroxyphenyl)carbonyl]-1-(3-pyrrolidinylpropyl)(3-piperidyl)3-hydroxyphenyl ketone (trans,trans)-1-[2-(dimethylamino)ethyl]-4-(3-fluoro-2-methylphenyl)-5-[(3-hydroxyphenyl)carbonyl](3-piperidyl)3-hydroxyphenyl ketone (trans,trans)-4-(3-fluoro-2-methylphenyl)-5-[(3-methoxyphenyl)carbonyl]-1-[5-(methylamino)pentyl](3-piperidyl)3-methoxyphenyl ketone (trans,trans)-4-(3-fluoro-2-methylphenyl)-5-[(3-hydroxyphenyl)carbonyl]-1-[3-(methylamino)propyl](3-piperidyl)3-hydroxyphenyl ketone (trans,trans)-1-[3-(dimethylamino)propyl]-4-(3-fluoro-2-methylphenyl)-5-[(3-hydroxyphenyl)carbonyl](3-piperidyl)3-hydroxyphenyl ketone (trans,trans)-4-(3-fluoro-2-methylphenyl)-1-(4-hydroxybutyl)-5-[(3-methoxyphenyl)carbonyl](3-piperidyl)3-methoxyphenyl ketone (trans,trans)-4-(3-fluoro-2-methylphenyl)-5-[(3-hydroxyphenyl)carbonyl]-1-(1-methyl(4-piperidyl))(3-piperidyl)3-hydroxyphenyl ketone 3-{(trans,trans)-3,5-bis[(3-hydroxyphenyl)carbonyl]-4-(3-fluoro-2-methylphenyl)piperidyl}thiolane-1,1-dione (trans,trans)-1-(2-amino-3-hydroxypropyl)-4-(3-fluoro-2-methylphenyl)-5-[(3-hydroxyphenyl)carbonyl](3-piperidyl)3-hydroxyphenyl ketone (trans,trans)-1-{2-[bis(methylethyl)amino]ethyl}-4-(3-fluoro-2-methylphenyl)-5-[(3-hydroxyphenyl)carbonyl](3-piperidyl)3-hydroxyphenyl ketone (trans,trans)-1-[2-(diethylamino)ethyl]-4-(3-fluoro-2-methylphenyl)-5-[(3-hydroxyphenyl)carbonyl](3-piperidyl)3-hydroxyphenyl ketone (trans,trans)-1-[2-(dimethylamino)-2-methylpropyl]-4-(3-fluoro-2-methylphenyl)-5-[(3-hydroxyphenyl)carbonyl](3-piperidyl)3-hydroxyphenyl ketone (trans,trans)-1-{1-[(dimethylamino)methyl]-2-hydroxyethyl}-4-(3-fluoro-2-methylphenyl)-5-[(3-methoxyphenyl)carbonyl](3-piperidyl)3-methoxyphenyl ketone 2-{(trans,trans)-3,5-bis[(3-hydroxyphenyl)carbonyl]-4-(3-fluoro-2-methylphenyl)piperidyl}-N-[2-(dimethylamino)ethyl]acetamide (trans,trans)-1-(2-amino-tert-butyl)-4-(3-fluoro-2-methylphenyl)-5-[(3-hydroxyphenyl)carbonyl](3-piperidyl)3-hydroxyphenyl ketone (trans,trans)-4-(3-fluoro-2-methylphenyl)-5-[(3-hydroxyphenyl)carbonyl]-1-[2-(methylamino)ethyl](3-piperidyl)2-chloro-6-fluorophenyl ketone 1-{(trans,trans)-3,5-bis[(3-hydroxyphenyl)carbonyl]-4-(3-fluoro-2-methylphenyl)piperidyl}-4-(dimethylamino)butan-1-one 1-{(trans,trans)-3,5-bis[(3-hydroxyphenyl)carbonyl]-4-(3-fluoro-2-methylphenyl)piperidyl}-2-piperidylethan-1-one (trans,trans)-4-(3-fluoro-2-methylphenyl)-5-[(3-hydroxyphenyl)carbonyl]-1-(3-piperidylcarbonyl)(3-piperidyl)3-hydroxyphenyl ketone 1-(2-{(trans,trans)-3,5-bis[(3-hydroxyphenyl)carbonyl]-4-(3-fluoro-2-methylphenyl)piperidyl}ethyl)-3-methylimidazolidin-2-one 1-[(2S)-2-(dimethylamino)propyl](trans,trans)-4-(3-fluoro-2-methylphenyl)-5-[(3-hydroxyphenyl)carbonyl](3-piperidyl)3-hydroxyphenyl ketone 1-[(2R)-2-(dimethylamino)-3-hydroxypropyl](trans,trans)-4-(3-fluoro-2-methylphenyl)-5-[(3-hydroxyphenyl)carbonyl](3-piperidyl)3-hydroxyphenyl ketone 1-((2R)-3-hydroxy-2-piperidylpropyl)(trans,trans)-4-(3-fluoro-2-methylphenyl)-5-[(3-hydroxyphenyl)carbonyl](3-piperidyl)3-hydroxyphenyl ketone 1-[(2R)-2-(cyclopentylamino)-3-hydroxypropyl](trans,trans)-4-(3-fluoro-2-methylphenyl)-5-[(3-hydroxyphenyl)carbonyl](3-piperidyl)3-hydroxyphenyl ketone (trans,trans)-1-[2-(dimethylamino)-isopropyl]-4-(3-fluoro-2-methylphenyl)-5-[(3-hydroxyphenyl)carbonyl](3-piperidyl)3-hydroxyphenyl ketone 2-{(trans,trans)-3,5-bis[(3-hydroxyphenyl)carbonyl]-4-(3-fluoro-2-methylphenyl)piperidyl}-2-methyl-1-(4-methylpiperazinyl)propan-1-one (trans,trans)-1-[2-(dimethylamino)-tert-butyl]-4-(3-fluoro-2-methylphenyl)-5-[(3-hydroxyphenyl)carbonyl](3-piperidyl)3-hydroxyphenyl ketone 2-{(trans,trans)-3,5-bis[(3-hydroxyphenyl)carbonyl]-4-(3-fluoro-2-methylphenyl)piperidyl}-N-[2-(dimethylamino)ethyl]propanamide 2-{(trans,trans)-3,5-bis[(3-hydroxyphenyl)carbonyl]-4-(3-fluoro-2-methylphenyl)piperidyl}-N-[2-(dimethylamino)ethyl]-3-hydroxypropanamide 2-{(trans,trans)-3,5-bis[(3-hydroxyphenyl)carbonyl]-4-(3-fluoro-2-methylphenyl)piperidyl}-1-piperazinylethan-1-one (2R)-3-amino-2-{3,5-bis[(3-hydroxyphenyl)carbonyl]-4-(3-fluoro-2-methylphenyl)piperidyl}propanamide (2S)-2-{(trans,trans)-3,5-bis[(3-hydroxyphenyl)carbonyl]-4-(3-fluoro-2-methylphenyl)piperidyl}-3-aminopropanamide 2-{3,5-bis[(3-hydroxyphenyl)carbonyl]-4-(3-fluoro-2-methylphenyl)piperidyl}-1-(4-methylpiperazinyl)propan-1-one (trans,trans)-1-{1-[(dimethylamino)methyl]-2-hydroxyethyl}-4-(3-fluoro-2-methylphenyl)-5-[(3-hydroxyphenyl)carbonyl](3-piperidyl)3-hydroxyphenyl ketone (trans,trans)-4-(3-fluoro-2-methylphenyl)-5-[(3-hydroxyphenyl)carbonyl]-1-(piperazin-2-ylcarbonyl)(3-piperidyl)3-hydroxyphenyl ketone 1-{(trans,trans)-3,5-bis[(3-hydroxyphenyl)carbonyl]-4-(3-fluoro-2-methylphenyl)piperidyl}-3,3-dimethylbutan-1-one (trans,trans,trans,trans)-4-(3-fluoro-2-methylphenyl)-2,6-dimethyl-5-(phenylcarbonyl)(3-piperidyl)phenyl ketone 2-[(trans,trans,trans,trans)-3,5-bis(phenylcarbonyl)-4-(3-fluoro-2-methylphenyl)-2,6-dimethylpiperidyl]-N,N-dimethylacetamide (trans,trans,trans,trans)-4-(3-fluoro-2-methylphenyl)-1-(2-methoxyethyl)-2,6-dimethyl-5-(phenylcarbonyl)(3-piperidyl)phenyl ketone {(trans,trans)-3,5-bis[(3-hydroxyphenyl)carbonyl]-4-(3-fluoro-2-methylphenyl)piperidyl}-N-[3-(dimethylamino)propyl]carboxamide (trans,trans)-4-(3-fluoro-2-methylphenyl)-5-[(3-hydroxyphenyl)carbonyl]-1-[(1-methyl(4-piperidyl))carbonyl](3-piperidyl)3-hydroxyphenyl ketone 4-(dimethylamino)butyl(trans,trans)-3,5-bis[(3-hydroxyphenyl)carbonyl]-4-(3-fluoro-2-methylphenyl)piperidinecarboxylate 1-{(trans,trans)-3,5-bis[(3-hydroxyphenyl)carbonyl]-4-(3-fluoro-2-methylphenyl)piperidyl}-3-piperidylpropan-1-one {(trans,trans)-3,5-bis[(3-hydroxyphenyl)carbonyl]-4-(3-fluoro-2-methylphenyl)piperidyl}-N-[3-(dimethylamino)propyl]-N-methylcarboxamide 1-(2-{(trans,trans)-3,5-bis[(3-hydroxyphenyl)carbonyl]-4-(3-fluoro-2-methylphenyl)piperidyl}ethyl)-3-[2-(dimethylamino)ethyl]imidazolidin-2-one 1-{(trans,trans)-4-(3-fluoro-2-methylphenyl)-5-[(2-fluorophenyl)carbonyl]-3-[(3-hydroxyphenyl)carbonyl]piperidyl}-4-(dimethylamino)butan-1-one 2-{(trans,trans)-3,5-bis[(3-hydroxyphenyl)carbonyl]-4-(3-fluoro-2-methylphenyl)piperidyl}-3-hydroxy-1-(4-methylpiperazinyl)propan-1-one (2R)-2-{(trans,trans)-3,5-bis[(3-hydroxyphenyl)carbonyl]-4-(3-fluoro-2-methylphenyl)piperidyl}-3-amino-1-(4-methylpiperazinyl)propan-1-one (2S)-2-{(trans,trans)-3,5-bis[(3-hydroxyphenyl)carbonyl]-4-(3-fluoro-2-methylphenyl)piperidyl}-3-amino-1-(4-methylpiperazinyl)propan-1-one 1-{(trans,trans)-3,5-bis[(3-hydroxyphenyl)carbonyl]-4-(3-fluoro-2-methylphenyl)piperidyl}-4-amino-2,2-dimethylbutan-1-one 1-{(trans,trans)-3,5-bis[(3-hydroxyphenyl)carbonyl]-4-(3-fluoro-2-methylphenyl)piperidyl}-4-(dimethylamino)-2,2-dimethylbutan-1-one {(trans,trans)-3,5-bis[(3-hydroxyphenyl)carbonyl]-4-(3-fluoro-2-methylphenyl)piperidyl}-N-[2-(dimethylamino)ethyl]-N-methylcarboxamide {(trans,trans)-3,5-bis[(3-hydroxyphenyl)carbonyl]-4-(3-fluoro-2-methylphenyl)piperidyl}-N-[2-(dimethylamino)ethyl]carboxamide 2-(dimethylamino)ethyl(trans,trans)-3,5-bis[(3-hydroxyphenyl)carbonyl]-4-(3-fluoro-2-methylphenyl)piperidinecarboxylate (trans,trans)-1-{[3-(dimethylamino)propyl]sulfonyl}-4-(3-fluoro-2-methylphenyl)-5-[(3-hydroxyphenyl)carbonyl](3-piperidyl)3-hydroxyphenyl ketone (trans,trans)-1-[(3-chloropropyl)sulfonyl]-4-(3-fluoro-2-methylphenyl)-5-[(3-hydroxyphenyl)carbonyl](3-piperidyl)3-hydroxyphenyl ketone 1-((2R)-2-amino-3-hydroxy-3-methylbutyl)(trans,trans)-4-(3-fluoro-2-methylphenyl)-5-[(3-hydroxyphenyl)carbonyl](3-piperidyl)3-hydroxyphenyl ketone 2-{(trans,trans)-3,5-bis[(3-hydroxyphenyl)carbonyl]-4-(3-fluoro-2-methylphenyl)piperidyl}-3-(dimethylamino)-1-(4-methylpiperazinyl)propan-1-one (2S)-2-{(trans,trans)-3,5-bis[(3-hydroxyphenyl)carbonyl]-4-(3-fluoro-2-methylphenyl)piperidyl}-3-(dimethylamino)-1-(4-methylpiperazinyl)propan-1-one (2R)-2-{(trans,trans)-3,5-bis[(3-hydroxyphenyl)carbonyl]-4-(3-fluoro-2-methylphenyl)piperidyl}-N-[2-(dimethylamino)ethyl]-3-[(methylsulfonyl)amino]propanamide (2R)-2-{(trans,trans)-3,5-bis[(3-hydroxyphenyl)carbonyl]-4-(3-fluoro-2-methylphenyl)piperidyl}-1-(4-methylpiperazinyl)-3-[(methylsulfonyl)amino]propan-1-one (2S)-2-{(trans,trans)-3,5-bis[(3-hydroxyphenyl)carbonyl]-4-(3-fluoro-2-methylphenyl)piperidyl}-1-(4-methylpiperazinyl)-3-[(methylsulfonyl)amino]propan-1-one 2-{(trans,trans)-3,5-bis[(3-hydroxyphenyl)carbonyl]-4-(3-fluoro-2-methylphenyl)piperidyl}-1-(4-methylpiperazinyl)ethan-1-one (2S)-2-(trifluoromethyl)pyrrolidinyl(trans,trans)-1-[4-(dimethylamino)butyl]-4-(3-fluoro-2-methylphenyl)-5-[(3-hydroxyphenyl)carbonyl](3-piperidyl)ketone (2R)-2-(trifluoromethyl)pyrrolidinyl(trans,trans)-4-(3-fluoro-2-methylphenyl)-5-[(3-hydroxyphenyl)carbonyl]-1-{2-[methyl(methylsulfonyl)amino]ethyl}(3-piperidyl)ketone (2S)-2-(trifluoromethyl)pyrrolidinyl(trans,trans)-4-(3-fluoro-2-methylphenyl)-5-[(3-hydroxyphenyl)carbonyl]-1-{2-[methyl(methylsulfonyl)amino]ethyl}(3-piperidyl)ketone 5-{[(2S)-2-(trifluoromethyl)pyrrolidinyl]carbonyl}(trans,trans)-4-(3-fluoro-2-methylphenyl)-1-[1-(2-methoxyethyl)(4-piperidyl)](3-piperidyl)3-hydroxyphenyl ketone 5-{[(2S)-2-(trifluoromethyl)pyrrolidinyl]carbonyl}(trans,trans)-4-(3-fluoro-2-methylphenyl)-1-(1-methyl(4-piperidyl))(3-piperidyl)3-hydroxyphenyl ketone (2S)-2-(trifluoromethyl)pyrrolidinyl(trans,trans)-4-(3-fluoro-2-methylphenyl)-5-[(3-hydroxyphenyl)carbonyl]-1-{2-[methyl(methylsulfonyl)amino]ethyl}(3-piperidyl)ketone (2R)-2-(trifluoromethyl)pyrrolidinyl(trans,trans)-4-(3-fluoro-2-methylphenyl)-1-{2-[(2-hydroxyethyl)(methylethyl)amino]ethyl}-5-[(3-hydroxyphenyl)carbonyl](3-piperidyl)ketone (2S)-2-(trifluoromethyl)pyrrolidinyl(trans,trans)-1-[2-(diethylamino)ethyl]-4-(3-fluoro-2-methylphenyl)-5-[(3-hydroxyphenyl)carbonyl](3-piperidyl)ketone (trans,trans)-4-(3-fluoro-2-methylphenyl)-5-[(3-hydroxyphenyl)carbonyl]-1-{2-[methyl(methylsulfonyl)amino]ethyl}(3-piperidyl)indolinyl ketone 5-{[(2S)-2-(trifluoromethyl)pyrrolidinyl]carbonyl}(trans,trans)-4-(3-fluoro-2-methylphenyl)-1-[1-(2-hydroxyethyl)(4-piperidyl)](3-piperidyl)3-hydroxyphenyl ketone (2S)-2-(trifluoromethyl)pyrrolidinyl(trans,trans)-1-{2-[4-(ethylsulfonyl)piperazinyl]ethyl}-4-(3-fluoro-2-methylphenyl)-5-[(3-hydroxyphenyl)carbonyl](3-piperidyl)ketone (2S)-2-(trifluoromethyl)pyrrolidinyl(trans,trans)-1-(2-azetidinylethyl)-4-(3-fluoro-2-methylphenyl)-5-[(3-hydroxyphenyl)carbonyl](3-piperidyl)ketone (2S)-2-(trifluoromethyl)pyrrolidinyl(trans,trans)-1-[2-(dimethylamino)ethyl]-4-(3-fluoro-2-methylphenyl)-5-[(3-hydroxyphenyl)carbonyl](3-piperidyl)ketone (2S)-2-(trifluoromethyl)pyrrolidinyl(trans,trans)-1-[2-(dimethylamino)ethyl]-4-(3-fluoro-2-methylphenyl)-5-[(3-hydroxyphenyl)carbonyl](3-piperidyl)ketone (2R)-2-(trifluoromethyl)pyrrolidinyl(trans,trans)-1-[2-(dimethylamino)ethyl]-4-(3-fluoro-2-methylphenyl)-5-[(3-hydroxyphenyl)carbonyl](3-piperidyl)ketone (trans,trans)-4-(3-fluoro-2-methylphenyl)-5-[(3-hydroxyphenyl)carbonyl]-1-{2-[methyl(methylsulfonyl)amino]ethyl}(3-piperidyl)1,2,5,6-tetrahydropyridyl ketone (2S)-2-(trifluoromethyl)pyrrolidinyl(trans,trans)-4-(3-fluoro-2-methylphenyl)-5-[(3-hydroxyphenyl)carbonyl]-1-[2-(methylamino)ethyl](3-piperidyl)ketone (trans,trans)-4-(3-fluoro-2-methylphenyl)-5-[(3-hydroxyphenyl)carbonyl]-1-{2-[methyl(methylsulfonyl)amino]ethyl}(3-piperidyl)2-methylpiperidyl ketone (2S)-2-(trifluoromethyl)pyrrolidinyl(trans,trans)-4-(3-fluoro-2-methylphenyl)-5-[(3-hydroxyphenyl)carbonyl](3-piperidyl)ketone (trans,trans)-4-(3-fluoro-2-methylphenyl)-5-[(3-hydroxyphenyl)carbonyl]-1-{2-[methyl(methylsulfonyl)amino]ethyl}(3-piperidyl)3-methylpiperidyl ketone (trans,trans)-4-(3-fluoro-2-methylphenyl)-1-(2-hydroxyisopropyl)-5-[(3-hydroxyphenyl)carbonyl](3-piperidyl)piperidyl ketone (trans,trans)-4-(3-fluoro-2-methylphenyl)-5-[(3-hydroxyphenyl)carbonyl]-1-{2-[methyl(methylsulfonyl)amino]ethyl}(3-piperidyl)piperidyl ketone (trans,trans)-4-(3-fluoro-2-methylphenyl)-1-(2-hydroxy-2-methylpropyl)-5-[(3-hydroxyphenyl)carbonyl](3-piperidyl)piperidyl ketone (trans,trans)-4-(3-fluoro-2-methylphenyl)-1-(5-hydroxypentyl)-5-[(3-hydroxyphenyl)carbonyl](3-piperidyl)piperidyl ketone (trans,trans)-4-(3-fluoro-2-methylphenyl)-5-[(3-hydroxyphenyl)carbonyl]-1-(2-methoxyethyl)(3-piperidyl)azaperhydroepinyl ketone (trans,trans)-4-(3-fluoro-2-methylphenyl)-1-(2-hydroxyethyl)-5-[(3-hydroxyphenyl)carbonyl](3-piperidyl)azaperhydroepinyl ketone ((trans,trans)-4-(3-fluoro-2-methylphenyl)-5-[(3-hydroxyphenyl)carbonyl]-1-{2-[methyl(methylsulfonyl)amino]ethyl}(3-piperidyl))-N-benzamide (trans,trans)-4-(3-fluoro-2-methylphenyl)-5-[(3-hydroxyphenyl)carbonyl]-1-{2-[methyl(methylsulfonyl)amino]ethyl}(3-piperidyl)3,3-dimethylpiperidyl ketone N-(2-{(trans,trans)-4-(3-fluoro-2-methylphenyl)-3-[(3-hydroxyphenyl)carbonyl]-5-(piperidylcarbonyl)piperidyl}ethyl)methoxy-N-methylcarboxamide (trans,trans)-4-(3-fluoro-2-methylphenyl)-5-[(3-hydroxyphenyl)carbonyl]-1-(2-methoxyethyl)(3-piperidyl)piperidyl ketone (trans,trans)-4-(3-fluoro-2-methylphenyl)-1-(3-hydroxybutyl)-5-[(3-hydroxyphenyl)carbonyl](3-piperidyl)piperidyl ketone (trans,trans)-4-(3-fluoro-2-methylphenyl)-5-[(3-hydroxyphenyl)carbonyl]-1-{2-[methyl(methylsulfonyl)amino]ethyl}(3-piperidyl)azaperhydroepinyl ketone methyl 2-[((trans,trans)-4-(3-fluoro-2-methylphenyl)-5-[(3-hydroxyphenyl)carbonyl]-1-{2-[methyl(methylsulfonyl)amino]ethyl}-3-piperidyl)carbonylamino]benzoate (trans,trans)-4-(3-fluoro-2-methylphenyl)-5-[(3-hydroxyphenyl)carbonyl]-1-{2-[methyl(methylsulfonyl)amino]ethyl}(3-piperidyl)azaperhydroocinyl ketone (trans,trans)-4-(3-fluoro-2-methylphenyl)-5-[(3-hydroxyphenyl)carbonyl]-1-{2-[(methylsulfonyl)amino]ethyl}(3-piperidyl)piperidyl ketone

[(trans,trans)-4-(3-fluoro-2-methylphenyl)-1-(2-methoxyethyl)-5-(phenylcarbonyl)(3-piperidyl)]-N-benzamide (trans,trans)-4-(3-fluoro-2-methylphenyl)-5-[(3-hydroxyphenyl)carbonyl]-1-{2-[methyl(methylsulfonyl)amino]ethyl}(3-piperidyl)3,3-difluoropiperidyl ketone (trans,trans)-4-(3-fluoro-2-methylphenyl)-1-(2-methoxyethyl)-5-(phenylcarbonyl)(3-piperidyl)piperidyl ketone methyl 1-[((trans,trans)-4-(3-fluoro-2-methylphenyl)-5-[(3-hydroxyphenyl)carbonyl]-1-{2-[methyl(methylsulfonyl)amino]ethyl}-3-piperidyl)carbonyl]piperidine-2-carboxylate (trans,trans)-4-(3-fluoro-2-methylphenyl)-1-(2-hydroxyethyl)-5-[(3-hydroxyphenyl)carbonyl](3-piperidyl)piperidyl ketone (trans,trans)-4-(3-fluoro-2-methylphenyl)-5-[(3-hydroxyphenyl)carbonyl]-1-{2-[methyl(methylsulfonyl)amino]ethyl}(3-piperidyl)2-azabicyclo[2.2.1]hept-2-yl ketone (trans,trans)-4-(3-fluoro-2-methylphenyl)-5-[(3-hydroxyphenyl)carbonyl]-1-{2-[methyl(methylsulfonyl)amino]ethyl}(3-piperidyl)4,4-difluoropiperidyl ketone (trans,trans)-4-(3-fluoro-2-methylphenyl)-5-[(3-hydroxyphenyl)carbonyl]-1-(4,4,4-trifluorobutyl)(3-piperidyl)piperidyl ketone (trans,trans)-4-(3-fluoro-2-methylphenyl)-5-[(3-hydroxyphenyl)carbonyl]-1-{2-[methyl(methylsulfonyl)amino]ethyl}(3-piperidyl)3-fluoropiperidyl ketone (trans,trans)-4-(3-fluoro-2-methylphenyl)-5-[(3-hydroxyphenyl)carbonyl]-1-{2-[methyl(methylsulfonyl)amino]ethyl}(3-piperidyl)4-methylpiperidyl ketone (2S)-2-(trifluoromethyl)pyrrolidinyl(trans,trans)-1-[2-(dimethylamino)ethyl]-4-(3-fluoro-2-methylphenyl)-5-[(3-hydroxyphenyl)carbonyl](3-piperidyl)ketone (2R)-2-(trifluoromethyl)pyrrolidinyl(trans,trans)-4-(3-fluoro-2-methylphenyl)-5-[(3-hydroxyphenyl)carbonyl]-1-{2-[methyl(methylsulfonyl)amino]ethyl}(3-piperidyl)ketone ethyl 1-[((trans,trans)-4-(3-fluoro-2-methylphenyl)-5-[(3-hydroxyphenyl)carbonyl]1-{2-[methyl(methylsulfonyl)amino]ethyl}-3-piperidyl)carbonyl]piperidine-3-carboxylate (trans,trans)-4-(3-fluoro-2-methylphenyl)-5-[(3-hydroxyphenyl)carbonyl]-1-{2-[methyl(methylsulfonyl)amino]ethyl}(3-piperidyl)3-pyrrolinyl ketone (trans,trans)-4-(3-fluoro-2-methylphenyl)-5-[(3-hydroxyphenyl)carbonyl]-1-(2-methoxyethyl)(3-piperidyl)pyrrolidinyl ketone (trans,trans)-4-(3-fluoro-2-methylphenyl)-5-[(3-hydroxyphenyl)carbonyl]-1-{2-[methyl(methylsulfonyl)amino]ethyl}(3-piperidyl)2-methylpyrrolidinyl ketone (trans,trans)-4-(3-fluoro-2-methylphenyl)-5-[(3-hydroxyphenyl)carbonyl]-1-{2-[methyl(methylsulfonyl)amino]ethyl}(3-piperidyl)2-(methoxymethyl)pyrrolidinyl ketone (trans,trans)-4-(3-fluoro-2-methylphenyl)-5-[(3-hydroxyphenyl)carbonyl]-1-{2-[methyl(methylsulfonyl)amino]ethyl}(3-piperidyl)isoindolin-2-yl ketone N-(2-{(trans,trans)-4-(3-fluoro-2-methylphenyl)-3-[(3-hydroxyphenyl)carbonyl]-5-(piperidylcarbonyl)piperidyl}-2-oxoethyl)methoxycarboxamide methyl(trans,trans)-4-(3-fluoro-2-methylphenyl)-3-[(3-hydroxyphenyl)carbonyl]-5-(piperidylcarbonyl)piperidinecarboxylate ethyl 2-({(trans,trans)-4-(3-fluoro-2-methylphenyl)-5-[(3-hydroxyphenyl)carbonyl]-1-(2-methoxyethyl)(3-piperidyl)}-N-methylcarbonylamino)acetate (trans,trans)-1-acetyl-4-(3-fluoro-2-methylphenyl)-3-[(3-hydroxyphenyl)carbonyl]-5-(piperidylcarbonyl)piperidine ((trans,trans)-4-(3-fluoro-2-methylphenyl)-5-[(3-hydroxyphenyl)carbonyl]-1-{2-[methyl(methylsulfonyl)amino]ethyl}(3-piperidyl))-N-(2,2,2-trifluoroethyl)carboxamide (trans,trans)-4-(3-fluoro-2-methylphenyl)-5-[(3-hydroxyphenyl)carbonyl]-1-{2-[methyl(methylsulfonyl)amino]ethyl}(3-piperidyl)4,4-dimethylpiperidyl ketone (trans,trans)-4-(3-fluoro-2-methylphenyl)-1-(2-methoxyethyl)-5-(phenylcarbonyl)(3-piperidyl)pyrrolidinyl ketone (2R)-2-(trifluoromethyl)pyrrolidinyl(trans,trans)-1-[2-(dimethylamino)ethyl]-4-(3-fluoro-2-methylphenyl)-5-[(3-hydroxyphenyl)carbonyl](3-piperidyl)ketone (trans,trans)-4-(3-fluoro-2-methylphenyl)-1-(2-hydroxyethyl)-5-[(3-hydroxyphenyl)carbonyl](3-piperidyl)pyrrolidinyl ketone (trans,trans)-4-(3-fluoro-2-methylphenyl)-5-[(3-hydroxyphenyl)carbonyl](3-piperidyl)piperidyl ketone (trans,trans)-4-(3-fluoro-2-methylphenyl)-1-(2-methoxyethyl)-5-(phenylcarbonyl)(3-piperidyl)azaperhydroepinyl ketone (trans,trans)-4-(3-fluoro-2-methylphenyl)-1-(2-methoxyethyl)-5-(phenylcarbonyl)(3-piperidyl)3-hydroxypiperidyl ketone ((trans,trans)-4-(3-fluoro-2-methylphenyl)-5-[(3-hydroxyphenyl)carbonyl]-1-{2-[methyl(methylsulfonyl)amino]ethyl}(3-piperidyl))-N-cyclopent-3-enylcarboxamide (trans,trans)-4-(3-fluoro-2-methylphenyl)-1-(2-methoxyethyl)-5-(phenylcarbonyl)(3-piperidyl)3,3-difluoropyrrolidinyl ketone {(trans,trans)-4-(3-fluoro-2-methylphenyl)-5-[(3-hydroxyphenyl)carbonyl]-1-(2-methoxyethyl)(3-piperidyl)}-N-methyl-N-propylcarboxamide (trans,trans)-4-(3-fluoro-2-methylphenyl)-5-[(3-hydroxyphenyl)carbonyl]-1-{2-[methyl(methylsulfonyl)amino]ethyl}(3-piperidyl)7-azabicyclo[2.2.1]hept-7-yl ketone (trans,trans)-4-(3-fluoro-2-methylphenyl)-5-[(3-hydroxyphenyl)carbonyl]-1-(2-methoxyethyl)(3-piperidyl)3-hydroxypiperidyl ketone (trans,trans)-4-(3-fluoro-2-methylphenyl)-1-(2-methoxyethyl)-5-(phenylcarbonyl)(3-piperidyl)3-(trifluoromethyl)pyrrolidinyl ketone

[(trans,trans)-4-(3-fluoro-2-methylphenyl)-1-(2-methoxyethyl)-5-(phenylcarbonyl)(3-piperidyl)]-N-cyclohexylcarboxamide

[(trans,trans)-4-(3-fluoro-2-methylphenyl)-1-(2-methoxyethyl)-5-(phenylcarbonyl)(3-piperidyl)]-N-methyl-N-propylcarboxamide (trans,trans)-4-(3-fluoro-2-methylphenyl)-5-[(3-hydroxyphenyl)carbonyl]-1-{2-[methyl(methylsulfonyl)amino]ethyl}(3-piperidyl)2-phenylpiperidyl ketone (trans,trans)-4-(3-fluoro-2-methylphenyl)-1-(2-methoxyethyl)-5-(phenylcarbonyl)(3-piperidyl)2-(hydroxymethyl)piperidyl ketone

[(trans,trans)-4-(3-fluoro-2-methylphenyl)-1-(2-methoxyethyl)-5-(phenylcarbonyl)(3-piperidyl)]-N-cyclohexyl-N-methylcarboxamide ((trans,trans)-4-(3-fluoro-2-methylphenyl)-5-[(3-hydroxyphenyl)carbonyl]-1-{2-[methyl(methylsulfonyl)amino]ethyl}(3-piperidyl))-N-methyl-N-benzamide 1-{(trans,trans)-4-(3-fluoro-2-methylphenyl)-3-[(3-hydroxyphenyl)carbonyl]-5-(piperidylcarbonyl)piperidyl}-2-aminoethan-1-one (trans,trans)-4-(3-fluoro-2-methylphenyl)-1-(2-methoxyethyl)-5-(phenylcarbonyl)(3-piperidyl)3-(trifluoromethyl)piperidyl ketone (trans,trans)-4-(3-fluoro-2-methylphenyl)-5-[(3-hydroxyphenyl)carbonyl]-1-{2-[methyl(methylsulfonyl)amino]ethyl}(3-piperidyl)3-phenylpiperidyl ketone (trans,trans)-4-(3-fluoro-2-methylphenyl)-5-[(3-hydroxyphenyl)carbonyl]-1-{2-[methyl(methylsulfonyl)amino]ethyl}(3-piperidyl)1,2,3,4-tetrahydroquinolyl ketone

[(trans,trans)-4-phenyl-5-(phenylcarbonyl)-1-benzyl(3-piperidyl)]-N-methoxy-N-methylcarboxamide (trans,trans)-4-(3-fluoro-2-methylphenyl)-5-[(3-hydroxyphenyl)carbonyl]-1-{2-[methyl(methylsulfonyl)amino]ethyl}(3-piperidyl)2-1,2,3,4-tetrahydroisoquinolyl ketone methyl 1-[((trans,trans)-4-(3-fluoro-2-methylphenyl)-5-[(3-hydroxyphenyl)carbonyl]-1-{2-[methyl(methylsulfonyl)amino]ethyl}-3-piperidyl)carbonyl]pyrrolidine-2-carboxylate (trans,trans)-4-(3-fluoro-2-methylphenyl)-1-(2-methoxyethyl)-5-(phenylcarbonyl)(3-piperidyl)3,5-dimethylmorpholin-4-yl ketone (trans,trans)-4-(3-fluoro-2-methylphenyl)-1-(2-methoxyethyl)-5-(phenylcarbonyl)(3-piperidyl)morpholin-4-yl ketone (trans,trans)-4-(3-fluoro-2-methylphenyl)-1-(2-methoxyethyl)-5-(phenylcarbonyl)(3-piperidyl)azetidinyl ketone (trans,trans)-4-(3-fluoro-2-methylphenyl)-1-(2-hydroxyethyl)-5-[(3-hydroxyphenyl)carbonyl]-(3-piperidyl) 3-hydroxypiperidyl ketone (trans,trans)-4-(3-fluoro-2-methylphenyl)-1-(2-methoxyethyl)-5-(phenylcarbonyl)(3-piperidyl)4-(trifluoromethyl)piperidyl ketone (trans,trans)-4-(3-fluoro-2-methylphenyl)-1-(2-methoxyethyl)-5-(phenylcarbonyl)(3-piperidyl)3-hydroxypyrrolidinyl ketone

[(trans,trans)-4-(3-fluoro-2-methylphenyl)-1-(2-methoxyethyl)-5-(phenylcarbonyl)(3-piperidyl)]-N-(2-methoxyethyl)-N-methylcarboxamide ((trans,trans)-4-(3-fluoro-2-methylphenyl)-5-[(3-hydroxyphenyl)carbonyl]-1-{2-[methyl(methylsulfonyl)amino]ethyl}(3-piperidyl))-N-(3-methylcyclohexyl)carboxamide

[(trans,trans)-4-(3-fluoro-2-methylphenyl)-1-(2-methoxyethyl)-5-(phenylcarbonyl)(3-piperidyl)]-N-(2-hydroxyethyl)-N-methylcarboxamide

[(trans,trans)-4-(3-fluoro-2-methylphenyl)-1-(2-methoxyethyl)-5-(phenylcarbonyl)(3-piperidyl)]-N-(tert-butyl)carboxamide {(trans,trans)-4-(3-fluoro-2-methylphenyl)-5-[(3-hydroxyphenyl)carbonyl]-1-(2-methoxyethyl)(3-piperidyl)}-N-(2-hydroxyethyl)-N-methylcarboxamide (trans,trans)-4-(3-fluoro-2-methylphenyl)-1-(2-methoxyethyl)-5-(phenylcarbonyl)(3-piperidyl)2-1,2,3,4-tetrahydroisoquinolyl ketone {1-[(((trans,trans)-4-(3-fluoro-2-methylphenyl)-5-[(3-hydroxyphenyl)carbonyl]-1-{2-[methyl(methylsulfonyl)amino]ethyl}(3-piperidyl))carbonyl]pyrrolidin-2-yl}-N-methylcarboxamide

[(trans,trans)-4-(3-fluoro-2-methylphenyl)-1-(2-methoxyethyl)-5-(phenylcarbonyl)(3-piperidyl)]-N,N-dimethylcarboxamide

[(trans,trans)-4-(3-fluoro-2-methylphenyl)-1-(2-methoxyethyl)-5-(phenylcarbonyl)(3-piperidyl)]-N-(2-hydroxyethyl)carboxamide ethyl(trans,trans)-4-(3-fluoro-2-methylphenyl)-5-[(3-hydroxyphenyl)carbonyl]-1-(2-methoxyethyl)piperidine-3-carboxylate and ethyl(trans,trans)-4-(3-fluoro-2-methylphenyl)-1-(2-methoxyethyl)-5-(phenylcarbonyl)piperidine-3-carboxylate.

The compounds of the invention can be synthesized utilizing techniques well known in the art from commercially available starting materials and reagents. For example, the compounds of the invention can be prepared as shown below:

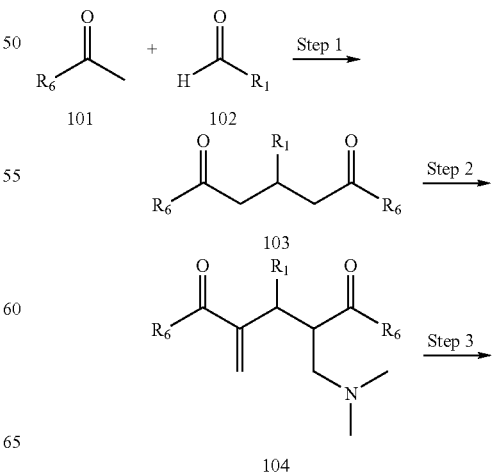

Reaction Scheme 1

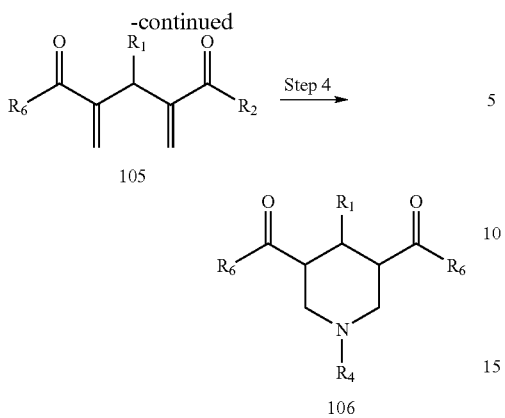

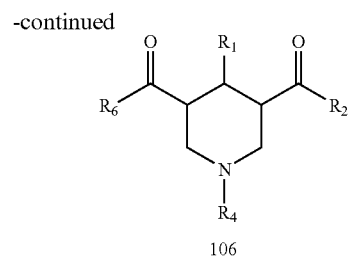

Referring to Reaction Scheme 1, Step 1, to a stirred solution of an excess, such as about 2.4 equivalents, of a compound of Formula 101 and a compound of Formula 102 in an inert solvent such as dichloromethane is added a base such as aqueous sodium hydroxide (for example, 50% aqueous sodium hydroxide) and tetrabutylammonium bromide. The resulting solution is stirred vigorously at room temperature for about 3 hour. The product, a compound of Formula 103, is isolated and optionally purified.

Referring to Reaction Scheme 1, Step 2, a mixture of a compound of Formula 103 and an excess, such as about 2.3 equivalents, of Eschenmoser's salt is taken up in acetic acid and the resulting suspension stirred at about 120° C. The product, a compound of Formula 104, is isolated and optionally purified.

Referring to Reaction Scheme 1, Step 3, a compound of Formula 104 and a base such as DIEA in an inert solvent such as acetonitrile is treated with about an equivalent of iodomethane. The mixture is stirred at room temperature for about 2 h. Base, such as aqueous potassium hydroxide, for example, 1 M potassium hydroxide, is added and the reaction heated to about 70° C. for about 30 min. The product, a compound of Formula 105, is isolated and optionally purified.

Referring to Reaction Scheme 1, Step 4, to a suspension of an excess, such as about 7 equivalents, of H-GlyNMe$_2$ TFA salt in an inert solvent such as DMF is added 1,8-diazabicyclo [5.4.0]-undec-7-ene (DBU) and the mixture stirred at about 80° C. until all the solid dissolved. A compound of Formula 105 is then added, and the stirring is continued at about 80° C. for about another 45 min. If a mixture of cis/trans and trans/trans isomers is obtained, that mixture can be converted to the trans/trans product by treatment with a polar, protic solvent such as methanol and aqueous base, such as aqueous potassium hydroxide, for example, 1 M potassium hydroxide, at about 75° C. for about 2 h. The product, a compound of Formula 106, is isolated and optionally purified.

Reaction Scheme 2

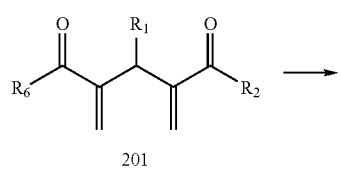

Referring to Reaction Scheme 2, Step 1, to a stirred mixture of a compound of Formula 201 in an inert solvent such as acetonitrile is added an excess (such as about 4.9 equivalents) of a compound of formula NH$_2$R$_4$. The solution is stirred for about 1 h and then treated with base, such as aqueous potassium hydroxide (e.g., 1 M aqueous potassium hydroxide). The mixture may be stirred at reflux for 1.5 h to achieve complete epimerization to a single diastereomeric (trans, trans) form by LCMS. The product, a compound of Formula 106, is isolated and optionally purified.

Reaction Scheme 3

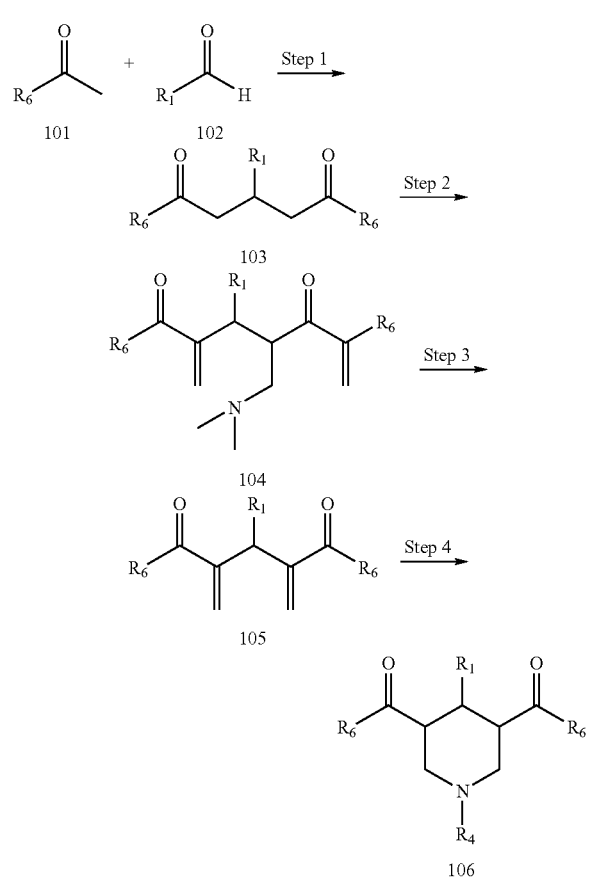

Referring to Reaction Scheme 3, Step 1, to a stirred solution of an excess such as greater than two equivalents (e.g., 2.4 equivalents) of a compound of Formula 101 and a compound of Formula 102 in an inert solvent such as dichloromethane is added base such as aqueous sodium hydroxide (e.g., 10% aqueous sodium hydroxide) and tetrabutylammonium bromide using a water/ice bath to maintain room temperature. The resulting mixture is stirred vigorously at room temperature for about 16 h. An additional portion of tetrabutylammonium bromide may be added and the mixture stirred an additional 3 h. The product, a compound of Formula 103, is isolated and optionally purified.

Referring to Reaction Scheme 3, Step 2, a mixture of a compound of Formula 103 and an excess such as about 4.6 equivalents of Eschenmoser's salt in a polar protic solvent such as acetic acid is stirred at about 120° C. under nitrogen for about 16 h. An additional amount of Eschenmoser's salt may be added and the mixture may be heated an additional 2 h. The product, a compound of Formula 104, is isolated and optionally purified.

Referring to Reaction Scheme 3, Step 3, to a stirred solution of a compound of Formula 104 in an inert solvent such as acetonitrile is added a base such as diisopropylethylamine followed by an excess (such as more than 10 equivalents, e.g., 12 equivalents) of iodomethane. The mixture is stirred at room temperature for about 16 h. To this mixture is added base, such as aqueous potassium hydroxide (e.g., 2 M aqueous potassium hydroxide) and the temperature is raised to about 75° C. for about 16 h. The product, a compound of Formula 105, is isolated and optionally purified.

Referring to Reaction Scheme 3, Step 4, a stirred mixture of a compound of Formula 105 in an inert solvent such as DMF is heated to about 80° C. An excess (e.g., 7 equivalents) of a compound of formula $NH_2R_4$ is added slowly over 10 min. The heated solution is stirred for about 45 min. The product, a compound of Formula 106, is isolated and optionally purified.

Reaction Scheme 4

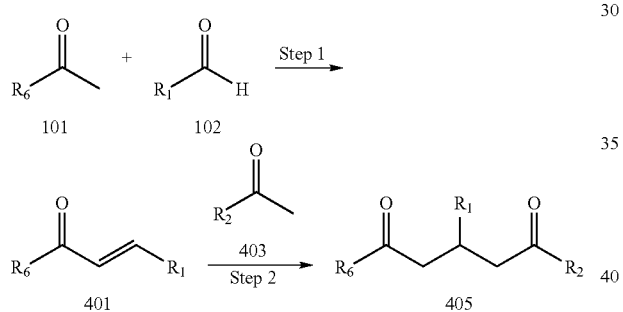

Referring to Reaction Scheme 4, Step 1, to a stirred solution of a compound of Formula 101 in an inert solvent such as IMS is added a compound of Formula 102. Base, such as aqueous sodium hydroxide (e.g., 10% aqueous sodium hydroxide) is added over about 40 min using a water bath to maintain a temperature between 18-25° C. The product, a compound of Formula 401, is isolated and optionally purified.

Referring to Reaction Scheme 4, Step 2, to a solution of a compound of Formula 401 in an inert solvent such as dichloromethane and base (such as aqueous sodium hydroxide, e.g., 50% aqueous sodium hydroxide) is added an excess (such as about 1.1 equivalents) of a compound of Formula 403 followed by tetrabutylammonium bromide. The mixture is stirred vigorously at room temperature for about 16 h. The product, a compound of Formula 405, is isolated and optionally purified.

Reaction Scheme 5

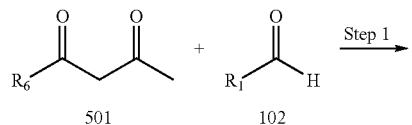

-continued

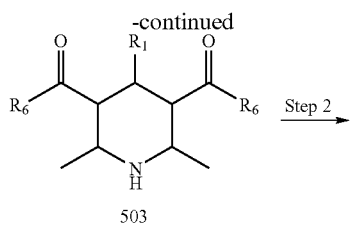

Referring to Reaction Scheme 5, Step 1, a mixture of a compound of Formula 501, an excess (such as about 2 equivalents) of a compound of Formula 102, and catalytic tris(trifluoromethylsulfonyloxy)ytterbium in ammonia solution (e.g., 7 N in methanol) is stirred under reflux for about 16 h. The dihydropyridine product with some ketone starting material may be isolated. That intermediate is dissolved in a mixture of TFA and triethylsilane and stirred for about 16 h. The product, a compound of Formula 503, is isolated and optionally purified.

Referring to Reaction Scheme 5, Step 2, a compound of Formula 503, an excess (such as about 1.5 equivalents) of a compound of formula $R_4X$ wherein X is a leaving group such as bromo, a base such as diisopropylethylamine in an inert solvent such as N-methylpyrrolidone is heated to about 150° C. in a microwave oven for about 30 min. The product, a compound of Formula 505, is isolated and optionally purified.

Reaction Scheme 6

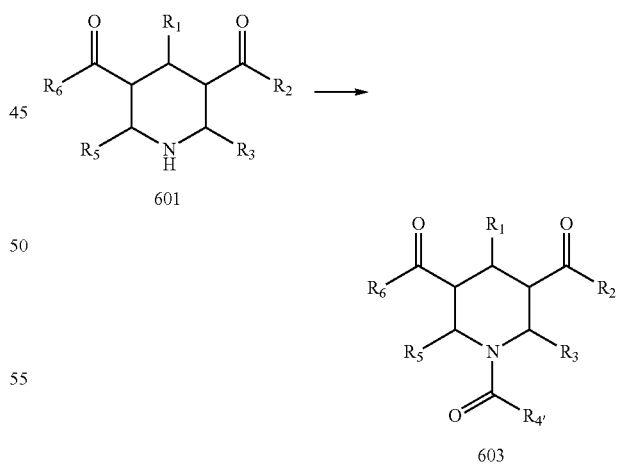

Referring to Reaction Scheme 6, to a solution of a compound of Formula 601 in an inert base such as acetonitrile are added an excess (such as about 1.5 equivalents) of a compound of formula $R_{4'}COOH$ (wherein $R_{4'}$ is alkyl, cycloalkyl, aryl, heteroaryl, or heterocycloalkyl, each of which is optionally substituted), an excess (such as about 1.5 equivalents) of HATU, and base such as diisopropylethylamine. The resulting mixture is stirred at room temperature for about 2 h. The product, a compound of Formula 603, is isolated and optionally purified.

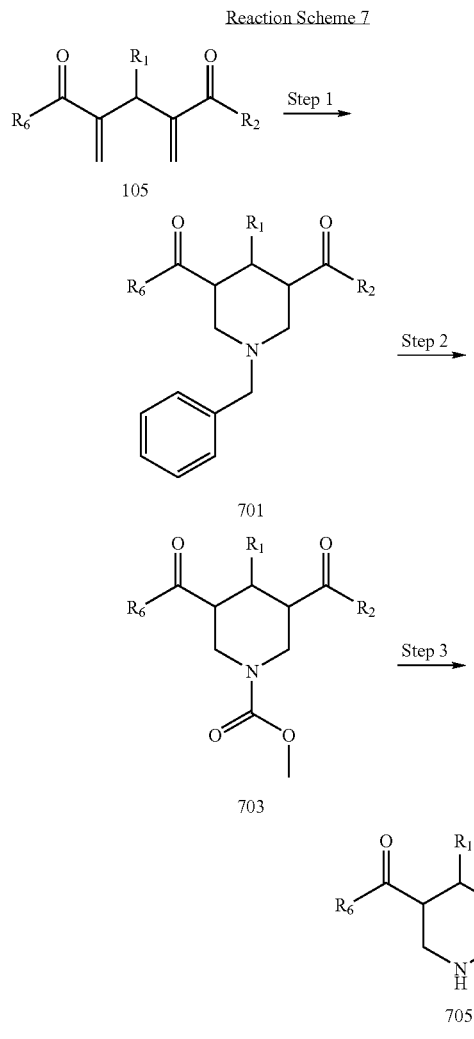

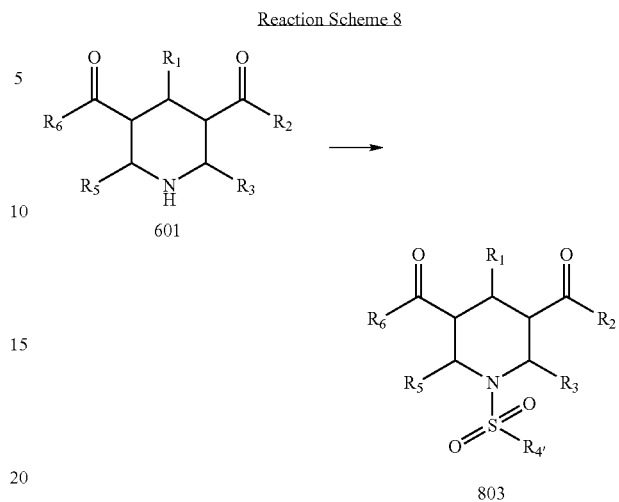

Referring to Reaction Scheme 8, to a solution of a compound of Formula 601 in an inert solvent such as THF are added an excess (such as about 1.5 equivalents) of a compound of Formula $ClSO_2R_{4'}$ (wherein $R_{4'}$ is alkyl, cycloalkyl, aryl, heteroaryl, or heterocycloalkyl, each of which is optionally substituted) and a base such as triethylamine. The resulting mixture is stirred at room temperature for about 1 h. The product, a compound of Formula 803, is isolated and optionally purified.

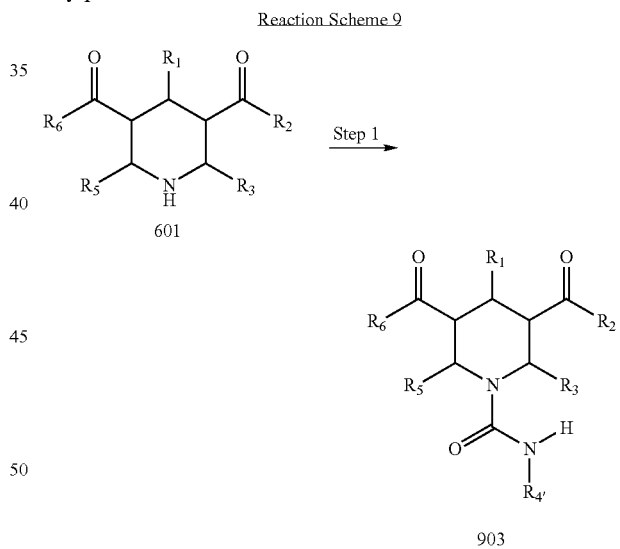

Referring to Reaction Scheme 7, Step 1, to a stirred mixture of a compound of Formula 105 in an inert solvent such as acetonitrile is added an excess (such as about 4 equivalents) of benzylamine. The solution is stirred for about 3 h. Following addition of aqueous base (such as 1 M aqueous potassium hydroxide), the solution is refluxed for about 16 h to achieve epimerization to mainly the (trans,trans) diastereoisomeric form by LCMS. The product, a compound of Formula 701, is isolated and optionally purified.

Referring to Reaction Scheme 7, Step 2, to a compound of Formula 701 is added an excess of methyl chloroformate. The reaction mixture is stirred at room temperature for about 2 h. The product, a compound of Formula 703, is isolated and optionally purified.

Referring to Reaction Scheme 7, Step 3, a compound of Formula 703 is treated with concentrated HBr (such as 48% HBr) and the mixture is stirred at room temperature for about 16 h. The product, a compound of Formula 705, is isolated and optionally purified.

Referring to Reaction Scheme 9, to a solution of a compound of Formula 601 in an inert solvent such as dichloromethane is slowly added a solution of triphosgene in an inert solvent such as dichloromethane. The resulting mixture is stirred at room temperature for about 15 min followed by addition of a base such as diisopropylethylamine. After stirring for about 15 min, a compound of Formula $NH_2R_{4'}$ (or a mono-alkylated derivative thereof, wherein $R_{4'}$ is alkyl, cycloalkyl, aryl, heteroaryl, or heterocycloalkyl, each of which is optionally substituted) is added and the mixture is stirred about 30 min. The product, a compound of Formula 903, is isolated and optionally purified.

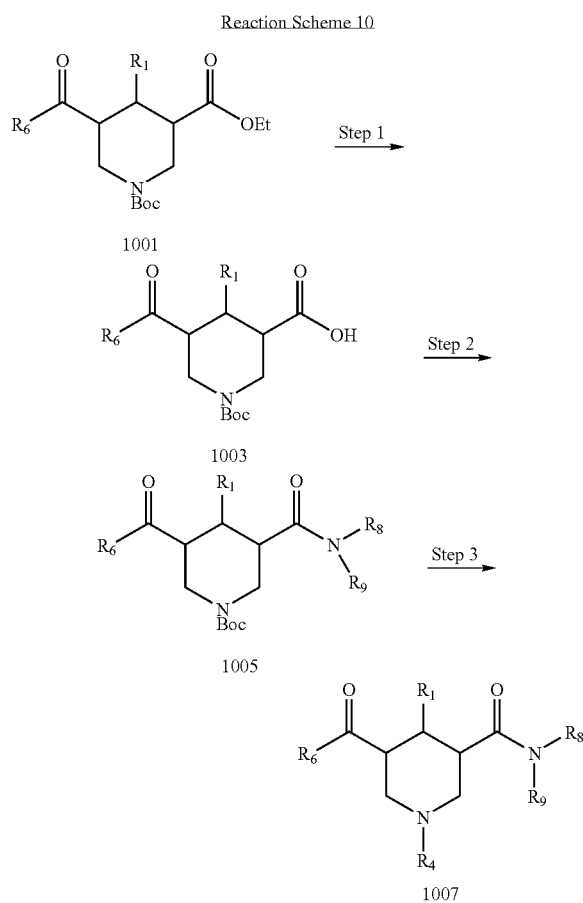

Reaction Scheme 10

Referring to Reaction Scheme 10, Step 1, to a stirred solution of a compound of Formula 1001 in a polar protic solvent such as methanol is added aqueous base (such as aqueous potassium hydroxide, e.g., 1M potassium hydroxide). The resulting solution is stirred at about 60° C. for about 16 h. The product, a compound of Formula 1003, is isolated and optionally purified.

Referring to Reaction Scheme 10, Step 2, a compound of Formula 1003 in an inert solvent such as dichloromethane is treated with an excess (such as about 3 equivalents) of oxalyl chloride followed by an excess (such as about 4.8 equivalents) of DMF. When gas evolution ceased, an excess of an amine of Formula $NHR_7R_8$ (or $NHR_9R_{10}$) is added followed by a base such as diisopropylethylamine. After about 5 min, the reaction is found to be complete by LCMS. The product, a compound of Formula 1005, is isolated and optionally purified.

Referring to Reaction Scheme 10, Step 3, a solution of a compound of Formula 1005 in an inert solvent is treated with HCl/dioxane solution at room temperature and the mixture is stirred overnight. The product is isolated and then treated with an aldehyde of Formula $HC(O)R_{4'}$ (where $R_{4'}$ is as described above) followed by $NaBH(OAc)_3$ in an inert solvent such as dichloromethane. After stirring 30 min at room temperature, the product, a compound of Formula 1007, is isolated and optionally purified.

In some embodiments, the chemical entities described herein are administered as a pharmaceutical composition or formulation. Accordingly, provided are pharmaceutical formulations comprising at least one chemical entity chosen from compounds of Formula 1 and pharmaceutically acceptable salts, solvates, chelates, non-covalent complexes, prodrugs, and mixtures thereof, together with at least one pharmaceutically acceptable vehicle chosen from carriers, adjuvants, and excipients.

Pharmaceutically acceptable vehicles must be of sufficiently high purity and sufficiently low toxicity to render them suitable for administration to the animal being treated. The vehicle can be inert or it can possess pharmaceutical benefits. The amount of vehicle employed in conjunction with the chemical entity is sufficient to provide a practical quantity of material for administration per unit dose of the chemical entity.

Exemplary pharmaceutically acceptable carriers or components thereof are sugars, such as lactose, glucose and sucrose; starches, such as corn starch and potato starch; cellulose and its derivatives, such as sodium carboxymethyl cellulose, ethyl cellulose, and methyl cellulose; powdered tragacanth; malt; gelatin; talc; solid lubricants, such as stearic acid and magnesium stearate; calcium sulfate; synthetic oils; vegetable oils, such as peanut oil, cottonseed oil, sesame oil, olive oil, and corn oil; polyols such as propylene glycol, glycerine, sorbitol, mannitol, and polyethylene glycol; alginic acid; phosphate buffer solutions; emulsifiers, such as the TWEENS; wetting agents, such sodium lauryl sulfate; coloring agents; flavoring agents; tableting agents; stabilizers; antioxidants; preservatives; pyrogen-free water; isotonic saline; and phosphate buffer solutions.

Optional active agents may be included in a pharmaceutical composition, which do not substantially interfere with the activity of the chemical entity of the present invention.

Effective concentrations of at least one chemical entity chosen from compounds of Formula 1 and pharmaceutically acceptable salts, solvates, chelates, non-covalent complexes, prodrugs, and mixtures thereof, are mixed with a suitable pharmaceutical acceptable vehicle. In instances in which the chemical entity exhibits insufficient solubility, methods for solubilizing compounds may be used. Such methods are known to those of skill in this art, and include, but are not limited to, using cosolvents, such as dimethylsulfoxide (DMSO), using surfactants, such as TWEEN, or dissolution in aqueous sodium bicarbonate.

Upon mixing or addition of the chemical entity described herein, the resulting mixture may be a solution, suspension, emulsion or the like. The form of the resulting mixture depends upon a number of factors, including the intended mode of administration and the solubility of the chemical entity in the chosen vehicle. The effective concentration sufficient for ameliorating the symptoms of the disease treated may be empirically determined.

Chemical entities described herein may be administered orally, topically, parenterally, intravenously, by intramuscular injection, by inhalation or spray, sublingually, transdermally, via buccal administration, rectally, as an ophthalmic solution, or by other means, in dosage unit formulations.

Dosage formulations suitable for oral use, include, for example, tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents, such as sweetening agents, flavoring agents, coloring agents and preserving agents, in order to provide pharmaceutically elegant and palatable preparations. In some embodiments, oral formulations contain from 0.1 to 99% of at least one chemical entity described herein. In some embodiments, oral formulations contain at least 5% (weight %) of at least one chemical entity described herein. Some embodiments contain from 25% to 50% or from 5% to 75% of at least one chemical entity described herein.

Orally administered compositions also include liquid solutions, emulsions, suspensions, powders, granules, elixirs, tinctures, syrups, and the like. The pharmaceutically acceptable carriers suitable for preparation of such compositions are well known in the art. Oral formulations may contain preservatives, flavoring agents, sweetening agents, such as sucrose or saccharin, taste-masking agents, and coloring agents.

Typical components of carriers for syrups, elixirs, emulsions and suspensions include ethanol, glycerol, propylene glycol, polyethylene glycol, liquid sucrose, sorbitol and water. Syrups and elixirs may be formulated with sweetening agents, for example glycerol, propylene glycol, sorbitol or sucrose. Such formulations may also contain a demulcent.

Chemical entities described herein can be incorporated into oral liquid preparations such as aqueous or oily suspensions, solutions, emulsions, syrups, or elixirs, for example. Moreover, formulations containing these chemical entities can be presented as a dry product for constitution with water or other suitable vehicle before use. Such liquid preparations can contain conventional additives, such as suspending agents (e.g., sorbitol syrup, methyl cellulose, glucose/sugar, syrup, gelatin, hydroxyethyl cellulose, carboxymethyl cellulose, aluminum stearate gel, and hydrogenated edible fats), emulsifying agents (e.g., lecithin, sorbitan monsoleate, or acacia), non-aqueous vehicles, which can include edible oils (e.g., almond oil, fractionated coconut oil, silyl esters, propylene glycol and ethyl alcohol), and preservatives (e.g., methyl or propyl p-hydroxybenzoate and sorbic acid).

For a suspension, typical suspending agents include methylcellulose, sodium carboxymethyl cellulose, AVICEL RC-591, tragacanth and sodium alginate; typical wetting agents include lecithin and polysorbate 80; and typical preservatives include methyl paraben and sodium benzoate.

Aqueous suspensions contain the active material(s) in admixture with excipients suitable for the manufacture of aqueous suspensions. Such excipients are suspending agents, for example sodium carboxymethylcellulose, methylcellulose, hydropropylmethylcellulose, sodium alginate, polyvinylpyrrolidone, gum tragacanth and gum acacia; dispersing or wetting agents; may be a naturally-occurring phosphatide, for example, lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol substitute, or condensation products of ethylene oxide with partial esters derived from fatty acids and hexitol anhydrides, for example polyethylene sorbitan substitute. The aqueous suspensions may also contain one or more preservatives, for example ethyl, or n-propyl p-hydroxybenzoate.

Oily suspensions may be formulated by suspending the active ingredients in a vegetable oil, for example peanut oil, olive oil, sesame oil or coconut oil, or in a mineral oil such as liquid paraffin. The oily suspensions may contain a thickening agent, for example beeswax, hard paraffin or cetyl alcohol. Sweetening agents such as those set forth above, and flavoring agents may be added to provide palatable oral preparations. These compositions may be preserved by the addition of an anti-oxidant such as ascorbic acid.

Pharmaceutical compositions of the invention may also be in the form of oil-in-water emulsions. The oily phase may be a vegetable oil, for example olive oil or peanut oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol, anhydrides, for example sorbitan monoleate, and condensation products of the said partial esters with ethylene oxide, for example polyoxyethylene sorbitan monoleate.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above.

Tablets typically comprise conventional pharmaceutically acceptable adjuvants as inert diluents, such as calcium carbonate, sodium carbonate, mannitol, lactose and cellulose; binders such as starch, gelatin and sucrose; disintegrants such as starch, alginic acid and croscarmellose; lubricants such as magnesium stearate, stearic acid and talc. Glidants such as silicon dioxide can be used to improve flow characteristics of the powder mixture. Coloring agents, such as the FD&C dyes, can be added for appearance. Sweeteners and flavoring agents, such as aspartame, saccharin, menthol, peppermint, and fruit flavors, can be useful adjuvants for chewable tablets. Capsules (including time release and sustained release formulations) typically comprise one or more solid diluents disclosed above. The selection of carrier components often depends on secondary considerations like taste, cost, and shelf stability.

Such compositions may also be coated by conventional methods, typically with pH or time-dependent coatings, such that the chemical entity is released in the gastrointestinal tract in the vicinity of the desired topical application, or at various times to extend the desired action. Such dosage forms typically include, but are not limited to, one or more of cellulose acetate phthalate, polyvinylacetate phthalate, hydroxypropyl methylcellulose phthalate, ethyl cellulose, Eudragit coatings, waxes and shellac.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin or olive oil.

Pharmaceutical compositions may be in the form of a sterile injectable aqueous or oleaginous suspension. This suspension may be formulated according to the known art using those suitable dispersing or wetting agents and suspending agents that have been mentioned above. The sterile injectable preparation may also be sterile injectable solution or suspension in a non-toxic parentally acceptable vehicle, for example as a solution in 1,3-butanediol. Among the acceptable vehicles that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid can be useful in the preparation of injectables.

Chemical entities described herein may be administered parenterally in a sterile medium. Parenteral administration includes subcutaneous injections, intravenous, intramuscular, intrathecal injection or infusion techniques. Chemical entities described herein, depending on the vehicle and concentration used, can either be suspended or dissolved in the vehicle. Advantageously, adjuvants such as local anesthetics, preservatives and buffering agents can be dissolved in the vehicle. In many compositions for parenteral administration the carrier comprises at least 90% by weight of the total composition. In some embodiments, the carrier for parenteral administration is chosen from propylene glycol, ethyl oleate, pyrrolidone, ethanol, and sesame oil.

Chemical entities described herein may also be administered in the form of suppositories for rectal administration of the drug. These compositions can be prepared by mixing the drug with a suitable non-irritating excipient that is solid at ordinary temperatures but liquid at rectal temperature and will therefore melt in the rectum to release the drug. Such materials include cocoa butter and polyethylene glycols.

Chemical entities described herein may be formulated for local or topical application, such as for topical application to the skin and mucous membranes, such as in the eye, in the form of gels, creams, and lotions and for application to the eye. Topical compositions may be in any form including, for example, solutions, creams, ointments, gels, lotions, milks, cleansers, moisturizers, sprays, skin patches, and the like.

Such solutions may be formulated as 0.01%-10% isotonic solutions, pH 5-7, with appropriate salts. Chemical entities described herein may also be formulated for transdermal administration as a transdermal patch.

Topical compositions comprising at least one chemical entity described herein can be admixed with a variety of carrier materials well known in the art, such as, for example, water, alcohols, aloe vera gel, allantoin, glycerine, vitamin A and E oils, mineral oil, propylene glycol, PPG-2 myristyl propionate, and the like.

Other materials suitable for use in topical carriers include, for example, emollients, solvents, humectants, thickeners and powders. Examples of each of these types of materials, which can be used singly or as mixtures of one or more materials, are as follows:

Representative emollients include stearyl alcohol, glyceryl monoricinoleate, glyceryl monostearate, propane-1,2-diol, butane-1,3-diol, mink oil, cetyl alcohol, iso-propyl isostearate, stearic acid, iso-butyl palmitate, isocetyl stearate, oleyl alcohol, isopropyl laurate, hexyl laurate, decyl oleate, octadecan-2-ol, isocetyl alcohol, cetyl palmitate, dimethylpolysiloxane, di-n-butyl sebacate, iso-propyl myristate, iso-propyl palmitate, iso-propyl stearate, butyl stearate, polyethylene glycol, triethylene glycol, lanolin, sesame oil, coconut oil, arachis oil, castor oil, acetylated lanolin alcohols, petroleum, mineral oil, butyl myristate, isostearic acid, palmitic acid, isopropyl linoleate, lauryl lactate, myristyl lactate, decyl oleate, and myristyl myristate; propellants, such as propane, butane, iso-butane, dimethyl ether, carbon dioxide, and nitrous oxide; solvents, such as ethyl alcohol, methylene chloride, iso-propanol, castor oil, ethylene glycol monoethyl ether, diethylene glycol monobutyl ether, diethylene glycol monoethyl ether, dimethyl sulphoxide, dimethyl formamide, tetrahydrofuran; humectants, such as glycerin, sorbitol, sodium 2-pyrrolidone-5-carboxylate, soluble collagen, dibutyl phthalate, and gelatin; and powders, such as chalk, talc, fullers earth, kaolin, starch, gums, colloidal silicon dioxide, sodium polyacrylate, tetra alkyl ammonium smectites, trialkyl aryl ammonium smectites, chemically modified magnesium aluminum silicate, organically modified montmorillonite clay, hydrated aluminum silicate, fumed silica, carboxyvinyl polymer, sodium carboxymethyl cellulose, and ethylene glycol monostearate.

Chemical entities described herein may also be topically administered in the form of liposome delivery systems, such as small unilamellar vesicles, large unilamellar vesicles, and multilamellar vesicles. Liposomes can be formed from a variety of phospholipids, such as cholesterol, stearylamine or phosphatidylcholines.

Other compositions useful for attaining systemic delivery of the chemical entity include sublingual, buccal and nasal dosage forms. Such compositions typically comprise one or more of soluble filler substances such as sucrose, sorbitol and mannitol, and binders such as acacia, microcrystalline cellulose, carboxymethyl cellulose, and hydroxypropyl methylcellulose. Glidants, lubricants, sweeteners, colorants, antioxidants and flavoring agents disclosed above may also be included.

Compositions for inhalation typically can be provided in the form of a solution, suspension or emulsion that can be administered as a dry powder or in the form of an aerosol using a conventional propellant (e.g., dichlorodifluoromethane or trichlorofluoromethane).

The compositions of the present invention may also optionally comprise an activity enhancer. The activity enhancer can be chosen from a wide variety of molecules that function in different ways to enhance or be independent of therapeutic effects of the chemical entities described herein. Particular classes of activity enhancers include skin penetration enhancers and absorption enhancers.

Pharmaceutical compositions of the invention may also contain additional active agents that can be chosen from a wide variety of molecules, which can function in different ways to enhance the therapeutic effects of at least one chemical entity described herein. These optional other active agents, when present, are typically employed in the compositions of the invention at a level ranging from 0.01% to 15%. Some embodiments contain from 0.1% to 10% by weight of the composition. Other embodiments contain from 0.5% to 5% by weight of the composition.

The invention includes packaged pharmaceutical formulations. Such packaged formulations include a pharmaceutical composition comprising at least one chemical entity chosen from compounds of Formula 1 and pharmaceutically acceptable salts, solvates, chelates, non-covalent complexes, prodrugs, and mixtures thereof, and instructions for using the composition to treat a mammal (typically a human patient). In some embodiments, the instructions are for using the pharmaceutical composition to treat a patient suffering from a disease responsive to inhibition of Btk activity and/or inhibition of B-cell activity. The invention can include providing prescribing information; for example, to a patient or health care provider, or as a label in a packaged pharmaceutical formulation. Prescribing information may include for example efficacy, dosage and administration, contraindication and adverse reaction information pertaining to the pharmaceutical formulation.

In all of the foregoing the chemical entities can be administered alone, as mixtures, or in combination with other active agents.

The chemical entities described herein can be used to treat cellular proliferation diseases. Such diseases include, but are not limited to, cancer (further discussed below), autoimmune disease, fungal disorders, arthritis, graft rejection, inflammatory bowel disease, cellular proliferation induced after medical procedures, including, but not limited to, surgery, angioplasty, and the like. Treatment includes inhibiting cellular proliferation. It is appreciated that in some cases the cells may not be in an abnormal state and still require treatment. Thus, in some embodiments, at least one chemical entity is administered to cells or individuals afflicted or subject to impending affliction with any one of these diseases or states.

The chemical entities provided herein can be used to treat cancer including solid tumors such as skin, breast, brain, cervical carcinomas, testicular carcinomas, etc. More particularly, cancers that can be treated include, but are not limited to:

Cardiac: sarcoma (angiosarcoma, fibrosarcoma, rhabdomyosarcoma, liposarcoma), myxoma, rhabdomyoma, fibroma, lipoma and teratoma;

Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma;

Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma);

Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma);

Liver: hepatoma (hepatocellular carcinoma), cholangiocarcinoma, hepatoblastoma, angiosarcoma, hepatocellular adenoma, hemangioma;

Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors;

Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma);

Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant tertoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma], fallopian tubes (carcinoma);

Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma];

Skin: malignant melanoma, basal cell carcinoma, squamous cell carcinoma, Karposi's sarcoma, moles dysplastic nevi, lipoma, angioma, dermatofibroma, keloids, psoriasis; and Adrenal glands: neuroblastoma.

As used herein, treatment of cancer includes treatment of cancerous cells.

The chemical entities provided herein may be demonstrated to inhibit tumor cell proliferation, cell transformation and tumorigenesis in vitro and in vivo using a variety of assays known in the art, or described herein. Such assays may use cells of a cancer cell line, or cells from a patient. Many assays well-known in the art can be used to assess such survival and/or growth; for example, cell proliferation can be assayed by measuring $^3$H-thymidine incorporation, by direct cell count, by detecting changes in transcription, translation or activity of known genes such as proto-oncogenes (e.g., fos, myc) or cell cycle markers (Rb, cdc2, cyclin A, D1, D2, D3, E, etc). The levels of such protein and mRNA and activity can be determined by any method well known in the art.

Cell proliferation may be measured by counting samples of a cell population over time (e.g., daily cell counts). Cells may be counted using a hemacytometer and light microscopy (e.g., HyLite hemacytometer, Hausser Scientific). Cell number may be plotted against time in order to obtain a growth curve for the population of interest. In one embodiment, cells are first mixed with the dye Trypan-blue (Sigma), such that living cells exclude the dye, and are counted as viable members of the population.

DNA content and/or mitotic index of the cells may be measured, for example, based on DNA ploidy value of the cell. For example, cells in the G1 phase of the cell cycle generally contain a 2N DNA ploidy value. Cells in which DNA has been replicated but have not progressed through mitosis (e.g., cells in S-phase) will exhibit a ploidy value higher than 2N and up to 4N DNA content. Ploidy value and cell-cycle kinetics may be further measured using propidum iodide assay (see, e.g., Turner, T., et al., 1998, Prostate 34:175-81). Alternatively, the DNA ploidy maybe determined by quantitation of DNA Feulgen staining (which binds to DNA in a stoichiometric manner) on a computerized microdensitometry staining system (see, e.g., Bacus, S., 1989, Am. J. Pathol. 135:783-92). In an another embodiment, DNA content may be analyzed by preparation of a chromosomal spread (Zabalou, S., 1994, Hereditas. 120:127-40; Pardue, M. L., 1994, Meth. Cell Biol. 44:333-351).

Detection of changes in length of the cell cycle or speed of cell cycle may also be used to measure inhibition of cell proliferation by the compounds of the invention. In one embodiment the length of the cell cycle is determined by the doubling time of a population of cells (e.g., using cells contacted or not contacted with one or more compounds of the invention). In another embodiment, FACS analysis is used to analyze the phase of cell cycle progression, or purify G1, S, and G2/M fractions (see e.g., Delia, D. et al., 1997, Oncogene 14:2137-47).

Lapse of cell cycle checkpoint(s), and/or induction of cell cycle checkpoint(s), may be examined by any method known in the art. Without limitation, a cell cycle checkpoint is a mechanism which ensures that certain cellular events occur in a particular order. Checkpoint genes are defined by mutations that allow late events to occur without prior completion of an early event (Weinert, T., and Hartwell, L., 1993, Genetics 134:63-80). Induction or inhibition of cell cycle checkpoint genes may be assayed, for example, by Western blot analysis, or by immunostaining, etc. Lapse of cell cycle checkpoints may be further assessed by the progression of a cell through the checkpoint without prior occurrence of specific events (e.g., progression into mitosis without complete replication of the genomic DNA).

The chemical entities provided herein can also be demonstrated to alter cell proliferation in cultured cells in vitro using methods that are well known in the art. Specific examples of cell culture models include, but are not limited to, for lung cancer, primary rat lung tumor cells (Swafford et al., 1997, Mol. Cell. Biol. 17:1366-1374) and large-cell undifferentiated cancer cell lines (Mabry et al., 1991, Cancer Cells 3:53-58); colorectal cell lines for colon cancer (Park and Gazdar, 1996, J. Cell Biochem. Suppl. 24:131-141); multiple established cell lines for breast cancer (Hambly et al., 1997, Breast Cancer Res. Treat. 43:247-258; Gierthy et al., 1997, Chemosphere 34:1495-1505; Prasad and Church, 1997, Biochem. Biophys. Res. Commun. 232:14-19); a number of well-characterized cell models for prostate cancer (Webber et al., 1996, Prostate, Part 1, 29:386-394; Part 2, 30:58-64; and Part 3, 30-136-142; Boulikas, 1997, Anticancer Res. 17:1471-1505); for genitourinary cancers, continuous human bladder cancer cell lines (Ribeiro et al., 1997, Int. J. Radiat. Biol. 72:11-20); organ cultures of transitional cell carcinomas (Booth et al., 1997, Lab Invest. 76:843-857) and rat progression models (Vet et al., 1997, Biochim. Biophys Acta 1360: 39-44); and established cell lines for leukemias and lymphomas (Drexler, 1994, Leuk. Res. 18:919-927; Tohyama, 1997, Int. J. Hematol. 65:309-317).

The chemical entities provided herein can also be demonstrated to inhibit cell growth (or mitosis) in vitro. In this embodiment, cells are contacted with one or more chemical entities provided herein, and examined for lethal phenotype.

The chemical entities provided herein can also be demonstrated to inhibit tumor formation in vivo. A vast number of animal models of hyperproliferative disorders, including tumorigenesis and metastatic spread, are known in the art (see Table 317-1, Chapter 317, "Principals of Neoplasia," in Harrison's Principals of Internal Medicine, 13th Edition, Isselbacher et al., eds., McGraw-Hill, New York, p. 1814; and Lovejoy et al., 1997, J. Pathol. 181:130-135). Specific examples include for lung cancer, transplantation of tumor nodules into rats (Wang et al., 1997, Ann. Thorac. Surg. 64:216-219) or establishment of lung cancer metastases in SCID mice depleted of NK cells (Yono and Sone, 1997, Gan To Kagaku Ryoho 24:489-494); for colon cancer, colon cancer transplantation of human colon cancer cells into nude mice (Gutman and Fidler, 1995, World J. Surg. 19:226-234), the cotton top tamarin model of human ulcerative colitis (Warren, 1996, Aliment. Pharmacol. Ther. Supp 12:45-47) and mouse models with mutations of the adenomatous polyposis tumor suppressor (Polakis, 1997, Biochim. Biophys. Acta 1332:F127-F147); for breast cancer, transgenic models of breast cancer (Dankfort and Muller, 1996, Cancer Treat. Res. 83:71-88; Amundadittir et al., 1996, Breast Cancer Res. Treat. 39:119-135) and chemical induction of tumors in rats (Russo and Russo, 1996, Breast Cancer Res. Treat. 39:7-20); for prostate cancer, chemically-induced and transgenic rodent models, and human xenograft models (Royai et al., 1996, Semin. Oncol. 23:35-40); for genitourinary cancers, induced bladder neoplasm in rats and mice (Oyasu, 1995, Food Chem. Toxicol. 33:747-755) and xenografts of human transitional cell carcinomas into nude rats (Jarrett et al., 1995, J. Endourol. 9:1-7); and for hematopoietic cancers, transplanted allogenic marrow in animals (Appelbaum, 1997, Leukemia 11(Suppl. 4):S15-S17). Further, general animal models applicable to many types of cancer have been described, including, but not restricted to, the p53-deficient mouse model (Donehower, 1996, Semin. Cancer Biol. 7:269-278), the Min mouse (Shoemaker et al., 1997, Biochem. Biophys. Acta, 1332:F25-F48), and immune responses to tumors in rat (Frey, 1997, Methods, 12:173-188).

For example, chemical entities provided herein can be administered to a test animal, preferably a test animal predisposed to develop a type of tumor, and the test animal subsequently examined for a decreased incidence of tumor formation in comparison with controls not administered the compound. Alternatively, chemical entities provided herein can be administered to test animals having tumors (e.g., animals in which tumors have been induced by introduction of malignant, neoplastic, or transformed cells, or by administration of a carcinogen) and subsequently examining the tumors in the test animals for tumor regression in comparison to controls not administered the chemical entity.

Another measure of inhibition is $GI_{50}$, defined as the concentration of the chemical entity that results in a decrease in the rate of cell growth by fifty percent. In some embodiments, the chemical entity has a $GI_{50}$ of less than about 1 mM; alternatively, the chemical entity has a $GI_{50}$ of less than about 20 µM, less than about 10 µM, less than about 1 µM, less than about 100 nM, or less than about 10 nM. Measurement of $GI_{50}$ is done using a cell proliferation assay such as described herein. Chemical entities provided herein were found to inhibit cell proliferation.

In vitro potency of chemical entities provided herein can be determined, for example, by assaying human ovarian cancer cells (SKOV3) for viability following a 72-hour exposure to a 9-point dilution series of compound. Cell viability is determined by measuring the absorbance of formazon, a product formed by the bioreduction of MTS/PMS, a commercially available reagent. Each point on the dose-response curve is calculated as a percent of untreated control cells at 72 hours minus background absorption (complete growth inhibition).

Anti-proliferative compounds that have been successfully applied in the clinic to treatment of cancer (cancer chemotherapeutics) have $GI_{50}$'s that vary greatly. For example, in A549 cells, paclitaxel $GI_{50}$ is 4 nM, doxorubicin is 63 nM, 5-fluorouracil is 1 µM, and hydroxyurea is 500 µM (data provided by National Cancer Institute, Developmental Therapeutic Program, http://dtp.nci.nih.gov/). Therefore, compounds that inhibit cellular proliferation, irrespective of the concentration demonstrating inhibition, have potential clinical usefulness.

Chemical entities provided herein may be administered, for example, as a pharmaceutically acceptable composition, to a patient. Depending upon the manner of introduction, the chemical entities may be formulated in a variety of ways as discussed below. The concentration of therapeutically active chemical entity in the formation may vary from about 0.1-10 wt. %.

The chemical entity may be administered alone or in combination with other treatments, i.e., radiation, or other chemotherapeutic agents such as the taxane class of agents that appear to act on microtubule formation or the camptothecin class of topoisomerase I inhibitors. When used, other chemotherapeutic agents may be administered before, concurrently, or after administration of at least one chemical entity provided herein. In some embodiments, at least one chemical entity provided herein is co-administered with one or more other chemotherapeutic agents. By "co-administer" it is meant that at least one chemical entity provided herein is administered to a patient such that the chemical entity as well as the co-administered compound may be found in the patient's bloodstream at the same time, regardless of when the compounds are actually administered, including simultaneously.

The following examples serve to more fully describe the manner of using the above-described invention. It is understood that these examples in no way serve to limit the true scope of this invention, but rather are presented for illustrative purposes.

All publications, including but not limited to patents and patent applications, cited in this specification are herein incorporated by reference as if each individual publication were specifically and individually indicated to be incorporated by reference herein as though fully set forth.

EXAMPLES

Example 1

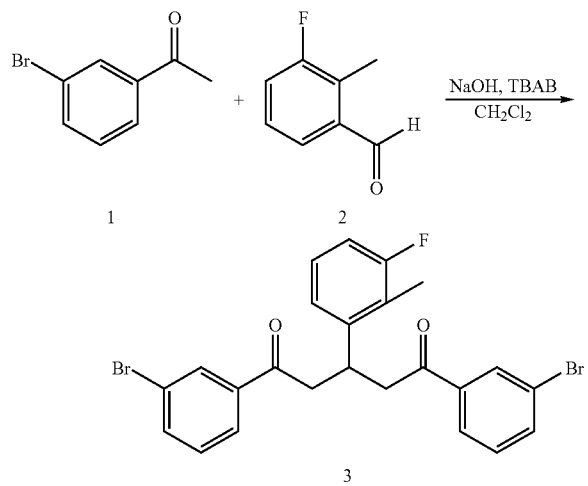

To a stirred solution of 3'-bromoacetophenone (20 g, 100 mmol) and 3-fluoro-2-methyl benzadehyde (5.8 g, 42 mmol) in dichloromethane was added 100 mL 50% aq NaOH and tetrabutylammonium bromide (0.2 g, 0.6 mmol). The resulting solution was stirred vigorously at room temperature for 3 hour. LCMS showed the reaction had completed. The reaction mixture was quenched with 1 N HCl cautiously and extracted with dichloromethane. The organic layer was washed with brine, dried and concentrated under reduced pressure. The crude product was recrystallized from ether/hexane to give 14 g of white solid in 65% yield. (characterized by LCMS and $^1$H NMR). LRMS (M+H$^+$) m/z=516.9

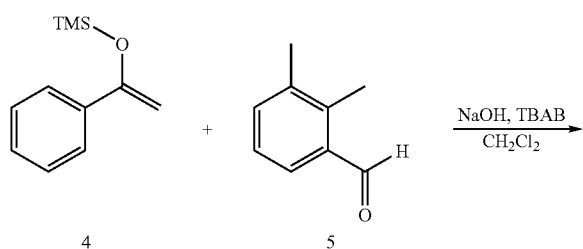

-continued

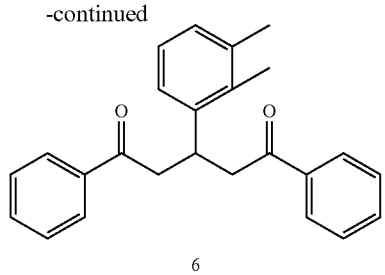

To a mixture of tetrabutylammonium bromide (1.08 g, 3.3 mmol) in dichloromethane (80 mL) and aqueous NaOH (50% w/w solution, 10 mL) was added 4 (13.7 mL, 67 mmol) and 5 (4.50 g, 33.5 mmol). The mixture was stirred at room temperature for 6 h followed by the addition of 1 M HCl (200 mL). The product was extracted with dichloromethane (250 mL) and the organic phase washed with 1 M HCl (200 mL), dried over Na2SO4 and concentrated under vacuum. The resulting thick yellow oil was purified over silica gel with ether and hexanes as eluent to give 6 (3.06 g, 26%) as a yellow solid, along with an additional 1.67 g of less pure material. LRMS (M+H$^+$) m/z=357.1

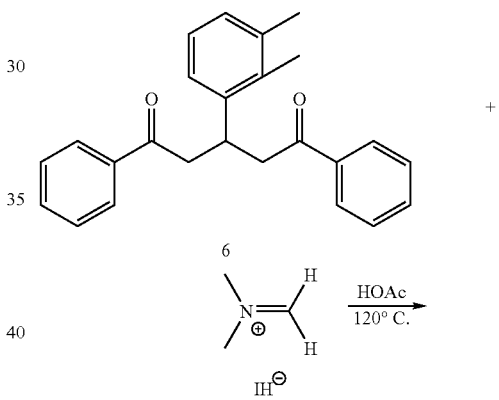

A mixture of 6 (21.94 g, 61.6 mmol) and Eschenmoser's salt (26.2 g, 141.7 mmol) was taken up in acetic acid (200 mL) and the resulting suspension stirred at 120° C. After 15 min, the mixture became a clear solution. Stirring was continued at 120° C. for 16 h at which time LC/MS showed complete conversion of starting material. The flask was cooled to room temperature and then diluted with ethyl acetate (500 mL). The resulting mixture was neutralized with Na$_2$CO$_3$ until pH 8 was reached. The layers were separated and organic layer evaporated to dryness. The resulting solid 7 (30.44 g) was carried on without further purification. LRMS (M+H$^+$) m/z=426.2

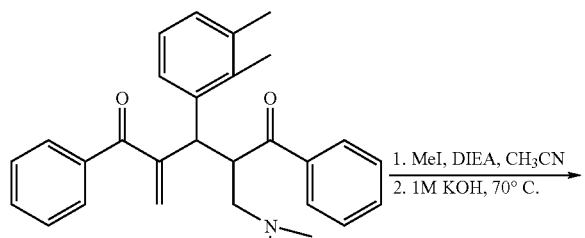

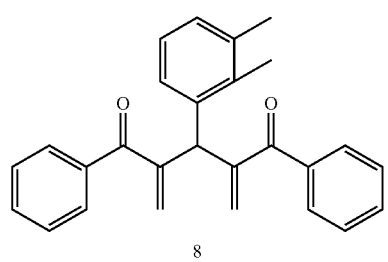

A suspension of 7 (26.19 g, 61.6 mmol) and DIEA (107 mL, 61.6 mmol) in acetonitrile 225 mL) was treated with iodomethane (38.3 mL, 61.6 mmol). The mixture was stirred at room temperature for 2 h. 1 M KOH (200 mL) was added and the reaction heated to 70° C. for 30 min. After cooling to room temperature, the product was extracted with ethyl acetate (2×250 mL) and the solvents removed under vacuum. The residue was purified over silica gel using ether and hexanes as eluent to give 8 (10.8 g, 29% from 6) as a white solid. LRMS (M+H$^+$) m/z=381.1

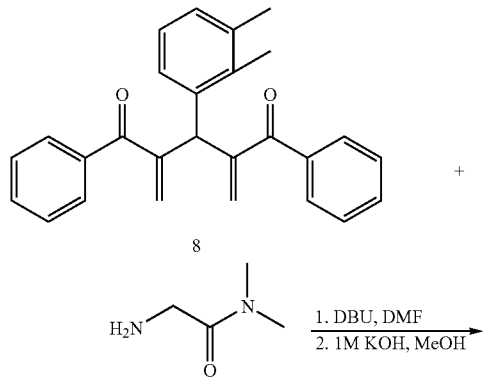

To a suspension of H-GlyNMe$_2$ TFA salt (10.0 g, 46.2 mmol) in DMF (50 mL) was added 1,8-diazabicyclo[5.4.0]-undec-7-ene (DBU) (9.85 mL, 66.0 mmol) and the mixture stirred at 80° C. until all the solid dissolved. Compound 8 (2.51 g, 6.60 mmol) was then added, and the stirring was continued at 80° C. for another 45 min, at which time LC/MS showed complete reaction to a 1:1 mixture of cis/trans and trans/trans isomers (confirmed by HNMR). After cooling to room temperature, most of the DMF was evaporated under vacuum. The resulting residue was partitioned between ethyl acetate and sodium bicarbonate, and the organic layer was dried over sodium sulfate, filtered and evaporated to dryness. The foamy white solid was then dissolved in a mixture of methanol (100 mL) and 1 M KOH (50 mL) and stirred at 75° C. for 2 h, at which point LC/MS showed complete conversion to the trans/trans product. The solution was cooled to room temperature and extracted with ethyl acetate (2×150 mL). The combined organic layers were dried over sodium sulfate and evaporated to dryness. The resulting foamy solid was purified over silica gel using ethyl acetate and hexanes as eluent to give desired product with a single impurity, which was removed by recrystallization from an ethyl acetate/hexanes mixture. Pure 9 (1.61 g, 51%) was obtained as white crystals. LRMS (M+H$^+$) m/z=483.2; m.p.=125-126° C.

Example 2

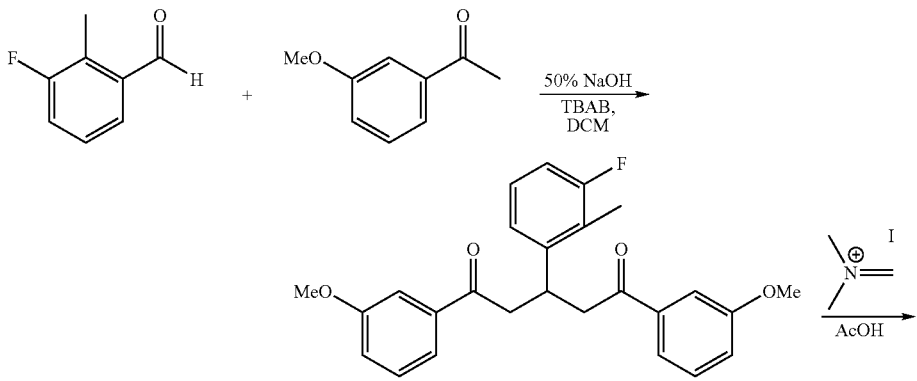

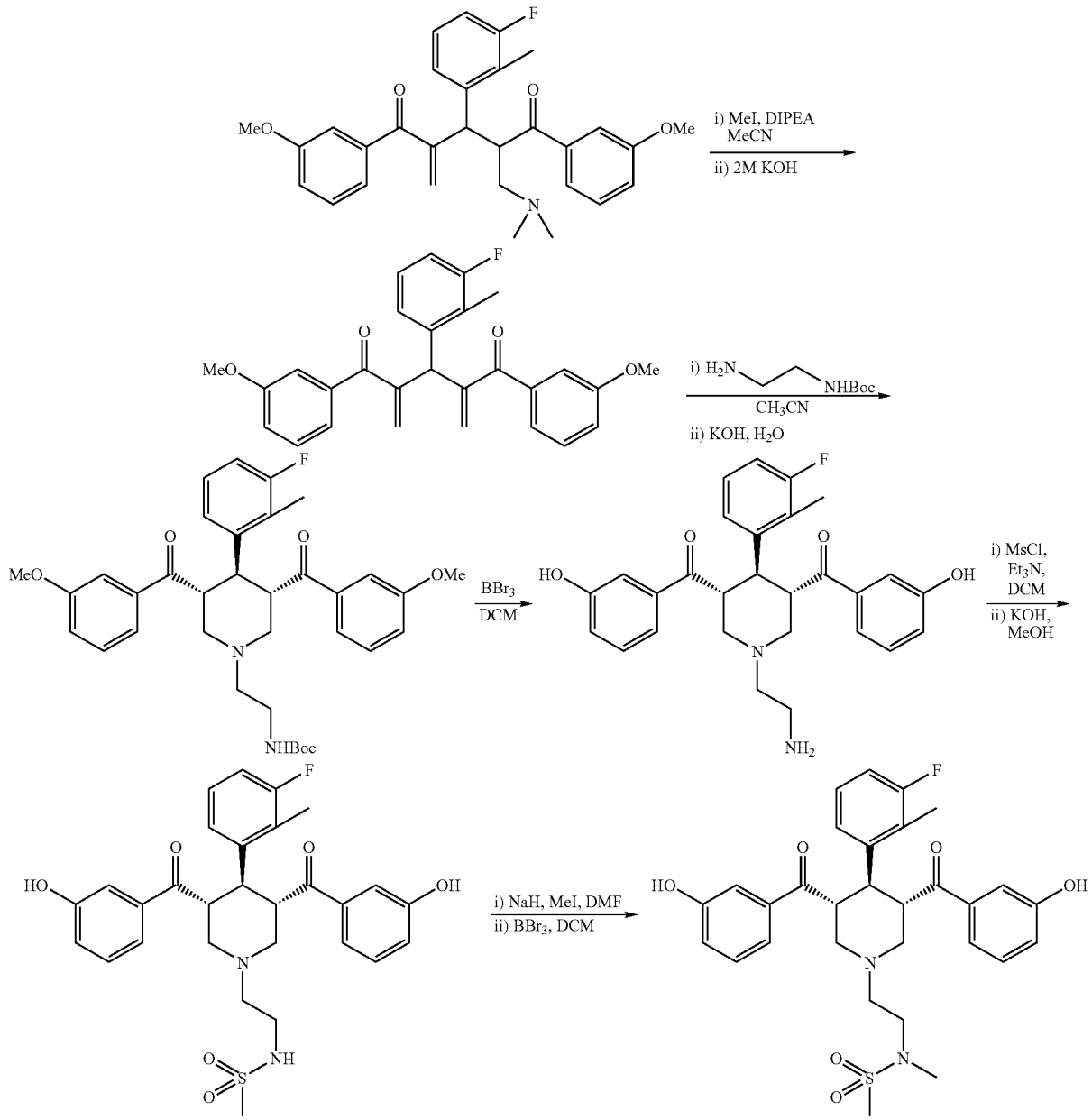

To a stirred solution of 3-fluoro-2-methylbenzaldehyde (75.0 g, 543 mmol) and 3'-methoxyacetophenone (179 g, 1.32 mol) in dichloromethane (1.5 L) was added 10% aq NaOH (750 mL) and tetrabutylammonium bromide (30.8 g, 95.7 mmol) portion-wise using a water/ice bath to maintain room temperature. The resulting mixture was stirred vigorously at room temperature for 16 h during which time a precipitate formed. An additional portion of tetrabutylammonium bromide (10.0 g, 31.1 mmol) was added and the mixture stirred an additional 3 h. The layers were separated, the aqueous phase was extracted with dichloromethane (500 mL), and the combined organic phases were washed with water. The organic layer was then dried over MgSO$_4$, filtered, and concentrated under vacuum to give 279.1 g of crude product as a viscous brown oil. Purification over silica gel using 25-50% EtOAc/hexanes followed by slurrying of the concentrated yellow oil with 50% ether/hexanes and 100% ether gave the desired product, 3-(3-fluoro-2-methylphenyl)-1,5-bis(3-methoxyphenyl)pentane-1,5-dione (71.6 g, 31.4% yield), (characterized by $^1$H NMR).

A mixture of 3-(3-fluoro-2-methylphenyl)-1,5-bis(3-methoxyphenyl)pentane-1,5-dione (71.6 g, 170 mmol) and (145 g, 782 mmol) in acetic acid (300 mL) was stirred at 120° C. under nitrogen for 16 h. An additional 5 g (27.0 mmol) of Eschenmoser's salt was added and the mixture heated an additional 2 h. The solution was allowed to cool to room temperature and concentrated in vacuo to give a brown solid. The residue slurried with water and then treated with NaOH (s) until the pH reached 10. EtOAc (100 mL) was added, and the pH was adjusted to 10 with NaOH (s). The vigorously stirred mixture was diluted with 200 mL of EtOAc followed by 300 mL of hexanes. The pale yellow solid was isolated by filtration, washed with water (200 mL), hexanes (200 mL), and ethyl acetate (100 mL), and dried under vacuum at 45° C. overnight to give 91 g of desired 2-((dimethylamino)methyl)-3-(3-fluoro-2-methylphenyl)-1,5-bis(3-methoxyphenyl)-4-methylenepentane-1,5-dione product as a crude yellow solid, (characterized by LCMS and $^1$H NMR), LRMS (M+H$^+$) m/z=490.5.

To a stirred solution of crude 2-((dimethylamino)methyl)-3-(3-fluoro-2-methylphenyl)-1,5-bis(3-methoxyphenyl)-4-methylenepentane-1,5-dione (91 g, 186 mmol) in acetonitrile (769 mL) was added diisopropylethylamine (65 mL, 376 mmol) followed by iodomethane (140 mL, 2.24 mol). The mixture was stirred at room temperature for 16 h. To this mixture was added 2 M KOH (307 mL, 614 mmol), and the temperature was raised to 75° C. for 16 h. The mixture was partitioned between dichloromethane and water. The layers were separated and the aqueous phase extracted with 500 mL dichloromethane. The combined organic layers were dried over MgSO$_4$, filtered, and evaporated to dryness. The residue was treated with 350 mL ether, isolated by filtration, and washed with 2×100 mL of ether. The ether layers were concentrated in vacuum to give 3-(3-fluoro-2-methylphenyl)-1,5-bis(3-methoxyphenyl)-2,4-dimethylenepentane-1,5-dione (63.8 g, 77% yield), (characterized by LCMS and $^1$H NMR). LRMS (M+H$^+$) m/z=445.3.

A stirred mixture of 3-(3-fluoro-2-methylphenyl)-1,5-bis(3-methoxyphenyl)-2,4-dimethylenepentane-1,5-dione (44 g, 99 mmol) in DMF (450 mL) was heated to 80° C. N-Boc-ethylenediamine (112 g, 694 mmol) was then added slowly over 10 min. The heated solution was stirred for 45 min, and then cooled to room temperature and concentrated under vacuum. The residue was dissolved in 1.3 L of methanol and treated with 1 M KOH (440 mL, 440 mmol). The mixture was stirred at reflux for 1.5 h to achieve complete epimerization to a single diastereomeric (trans,trans) form by LCMS. The mixture was allowed to cool to room temperature and concentrated under vacuum. The residue was dissolved in 1.8 L of EtOAc, washed with water (400 mL), dried with MgSO$_4$, filtered, and concentrated under vacuum. The crude product was purified over silica gel using 25-50% EtOAc/hexanes to give tert-butyl 2-((trans,trans)-4-(3-fluoro-2-methylphenyl)-3,5-bis(3-methoxybenzoyl)piperidin-1-yl)ethylcarbamate (49.9 g, 83% yield) after drying under vacuum at 45° C. overnight, (characterized by $^1$H NMR).

To a solution of tert-butyl 2-((trans,trans)-4-(3-fluoro-2-methylphenyl)-3,5-bis(3-methoxybenzoyl)piperidin-1-yl) ethylcarbamate (49.9 g, 82.6 mmol) in dichloromethane (1.4 L) under nitrogen was added Boron tribromide (413 mL, 1.0 M in dichloromethane, 413 mmol) dropwise to maintain room temperature. The resulting solution was stirred for 3 h and then quenched with 1.8 L of ice water at 0° C., producing a mild exotherm. The organic layer was separated and the aqueous layer neutralized with NaHCO$_3$ to pH 7. After extraction of the aqueous layer with EtOAc and dichloromethane, the organic phases were combined, dried over MgSO$_4$, and concentrated under vacuum to crude product as a foam. The residue was resuspended in ether and evaporated to generate give 55 g (>100% yield) of a drier foam. The crude ((trans,trans)-1-(2-aminoethyl)-4-(3-fluoro-2-methylphenyl)piperidine-3,5-diyl)bis((3-hydroxyphenyl)methanone) was taken on to the next step without further purification, (characterized by LCMS and $^1$H NMR). LRMS (M+H$^+$) m/z=477.7.

A portion of ((trans,trans)-1-(2-aminoethyl)-4-(3-fluoro-2-methylphenyl)piperidine-3,5-diyl)bis((3-hydroxyphenyl) methanone) (32 g, 67 mmol) was dissolved in dichloromethane (768 mL) and triethylamine (56.2 mL, 403 mmol) and cooled with an ice water bath. Methanesulfonyl chloride (31.2 mL, 403 mmol) was added slowly maintaining the temperature below 30° C. The mixture was stirred an additional 3 h at room temperature and concentrated in vacuo. The residue was dissolved in MeOH (1 L) and treated with 3 M KOH (330 mmol). Stirring for 2.5 h at reflux was sufficient to produce the desired product by HPLC. The mixture was cooled to room temperature and concentrated under vacuum The pH of the remaining aqueous phase was adjusted to 7 with 1 M HCl followed by extraction with EtOAc (1 L). The organic phase was dried over MgSO$_4$, filtered, and evaporated to dryness. The residue was purified over silica gel using 90-100% EtOAc/hexanes. Mixed fractions were slurried with ether and then recrystallized with hot EtOAc/hexanes to yield a total of 8.3 g (22% overall yield over 2 steps) of desired N-(2-((trans,trans)-4-(3-fluoro-2-methylphenyl)-3,5-bis(3-hydroxybenzoyl)piperidin-1-yl)ethyl)methanesulfonamide, (characterized by $^1$H NMR).

A solution of N-(2-((trans,trans)-4-(3-fluoro-2-methylphenyl)-3,5-bis(3-hydroxybenzoyl)piperidin-1-yl)ethyl) methanesulfonamide (2.3 g, 4.1 mmol) in DMF (23 mL) was added to a mixture of sodium hydride (0.52 g, 21.8 mmol) in DMF (23 mL) over 5 min. The solution was stirred for 15 min and treated with a mixture of methyl iodide (1.5 g, 21.8 mmol) in DMF (4 mL). The reaction was stirred for 45 min and then partitioned between water (150 mL) and EtOAc (200 mL). The organics were separated, washed with saturated NaCl (100 mL), dried over MgSO$_4$, and evaporated in vacuo. The resultant oil was dissolved in dichloromethane (50 mL) and treated with Boron tribromide (25 mL, 1.0 M in dichloromethane, 25 mmol) (added slowly under nitrogen) for 20 min. The reaction was poured onto ice and the mixture neutralized with Na$_2$CO$_3$ to pH 7. The product was extracted with EtOAc, dried over MgSO$_4$, and concentrated afford a yellow oil. Purification over silica gel using 85% EtOAc/hexanes gave N-(2-((trans,trans)-4-(3-fluoro-2-methylphenyl)-3,5-bis(3-hydroxybenzoyl)piperidin-1-yl)ethyl)-N-methyl-methanesulfonamide (1.2 g, 52% yield), (characterized by LCMS and $^1$H NMR), LRMS (M+H$^+$) m/z=569.8.

Example 3

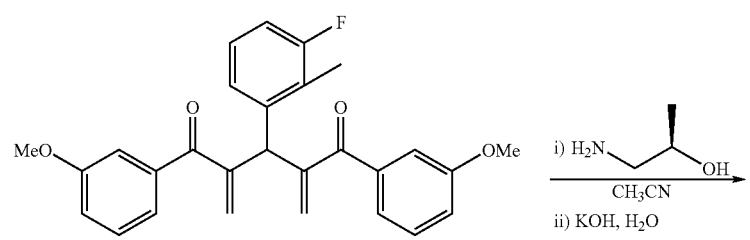

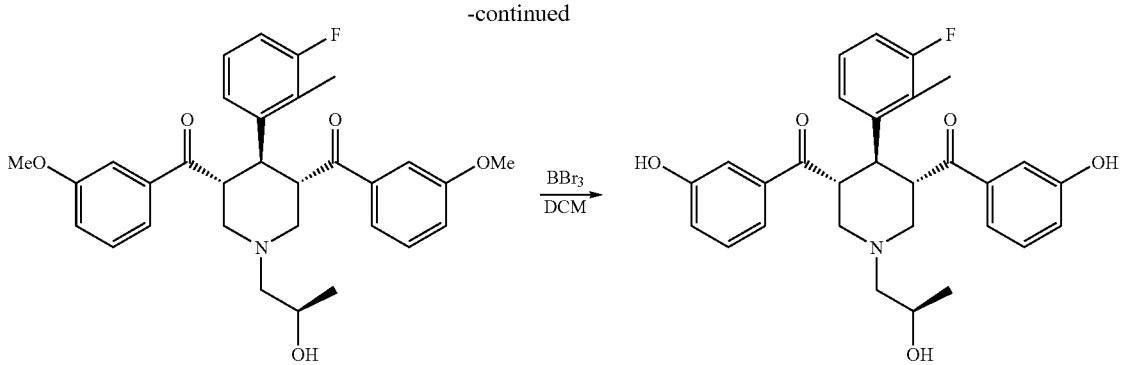

To a stirred mixture of 3-(3-fluoro-2-methylphenyl)-1,5-bis(3-methoxyphenyl)-2,4-dimethylenepentane-1,5-dione (19 g, 43 mmol) in acetonitrile (190 mL) was added R-(−)-1-amino-2-propanol (17 mL, 210 mmol). The solution was stirred for 1 h and then treated with 1 M KOH (190 mL). The mixture was stirred at reflux for 1.5 h to achieve complete epimerization to a single diastereomeric (trans,trans) form by LCMS. The mixture was allowed to cool to room temperature and partitioned between EtOAc and brine (400 mL each). The aqueous phase was extracted with EtOAc (400 mL) and the combined layers dried with MgSO$_4$, filtered, and concentrated under vacuum. The 24 g of crude solid product was purified over silica gel using 60% EtOAc/hexanes to give ((trans,trans)-4-(3-fluoro-2-methylphenyl)-1-((R)-2-hydroxypropyl)piperidine-3,5-diyl)bis((3-methoxyphenyl)methanone) (16.1 g, 72% yield) (characterized by LCMS and $^1$H NMR), LRMS (M+H$^+$) m/z=520.8.

A solution of ((trans,trans)-4-(3-fluoro-2-methylphenyl)-1-((R)-2-hydroxypropyl)piperidine-3,5-diyl)bis((3-methoxyphenyl)methanone) (25.8 g, 51.1 mmol) in dichloromethane (516 mL) under nitrogen was cooled over a water ice bath. To it was added boron tribromide (255 mL, 1 M in DCM, 255 mmol) at 0° C. dropwise over 15 min to maintain room temperature. The resulting solution was stirred for 30 min at room temperature and then quenched carefully with ice water not letting the temperature get above 15° C. The layers were separated and the aqueous layer was neutralized with NaHCO$_3$ to pH 7 and extracted with EtOAc (1 L). The organic phase dried over MgSO$_4$, filtered, and evaporated to dryness. The residue was purified over silica gel using 75% EtOAc/hexanes to give pure((trans,trans)-4-(3-fluoro-2-methylphenyl)-1-((R)-2-hydroxypropyl)piperidine-3,5-diyl)bis((3-hydroxyphenyl)methanone) (7.3 g, 29% yield) as a foam along with an additional 13 g of less pure material (characterized by LCMS and $^1$H NMR), LRMS (M+H$^+$) m/z=492.7.

Example 4

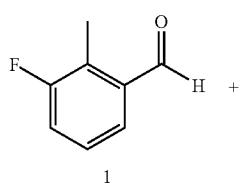

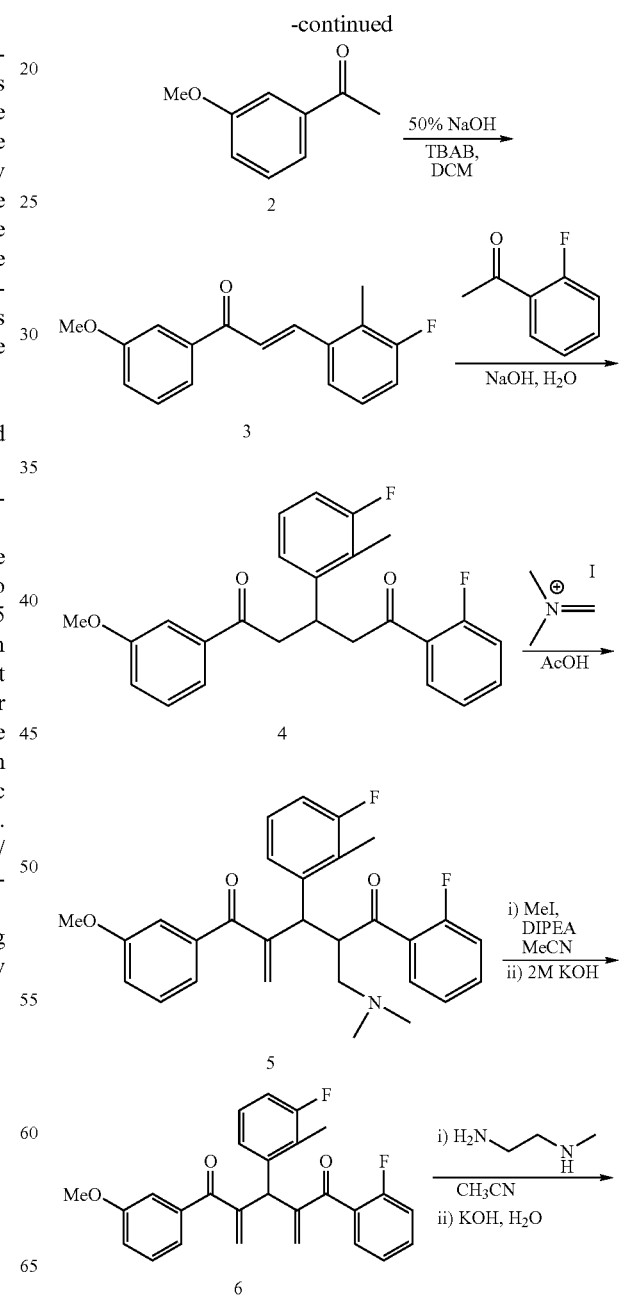

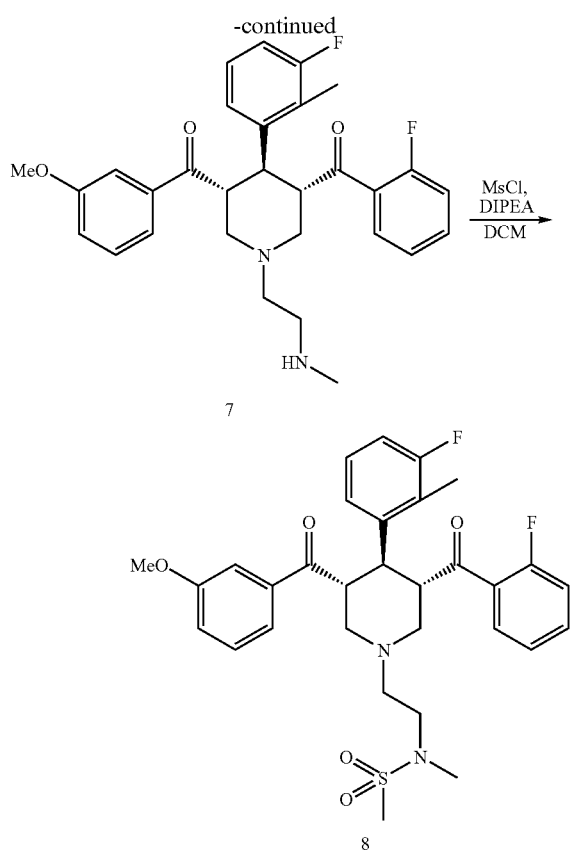

To a stirred solution of 3-fluoro-2-methylbenzaldehyde (150 g, 1.2 mol) in IMS (600 mL) was added 3-methoxyacetophenone (163 g, 1.2 mol). NaOH (10% aq, 750 mL) was added over 40 min using a water bath to maintain a temperature between 18-25° C. The mixture was stirred vigorously at room temperature for 15 h and a thick precipitate was formed. The solid was isolated by filtration, broken up with a mortar and pestle, and washed IMS and water. After drying at 45° C. for 48 h, 273 g (84% yield), the desired product (E)-3-(3-fluoro-2-methylphenyl)-1-(3-methoxyphenyl)prop-2-en-1-one was obtained (characterized by LCMS and $^1$H NMR, LRMS (M+H$^+$) m/z=271.1.

To a solution of (E)-3-(3-fluoro-2-methylphenyl)-1-(3-methoxyphenyl)prop-2-en-1-one (60.6 g, 224 mmol) in dichloromethane (3.53 L) and 50% aqueous NaOH (2.41 L) was added 2-fluoroacetophenone (33.3 mL, 239 mmol) followed by tetrabutylammonium bromide (12.1 g, 38.4 mmol). The mixture was stirred vigorously at room temperature for 16 h, then partitioned between saturated NaCl (1.5 L) and ethyl acetate (2 L) and the product extracted with EtOAc. The organic layer was dried over MgSO$_4$ and concentrated in vacuo to give 122 g of crude product. The product was purified over silica gel using 10% EtOAc/hexanes to give 38.3 g (42% yield) of the desired product, 3-(3-fluoro-2-methylphenyl)-1-(2-fluorophenyl)-5-(3-methoxyphenyl)pentane-1,5-dione (characterized by LCMS and $^1$H NMR), LRMS (M+H$^+$) m/z=409.4.

A mixture of 3-(3-fluoro-2-methylphenyl)-1-(2-fluorophenyl)-5-(3-methoxyphenyl)pentane-1,5-dione (8.4 g, 20.6 mmol) and Eschenmoser's salt (17.6 g, 94.9 mmol) in acetic acid (86 mL) was stirred at 120° C. under nitrogen for 16 h. An additional 3.8 g (20 mmol) of Eschenmoser's salt was added and the mixture heated an additional 5 h. The solution was allowed to cool to room temperature and concentrated in vacuo. The residue was dissolved in EtOAc (30 mL) and 9:1 hexanes/EtOAc, and then treated with 10% NaOH until the pH reached 11 (150 mL). After 30 min, the resulting brown solid was collected by filtration, triturated with EtOAc (3×50 mL), and dried under vacuum at 40° C. to give 2-((dimethylamino)methyl)-3-(3-fluoro-2-methylphenyl)-1-(2-fluorophenyl)-5-(3-methoxyphenyl)-4-methylenepentane-1,5-dione product (7.5 g, 76% crude yield) as a yellow solid (characterized by LCMS and $^1$H NMR, LRMS (M+H$^+$) m/z=478.7.

To a solution of crude 2-((dimethylamino)methyl)-3-(3-fluoro-2-methylphenyl)-1-(2-fluorophenyl)-5-(3-methoxyphenyl)-4-methylenepentane-1,5-dione (7.5 g, 15.7 mmol) in acetonitrile (60 mL) was added iodomethane (11.7 mL, 187 mmol) and diisopropylethylamine (5.4 mL, 31.3 mmol). The mixture was stirred at room temperature for 2 h, during which time a precipitate formed. To this heterogeneous mixture was added 2 M KOH (26 mL, 52 mmol), and the resulting mixture was refluxed for 6 h and then allowed to stand for 48 h. The mixture was partitioned between dichloromethane and water. The layers were separated and the aqueous phase extracted twice with dichloromethane. The combined organic layers were dried over MgSO$_4$ and evaporated to dryness. The residue was purified over silica gel using 30% EtOAc/hexanes to give 3-(3-fluoro-2-methylphenyl)-1-(2-fluorophenyl)-5-(3-methoxyphenyl)-2,4-dimethylenepentane-1,5-dione (3.2 g, 47% yield), (characterized by LCMS and $^1$H NMR), LRMS (M+H$^+$) m/z=433.4.

To a mixture of 3-(3-fluoro-2-methylphenyl)-1-(2-fluorophenyl)-5-(3-methoxyphenyl)-2,4-dimethylenepentane-1,5-dione (29.6 g, 68.5 mmol) in acetonitrile (288 mL) at room temperature was added N-methylethylenediamine (29.8 mL, 398 mmol). The solution was stirred for 1.5 h resulting in complete conversion of starting material to product as a mixture of diastereomers. An excess of 1 M KOH (290 mL) was added and the mixture was stirred at reflux for 2 h to achieve complete epimerization to a single diastereomer (trans,trans) by LCMS. The mixture was allowed to cool to room temperature, diluted with saturated NaCl (600 mL) solution, and extracted with EtOAc (2×500 mL). The organic phase was dried over MgSO$_4$ and the solvents were removed under vacuum to give crude ((trans,trans)-4-(3-fluoro-2-methylphenyl)-5-(2-fluorobenzoyl)-1-(2-(methylamino)ethyl)piperidin-3-yl)(3-methoxyphenyl)methanone (32.5 g), which was used in the next step without further purification (characterized by LCMS and $^1$H NMR, LRMS (M+H$^+$) m/z=507.7.

A mixture of crude ((trans,trans)-4-(3-fluoro-2-methylphenyl)-5-(2-fluorobenzoyl)-1-(2-(methylamino)ethyl)piperidin-3-yl)(3-methoxyphenyl)methanone (32.5 g, 69.6 mmol) in dichloromethane (250 mL) under nitrogen was treated with diisopropylethylamine (14.5 mL, 84.0 mmol) and methanesulfonyl chloride (10.8 mmol, 139 mmol) at room temperature. The resulting solution was stirred for 2 h and then diluted with saturated NaHCO$_3$ (300 mL). After extraction with EtOAc (2×300 mL), the organic phases were combined, dried over MgSO$_4$, and concentrated under vacuum to give 36.1 g of crude product. The residue was purified over silica gel using 10% EtOAc/dichloromethane followed by 100% EtOAc and then MeOH to give N-(2-((trans,trans)-4-(3-fluoro-2-methylphenyl)-3-(2-fluorobenzoyl)-5-(3-methoxybenzoyl)piperidin-1-yl)ethyl)-N-methylmethanesulfonamide (14.7 g, 36% yield over two steps (characterized by LCMS and $^1$H NMR). LRMS (M+H$^+$) m/z=585.9.

Example 5

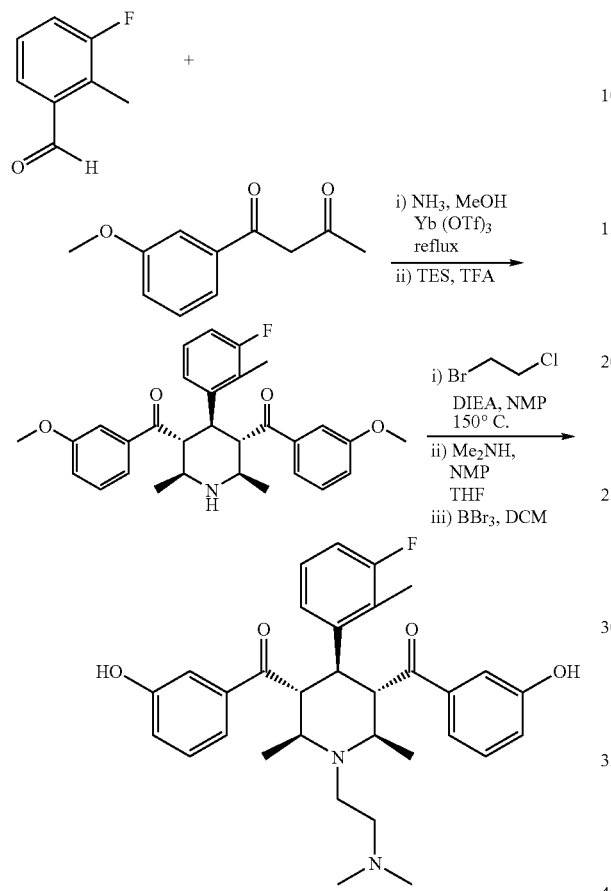

A mixture of 3-fluoro-2-methylbenzaldehyde (2.0 g, 14.5 mmol), 1-(3-methoxyphenyl)butane-1,3-dione (5.56 g, 28.9 mmol) and catalytic tris(trifluoromethylsulfonyloxy)ytterbium (~50 mg) in 40 mL of ammonia solution (7 N in methanol) was stirred under reflux for 16 h. The solvents were removed under vacuum, and the residue was purified over silica gel using 10-80% EtOAc/hexanes to give 1.2 g of dihydropyridine product with some ketone starting material present (characterized by LCMS and $^1$H NMR, LRMS (M+H$^+$) m/z=486.1. The dried product was dissolved in a mixture of TFA (20 mL) and triethylsilane (20 mL) and stirred for 16 h. The solvents were removed under vacuum and the residue resuspended in EtOAc. After washing with saturated NaHCO$_3$ and evaporating to dryness, the product was purified over silica gel using 10-100% EtOAc/hexanes to get pure desired (trans,trans,trans,trans)-4-(3-fluoro-2-methylphenyl)-2,6-dimethylpiperidine-3,5-diyl)bis((3-methoxyphenyl)methanone product (0.32 g, 4.5% yield) (characterized by LCMS and $^1$H NMR, LRMS (M+H$^+$) m/z=490.2.

A portion of (trans,trans,trans,trans)-4-(3-fluoro-2-methylphenyl)-2,6-dimethylpiperidine-3,5-diyl)bis((3-methoxyphenyl)methanone (200 mg, 0.41 mmol), 1-bromo-2-chloroethane (0.1 mL, 0.6 mmol), and diisopropylethylamine (0.1 mL, 0.6 mmol) in N-methylpyrrolidone (1 mL) was heated to 150° C. in a microwave oven for 30 min. The mixture was diluted in EtOAc, washed with saturated NaHCO$_3$, dried over Na$_2$SO$_4$, and evaporated to dryness. The residue was resuspended in dimethylamine solution (0.2 mL, 2 M in THF, 0.4 mmol) and NMP (1 mL), and heated to 120° C. for 30 min. The solution was diluted with EtOAc, washed with saturated NaHCO$_3$, dried over Na$_2$SO$_4$, and concentrated under vacuum. This residue was redissolved in dichloromethane (10 mL) and treated with boron tribromide (2 mL, 1 M in dichloromethane, 2 mmol) at room temperature. After stirring 30 min, the reaction was quenched with methanol and the solvents removed under vacuum. Purification of the crude product by reverse phase chromatography (HPLC, C18) using acetonitrile and water with 0.1% TFA buffer gave pure desired (trans,trans,trans,trans)-1-(2-(dimethylamino)ethyl)-4-(3-fluoro-2-methylphenyl)-2,6-dimethylpiperidine-3,5-diyl)bis((3-hydroxyphenyl)methanone (5.3 mg, 2.4% yield) (characterized by LCMS and $^1$H NMR, LRMS (M+H$^+$) m/z=533.2.

Example 6

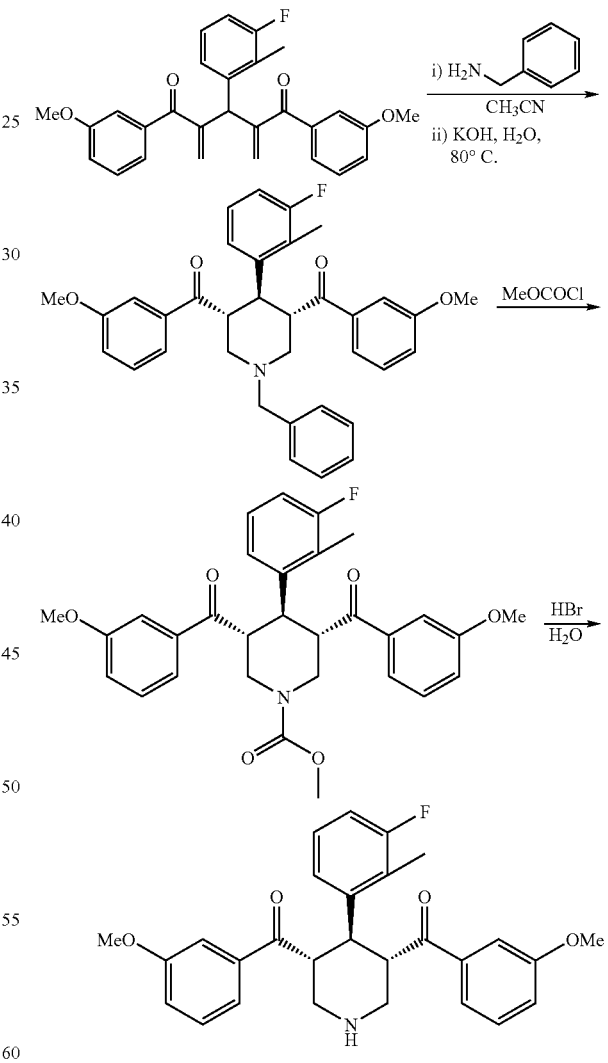

To a stirred mixture of 3-(3-fluoro-2-methylphenyl)-1,5-bis(3-methoxyphenyl)-2,4-dimethylenepentane-1,5-dione (9.8 g, 22 mmol) in acetonitrile (100 mL) was added benzylamine (16.5 mL, 87.9 mmol). The solution was stirred for 3 h. Following addition of 1 M KOH (30 mL), the solution was refluxed for 16 h to achieve epimerization to mainly the (trans,trans) diastereoisomeric form by LCMS. The mixture was allowed to cool to room temperature and partitioned between EtOAc and brine. The aqueous phase was extracted with EtOAc, and the combined layers were concentrated under vacuum. The crude (trans,trans)-1-benzyl-4-(3-fluoro-2-methylphenyl)piperidine-3,5-diyl)bis((3-methoxyphenyl)methanone was used in the next step without further purification (characterized by LCMS). LRMS (M+H$^+$) m/z=552.2.

To solid (trans,trans)-1-benzyl-4-(3-fluoro-2-methylphenyl)piperidine-3,5-diyl)bis((3-methoxyphenyl)methanone (4.0 g, 7.24 mmol) was added methyl chloroformate (20 mL). The reaction mixture stirred at room temperature for 2 h, after which the solvents were removed under vacuum. 1 M HCl solution (200 mL) was added and the product was extracted with EtOAc (2×200 mL). The combined organics were dried over MgSO4 and concentrated under vacuum. The resulting (trans,trans)-methyl 4-(3-fluoro-2-methylphenyl)-3,5-bis(3-methoxybenzoyl)piperidine-1-carboxylate as a yellow oil was placed under high vacuum overnight and then used in the next step without purification (characterized by LCMS). LRMS (M+H$^+$) m/z=520.1.

A portion of the crude (trans,trans)-methyl 4-(3-fluoro-2-methylphenyl)-3,5-bis(3-methoxybenzoyl)piperidine-1-carboxylate (3.54 g, 6.42 mmol) was treated with concentrated HBr (48%, 10 mL) and the mixture stirred at room temperature for 16 h. 10% NaOH was added to bring the pH to 10. The product was extracted with EtOAc (3×150 mL), and the combined organic phases were concentrated to dryness under vacuum. The residue was partially purified over silica gel using 1-60% EtOAc/hexanes to still impure (trans,trans)-4-(3-fluoro-2-methylphenyl)piperidine-3,5-diyl)bis((3-methoxyphenyl)methanone (characterized by LCMS). LRMS (M+H$^+$) m/z=462.2.

Example 7

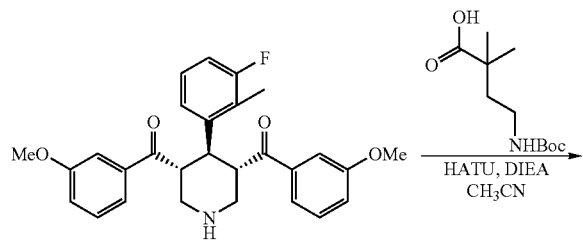

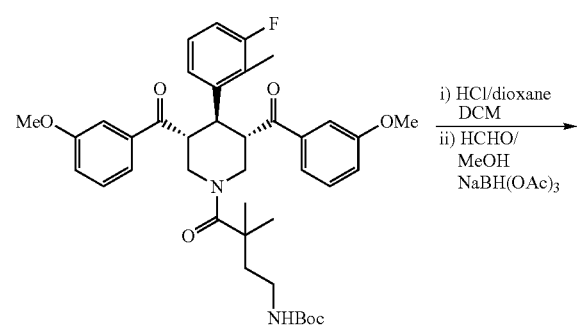

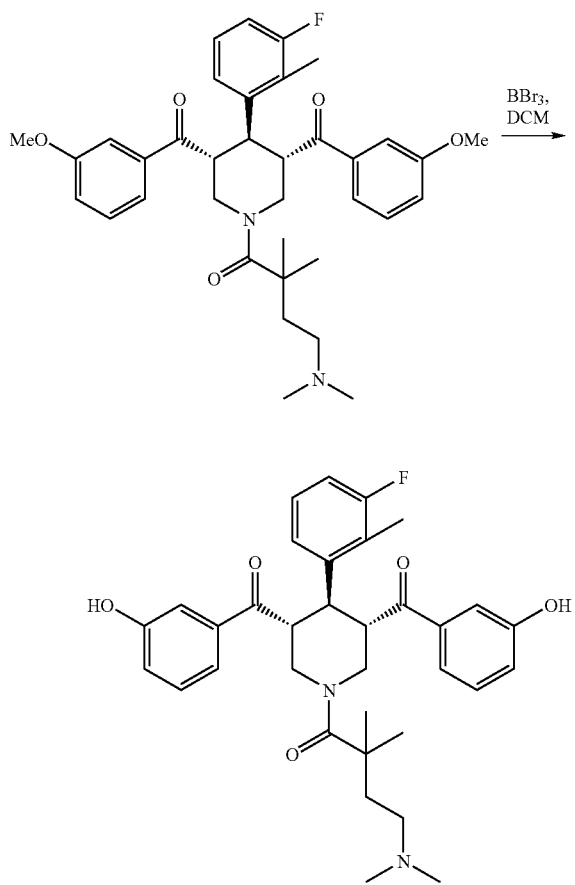

To a solution of (trans,trans)-4-(3-fluoro-2-methylphenyl)piperidine-3,5-diyl)bis((3-methoxyphenyl)methanone (0.17 g, 0.37 mmol) in acetonitrile (5 mL) were added 4-(tert-butoxycarbonylamino)-2,2-dimethylbutanoic acid (0.13 g, 0.56 mmol), HATU (0.21 g, 0.55 mmol) and diisopropylethylamine (0.1 mL, 0.57 mmol). The resulting mixture was stirred at room temperature for 2 h. The reaction was diluted with saturated NaCl (40 mL) and extracted with EtOAc (3×40 mL). The combined organic layers were dried over Na$_2$SO$_4$ and concentrated to dryness. Partial purification over silica gel using 1-60% EtOAc/hexanes gave tert-butyl 4-((trans,trans)-4-(3-fluoro-2-methylphenyl)-3,5-bis(3-methoxybenzoyl)piperidin-1-yl)-3,3-dimethyl-4-oxobutylcarbamate as a white solid which was placed under high vacuum overnight and taken on to the next step without further purification (characterized by LCMS).

A mixture of tert-butyl 4-((trans,trans)-4-(3-fluoro-2-methylphenyl)-3,5-bis(3-methoxybenzoyl)piperidin-1-yl)-3,3-dimethyl-4-oxobutylcarbamate (118 mg, 0.27 mmol) in dichloromethane (5 mL) was treated with HCl/dioxane solution (4 M, 5 mL) at room temperature. After stirring for 1 h, the solvents were removed under vacuum to give a white solid that was placed under high vacuum for 1 h. The solid was resuspended methanol (5 mL) and to the mixture was added aqueous formaldehyde (37% weight, 2 mL). NaBH(OAc)$_3$ was then added portion wise with stirring until the reaction was complete by LCMS. 1 M KOH (40 mL) was added and the mixture extracted with EtOAc (3×40 mL). The combined organic layers were dried over Na$_2$SO$_4$ and concentrated to dryness. The residue was placed under high vacuum for 1 h to give crude desired (trans,trans)-1-(4-(dimethylamino)-2,2-dimethylbutanoyl)-4-(3-fluoro-2-methylphenyl)piperidine-3,5-diyl)bis((3-methoxyphenyl)methanone (56 mg, 34% yield), which was used without further purification in the next step purification (characterized by LCMS).

To a mixture of (trans,trans)-1-(4-(dimethylamino)-2,2-dimethylbutanoyl)-4-(3-fluoro-2-methylphenyl)piperidine-3,5-diyl)bis((3-methoxyphenyl)methanone (56 mg, 0.10 mmol) in dichloromethane (3 mL) was added boron tribromide (0.125 g, 0.5 mmol) at room temperature. The mixture was stirred 30 min and then quenched with methanol. The solvents were removed under vacuum and the residue was taken up in DMF (1.7 mL) and purified by reverse phase chromatography (HPLC, C18) using 10% acetonitrile/water with 0.1% TFA buffer to give clean desired (trans,trans)-1-(4-(dimethylamino)-2,2-dimethylbutanoyl)-4-(3-fluoro-2-methylphenyl)piperidine-3,5-diyl)bis((3-hydroxyphenyl)methanone (14 mg, 24% yield) (characterized by LCMS and $^1$H NMR). LRMS (M+H$^+$) m/z=575.2.

Example 8

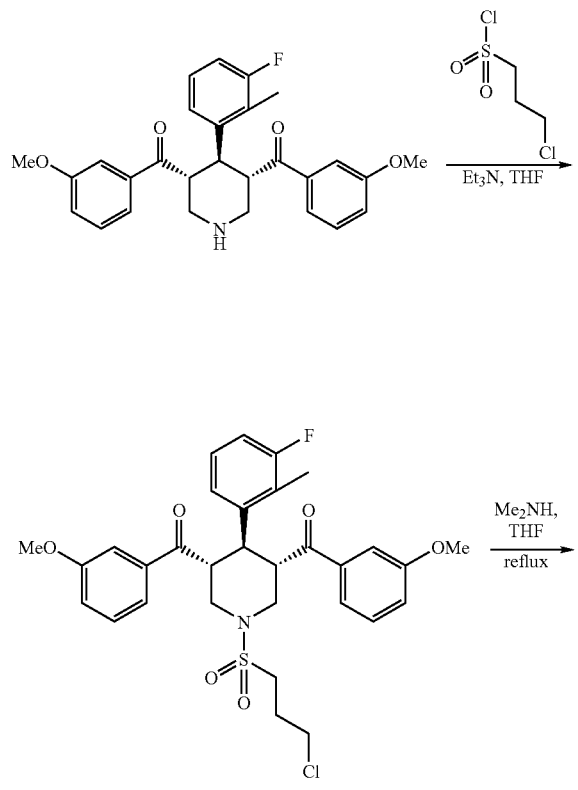

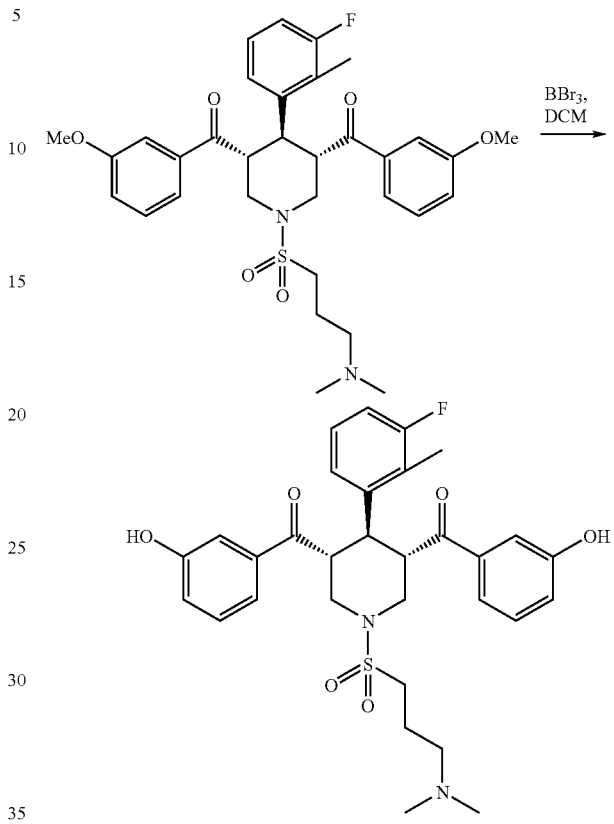

To a solution of (trans,trans)-4-(3-fluoro-2-methylphenyl)piperidine-3,5-diyl)bis((3-methoxyphenyl)methanone (0.31 g, 0.67 mmol) in THF (5 mL) were added 3-chloropropane-1-sulfonyl chloride (0.178 g, 1.0 mmol) and triethylamine (0.3 mL, 2.2 mmol). The resulting mixture was stirred at room temperature for 1 h. The reaction was diluted with saturated NaCl (50 mL) and extracted with EtOAc (3×50 mL). The combined organic layers were dried over Na$_2$SO$_4$ and concentrated under vacuum. Partial purification over silica gel using 1-60% EtOAc/hexanes gave (trans,trans)-1-(3-chloropropylsulfonyl)-4-(3-fluoro-2-methylphenyl)piperidine-3,5-diyl)bis((3-methoxyphenyl)methanone (0.105 g, 26% yield) as a thick yellowish oil (characterized by LCMS).

A solution of (trans,trans)-1-(3-chloropropylsulfonyl)-4-(3-fluoro-2-methylphenyl)piperidine-3,5-diyl)bis((3-methoxyphenyl)methanone (0.105 g, 0.17 mmol) in THF (4 mL) was treated with dimethylamine (2.0 M in THF, 0.85 mL, 1.7 mmol) at reflux for 16 h. The solution was allowed to cool to room temperature and diluted with NaHCO$_3$ solution (10% weight, 40 mL). Extraction with EtOAc (3×40 mL) was followed by drying of the combined layers over Na$_2$SO$_4$ and evaporation to dryness. The crude (trans,trans)-1-(3-(dimethylamino)propylsulfonyl)-4-(3-fluoro-2-methylphenyl)piperidine-3,5-diyl)bis((3-methoxyphenyl)methanone product (0.12 g, ~50% pure) was taken to the next step without further purification.

To a mixture of (trans,trans)-1-(3-(dimethylamino)propylsulfonyl)-4-(3-fluoro-2-methylphenyl)piperidine-3,5-diyl)

bis((3-methoxyphenyl)methanone (0.12 g) in dichloromethane (5 mL) was added boron tribromide (0.25 g, 1.0 mmol) at room temperature. The mixture was stirred 30 min and then quenched with methanol. The solvents were removed under vacuum and the residue was taken up in DMF (1.7 mL) and purified by reverse phase chromatography (HPLC, C18) using 10% acetonitrile/water with 0.1% TFA buffer to give clean desired (trans,trans)-1-(3-(dimethylamino)propylsulfonyl)-4-(3-fluoro-2-methylphenyl)piperidine-3,5-diyl)bis((3-hydroxyphenyl)methanone (16.2 mg, 24% yield) (characterized by LCMS and $^1$H NMR). LRMS (M+H$^+$) m/z=583.2.

Example 9

To a mixture of (trans,trans)-N-(2-(dimethylamino)ethyl)-4-(3-fluoro-2-methylphenyl)-3,5-bis(3-methoxybenzoyl)-N-methylpiperidine-1-carboxamide (0.12 g, 0.22 mmol) in dichloromethane (5 mL) was added boron tribromide (0.25 g, 1.0 mmol) at room temperature. The mixture was stirred 30 min and then quenched with methanol. The solvents were removed under vacuum and the residue was taken up in DMF (1.7 mL) and purified by reverse phase chromatography (HPLC, C18) using 10% acetonitrile/water with 0.1% TFA buffer to give clean desired (trans,trans)-N-(2-(dimethylamino)ethyl)-4-(3-fluoro-2-methylphenyl)-3,5-bis(3-hydroxybenzoyl)-N-methylpiperidine-1-carboxamide (42 mg, 34% yield) (characterized by LCMS and $^1$H NMR). LRMS (M+H$^+$) m/z=562.2.

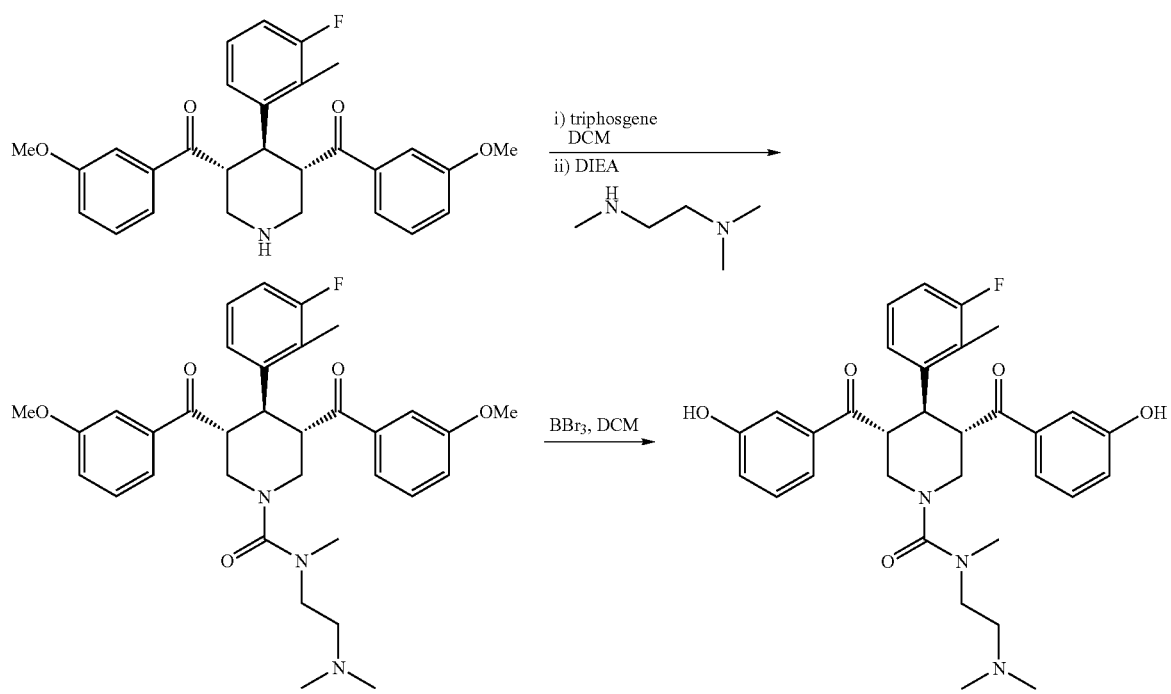

To a solution of (trans,trans)-4-(3-fluoro-2-methylphenyl)piperidine-3,5-diyl)bis((3-methoxyphenyl)methanone (0.19 g, 0.42 mmol) in dichloromethane (2 mL) was slowly added a solution of triphosgene (0.13 g, 0.42 mmol) in dichloromethane (2 mL). The resulting mixture was stirred at room temperature for 15 min followed by addition of diisopropylethylamine (0.35 mL, 2.0 mmol). After stirring 15 min, N1,N1,N2-trimethylethane-1,2-diamine (0.072 mL, 0.63 mmol) was added and the mixture stirred a further 30 min. The reaction was diluted with saturated NaCl (40 mL) and extracted with EtOAc (3×40 mL). The combined organic layers were concentrated under vacuum and the residue purified over silica gel using 1-100% EtOAc/hexanes to give (trans,trans)-N-(2-(dimethylamino)ethyl)-4-(3-fluoro-2-methylphenyl)-3,5-bis(3-methoxybenzoyl)-N-methylpiperidine-1-carboxamide (0.13 g, 52% yield) as a yellow oil (characterized by LCMS).

Example 10

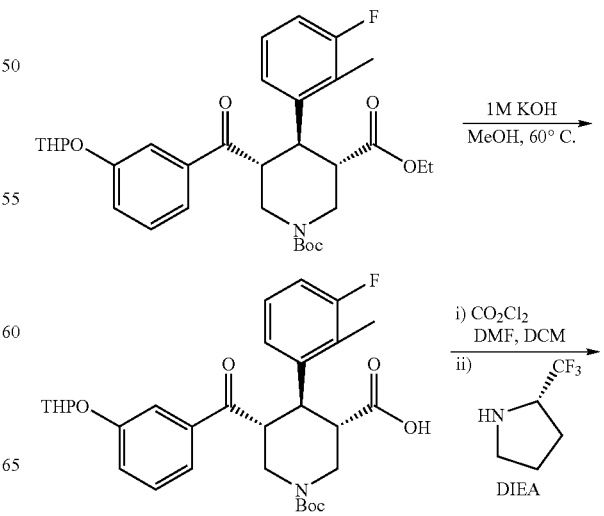

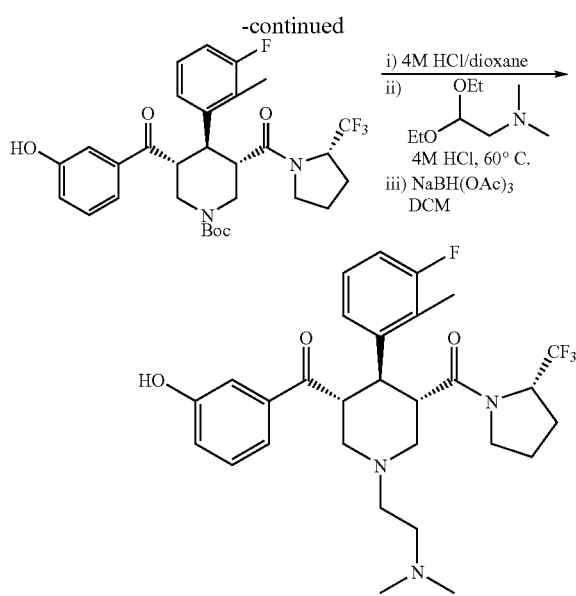

To a stirred solution of (trans,trans)-1-tert-butyl 3-ethyl 4-(3-fluoro-2-methylphenyl)-5-(3-(tetrahydro-2H-pyran-2-yloxy)benzoyl)piperidine-1,3-dicarboxylate (244 mg, 0.429 mmol) in methanol (10 mL) was added 1 M KOH (2.0 mL, 1.5 mmol). The resulting solution was stirred at 60° C. for 16 h. The methanol was removed under vacuum and the remaining aqueous phase was diluted with water (15 mL). The pH was adjusted to 3-4 with HCl solution which resulted in formation of a white precipitate. The mixture was extracted with EtOAc and the organic phase was washed with saturated NaCl, dried over $Na_2SO_4$ and concentrated to give (trans,trans)-1-(tert-butoxycarbonyl)-4-(3-fluoro-2-methylphenyl)-5-(3-(tetrahydro-2H-pyran-2-yloxy)benzoyl)piperidine-3-carboxylic acid (227 mg, 98% yield) as a white, foamy solid (characterized by LCMS). LRMS (M+H$^+$-Boc) m/z=442.

A portion of (trans,trans)-1-(tert-butoxycarbonyl)-4-(3-fluoro-2-methylphenyl)-5-(3-(tetrahydro-2H-pyran-2-yloxy)benzoyl)piperidine-3-carboxylic acid (71 mg, 0.131 mmol) in anhydrous dichloromethane (15 mL) was treated with oxalyl chloride (0.050 mL, 0.393 mmol) followed by DMF (0.041 mL, 0.524 mmol). When gas evolution ceased, (S)-2-(trifluoromethyl)pyrrolidine (91 mg, 0.655 mmol) was added, followed by diisopropylethylamine (0.114 mL, 0.655 mmol). After 5 min, the reaction was found to be complete by LCMS (C18, 1-100% acetonitrile/water gradient). The reaction was quenched with saturated NaHCO$_3$ and the layers separated. The organic phase was washed sequentially with 0.5 M HCl and saturated NaCl, dried over Na$_2$SO$_4$, and evaporated to dryness to yield 80 mg of a white foamy solid. The residue was purified over silica gel using 15% EtOAc/dichloromethane to give the desired (trans,trans)-tert-butyl 4-(3-fluoro-2-methylphenyl)-3-(3-hydroxybenzoyl)-5-((S)-2-(trifluoromethyl)pyrrolidine-1-carbonyl)piperidine-1-carboxylate diastereoisomers (higher running product on TLC (15% EtOAc/CH$_2$Cl$_2$)=29 mg, 40% yield; lower running product on TLC=8 mg, 6% yield) (characterized by LCMS).

A solution of the higher running product of (trans,trans)-tert-butyl 4-(3-fluoro-2-methylphenyl)-3-(3-hydroxybenzoyl)-5-((S)-2-(trifluoromethyl)pyrrolidine-1-carbonyl)piperidine-1-carboxylate (29 mg, 0.050 mmol) in THF (0.5 mL) was treated with HCl/dioxane solution (4 M, 5 mL) at room temperature and the mixture stirred overnight. The solvents were evaporated and the residue partitioned between EtOAc and saturated NaHCO$_3$. The layers were separated and the organic phase was extracted with EtOAc. The combined organic layers were combined, dried over Na$_2$SO$_4$, and concentrated under vacuum to give 24 mg of a glassy solid. In a separate flask, (dimethylamino)acetaldehyde diethyl acetal (1 g) was dissolved in 4 M HCl/dioxane solution (50 mL). Water (15 mL) was added and the resulting mixture stirred at 60° C. for 30 min. The organic solvent was removed under vacuum and the pH of the remaining aqueous phase was adjusted with 1 M KOH to pH 15. The mixture was extracted with dichloromethane, dried over Na$_2$SO$_4$, and concentrated under vacuum until ~20 mL remained. The piperidine (24 mg) from above was treated with 1 mL of the above aldehyde/dichloromethane solution followed by NaBH(OAc)$_3$ (75 mg, excess) in dichloromethane (3 mL). After stirring 30 min at room temperature, the reaction was quenched with NaHCO$_3$ and the layers separated. The organic phase was washed with NaHCO$_3$, dried over Na$_2$SO$_4$ and evaporated to dryness. The residue was purified over silica gel using 10% MeOH/dichloromethane to give pure desired ((trans,trans)-1-(2-(dimethylamino)ethyl)-4-(3-fluoro-2-methylphenyl)-5-((S)-2-(trifluoromethyl)pyrrolidine-1-carbonyl)piperidin-3-yl)(3-hydroxyphenyl)methanone (11 mg, 40% yield) (characterized by LCMS and $^1$H NMR, LRMS (M+H$^+$) m/z=550.2.

Example 11

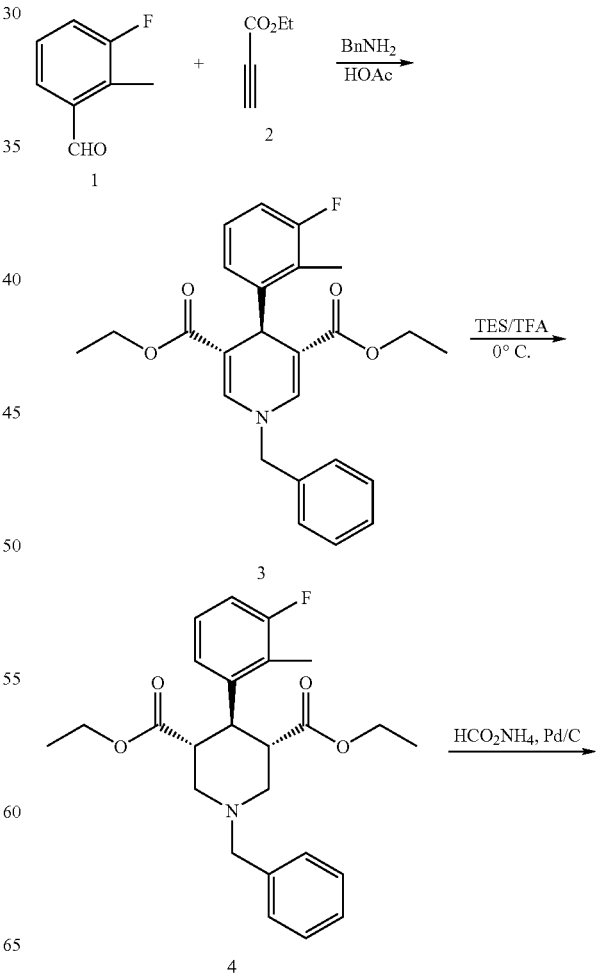

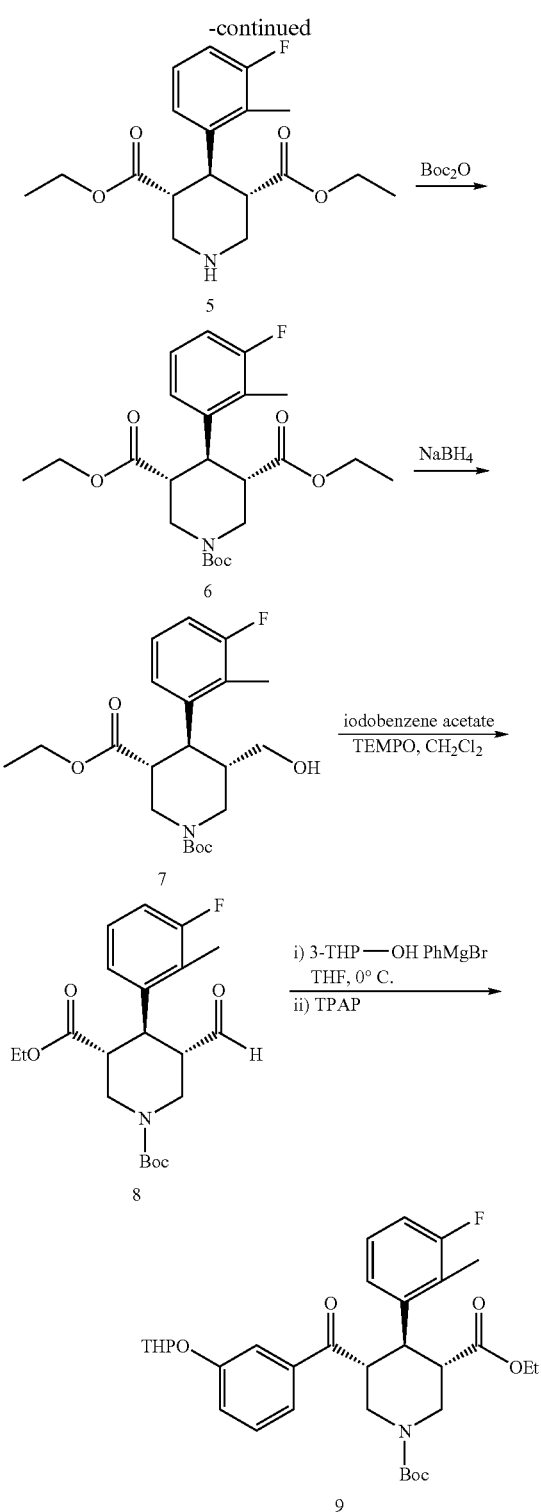

reached) and stirred for 30 min at this temperature. The reaction mixture was then poured onto ice (ca 2 kg), and the resultant crude yellow solid was isolated by filtration. The yellow solid was broken into a fine powder and triturated with hexanes, followed by drying in vacuo overnight to give 154 g (72%) of 1-benzyl-4-(3-fluoro-2-methylphenyl)-1,4-dihydropyridine-3,5-dicarboxylate 3 as a pale yellow powder (characterized by LCMS and $^1$H NMR, LRMS (M+H$^+$) m/z=424.2).

A 3-L round-bottomed flask containing diethyl 1-benzyl-4-(3-fluoro-2-methylphenyl)-1,4-dihydropyridine-3,5-dicarboxylate (3, 236 g, 557 mmol, 1.0 equiv) was cooled to 0° C. Trifluoroacetic acid (1.5 L) was then added and the mixture stirred for 10 min, followed by the addition of triethylsilane (270 mL, 1670 mmol, 3 equiv). The reaction was stirred at ca 10° C. for 2 h. This reaction was then combined with a pilot scale reaction at the same stage (starting from 59 g of 3 using the same condition outlined above). The combined reaction mixtures were concentrated and diluted with ethyl acetate (1 L) and a saturated solution of potassium carbonate (300 mL). The organic layer was separated, dried over Na$_2$SO$_4$, filtered, and concentrated. The residue was dissolved in Dichloromethane and purified by silica gel chromatography (2-8% EtOAc/hexanes) to afford 131 g of (trans,trans)-diethyl 1-benzyl-4-(3-fluoro-2-methylphenyl)piperidine-3,5-dicarboxylate 4 as a pale yellow oil (LRMS (M+H (m/z)=428.2, also characterized by $^1$H NMR) and 92 g of the corresponding cis/trans isomer. The cis/trans isomer was isomerized by refluxing with sodium ethoxide in ethanol for several hours, yielding 76 g of 4 (207 g, 70% combined yield).

To a 2 L round bottom flask was added (trans,trans)-diethyl 1-benzyl-4-(3-fluoro-2-methylphenyl)piperidine-3,5-dicarboxylate (4, 131 g, 306 mmol, 1.0 equiv), ammonium formate (95.5 g, 1510 mmol, 4.9 equiv), methanol (1 L), and 10% Pd/C (13 g). The reaction mixture was refluxed for 1 hour. After cooling to room temperature, the reaction was filtered, concentrated, and redissolved in ethyl acetate (600 mL). The mixture was washed with water (250 mL), and the organic layer was dried over Na$_2$SO$_4$, filtered, and concentrated to afford a viscous oil. The crude amine was dissolved in methanol, and di tert-butyl dicarbonate (74.0 g, 368 mmol) and triethylamine (53.3 mL) were added. After stirring the reaction overnight, the reaction was concentrated and purified by silica gel chromatography (5-10% EtOAc/hexanes) to give 118 g (88%) of (trans,trans)-1-tert-butyl 3,5-diethyl 4-(3-fluoro-2-methylphenyl)piperidine-1,3,5-tricarboxylate 6 as a white solid (characterized by LCMS and $^1$H NMR, LRMS (M+H$^+$-Boc) m/z=338).

A 2-L round bottom flask was charged with (trans, trans)-1-tert-butyl 3,5-diethyl 4-(6,3-fluoro-2-methylphenyl)piperidine-1,3,5-tricarboxylate (124.5 g, 285 mol, 1.0 equiv), sodium borohydride (108 g, 2.85 mol, 10.0 equiv), and ethanol (1 L). The reaction mixture was heated to 60° C. for 2 h. The reaction was then poured onto ice (ca 1 kg), followed by the addition of ethyl acetate (2 L) and saturated sodium chloride solution (500 mL). The organic layer was separated, and the aqueous layers were washed with ethyl acetate (3×250 mL). The combined organic layers were then dried over Na$_2$SO$_4$, filtered, and concentrated. The crude residue was dissolved in Dichloromethane and purified by silica gel chromatography (20-35% EtOAc/hexanes) to yield 58.5 g of (trans,trans)-1-tert-butyl 3-ethyl 4-(3-fluoro-2-methylphenyl)-5-(hydroxymethyl)piperidine-1,3-dicarboxylate 7 (70% yield based on recovered starting material, LRMS (M+H-t-Bu (m/z)=340) as a white solid and 38 g of recovered starting material 6.

A 2-L round bottom flask was charged with 2-methyl-3-fluorobenzaldehyde (75.3 g, 509 mmol, 1.0 equiv) and ethyl propiolate (100 g, 1.02 mol, 2.0 equiv), and the mixture was cooled to 0° C. Benzylamine (55.6 mL, 509 mmol, 1.0 equiv) was then slowly added, inducing a brief exotherm. Acetic acid was added to the mixture, and the reaction was heated to 110° C. (another exotherm occurs when this temperature is To a 1-L round bottomed flask was added (trans,trans)-1-tert-butyl 3-ethyl 4-(3-fluoro-2-methylphenyl)-5-(hydroxymethyl)piperidine-1,3-dicarboxylate (7, 55 g, 139 mmol, 1 equiv) and Dichloromethane (350 mL) The mixture was cooled to 0° C., and iodobenzene diacetate (89.7 g, 278 mmol, 2 equiv) and TEMPO (7.16 g, 46 mmol, 0.33 equiv) were added. The reaction was allowed to warm to room temperature and was stirred for 1.5 h. The reaction was diluted with Dichloromethane (300 mL) and washed with saturated sodium thiosulfate solution and saturated sodium bicarbonate solution. The organic layer was separated and then dried over $Na_2SO_4$, filtered, and concentrated. The crude residue was dissolved in Dichloromethane and purified by silica gel chromatography (10-20% EtOAc/hexanes) to yield 47.5 g (87%) of tert (trans,trans)-1-tert-butyl 3-ethyl 4-(3-fluoro-2-methylphenyl)-5-formylpiperidine-1,3-dicarboxylate 8 as a clear oil, (M+H-t-Bu (m/z)=338.2).

To a 250-mL round-bottomed flask was added tert (trans,trans)-1-tert-butyl 3-ethyl 4-(3-fluoro-2-methylphenyl)-5-formylpiperidine-1,3-dicarboxylate (8, 4.5 g, 11.5 mmol, 1.0 equiv) and THF (100 mL). The reaction was cooled to 0° C. and (3-(tetrahydro-2H-pyran-2-yloxy)phenyl)magnesium bromide (0.25 M, 52.7 mL, 13.1 mmol, 1.15 equiv) was added over 3 min. The reaction was stirred for 1 h at 0° C. The reaction was quenched by the addition of ammonium chloride, followed by the addition of ethyl acetate (300 mL). The organic layer was separated and dried over $Na_2SO_4$, filtered, and concentrated. The crude residue was dissolved in Dichloromethane and purified by silica gel chromatography (20% EtOAc/hexanes) to afford 5.8 g of (trans,trans)-1-tert-butyl 3-ethyl 4-(3-fluoro-2-methylphenyl)-5-((S)-hydroxy(3-(tetrahydro-2H-pyran-2-yloxy)phenyl)methyl)piperidine-1,3-dicarboxylate 9 as an oil (M+H-Boc (m/z)=472).

To a 500-mL round-bottomed flask was added (trans,trans)-1-tert-butyl 3-ethyl 4-(3-fluoro-2-methylphenyl)-5-((S)-hydroxy(3-(tetrahydro-2H-pyran-2-yloxy)phenyl)methyl)piperidine-1,3-dicarboxylate (9, 12.5 g, 21.9 mmol, 1.0 equiv), dichloromethane (200 mL), and Dess-Martin periodinane (9.47 g, 22.3 mmol, 1.02 equiv). The reaction was stirred for 30 min at rt. The reaction was diluted with Dichloromethane and washed with saturated sodium thiosulfate solution. The organic layer was separated and then dried over $Na_2SO_4$, filtered, and concentrated. The crude residue was dissolved in dichloromethane and purified by silica gel chromatography (5-15% EtOAc/hexanes) to yield 9.6 g (77%) of (trans, trans)-1-tert-butyl 3-ethyl 4-(3-fluoro-2-methylphenyl)-5-(3-(tetrahydro-2H-pyran-2-yloxy)benzoyl)piperidine-1,3-dicarboxylate 10 as a clear oil, (M+H-Boc (m/z)= 470.3).

Example 12

Using procedures similar to those described herein, the compounds in the following two tables were synthesized and tested for activity.

| Object MW | m/z Value | Ion | Chemical Name |
|---|---|---|---|
| 413.51 | 414 | (M + 1) | (cis,trans)-1-(2-hydroxyethyl)-4-phenyl-5-(phenylcarbonyl)(3-piperidyl) phenyl ketone |
| 437.57 | 438.2 | (M + 1) | (cis,trans)-1-cyclopentyl-4-phenyl-5-(phenylcarbonyl)(3-piperidyl) phenyl ketone |
| 427.53 | 428.2 | (M + 1) | (cis,trans)-1-(3-hydroxypropyl)-4-phenyl-5-(phenylcarbonyl)(3-piperidyl) phenyl ketone |
| 459.58 | 460.1 | (M + 1) | (cis,trans)-4-phenyl-5-(phenylcarbonyl)-1-benzyl(3-piperidyl) phenyl ketone |
| 411.54 | 412.2 | (M + 1) | (cis,cis)-4-phenyl-5-(phenylcarbonyl)-1-propyl(3-piperidyl) phenyl ketone |
| 427.53 | 428.2 | (M + 1) | (cis,trans)-1-((1S)-2-hydroxy-isopropyl)-4-phenyl-5-(phenylcarbonyl)(3-piperidyl)phenyl ketone |
| 427.53 | 428.1 | (M + 1) | (cis,cis)-1-(2-methoxyethyl)-4-phenyl-5-(phenylcarbonyl)(3-piperidyl) phenyl ketone |
| 427.53 | 428.2 | (M + 1) | (cis,trans)-1-(2-methoxyethyl)-4-phenyl-5-(phenylcarbonyl)(3-piperidyl) phenyl ketone |
| 427.53 | 428.2 | (M + 1) | 1-((1R)-2-hydroxy-isopropyl)(cis,trans)-4-phenyl-5-(phenylcarbonyl)(3-piperidyl) phenyl ketone |
| 455.54 | 470.2 | (M + 1) | ethyl 3-[(cis,cis)-3,5-bis(phenylcarbonyl)-4-phenylpiperidyl]propanoate |
| 427.53 | 428.1 | (M + 1) | (cis,trans)-1-((2S)-2-hydroxypropyl)-4-phenyl-5-(phenylcarbonyl)(3-piperidyl) phenyl ketone |
| 453.57 | 454.2 | (M + 1) | (cis,cis)-1-(oxolan-2-ylmethyl)-4-phenyl-5-(phenylcarbonyl)(3-piperidyl) phenylketone |
| 453.57 | 454.2 | (M + 1) | (cis,trans)-1-(oxolan-2-ylmethyl)-4-phenyl-5-(phenylcarbonyl)(3-piperidyl) phenylketone |
| 443.53 | 444.1 | (M + 1) | (cis,cis)-1-[2-hydroxy-1-(hydroxymethyl)ethyl]-4-phenyl-5-(phenylcarbonyl)(3-piperidyl) phenyl ketone |
| 443.53 | 444.1 | (M + 1) | (cis,trans)-1-[2-hydroxy-1-(hydroxymethyl)ethyl]-4-phenyl-5-(phenylcarbonyl)(3-piperidyl) phenyl ketone |
| 482.61 | 483.2 | (M + 1) | (cis,cis)-1-(2-morpholin-4-ylethyl)-4-phenyl-5-(phenylcarbonyl)(3-piperidyl) phenyl ketone |
| 482.61 | 483.2 | (M + 1) | (cis,trans)-1-(2-morpholin-4-ylethyl)-4-phenyl-5-(phenylcarbonyl)(3-piperidyl) phenyl ketone |
| 440.58 | 441.2 | (M + 1) | (cis,cis)-1-[2-(dimethylamino)ethyl]-4-phenyl-5-(phenylcarbonyl)(3-piperidyl) phenyl ketone |
| 440.58 | 441.2 | (M + 1) | (cis,trans)-1-[2-(dimethylamino)ethyl]-4-phenyl-5-(phenylcarbonyl)(3-piperidyl) phenyl ketone |
| 437.57 | 438.2 | (M + 1) | (cis,cis)-1-cyclopentyl-4-phenyl-5-(phenylcarbonyl)(3-piperidyl) phenyl ketone |

| Object MW | m/z Value | Ion | Chemical Name |
|---|---|---|---|
| 469.57 | 470 | (M + 1) | ethyl 3-[(cis,trans)-3,5-bis(phenylcarbonyl)-4-phenylpiperidyl]propanoate |
| 440.53 | 441 | (M + 1) | 2-[(cis,trans)-3,5-bis(phenylcarbonyl)-4-phenylpiperidyl]-N-methylacetamide |
| 427.53 | 428.2 | (M + 1) | 1-((2S)-2-hydroxypropyl)(cis,cis)-4-phenyl-5-(phenylcarbonyl)(3-piperidyl) phenyl ketone |
| 496.64 | 497 | (M + 1) | 2-[3,5-bis(phenylcarbonyl)-4-phenylpiperidyl]-3,3-dimethyl-N-methylbutanamide |
| 480.6 | 481 | (M + 1) | 3-[(cis,cis)-3,5-bis(phenylcarbonyl)-4-phenylpiperidyl]azaperhydroepin-2-one |
| 455.59 | 456 | (M + 1) | (cis,cis)-1-[2-hydroxy-1-(methylethyl)ethyl]-4-phenyl-5-(phenylcarbonyl)(3-piperidyl) phenyl ketone |
| 441.56 | 444.2 | (M + 1) | (cis,trans)-4-(2,3-dimethylphenyl)-1-(2-hydroxyethyl)-5-(phenylcarbonyl)(3-piperidyl) phenyl ketone |
| 455.59 | 456.2 | (M + 1) | (cis,trans)-4-(2,3-dimethylphenyl)-1-(3-hydroxypropyl)-5-(phenylcarbonyl)(3-piperidyl) phenyl ketone |
| 510.67 | 511.3 | (M + 1) | (cis,trans)-4-(2,3-dimethylphenyl)-1-(2-morpholin-4-ylethyl)-5-(phenylcarbonyl)(3-piperidyl) phenyl ketone |
| 509.68 | 510.3 | (M + 1) | (cis,trans)-4-(2,3-dimethylphenyl)-5-(phenylcarbonyl)-1-(2-piperazinylethyl)(3-piperidyl) phenyl ketone |
| 551.72 | 552.3 | (M + 1) | 4-{2-[(cis,trans)-4-(2,3-dimethylphenyl)-3,5-bis(phenylcarbonyl)piperidyl]ethyl}-1-acetylpiperazine |
| 468.59 | 469.2 | (M + 1) | 2-[(cis,trans)-4-(2,3-dimethylphenyl)-3,5-bis(phenylcarbonyl)piperidyl]-N-methylacetamide |
| 471.59 | 472.2 | (M + 1) | (cis,trans)-4-(2,3-dimethylphenyl)-1-[2-hydroxy-1-(hydroxymethyl)ethyl]-5-(phenylcarbonyl)(3-piperidyl) phenyl ketone |
| 453.57 | 454.2 | (M + 1) | 1-[(cis,trans)-4-(2,3-dimethylphenyl)-3,5-bis(phenylcarbonyl)piperidyl]propan-1-one |
| 482.61 | 483.2 | (M + 1) | 2-[(trans,trans)-4-(2,3-dimethylphenyl)-3,5-bis(phenylcarbonyl)piperidyl]-N,N-dimethylacetamide |
| 423.55 | 438.2 | (M + 1) | 4-(2,3-dimethylphenyl)-5-(phenylcarbonyl)-1-prop-2-enyl(3-piperidyl) phenyl ketone |
| 546.65 | 547.2 | (M + 1) | (cis,trans)-4-(2,3-dimethylphenyl)-5-[(3-fluorophenyl)carbonyl]-1-(2-morpholin-4-ylethyl)(3-piperidyl) 3-fluorophenyl ketone |
| 477.54 | 478.2 | (M + 1) | (cis,trans)-4-(2,3-dimethylphenyl)-5-[(3-fluorophenyl)carbonyl]-1-(2-hydroxyethyl)(3-piperidyl) 3-fluorophenyl ketone |
| 504.61 | 505.2 | (M + 1) | (cis,trans)-1-[2-(dimethylamino)ethyl]-4-(2,3-dimethylphenyl)-5-[(3-fluorophenyl)carbonyl](3-piperidyl) 3-fluorophenyl ketone |
| 560.67 | 561.2 | (M + 1) | (cis,trans)-4-(2,3-dimethylphenyl)-5-[(3-fluorophenyl)carbonyl]-1-(3-morpholin-4-ylpropyl)(3-piperidyl) 3-fluorophenyl ketone |
| 573.72 | 574.3 | (M + 1) | (cis,trans)-4-(2,3-dimethylphenyl)-5-[(3-fluorophenyl)carbonyl]-1-[3-(4-methylpiperazinyl)propyl](3-piperidyl) 3-fluorophenyl ketone |
| 545.66 | 546.2 | (M + 1) | (cis,trans)-4-(2,3-dimethylphenyl)-5-[(3-fluorophenyl)carbonyl]-1-(2-piperazinylethyl)(3-piperidyl) 3-fluorophenyl ketone |
| 558.66 | 559.2 | (M + 1) | 1-(3-{(cis,trans)-3,5-bis[(3-fluorophenyl)carbonyl]-4-(2,3-dimethylphenyl)piperidyl}propyl)pyrrolidin-2-one |
| 558.66 | 559.2 | (M + 1) | 1-(3-{(trans,trans)-3,5-bis[(3-fluorophenyl)carbonyl]-4-(2,3-dimethylphenyl)piperidyl}propyl)pyrrolidin-2-one |
| 524.69 | 525.3 | (M + 1) | (cis,trans)-4-(2,3-dimethylphenyl)-1-(3-morpholin-4-ylpropyl)-5-(phenylcarbonyl)(3-piperidyl) phenyl ketone |
| 537.73 | 538.3 | (M + 1) | (cis,trans)-4-(2,3-dimethylphenyl)-1-[3-(4-methylpiperazinyl)propyl]-5-(phenylcarbonyl)(3-piperidyl) phenyl ketone |
| 468.63 | 469.3 | (M + 1) | (cis,trans)-1-[2-(dimethylamino)ethyl]-4-(2,3-dimethylphenyl)-5-(phenylcarbonyl)(3-piperidyl) phenyl ketone |
| 522.68 | 523.3 | (M + 1) | 1-{3-[(cis,trans)-4-(2,3-dimethylphenyl)-3,5-bis(phenylcarbonyl)piperidyl]propyl}pyrrolidin-2-one |
| 502.65 | 503.3 | (M + 1) | (cis,trans)-4-(2,3-dimethylphenyl)-5-(phenylcarbonyl)-1-(2-(3-pyridyl)ethyl)(3-piperidyl) phenyl ketone |
| 482.66 | 483.3 | (M + 1) | (cis,trans)-1-[3-(dimethylamino)propyl]-4-(2,3-dimethylphenyl)-5-(phenylcarbonyl)(3-piperidyl) phenyl ketone |
| 505.65 | 506.3 | (M + 1) | (cis,trans)-4-(2,3-dimethylphenyl)-1-(3-imidazolylpropyl)-5-(phenylcarbonyl)(3-piperidyl) phenyl ketone |
| 491.62 | 492.2 | (M + 1) | (cis,trans)-4-(2,3-dimethylphenyl)-1-(2-imidazolylethyl)-5-(phenylcarbonyl)(3-piperidyl) phenyl ketone |
| 522.72 | 523.3 | (M + 1) | (cis,trans)-4-(2,3-dimethylphenyl)-5-(phenylcarbonyl)-1-(3-piperidylpropyl)(3-piperidyl) phenyl ketone |
| 469.61 | 470.2 | (M + 1) | (cis,trans)-4-(2,3-dimethylphenyl)-1-(4-hydroxybutyl)-5-(phenylcarbonyl)(3-piperidyl) phenyl ketone |
| 508.69 | 509.3 | (M + 1) | (cis,trans)-4-(2,3-dimethylphenyl)-5-(phenylcarbonyl)-1-(2-(2-piperidyl)ethyl)(3-piperidyl) phenyl ketone |
| 454.6 | 455.3 | (M + 1) | (cis,trans)-1-(3-aminopropyl)-4-(2,3-dimethylphenyl)-5-(phenylcarbonyl)(3-piperidyl) phenyl ketone |
| 440.58 | 441.2 | (M + 1) | (cis,trans)-1-(2-aminoethyl)-4-(2,3-dimethylphenyl)-5-(phenylcarbonyl)(3-piperidyl) phenyl ketone |

-continued

| Object MW | m/z Value | Ion | Chemical Name |
|---|---|---|---|
| 476.56 | 477.2 | (M + 1) | (cis,trans)-1-(2-aminoethyl)-4-(2,3-dimethylphenyl)-5-[(3-fluorophenyl)carbonyl](3-piperidyl) 3-fluorophenyl ketone |
| 482.61 | 483.2 | (M + 1) | 2-[(cis,trans)-4-(2,3-dimethylphenyl)-3,5-bis(phenylcarbonyl)piperidyl]-N,N-dimethylacetamide |
| 454.56 | 455 | (M + 1) | 2-[(cis,trans)-3,5-bis(phenylcarbonyl)-4-phenylpiperidyl]-N,N-dimethylacetamide |
| 397.51 | 398.2 | (M + 1) | (cis,trans)-4-(2,3-dimethylphenyl)-5-(phenylcarbonyl)(3-piperidyl) phenyl ketone |
| 469.57 | 470.2 | (M + 1) | 1-[4-(2,3-dimethylphenyl)-3,5-bis(phenylcarbonyl)piperidyl]-3-hydroxypropan-1-one |
| 439.55 | 440.2 | (M + 1) | 1-acetyl-4-(2,3-dimethylphenyl)-3,5-bis(phenylcarbonyl)piperidine |
| 496.6 | 497.3 | (M + 1) | N-{2-[4-(2,3-dimethylphenyl)-3,5-bis(phenylcarbonyl)piperidyl]-2-oxoethyl}acetamide |
| 482.61 | 483.25 | (M + 1) | 2-(dimethylamino)-1-[4-(2,3-dimethylphenyl)-3,5-bis(phenylcarbonyl)piperidyl]ethan-1-one |
| 455.54 | 456.2 | (M + 1) | 1-[4-(2,3-dimethylphenyl)-3,5-bis(phenylcarbonyl)piperidyl]-2-hydroxyethan-1-one |
| 455.54 | 456.2 | (M + 1) | 2-[(cis,trans)-4-(2,3-dimethylphenyl)-3,5-bis(phenylcarbonyl)piperidyl]acetic acid |
| 565.7 | 566.2 | (M + 1) | 4-{2-[(cis,trans)-4-(2,3-dimethylphenyl)-3,5-bis(phenylcarbonyl)piperidyl]acetyl}-1-acetylpiperazine |
| 539.71 | 540.3 | (M + 1) | 2-[(cis,trans)-4-(2,3-dimethylphenyl)-3,5-bis(phenylcarbonyl)piperidyl]-N-[2-(dimethylamino)ethyl]-N-methylacetamide |
| 455.54 | 456.2 | (M + 1) | 2-[(trans,trans)-4-(2,3-dimethylphenyl)-3,5-bis(phenylcarbonyl)piperidyl]acetic acid |
| 498.61 | 499.2 | (M + 1) | 2-[(trans,trans)-4-(2,3-dimethylphenyl)-3,5-bis(phenylcarbonyl)piperidyl]-N-(2-hydroxyethyl)acetamide |
| 510.67 | 511.3 | (M + 1) | (cis,cis)-4-(2,3-dimethylphenyl)-1-(2-morpholin-4-ylethyl)-5-(phenylcarbonyl)(3-piperidyl) phenyl ketone |
| 510.67 | 511.2 | (M + 1) | (trans,trans)-4-(2,3-dimethylphenyl)-1-(2-morpholin-4-ylethyl)-5-(phenylcarbonyl)(3-piperidyl) phenyl ketone |
| 518.59 | 519 | (M + 1) | 2-{(trans,trans)-3,5-bis[(3-fluorophenyl)carbonyl]-4-(2,3-dimethylphenyl)piperidyl}-N,N-dimethylacetamide |
| 566.73 | 567.3 | (M + 1) | 2-[(trans,trans)-4-(2,3-dimethylphenyl)-3,5-bis(phenylcarbonyl)piperidyl]-N-(2-piperazinylethyl)acetamide |
| 567.72 | 568.2 | (M + 1) | 2-[(trans,trans)-4-(2,3-dimethylphenyl)-3,5-bis(phenylcarbonyl)piperidyl]-N-(2-morpholin-4-ylethyl)acetamide |
| 523.67 | 524.3 | (M + 1) | 2-[(trans,trans)-4-(2,3-dimethylphenyl)-3,5-bis(phenylcarbonyl)piperidyl]-1-piperazinylethan-1-one |
| 565.7 | 566.2 | (M + 1) | 4-{2-[(trans,trans)-4-(2,3-dimethylphenyl)-3,5-bis(phenylcarbonyl)piperidyl]acetyl}-1-acetylpiperazine |
| 608.77 | 609.3 | (M + 1) | 2-[(trans,trans)-4-(2,3-dimethylphenyl)-3,5-bis(phenylcarbonyl)piperidyl]-N-[2-(4-acetylpiperazinyl)ethyl]acetamide |
| 539.71 | 540.3 | (M + 1) | 2-[(trans,trans)-4-(2,3-dimethylphenyl)-3,5-bis(phenylcarbonyl)piperidyl]-N-[2-(dimethylamino)ethyl]-N-methylacetamide |
| 468.59 | 469.2 | (M + 1) | 2-[(trans,trans)-4-(2,3-dimethylphenyl)-3,5-bis(phenylcarbonyl)piperidyl]-N-methylacetamide |
| 537.69 | 538.3 | (M + 1) | 2-[(trans,trans)-4-(2,3-dimethylphenyl)-3,5-bis(phenylcarbonyl)piperidyl]-1-(4-methylpiperazinyl)ethan-1-one |
| 524.65 | 525.2 | (M + 1) | 2-[(trans,trans)-4-(2,3-dimethylphenyl)-3,5-bis(phenylcarbonyl)piperidyl]-1-morpholin-4-ylethan-1-one |
| 504.57 | 505.2 | (M + 1) | 2-{(trans,trans)-3,5-bis[(3-fluorophenyl)carbonyl]-4-(2,3-dimethylphenyl)piperidyl}-N-methylacetamide |
| 454.56 | 455.2 | (M + 1) | 2-[(trans,trans)-4-(2,3-dimethylphenyl)-3,5-bis(phenylcarbonyl)piperidyl]acetamide |
| 441.56 | 442.2 | (M + 1) | (trans,trans)-4-(2,3-dimethylphenyl)-1-(2-hydroxyethyl)-5-(phenylcarbonyl)(3-piperidyl) phenyl ketone |
| 455.59 | 456.2 | (M + 1) | (trans,trans)-4-(2,3-dimethylphenyl)-1-(3-hydroxypropyl)-5-(phenylcarbonyl)(3-piperidyl) phenyl ketone |
| 540.69 | 541.4 | (M + 1) | N-{2-[(trans,trans)-4-(2,3-dimethylphenyl)-3,5-bis(phenylcarbonyl)piperidyl]ethyl}(tert-butoxy)carboxamide |
| 468.63 | 469.4 | (M + 1) | (trans,trans)-1-[2-(dimethylamino)ethyl]-4-(2,3-dimethylphenyl)-5-(phenylcarbonyl)(3-piperidyl) phenyl ketone |
| 469.57 | 470.3 | (M + 1) | 3-[(trans,trans)-4-(2,3-dimethylphenyl)-3,5-bis(phenylcarbonyl)piperidyl]propanoic acid |
| 537.73 | 538.4 | (M + 1) | (trans,trans)-4-(2,3-dimethylphenyl)-1-[3-(4-methylpiperazinyl)propyl]-5-(phenylcarbonyl)(3-piperidyl) phenyl ketone |
| 440.58 | 441.4 | (M + 1) | (trans,trans)-1-(2-aminoethyl)-4-(2,3-dimethylphenyl)-5-(phenylcarbonyl)(3-piperidyl) phenyl ketone |
| 486.58 | 487.2 | (M + 1) | 2-[(trans,trans)-3,5-bis(phenylcarbonyl)-4-(3-fluoro-2-methylphenyl)piperidyl]-N,N-dimethylacetamide |

-continued

| Object MW | m/z Value | Ion | Chemical Name |
|---|---|---|---|
| 471.59 | 472 | (M + 1) | (trans,trans)-4-(2,3-dimethylphenyl)-1-[2-hydroxy-1-(hydroxymethyl)ethyl]-5-(phenylcarbonyl)(3-piperidyl) phenyl ketone |
| 522.72 | 523.2 | (M + 1) | (trans,trans)-4-(2,3-dimethylphenyl)-5-(phenylcarbonyl)-1-(3-piperidylpropyl)(3-piperidyl) phenyl ketone |
| 496.64 | 497.2 | (M + 1) | 3-[(trans,trans)-4-(2,3-dimethylphenyl)-3,5-bis(phenylcarbonyl)piperidyl]-N,N-dimethylpropanamide |
| 556.65 | 557 | (M + 1) | methyl (N-{2-[(trans,trans)-4-(2,3-dimethylphenyl)-3,5-bis(phenylcarbonyl)piperidyl]ethyl}methoxycarbonylamino)formate |
| 482.61 | 483.2 | (M + 1) | N-{2-[(trans,trans)-4-(2,3-dimethylphenyl)-3,5-bis(phenylcarbonyl)piperidyl]ethyl}acetamide |
| 488.55 | 489.2 | (M + 1) | 2-[(trans,trans)-3,5-bis(2-pyridylcarbonyl)-4-(3-fluoro-2-methylphenyl)piperidyl]-N,N-dimethylacetamide |
| 460.5 | 461.1 | (M + 1) | 2-[(trans,trans)-3,5-bis(2-pyridylcarbonyl)-4-(3-fluoro-2-methylphenyl)piperidyl]acetamide |
| 474.53 | 475.2 | (M + 1) | 2-[(trans,trans)-3,5-bis(2-pyridylcarbonyl)-4-(3-fluoro-2-methylphenyl)piperidyl]-N-methylacetamide |
| 498.61 | 499.2 | (M + 1) | N-{2-[(trans,trans)-4-(2,3-dimethylphenyl)-3,5-bis(phenylcarbonyl)piperidyl]ethyl}methoxycarboxamide |
| 489.01 | 489.4 | (M + 1) | 2-[(trans,trans)-3,5-bis(phenylcarbonyl)-4-(2-chlorophenyl)piperidyl]-N,N-dimethylacetamide |
| 600.74 | 601.5 | (M + 1) | N-{2-[(trans,trans)-4-(2,3-dimethylphenyl)-3,5-bis(phenylcarbonyl)piperidyl]ethyl}-2-[2-(2-methoxyethoxy)ethoxy]acetamide |
| 468.59 | 469.4 | (M + 1) | 2-[(trans,trans)-3,5-bis(phenylcarbonyl)-4-(2-methylphenyl)piperidyl]-N,N-dimethylacetamide |
| 469.57 | 470.4 | (M + 1) | 2-[(trans,trans)-3,5-bis(phenylcarbonyl)-4-(3-methyl(4-pyridyl))piperidyl]-N,N-dimethylacetamide |
| 503.03 | 503.2 | (M + 1) | 2-[(trans,trans)-3,5-bis(phenylcarbonyl)-4-(3-chloro-2-methylphenyl)piperidyl]-N,N-dimethylacetamide |
| 426.51 | 427 | (M + 1) | 2-[(trans,trans)-3,5-bis(phenylcarbonyl)-4-phenylpiperidyl]acetamide |
| 454.56 | 455 | (M + 1) | 2-[(trans,trans)-3,5-bis(phenylcarbonyl)-4-phenylpiperidyl]-N,N-dimethylacetamide |
| 595.73 | 596 | (M + 1) | tert-butyl 4-{2-[(trans,trans)-3,5-bis(phenylcarbonyl)-4-phenylpiperidyl]acetyl}piperazinecarboxylate |
| 476.61 | 477.2 | (M + 1) | 2-[(trans,trans)-3,5-bis(phenylcarbonyl)-4-cyclohexylpiperidyl]-N-(2-hydroxyethyl)acetamide |
| 515.69 | 516.3 | (M + 1) | 2-[(trans,trans)-3,5-bis(phenylcarbonyl)-4-cyclohexylpiperidyl]-1-(4-methylpiperazinyl)ethan-1-one |
| 501.66 | 502.3 | (M + 1) | 2-[(trans,trans)-3,5-bis(phenylcarbonyl)-4-cyclohexylpiperidyl]-1-piperazinylethan-1-one |
| 460.61 | 461.2 | (M + 1) | 2-[(trans,trans)-3,5-bis(phenylcarbonyl)-4-cyclohexylpiperidyl]-N,N-dimethylacetamide |
| 502.64 | 503.2 | (M + 1) | 2-[(trans,trans)-3,5-bis(phenylcarbonyl)-4-cyclohexylpiperidyl]-1-morpholin-4-ylethan-1-one |
| 493.6 | 494.2 | (M + 1) | 2-[(trans,trans)-3,5-bis(phenylcarbonyl)-4-(3-cyano-2-methylphenyl)piperidyl]-N,N-dimethylacetamide |
| 685.42 | 686 | (M + 1) | 2-{(trans,trans)-3,5-bis[(4-bromophenyl)carbonyl]-4-(3-fluoro-2-methylphenyl)piperidyl}-1-piperazinylethan-1-one |
| 490.54 | 491.3 | (M + 1) | 2-[(trans,trans)-4-(2,3-difluorophenyl)-3,5-bis(phenylcarbonyl)piperidyl]-N,N-dimethylacetamide |
| 472.55 | 473.3 | (M + 1) | 2-[(trans,trans)-3,5-bis(phenylcarbonyl)-4-(2-fluorophenyl)piperidyl]-N,N-dimethylacetamide |
| 499.6 | 500.6 | (M + 1) | 2-[(trans,trans)-3,5-bis(phenylcarbonyl)-4-(1-methylimidazol-2-yl)piperidyl]-1-piperazinylethan-1-one |
| 495.61 | 496 | (M + 1) | 2-[(trans,trans)-3,5-bis(phenylcarbonyl)-4-phenylpiperidyl]-1-piperazinylethan-1-one |
| 411.54 | 412 | (M + 1) | (trans,trans)-4-(2,3-dimethylphenyl)-1-methyl-5-(phenylcarbonyl)(3-piperidyl) phenyl ketone |
| 397.51 | 398 | (M + 1) | (trans,trans)-1-methyl-4-(3-methylphenyl)-5-(phenylcarbonyl)(3-piperidyl) phenyl ketone |
| 526.62 | 527.2 | (M + 1) | methyl 3-{(trans,trans)-1-[(N,N-dimethylcarbamoyl)methyl]-3,5-bis(phenylcarbonyl)(4-piperidyl)}-2-methylbenzoate |
| 594.48 | 595.1 | (M + 1) | 2-[(trans,trans)-3,5-bis(phenylcarbonyl)-4-(3-iodo-2-methylphenyl)piperidyl]-N,N-dimethylacetamide |
| 489.01 | 489.1 | (M + 1) | 2-[(trans,trans)-3,5-bis(phenylcarbonyl)-4-(3-chlorophenyl)piperidyl]-N,N-dimethylacetamide |
| 458.55 | 459.2 | (M + 1) | 2-[(trans,trans)-3,5-bis(phenylcarbonyl)-4-(1-methylimidazol-2-yl)piperidyl]-N,N-dimethylacetamide |
| 431.95 | 432.2 | (M + 1) | (trans,trans)-4-(3-chloro-2-methylphenyl)-1-methyl-5-(phenylcarbonyl)(3-piperidyl) phenyl ketone |
| 458.55 | 459.4 | (M + 1) | 2-[(trans,trans)-3,5-bis(phenylcarbonyl)-4-(1-methylpyrazol-5-yl)piperidyl]-N,N-dimethylacetamide |
| 472.58 | 473.4 | (M + 1) | 2-[(trans,trans)-4-(1,5-dimethylpyrazol-4-yl)-3,5-bis(phenylcarbonyl)piperidyl]-N,N-dimethylacetamide |

-continued

| Object MW | m/z Value | Ion | Chemical Name |
|---|---|---|---|
| 429.53 | 430.1 | (M + 1) | (trans,trans)-4-(3-fluoro-2-methylphenyl)-1-methyl-5-(1,3-thiazol-2-ylcarbonyl)(3-piperidyl) 1,3-thiazol-2-yl ketone |
| 459.56 | 460.1 | (M + 1) | (trans,trans)-4-(3-fluoro-2-methylphenyl)-1-(2-hydroxyethyl)-5-(1,3-thiazol-2-ylcarbonyl)(3-piperidyl) 1,3-thiazol-2-yl ketone |
| 472.56 | 473.1 | (M + 1) | 2-[(trans,trans)-3,5-bis(1,3-thiazol-2-ylcarbonyl)-4-(3-fluoro-2-methylphenyl)piperidyl]acetamide |
| 486.58 | 487.05 | (M + 1) | 2-[(trans,trans)-3,5-bis(1,3-thiazol-2-ylcarbonyl)-4-(3-fluoro-2-methylphenyl)piperidyl]-N-methylacetamide |
| 500.61 | 501.05 | (M + 1) | 2-[(trans,trans)-3,5-bis(1,3-thiazol-2-ylcarbonyl)-4-(3-fluoro-2-methylphenyl)piperidyl]-N,N-dimethylacetamide |
| 425.56 | 426 | (M + 1) | (trans,trans)-4-(2,3-dimethylphenyl)-1-ethyl-5-(phenylcarbonyl)(3-piperidyl) phenylketone |
| 439.59 | 440 | (M + 1) | (trans,trans)-4-(2,3-dimethylphenyl)-5-(phenylcarbonyl)-1-propyl(3-piperidyl) phenyl ketone |
| 468.59 | 469 | (M + 1) | 2-[(trans,trans)-3,5-bis(phenylcarbonyl)-4-(3-methylphenyl)piperidyl]-N,N-dimethylacetamide |
| 509.6 | 510 | (M + 1) | 4-{2-[(trans,trans)-3,5-bis(phenylcarbonyl)-4-phenylpiperidyl]acetyl}piperazin-2-one |
| 503.03 | 503.3 | (M + 1) | 2-[(trans,trans)-3,5-bis(phenylcarbonyl)-4-(2-chloro-3-methylphenyl)piperidyl]-N,N-dimethylacetamide |
| 507 | 507.2 | (M + 1) | 2-[(trans,trans)-3,5-bis(phenylcarbonyl)-4-(2-chloro-3-fluorophenyl)piperidyl]-N,N-dimethylacetamide |
| 431.53 | 432.4 | (M + 1) | (trans,trans)-4-(1,5-dimethylpyrazol-4-yl)-1-(2-hydroxyethyl)-5-(phenylcarbonyl)(3-piperidyl) phenyl ketone |
| 428.52 | 429.4 | (M + 1) | (trans,trans)-1-(2-hydroxyethyl)-4-(3-methyl(2-pyridyl))-5-(phenylcarbonyl)(3-piperidyl) phenyl ketone |
| 546.63 | 547.2 | (M + 1) | 2-{(trans,trans)-3,5-bis[(3-methoxyphenyl)carbonyl]-4-(3-fluoro-2-methylphenyl)piperidyl}-N,N-dimethylacetamide |
| 532.6 | 533.2 | (M + 1) | 2-{(trans,trans)-3,5-bis[(3-methoxyphenyl)carbonyl]-4-(3-fluoro-2-methylphenyl)piperidyl}-N-methylacetamide |
| 518.58 | 519.1 | (M + 1) | 2-{(trans,trans)-3,5-bis[(3-hydroxyphenyl)carbonyl]-4-(3-fluoro-2-methylphenyl)piperidyl}-N,N-dimethylacetamide |
| 504.55 | 505.1 | (M + 1) | 2-{(trans,trans)-3,5-bis[(3-hydroxyphenyl)carbonyl]-4-(3-fluoro-2-methylphenyl)piperidyl}-N-methylacetamide |
| 644.37 | 645 | (M + 1) | 2-{(trans,trans)-3,5-bis [(2-bromophenyl)carbonyl]-4-(3-fluoro-2-methylphenyl)piperidyl}-N,N-dimethylacetamide |
| 603.32 | 603.95 | (M + 1) | (trans,trans)-5-[(2-bromophenyl)carbonyl]-4-(3-fluoro-2-methylphenyl)-1-(2-hydroxyethyl)(3-piperidyl) 2-bromophenyl ketone |
| 601.34 | 602.05 | (M + 1) | (trans,trans)-5-[(2-bromophenyl)carbonyl]-4-(3-fluoro-2-methylphenyl)-1-propyl(3-piperidyl) 2-bromophenyl ketone |
| 590.48 | 591.1 | (M + 1) | 2-{(trans,trans)-5-[(2-bromophenyl)carbonyl]-3-[(2-cyanophenyl)carbonyl]-4-(3-fluoro-2-methylphenyl)piperidyl}-N,N-dimethylacetamide |
| 512.6 | 513.4 | (M + 1) | 3-{(trans,trans)-1-[(N,N-dimethylcarbamoyl)methyl]-3,5-bis(phenylcarbonyl)(4-piperidyl)}-2-methylbenzoic acid |
| 580.46 | 581.2 | (M + 1) | 2-[(trans,trans)-3,5-bis(phenylcarbonyl)-4-(2-iodophenyl)piperidyl]-N,N-dimethylacetamide |
| 489.01 | 489.2 | (M + 1) | 2-[(trans,trans)-3,5-bis(phenylcarbonyl)-4-(4-chlorophenyl)piperidyl]-N,N-dimethylacetamide |
| 472.55 | 473.2 | (M + 1) | 2-[(trans,trans)-3,5-bis(phenylcarbonyl)-4-(4-fluorophenyl)piperidyl]-N,N-dimethylacetamide |
| 472.55 | 473.2 | (M + 1) | 2-[(trans,trans)-3,5-bis(phenylcarbonyl)-4-(3-fluorophenyl)piperidyl]-N,N-dimethylacetamide |
| 441.56 | 442.4 | (M + 1) | (trans,trans)-4-(2,6-dimethylphenyl)-1-(2-hydroxyethyl)-5-(phenylcarbonyl)(3-piperidyl) phenyl ketone |
| 522.56 | 523.4 | (M + 1) | 2-{(trans,trans)-3,5-bis(phenylcarbonyl)-4-[3-(trifluoromethyl)phenyl]piperidyl}-N,N-dimethylacetamide |
| 479.57 | 480.2 | (M + 1) | 2-[(trans,trans)-3,5-bis(phenylcarbonyl)-4-(2-cyanophenyl)piperidyl]-N,N-dimethylacetamide |
| 488.55 | 489.1 | (M + 1) | 2-[(trans,trans)-3,5-bis(4-pyridylcarbonyl)-4-(3-fluoro-2-methylphenyl)piperidyl]-N,N-dimethylacetamide |
| 505.58 | 506.1 | (M + 1) | (trans,trans)-4-(3-fluoro-2-methylphenyl)-1-(2-hydroxyethyl)-5-[(3-methoxyphenyl)carbonyl](3-piperidyl) 3-methoxyphenyl ketone |
| 477.52 | 478.1 | (M + 1) | (trans,trans)-4-(3-fluoro-2-methylphenyl)-1-(2-hydroxyethyl)-5-[(3-hydroxyphenyl)carbonyl](3-piperidyl) 3-hydroxyphenyl ketone |
| 505.58 | 506.1 | (M + 1) | (trans,trans)-4-(3-fluoro-2-methylphenyl)-1-(2-hydroxyethyl)-5-[(2-methoxyphenyl)carbonyl](3-piperidyl) 2-methoxyphenyl ketone |
| 487.63 | 488 | (M + 1) | (trans,trans)-4-(2,3-dimethylphenyl)-5-(phenylcarbonyl)-1-benzyl(3-piperidyl) phenyl ketone |
| 468.59 | 469 | (M + 1) | 2-[(trans,trans)-3,5-bis(phenylcarbonyl)-4-(4-methylphenyl)piperidyl]-N,N-dimethylacetamide |
| 468.59 | 469 | (M + 1) | 2-[(cis,trans)-3,5-bis(phenylcarbonyl)-4-(4-methylphenyl)piperidyl]-N,N-dimethylacetamide |
| 426.55 | 427 | (M + 1) | (cis,trans)-1-(2-aminoethyl)-4-(4-methylphenyl)-5-(phenylcarbonyl)(3-piperidyl) phenyl ketone |

| Object MW | m/z Value | Ion | Chemical Name |
|---|---|---|---|
| 546.63 | 547.2 | (M + 1) | 2-{(trans,trans)-3,5-bis [(2-methoxyphenyl)carbonyl]-4-(3-fluoro-2-methylphenyl)piperidyl}-N,N-dimethylacetamide |
| 518.58 | 519.1 | (M + 1) | 2-{(trans,trans)-3,5-bis [(2-hydroxyphenyl)carbonyl]-4-(3-fluoro-2-methylphenyl)piperidyl}-N,N-dimethylacetamide |
| 477.52 | 478.1 | (M + 1) | (trans,trans)-4-(3-fluoro-2-methylphenyl)-1-(2-hydroxyethyl)-5-[(2-hydroxyphenyl)carbonyl](3-piperidyl) 2-hydroxyphenyl ketone |
| 505.58 | 506.1 | (M + 1) | (trans,trans)-4-(3-fluoro-2-methylphenyl)-1-(2-hydroxyethyl)-5-[(4-methoxyphenyl)carbonyl](3-piperidyl) 4-methoxyphenyl ketone |
| 546.63 | 547.2 | (M + 1) | 2-{(trans,trans)-3,5-bis[(4-methoxyphenyl)carbonyl]-4-(3-fluoro-2-methylphenyl)piperidyl}-N,N-dimethylacetamide |
| 477.52 | 478.1 | (M + 1) | (trans,trans)-4-(3-fluoro-2-methylphenyl)-1-(2-hydroxyethyl)-5-[(4-hydroxyphenyl)carbonyl](3-piperidyl) 4-hydroxyphenyl ketone |
| 518.58 | 519.2 | (M + 1) | 2-{(trans,trans)-3,5-bis[(4-hydroxyphenyl)carbonyl]-4-(3-fluoro-2-methylphenyl)piperidyl}-N,N-dimethylacetamide |
| 587.64 | 588.2 | (M + 1) | methyl 3-({(trans,trans)-1-[(N,N-dimethylcarbamoyl)methyl]-5-[(3-carbamoylphenyl)carbonyl]-4-(3-fluoro-2-methylphenyl)-3-piperidyl}carbonyl)benzoate |
| 441.56 | 442 | (M + 1) | (trans,trans)-4-(3,4-dimethylphenyl)-1-(2-hydroxyethyl)-5-(phenylcarbonyl)(3-piperidyl) phenyl ketone |
| 482.61 | 483.2 | (M + 1) | 2-[trans,trans)-4-(3,4-dimethylphenyl)-3,5-bis(phenylcarbonyl)piperidyl]-N,N-dimethylacetamide |
| 418.57 | 419 | (M + 1) | (trans,trans)-1-(2-aminoethyl)-4-cyclohexyl-5-(phenylcarbonyl)(3-piperidyl) phenyl ketone |
| 471.65 | 472.2 | (M + 1) | (trans,trans)-5-(cyclohexylcarbonyl)-4-(3-fluoro-2-methylphenyl)-1-(2-methoxyethyl)(3-piperidyl) cyclohexyl ketone |
| 428.52 | 429 | (M + 1) | (trans,trans)-1-(2-hydroxyethyl)-4-(6-methyl(2-pyridyl))-5-(phenylcarbonyl)(3-piperidyl) phenyl ketone |
| 469.57 | 470 | (M + 1) | 2-[(trans,trans)-3,5-bis(phenylcarbonyl)-4-(6-methyl(2-pyridyl))piperidyl]-N,N-dimethylacetamide |
| 460.61 | 461 | (M + 1) | N-{2-[(trans,trans)-3,5-bis(phenylcarbonyl)-4-cyclohexylpiperidyl]ethyl}acetamide |
| 555.71 | 556.2 | (M + 1) | N-{2-[(trans,trans)-4-(2,3-dimethylphenyl)-3-((hydroxyimino)phenylmethyl)-5-(phenylcarbonyl)piperidyl]ethyl}(tert-butoxy)carboxamide |
| 455.59 | 456.2 | (M + 1) | (trans,trans)-1-(2-aminoethyl)-4-(2,3-dimethylphenyl)-5-((hydroxyimino)phenylmethyl)(3-piperidyl) phenyl ketone |
| 602.65 | 603.2 | (M + 1) | methyl 3-[((trans,trans)-1-[(N,N-dimethylcarbamoyl)methyl]-4-(3-fluoro-2-methylphenyl)-5-{[3-(methoxycarbonyl)phenyl]carbonyl}-3-piperidyl)carbonyl]benzoate |
| 425.46 | 426.1 | (M + 1) | (trans,trans)-4-(3-fluoro-2-methylphenyl)-1-(2-hydroxyethyl)-5-(pyrazol-3-ylcarbonyl)(3-piperidyl) pyrazol-3-yl ketone |
| 439.48 | 440.1 | (M + 1) | (trans,trans)-4-(3-fluoro-2-methylphenyl)-1-(2-methoxyethyl)-5-(pyrazol-3-ylcarbonyl)(3-piperidyl) pyrazol-3-yl ketone |
| 498.61 | 499 | (M + 1) | 2-{(trans,trans)-3,5-bis(phenylcarbonyl)-4-[3-(hydroxymethyl)-2-methylphenyl]piperidyl}-N,N-dimethylacetamide |
| 470.61 | 471.2 | (M + 1) | 2-[(trans,trans)-3,5-bis((hydroxyimino)phenylmethyl)-4-(2,3-dimethylphenyl)piperidyl]ethylamine |
| 519.6 | 520.2 | (M + 1) | (trans,trans)-4-(3-fluoro-2-methylphenyl)-5-{[3-(hydroxymethyl)phenyl]carbonyl}-1-(2-methoxyethyl)(3-piperidyl) 3-(hydroxymethyl)phenyl ketone |
| 476.54 | 477 | (M + 1) | (trans,trans)-1-(2-aminoethyl)-4-(3-fluoro-2-methylphenyl)-5-[(3-hydroxyphenyl)carbonyl](3-piperidyl) 3-hydroxyphenyl ketone |
| 490.57 | 491 | (M + 1) | (trans,trans)-1-(2-aminoethyl)-4-(3-fluoro-2-methylphenyl)-5-[(3-methoxyphenyl)carbonyl](3-piperidyl) 3-hydroxyphenyl ketone |
| 507.55 | 508.1 | (M + 1) | (trans,trans)-4-(3-fluoro-2-methylphenyl)-1-(2-hydroxyethyl)-5-[(6-methoxy(2-pyridyl))carbonyl](3-piperidyl) 6-methoxy(2-pyridyl) ketone |
| 704.88 | 706 | (M + 1) | N-{2-[(trans,trans)-4-(2,3-dimethylphenyl)-3,5-bis(phenylcarbonyl)piperidyl]ethyl}-2-[(3,5,6-trimethyl-1,7-dioxo(3-pyrazolino[1,2-a]3-pyrazolin-2-yl))methylthio]acetamide |
| 718.84 | 717 | (M + 1) | N-{2-[(trans,trans)-4-(2,3-dimethylphenyl)-3,5-bis(phenylcarbonyl)piperidyl]ethyl}-6-[(7-nitrobenzo[2,3-c]1,2,5-oxadiazol-4-yl)amino]hexanamide |
| 787.02 | 787 | (M + 1) | N-{2-[(trans,trans)-4-(2,3-dimethylphenyl)-3,5-bis(phenylcarbonyl)piperidyl]ethyl}-6-({[5-(dimethylamino)naphthyl]sulfonyl}amino)hexanamide |
| 514.42 | 515.1 | (M + 1) | (trans,trans)-5-[(2-chlorophenyl)carbonyl]-4-(3-fluoro-2-methylphenyl)-1-(2-hydroxyethyl)(3-piperidyl) 2-chlorophenyl ketone |
| 664.69 | 665 | (M + 1) | N-{2-[(trans,trans)-4-(2,3-dimethylphenyl)-3,5-bis(phenylcarbonyl)piperidyl]ethyl}(6,8-difluoro-7-hydroxy-2-oxochromen-3-yl)carboxamide |
| 669.81 | 670 | (M + 1) | N-{2-[(trans,trans)-4-(2,3-dimethylphenyl)-3,5-bis(phenylcarbonyl)piperidyl]ethyl}-2-[7-(dimethylamino)-2-oxochromen-4-yl]acetamide |

| Object MW | m/z Value | Ion | Chemical Name |
|---|---|---|---|
| 491.55 | 492.2 | (M + 1) | 1-((2S)-2-hydroxypropyl)(trans,trans)-4-(3-fluoro-2-methylphenyl)-5-[(3-hydroxyphenyl)carbonyl](3-piperidyl) 3-hydroxyphenyl ketone |
| 519.6 | 520.2 | (M + 1) | 1-((2R)-2-hydroxypropyl)(trans,trans)-4-(3-fluoro-2-methylphenyl)-5-[(3-methoxyphenyl)carbonyl](3-piperidyl) 3-methoxyphenyl ketone |
| 491.55 | 492.2 | (M + 1) | 1-((2R)-2-hydroxypropyl)(trans,trans)-4-(3-fluoro-2-methylphenyl)-5-[(3-hydroxyphenyl)carbonyl](3-piperidyl) 3-hydroxyphenyl ketone |
| 535.6 | 536.2 | (M + 1) | (trans,trans)-1-(2,3-dihydroxypropyl)-4-(3-fluoro-2-methylphenyl)-5-[(3-methoxyphenyl)carbonyl](3-piperidyl) 3-methoxyphenyl ketone |
| 507.55 | 508.1 | (M + 1) | (trans,trans)-1-(2,3-dihydroxypropyl)-4-(3-fluoro-2-methylphenyl)-5-[(3-hydroxyphenyl)carbonyl](3-piperidyl) 3-hydroxyphenyl ketone |
| 534.62 | 535.2 | (M + 1) | (trans,trans)-1-(3-amino-2-hydroxypropyl)-4-(3-fluoro-2-methylphenyl)-5-[(3-methoxyphenyl)carbonyl](3-piperidyl) 3-methoxyphenyl ketone |
| 506.57 | 507.1 | (M + 1) | (trans,trans)-1-(3-amino-2-hydroxypropyl)-4-(3-fluoro-2-methylphenyl)-5-[(3-hydroxyphenyl)carbonyl](3-piperidyl) 3-hydroxyphenyl ketone |
| 532.6 | 519.1 | (M + 1) | N-(2-{(trans,trans)-3,5-bis[(3-hydroxyphenyl)carbonyl]-4-(3-fluoro-2-methylphenyl)piperidyl}ethyl)-N-methylacetamide |
| 532.65 | 533.2 | (M + 1) | (trans,trans)-1-[2-(dimethylamino)ethyl]-4-(3-fluoro-2-methylphenyl)-5-[(3-methoxyphenyl)carbonyl](3-piperidyl) 3-methoxyphenyl ketone |
| 504.59 | 519.2 | (M + 1) | (trans,trans)-1-[2-(dimethylamino)ethyl]-4-(3-fluoro-2-methylphenyl)-5-[(3-methoxyphenyl)carbonyl](3-piperidyl) 3-hydroxyphenyl ketone |
| 574.68 | 575.2 | (M + 1) | (trans,trans)-4-(3-fluoro-2-methylphenyl)-5-[(3-methoxyphenyl)carbonyl]-1-(2-morpholin-4-ylethyl)(3-piperidyl) 3-methoxyphenyl ketone |
| 541.61 | 542.2 | (M + 1) | (trans,trans)-4-(3-fluoro-2-methylphenyl)-5-[(3-methoxyphenyl)carbonyl]-1-(pyrazol-5-ylmethyl)(3-piperidyl) 3-methoxyphenyl ketone |
| 513.56 | 514.1 | (M + 1) | (trans,trans)-4-(3-fluoro-2-methylphenyl)-5-[(3-hydroxyphenyl)carbonyl]-1-(pyrazol-5-ylmethyl)(3-piperidyl) 3-hydroxyphenyl ketone |
| 519.6 | 520.2 | (M + 1) | 1-((1S)-2-hydroxy-isopropyl)(trans,trans)-4-(3-fluoro-2-methylphenyl)-5-[(3-methoxyphenyl)carbonyl](3-piperidyl) 3-methoxyphenyl ketone |
| 491.55 | 492.2 | (M + 1) | 1-((1S)-2-hydroxy-isopropyl)(trans,trans)-4-(3-fluoro-2-methylphenyl)-5-[(3-hydroxyphenyl)carbonyl](3-piperidyl) 3-hydroxyphenyl ketone |
| 519.6 | 520.2 | (M + 1) | 1-((1R)-2-hydroxy-isopropyl)(trans,trans)-4-(3-fluoro-2-methylphenyl)-5-[(3-methoxyphenyl)carbonyl](3-piperidyl) 3-methoxyphenyl ketone |
| 541.56 | 542.1 | (M + 1) | (trans,trans)-5-[(2-fluoro-5-methoxyphenyl)carbonyl]-4-(3-fluoro-2-methylphenyl)-1-(2-hydroxyethyl)(3-piperidyl) 2-fluoro-5-methoxyphenyl ketone |
| 518.58 | 519.1 | (M + 1) | N-(2-{(trans,trans)-3,5-bis[(3-hydroxyphenyl)carbonyl]-4-(3-fluoro-2-methylphenyl)piperidyl}ethyl)acetamide |
| 554.63 | 555.1 | (M + 1) | (trans,trans)-4-(3-fluoro-2-methylphenyl)-5-[(3-hydroxyphenyl)carbonyl]-1-{2-[(methylsulfonyl)amino]ethyl}(3-piperidyl) 3-hydroxyphenyl ketone |
| 534.58 | 535.1 | (M + 1) | N-(2-{(trans,trans)-3,5-bis[(3-hydroxyphenyl)carbonyl]-4-(3-fluoro-2-methylphenyl)piperidyl}ethyl)methoxycarboxamide |
| 481.51 | 482.1 | (M + 1) | (trans,trans)-4-(3-fluoro-2-methylphenyl)-5-[(2-fluorophenyl)carbonyl]-1-(2-hydroxyethyl)(3-piperidyl) 2-fluorophenyl ketone |
| 490.57 | 491.2 | (M + 1) | (trans,trans)-4-(3-fluoro-2-methylphenyl)-5-[(3-hydroxyphenyl)carbonyl]-1-[2-(methylamino)ethyl](3-piperidyl) 3-hydroxyphenyl ketone |
| 568.66 | 569.2 | (M + 1) | (trans,trans)-4-(3-fluoro-2-methylphenyl)-5-[(3-hydroxyphenyl)carbonyl]-1-{2-[methyl(methylsulfonyl)amino]ethyl}(3-piperidyl) 3-hydroxyphenyl ketone |
| 548.6 | 549.2 | (M + 1) | N-(2-{(trans,trans)-3,5-bis[(3-hydroxyphenyl)carbonyl]-4-(3-fluoro-2-methylphenyl)piperidyl}ethyl)methoxy-N-methylcarboxamide |
| 482.61 | 483.3 | (M + 1) | 2-[(trans,trans)-3,5-bis(phenylcarbonyl)-4-(3-ethylphenyl)piperidyl]-N,N-dimethylacetamide |
| 441.56 | 442.2 | (M + 1) | (trans,trans)-4-(3-ethylphenyl)-1-(2-hydroxyethyl)-5-(phenylcarbonyl)(3-piperidyl) phenyl ketone |
| 448.6 | 449.2 | (M + 1) | 2-[(trans,trans)-3,5-bis(phenylcarbonyl)-4-(2-methylbutyl)piperidyl]-N,N-dimethylacetamide |

-continued

| Object MW | m/z Value | Ion | Chemical Name |
|---|---|---|---|
| 407.55 | 408.2 | (M + 1) | (trans,trans)-1-(2-hydroxyethyl)-4-(2-methylbutyl)-5-(phenylcarbonyl)(3-piperidyl) phenyl ketone |
| 513.5 | 514.1 | (M + 1) | (trans,trans)-5-[(2-fluoro-3-hydroxyphenyl)carbonyl]-4-(3-fluoro-2-methylphenyl)-1-(2-hydroxyethyl)(3-piperidyl) 2-fluoro-3-hydroxyphenyl ketone |
| 527.53 | 528.1 | (M + 1) | (trans,trans)-5-[(2-fluoro-3-hydroxyphenyl)carbonyl]-4-(3-fluoro-2-methylphenyl)-1-(2-hydroxyethyl)(3-piperidyl) 2-fluoro-3-methoxyphenyl ketone |
| 533.63 | 534.2 | (M + 1) | (trans,trans)-4-(3-fluoro-2-methylphenyl)-1-(2-hydroxy-2-methylpropyl)-5-[(3-methoxyphenyl)carbonyl](3-piperidyl) 3-methoxyphenyl ketone |
| 505.58 | 506.2 | (M + 1) | (trans,trans)-4-(3-fluoro-2-methylphenyl)-1-(2-hydroxy-2-methylpropyl)-5-[(3-hydroxyphenyl)carbonyl](3-piperidyl) 3-hydroxyphenyl ketone |
| 459.55 | 460.3 | (M + 1) | (trans,trans)-4-(3-fluoro-2-methylphenyl)-1-(2-methoxyethyl)-5-(phenylcarbonyl)(3-piperidyl) phenyl ketone |
| 491.55 | 492.1 | (M + 1) | (trans,trans)-4-(3-fluoro-2-methylphenyl)-5-[(3-hydroxyphenyl)carbonyl]-1-(2-methoxyethyl)(3-piperidyl) 3-hydroxyphenyl ketone |
| 491.55 | 492.1 | (M + 1) | (trans,trans)-4-(3-fluoro-2-methylphenyl)-1-(2-hydroxyethyl)-5-[(3-methoxyphenyl)carbonyl](3-piperidyl) 3-hydroxyphenyl ketone |
| 505.58 | 506.2 | (M + 1) | (trans,trans)-4-(3-fluoro-2-methylphenyl)-1-(2-methoxyethyl)-5-[(3-methoxyphenyl)carbonyl](3-piperidyl) 3-hydroxyphenyl ketone |
| 507.57 | 508.2 | (M + 1) | (trans,trans)-4-(3-fluoro-2-methylphenyl)-1-(2-methoxyethyl)-5-[(3-methoxyphenyl)carbonyl](3-piperidyl) 2-fluorophenyl ketone |
| 479.52 | 480.1 | (M + 1) | (trans,trans)-4-(3-fluoro-2-methylphenyl)-1-(2-hydroxyethyl)-5-[(3-hydroxyphenyl)carbonyl](3-piperidyl) 2-fluorophenyl ketone |
| 507.55 | 508.1 | (M + 1) | (trans,trans)-1-(2,3-dihydroxypropyl)-4-(3-fluoro-2-methylphenyl)-5-[(3-hydroxyphenyl)carbonyl](3-piperidyl) 3-hydroxyphenyl ketone |
| 491.55 | 492.1 | (M + 1) | 1-((1R)-2-hydroxy-isopropyl)(trans,trans)-4-(3-fluoro-2-methylphenyl)-5-[(3-hydroxyphenyl)carbonyl](3-piperidyl) 3-hydroxyphenyl ketone |
| 550.59 | 551.1 | (M + 1) | N-(2-{(trans,trans)-4-(3-fluoro-2-methylphenyl)-5-[(2-fluorophenyl)carbonyl]-3-[(3-methoxyphenyl)carbonyl]piperidyl}ethyl)methoxycarboxamide |
| 570.65 | 571.2 | (M + 1) | (trans,trans)-4-(3-fluoro-2-methylphenyl)-5-[(3-methoxyphenyl)carbonyl]-1-{2-[(methylsulfonyl)amino]ethyl}(3-piperidyl) 2-fluorophenyl ketone |
| 584.67 | 585.2 | (M + 1) | (trans,trans)-4-(3-fluoro-2-methylphenyl)-5-[(3-methoxyphenyl)carbonyl]-1-{2-[methyl(methylsulfonyl)amino]ethyl}(3-piperidyl) 2-fluorophenyl ketone |
| 506.58 | 507.1 | (M + 1) | (trans,trans)-4-(3-fluoro-2-methylphenyl)-5-[(3-methoxyphenyl)carbonyl]-1-[2-(methylamino)ethyl](3-piperidyl) 2-fluorophenyl ketone |
| 572.67 | 573.1 | (M + 1) | 1-(2-{(trans,trans)-3,5-bis[(3-methoxyphenyl)carbonyl]-4-(3-fluoro-2-methylphenyl)piperidyl}ethyl)pyrrolidin-2-one |
| 544.61 | 545.1 | (M + 1) | 1-(2-{(trans,trans)-3,5-bis[(3-hydroxyphenyl)carbonyl]-4-(3-fluoro-2-methylphenyl)piperidyl}ethyl)pyrrolidin-2-one |
| 687.86 | 688.3 | (M + 1) | N-{2-[(trans,trans)-4-(2,3-dimethylphenyl)-3,5-bis(phenylcarbonyl)piperidyl]ethyl}-3-(2-{2-[2-(2-aminoethoxy)ethoxy]ethoxy}ethoxy)propanamide |
| 555.49 | 556.1 | (M + 1) | (trans,trans)-4-(2,3-dichlorophenyl)-5-[(3-methoxyphenyl)carbonyl]-1-[2-(methylamino)ethyl](3-piperidyl) 3-methoxyphenyl ketone |
| 510.98 | 540.15 | (M + 1) | (trans,trans)-4-(3-chloro-2-fluorophenyl)-5-[(3-methoxyphenyl)carbonyl]-1-[2-(methylamino)ethyl](3-piperidyl) 3-methoxyphenyl ketone |
| 514.4 | 515.1 | (M + 1) | (trans,trans)-4-(2,3-dichlorophenyl)-1-(2-hydroxyethyl)-5-[(3-hydroxyphenyl)carbonyl](3-piperidyl) 3-hydroxyphenyl ketone |
| 497.94 | 498.55 | (M + 1) | (trans,trans)-4-(3-chloro-2-fluorophenyl)-1-(2-hydroxyethyl)-5-[(3-hydroxyphenyl)carbonyl](3-piperidyl) 3-hydroxyphenyl ketone |
| 548.6 | 549.1 | (M + 1) | N-(2-{(trans,trans)-3,5-bis[(3-hydroxyphenyl)carbonyl]-4-(3-fluoro-2-methylphenyl)piperidyl}-isopropyl)methoxycarboxamide |
| 568.66 | 569.1 | (M + 1) | (trans,trans)-4-(3-fluoro-2-methylphenyl)-5-[(3-hydroxyphenyl)carbonyl]-1-{2-[(methylsulfonyl)amino]propyl}(3-piperidyl) 3-hydroxyphenyl ketone |
| 548.6 | 549.2 | (M + 1) | N-((1S)-2-{(trans,trans)-3,5-bis[(3-hydroxyphenyl)carbonyl]-4-(3-fluoro-2-methylphenyl)piperidyl}-isopropyl)methoxycarboxamide |
| 562.63 | 563.2 | (M + 1) | N-(2-{(trans,trans)-3,5-bis[(3-hydroxyphenyl)carbonyl]-4-(3-fluoro-2-methylphenyl)piperidyl}-tert-butyl)methoxycarboxamide |
| 562.63 | 563.2 | (M + 1) | N-(2-{(trans,trans)-3,5-bis[(3-hydroxyphenyl)carbonyl]-4-(3-fluoro-2-methylphenyl)piperidyl}-isopropyl)methoxy-N-methylcarboxamide |

-continued

| Object MW | m/z Value | Ion | Chemical Name |
|---|---|---|---|
| 582.68 | 583.2 | (M + 1) | (trans,trans)-4-(3-fluoro-2-methylphenyl)-5-[(3-hydroxyphenyl)carbonyl]-1-{2-[methyl(methylsulfonyl)amino]propyl}(3-piperidyl) 3-hydroxyphenyl ketone |
| 568.66 | 569.1 | (M + 1) | 1-{(2S)-2-[(methylsulfonyl)amino]propyl}(trans,trans)-4-(3-fluoro-2-methylphenyl)-5-[(3-hydroxyphenyl)carbonyl](3-piperidyl) 3-hydroxyphenyl ketone |
| 546.6 | 547.2 | (M + 1) | 1-(2-{(trans,trans)-4-(3-fluoro-2-methylphenyl)-5-[(2-fluorophenyl)carbonyl]-3-[(3-hydroxyphenyl)carbonyl]piperidyl}ethyl)pyrrolidin-2-one |
| 605.53 | 607 | (M + 1) | (trans,trans)-4-(2,3-dichlorophenyl)-5-[(3-hydroxyphenyl)carbonyl]-1-{2-[methyl(methylsulfonyl)amino]ethyl}(3-piperidyl) 3-hydroxyphenyl ketone |
| 589.07 | 590.25 | (M + 1) | (trans,trans)-4-(3-chloro-2-fluorophenyl)-5-[(3-hydroxyphenyl)carbonyl]-1-{2-[methyl(methylsulfonyl)amino]ethyl}(3-piperidyl) 3-hydroxyphenyl ketone |
| 585.48 | 586 | (M + 1) | N-(2-{(trans,trans)-4-(2,3-dichlorophenyl)-3,5-bis[(3-hydroxyphenyl)carbonyl]piperidyl}ethyl)methoxy-N methylcarboxamide |
| 569.02 | 569.3 | (M + 1) | N-(2-{(trans,trans)-3,5-bis[(3-hydroxyphenyl)carbonyl]-4-(3-chloro-2-fluorophenyl)piperidyl}ethyl)methoxy-N-methylcarboxamide |
| 568.66 | 569.3 | (M + 1) | (trans,trans)-4-(2-fluoro-3-methylphenyl)-5-[(3-hydroxyphenyl)carbonyl]-1-{2-[methyl(methylsulfonyl)amino]ethyl}(3-piperidyl) 3-hydroxyphenyl ketone |
| 548.6 | 549.25 | (M + 1) | N-(2-{(trans,trans)-3,5-bis[(3-hydroxyphenyl)carbonyl]-4-(2-fluoro-3-methylphenyl)piperidyl}ethyl)methoxy-N-methylcarboxamide |
| 477.52 | 478.25 | (M + 1) | (trans,trans)-4-(2-fluoro-3-methylphenyl)-1-(2-hydroxyethyl)-5-[(3-hydroxyphenyl)carbonyl](3-piperidyl) 3-hydroxyphenyl ketone |
| 547.62 | 548.2 | (M + 1) | N-(2-{(trans,trans)-3,5-bis[(3-hydroxyphenyl)carbonyl]-4-(3-fluoro-2-methylphenyl)piperidyl}ethyl)-N-methyl(methylamino)carboxamide |
| 490.52 | 491.1 | (M + 1) | 2-{(trans,trans)-3,5-bis[(3-hydroxyphenyl)carbonyl]-4-(3-fluoro-2-methylphenyl)piperidyl}acetamide |
| 546.63 | 547.2 | (M + 1) | 2-{(trans,trans)-3,5-bis[(3-hydroxyphenyl)carbonyl]-4-(3-fluoro-2-methylphenyl)piperidyl}-4-methylpentanamide |
| 563.62 | 564.2 | (M + 1) | (trans,trans)-1-(benzimidazol-2-ylmethyl)-4-(3-fluoro-2-methylphenyl)-5-[(3-hydroxyphenyl)carbonyl](3-piperidyl) 3-hydroxyphenyl ketone |
| 495.51 | 496.25 | (M + 1) | (trans,trans)-4-(2,6-difluoro-3-methylphenyl)-1-(2-hydroxyethyl)-5-[(3-hydroxyphenyl)carbonyl](3-piperidyl) 3-hydroxyphenyl ketone |
| 533.59 | 534.2 | (M + 1) | N-(2-{(trans,trans)-3,5-bis[(3-hydroxyphenyl)carbonyl]-4-(3-fluoro-2-methylphenyl)piperidyl}ethyl)amino-N-methylamide |
| 504.59 | 505.2 | (M + 1) | (trans,trans)-1-(2-aminoethyl)-4-(3-fluoro-2-methylphenyl)-5-[(3-methoxyphenyl)carbonyl](3-piperidyl) 3-methoxyphenyl ketone |
| 516.6 | 517.2 | (M + 1) | (trans,trans)-4-(3-fluoro-2-methylphenyl)-5-[(3-hydroxyphenyl)carbonyl]-1-(4-piperidyl)(3-piperidyl) 3-hydroxyphenyl ketone |
| 594.69 | 595.2 | (M + 1) | (trans,trans)-4-(3-fluoro-2-methylphenyl)-5-[(3-hydroxyphenyl)carbonyl]-1-[1-(methylsulfonyl)(4-piperidyl)](3-piperidyl) 3-hydroxyphenyl ketone |
| 586.65 | 587.25 | (M + 1) | (trans,trans)-4-(2,6-difluoro-3-methylphenyl)-5-[(3-hydroxyphenyl)carbonyl]-1-{2-[methyl(methylsulfonyl)ammo]ethyl}(3-piperidyl) 3-hydroxyphenyl ketone |
| 566.59 | 567.25 | (M + 1) | N-(2-{(trans,trans)-4-(2,6-difluoro-3-methylphenyl)-3,5-bis[(3-hydroxyphenyl)carbonyl]piperidyl}ethyl)methoxy-N-methylcarboxamide |
| 632.69 | 633.2 | (M + 1) | (trans,trans)-5-[(2-fluoro-3-methoxyphenyl)carbonyl]-4-(3-fluoro-2-methylphenyl)-1-{2-[methyl(methylsulfonyl)amino]ethyl}(3-piperidyl) 2-fluoro-3-methoxyphenyl ketone |
| 590.61 | 591.2 | (M + 1) | (trans,trans)-5-[(2-fluoro-3-hydroxyphenyl)carbonyl]-4-(3-fluoro-2-methylphenyl)-1-{2-[(methylsulfonyl)amino]ethyl}(3-piperidyl) 2-fluoro-3-hydroxyphenyl ketone |
| 519.56 | 520.2 | (M + 1) | N-(2-{(trans,trans)-3,5-bis[(3-hydroxyphenyl)carbonyl]-4-(3-fluoro-2-methylphenyl)piperidyl}ethyl)aminoamide |
| 583.67 | 584.2 | (M + 1) | (trans,trans)-1-(2-{[(dimethylamino)sulfonyl]amino}ethyl)-4-(3-fluoro-2-methylphenyl)-5-[(3-hydroxyphenyl)carbonyl](3-piperidyl) 3-hydroxyphenyl ketone |
| 597.7 | 598.2 | (M + 1) | (trans,trans)-1-(2-{[(dimethylamino)sulfonyl]methylamino}ethyl)-4-(3-fluoro-2-methylphenyl)-5-[(3-hydroxyphenyl)carbonyl](3-piperidyl) 3-hydroxyphenyl ketone |

-continued

| Object MW | m/z Value | Ion | Chemical Name |
|---|---|---|---|
| 572.71 | 573.3 | (M + 1) | (trans,trans)-4-(3-fluoro-2-methylphenyl)-5-[(3-hydroxyphenyl)carbonyl]-1-(2,2,6,6-tetramethyl(4-piperidyl))(3-piperidyl) 3-hydroxyphenyl ketone |
| 525.56 | 526.1 | (M + 1) | (trans,trans)-4-(3-fluoro-2-methylphenyl)-1-(2-methoxyethyl)-5-[(3-methoxyphenyl)carbonyl](3-piperidyl) 2,3-difluorophenyl ketone |
| 526.55 | 527.1 | (M + 1) | (trans,trans)-5-[(2-fluoro-3-hydroxyphenyl)carbonyl]-4-(3-fluoro-2-methylphenyl)-1-[2-(methylamino)ethyl](3-piperidyl) 2-fluoro-3-hydroxyphenyl ketone |
| 512.52 | 513.1 | (M + 1) | (trans,trans)-1-(2-aminoethyl)-5-[(6-fluoro-3-hydroxyphenyl)carbonyl]-4-(3-fluoro-2-methylphenyl)(3-piperidyl) 6-fluoro-3-hydroxyphenyl ketone |
| 497.51 | 498.1 | (M + 1) | (trans,trans)-4-(3-fluoro-2-methylphenyl)-1-(2-hydroxyethyl)-5-[(3-hydroxyphenyl)carbonyl](3-piperidyl) 2,3-difluorophenyl ketone |
| 573.58 | 574.1 | (M + 1) | (trans,trans)-4-(3-fluoro-2-methylphenyl)-5-[(3-methoxyphenyl)carbonyl]-1-(3,3,3-trifluoro-2-hydroxypropyl)(3-piperidyl) 3-methoxyphenyl ketone |
| 545.52 | 546.2 | (M + 1) | (trans,trans)-4-(3-fluoro-2-methylphenyl)-5-[(3-hydroxyphenyl)carbonyl]-1-(3,3,3-trifluoro-2-hydroxypropyl)(3-piperidyl) 3-hydroxyphenyl ketone |
| 573.65 | 574.2 | (M + 1) | 1-(2-{(trans,trans)-3,5-bis[(3-methoxyphenyl)carbonyl]-4-(3-fluoro-2-methylphenyl)piperidyl}ethyl)imidazolidin-2-one |
| 545.6 | 546.2 | (M + 1) | 1-(2-{(trans,trans)-3,5-bis[(3-hydroxyphenyl)carbonyl]-4-(3-fluoro-2-methylphenyl)piperidyl}ethyl)imidazolidin-2-one |
| 530.63 | 531.2 | (M + 1) | 1-((2R)-2-aminocyclohexyl)(trans,trans)-4-(3-fluoro-2-methylphenyl)-5-[(3-hydroxyphenyl)carbonyl](3-piperidyl) 3-hydroxyphenyl ketone |
| 530.63 | 531.2 | (M + 1) | (trans,trans)-1-(2-aminocyclohexyl)-4-(3-fluoro-2-methylphenyl)-5-[(3-hydroxyphenyl)carbonyl](3-piperidyl) 3-hydroxyphenyl ketone |
| 608.72 | 609.2 | (M + 1) | (trans,trans)-4-(3-fluoro-2-methylphenyl)-5-[(3-hydroxyphenyl)carbonyl]-1-{2-[(methylsulfonyl)amino]cyclohexyl}(3-piperidyl) 3-hydroxyphenyl ketone |
| 604.64 | 605.2 | (M + 1) | (trans,trans)-5-[(2-fluoro-3-hydroxyphenyl)carbonyl]-4-(3-fluoro-2-methylphenyl)-1-{2-[methyl(methylsulfonyl)amino]ethyl}(3-piperidyl) 2-fluoro-3-hydroxyphenyl ketone |
| 523.59 | 524.1 | (M + 1) | (trans,trans)-4-(3-fluoro-2-methylphenyl)-5-[(3-hydroxyphenyl)carbonyl]-1-benzyl(3-piperidyl) 3-hydroxyphenyl ketone |
| 502.58 | 503.2 | (M + 1) | (trans,trans)-4-(3-fluoro-2-methylphenyl)-5-[(3-hydroxyphenyl)carbonyl]-1-pyrrolidin-3-yl(3-piperidyl) 3-hydroxyphenyl ketone |
| 580.67 | 581.1 | (M + 1) | (trans,trans)-4-(3-fluoro-2-methylphenyl)-5-[(3-hydroxyphenyl)carbonyl]-1-[1-(methylsulfonyl)pyrrolidin-3-yl](3-piperidyl) 3-hydroxyphenyl ketone |
| 560.61 | 561.2 | (M + 1) | methyl 3-{(trans,trans)-3,5-bis[(3-hydroxyphenyl)carbonyl]-4-(3-fluoro-2-methylphenyl)piperidyl}pyrrolidinecarboxylate |
| 544.61 | 545.2 | (M + 1) | 3-{(trans,trans)-3,5-bis[(3-hydroxyphenyl)carbonyl]-4-(3-fluoro-2-methylphenyl)piperidyl}-1-acetylpyrrolidine |
| 545.6 | 546.2 | (M + 1) | 3-{(trans,trans)-3,5-bis[(3-hydroxyphenyl)carbonyl]-4-(3-fluoro-2-methylphenyl)piperidyl}pyrrolidinecarboxamide |
| 559.63 | 560.2 | (M + 1) | (3-{(trans,trans)-3,5-bis[(3-hydroxyphenyl)carbonyl]-4-(3-fluoro-2-methylphenyl)piperidyl}pyrrolidinyl)-N-methylcarboxamide |
| 609.71 | 610.2 | (M + 1) | (trans,trans)-1-{1-[(dimethylamino)sulfonyl]pyrrolidin-3-yl}-4-(3-fluoro-2-methylphenyl)-5-[(3-hydroxyphenyl)carbonyl](3-piperidyl) 3-hydroxyphenyl ketone |
| 536.61 | 537.2 | (M + 1) | (trans,trans)-4-(3-fluoro-2-methylphenyl)-5-[(3-methoxyphenyl)carbonyl]-1-[2-(methylamino)ethyl](3-piperidyl) 2-fluoro-3-methoxyphenyl ketone |
| 495.51 | 496.1 | (M + 1) | (trans,trans)-4-(3-fluoro-2-methylphenyl)-1-(2-hydroxyethyl)-5-[(3-hydroxyphenyl)carbonyl](3-piperidyl) 2-fluoro-3-hydroxyphenyl ketone |
| 508.56 | 509.1 | (M + 1) | (trans,trans)-4-(3-fluoro-2-methylphenyl)-5-[(3-hydroxyphenyl)carbonyl]-1-[2-(methylamino)ethyl](3-piperidyl) 2-fluoro-3-hydroxyphenyl ketone |
| 567.63 | 568.1 | (M + 1) | 4-{(trans,trans)-3,5-bis[(3-hydroxyphenyl)carbonyl]-4-(3-fluoro-2-methylphenyl)piperidyl}-3-hydroxythiolane-1,1-dione |
| 569.64 | 570.1 | (M + 1) | (2-{(trans,trans)-3,5-bis[(3-hydroxyphenyl)carbonyl]-4-(3-fluoro-2-methylphenyl)piperidyl}ethyl)aminomethylsulfonamide |
| 530.63 | 531.2 | (M + 1) | (trans,trans)-4-(3-fluoro-2-methylphenyl)-5-[(3-hydroxyphenyl)carbonyl]-1-(3-piperidylmethyl)(3-piperidyl) 3-hydroxyphenyl ketone |
| 516.6 | 517.2 | (M + 1) | (trans,trans)-4-(3-fluoro-2-methylphenyl)-5-[(3-hydroxyphenyl)carbonyl]-1-(3-piperidyl)(3-piperidyl) 3-hydroxyphenyl ketone |

-continued

| Object MW | m/z Value | Ion | Chemical Name |
|---|---|---|---|
| 560.55 | 561.2 | (M + 1) | (trans,trans)-4-(3-fluoro-2-methylphenyl)-5-[(3-hydroxyphenyl)carbonyl]-1-[2-(methylamino)ethyl](3-piperidyl) 2-fluoro-3-(trifluoromethyl)phenyl ketone |
| 506.58 | 507.1 | (M + 1) | (trans,trans)-4-(3-fluoro-2-methylphenyl)-5-[(3-hydroxyphenyl)carbonyl]-1-[2-(methylamino)ethyl](3-piperidyl) 2-fluoro-3-methylphenyl ketone |
| 493.54 | 494.1 | (M + 1) | (trans,trans)-4-(3-fluoro-2-methylphenyl)-1-(2-hydroxyethyl)-5-[(3-hydroxyphenyl)carbonyl](3-piperidyl) 2-fluoro-3-methylphenyl ketone |
| 533.65 | 534.1 | (M + 1) | (trans,trans)-4-(3-fluoro-2-methylphenyl)-5-[(3-hydroxyphenyl)carbonyl]-1-thian-4-yl(3-piperidyl) 3-hydroxyphenyl ketone |
| 531.61 | 532.2 | (M + 1) | (trans,trans)-4-(3-fluoro-2-methylphenyl)-1-(4-hydroxycyclohexyl)-5-[(3-hydroxyphenyl)carbonyl](3-piperidyl) 3-hydroxyphenyl ketone |
| 516.6 | 517.2 | (M + 1) | (trans,trans)-4-(3-fluoro-2-methylphenyl)-5-[(3-hydroxyphenyl)carbonyl]-1-(pyrrolidin-2-ylmethyl)(3-piperidyl) 3-hydroxyphenyl ketone |
| 532.65 | 533.2 | (M + 1) | (trans,trans)-1-(4-aminobutyl)-4-(3-fluoro-2-methylphenyl)-5-[(3-methoxyphenyl)carbonyl](3-piperidyl) 3-methoxyphenyl ketone |
| 504.59 | 505.1 | (M + 1) | (trans,trans)-1-(4-aminobutyl)-4-(3-fluoro-2-methylphenyl)-5-[(3-hydroxyphenyl)carbonyl](3-piperidyl) 3-hydroxyphenyl ketone |
| 548.6 | 549.3 | (M + 1) | 2-{(trans,trans)-3,5-bis[(3-hydroxyphenyl)carbonyl]-4-(3-fluoro-2-methylphenyl)piperidyl}-3-(dimethylamino)propanoic acid |
| 503.56 | 504.1 | (M + 1) | (trans,trans)-1-acetyl-3,5-bis[(3-methoxyphenyl)carbonyl]-4-(3-fluoro-2-methylphenyl)piperidine |
| 597.12 | 598.1 | (M + 1) | (trans,trans)-4-(3-fluoro-2-methylphenyl)-1-(2-methoxyethyl)-5-[(3-methoxyphenyl)carbonyl](3-piperidyl) 3-chloro-2-[(2-methoxyethyl)amino]phenyl ketone |
| 595.15 | 596.1 | (M + 1) | (trans,trans)-4-(3-fluoro-2-methylphenyl)-5-[(3-methoxyphenyl)carbonyl]-1-[2-(methylamino)ethyl](3-piperidyl) 3-chloro-2-{[2-(methylamino)ethyl]amino}phenyl ketone |
| 547.62 | 548.2 | (M + 1) | 2-{(trans,trans)-3,5-bis[(3-hydroxyphenyl)carbonyl]-4-(3-fluoro-2-methylphenyl)piperidyl}-3-(dimethylamino)propanamide |
| 575.67 | 576.2 | (M + 1) | 2-{(trans,trans)-3,5-bis[(3-hydroxyphenyl)carbonyl]-4-(3-fluoro-2-methylphenyl)piperidyl}-3-(dimethylamino)-N,N-dimethylpropanamide |
| 532.65 | 533.2 | (M + 1) | (trans,trans)-1-[4-(dimethylamino)butyl]-4-(3-fluoro-2-methylphenyl)-5-[(3-hydroxyphenyl)carbonyl](3-piperidyl) 3-hydroxyphenyl ketone |
| 518.62 | 519.1 | (M + 1) | (trans,trans)-4-(3-fluoro-2-methylphenyl)-5-[(3-hydroxyphenyl)carbonyl]-1-[4-(methylamino)butyl](3-piperidyl) 3-hydroxyphenyl ketone |
| 547.62 | 548 | (M + 1) | 2-{(trans,trans)-3,5-bis[(3-hydroxyphenyl)carbonyl]-4-(3-fluoro-2-methylphenyl)piperidyl}-N-[2-(methylamino)ethyl]acetamide |
| 533.59 | 534 | (M + 1) | 2-{(trans,trans)-3,5-bis[(3-hydroxyphenyl)carbonyl]-4-(3-fluoro-2-methylphenyl)piperidyl}-N-(2-aminoethyl)acetamide |
| 518.58 | 519.1 | (M + 1) | 1-{(trans,trans)-3,5-bis[(3-hydroxyphenyl)carbonyl]-4-(3-fluoro-2-methylphenyl)piperidyl}-3-(methylamino)propan-1-one |
| 581.12 | 581.2 | (M + 1) | (trans,trans)-4-(3-fluoro-2-methylphenyl)-5-[(3-hydroxyphenyl)carbonyl]-1-[2-(methylamino)ethyl](3-piperidyl) 3-chloro-2-{[2-(methylamino)ethyl]amino}phenyl ketone |
| 475.51 | 476.1 | (M + 1) | (trans,trans)-1-acetyl-3,5-bis[(3-hydroxyphenyl)carbonyl]-4-(3-fluoro-2-methylphenyl)piperidine |
| 513.96 | 514.1 | (M + 1) | (trans,trans)-4-(3-fluoro-2-methylphenyl)-1-(2-hydroxyethyl)-5-[(3-hydroxyphenyl)carbonyl](3-piperidyl) 3-chloro-2-fluorophenyl ketone |
| 632.72 | 634.2 | (M + 1) | N-(2-{(trans,trans)-3,5-bis[(3-methoxyphenyl)carbonyl]-4-(3-fluoro-2-methylphenyl)piperidyl}-2-oxoethyl)(tert-butoxy)-N-methylcarboxamide |
| 546.67 | 547.2 | (M + 1) | (trans,trans)-1-(5-aminopentyl)-4-(3-fluoro-2-methylphenyl)-5-[(3-methoxyphenyl)carbonyl](3-piperidyl) 3-methoxyphenyl ketone |
| 518.62 | 519.1 | (M + 1) | (trans,trans)-1-(5-aminopentyl)-4-(3-fluoro-2-methylphenyl)-5-[(3-hydroxyphenyl)carbonyl](3-piperidyl) 3-hydroxyphenyl ketone |
| 546.67 | 547.2 | (M + 1) | (trans,trans)-1-[5-(dimethylamino)pentyl]-4-(3-fluoro-2-methylphenyl)-5-[(3-hydroxyphenyl)carbonyl](3-piperidyl) 3-hydroxyphenyl ketone |
| 490.52 | 491.1 | (M + 1) | 1-{(trans,trans)-3,5-bis[(3-hydroxyphenyl)carbonyl]-4-(3-fluoro-2-methylphenyl)piperidyl}-2-aminoethan-1-one |
| 561.64 | 562.3 | (M + 1) | 2-{(trans,trans)-3,5-bis[(3-hydroxyphenyl)carbonyl]-4-(3-fluoro-2-methylphenyl)piperidyl}-3-(dimethylamino)-N-methylpropanamide |
| 586.74 | 587.3 | (M + 1) | (trans,trans)-4-(3-fluoro-2-methylphenyl)-5-[(3-hydroxyphenyl)carbonyl]-1-(1,2,2,6,6-pentamethyl(4-piperidyl))(3-piperidyl) 3-hydroxyphenyl ketone |
| 504.55 | 505.1 | (M + 1) | 1-{(trans,trans)-3,5-bis[(3-hydroxyphenyl)carbonyl]-4-(3-fluoro-2-methylphenyl)piperidyl}-2-(methylamino)ethan-1-one |

-continued

| Object MW | m/z Value | Ion | Chemical Name |
|---|---|---|---|
| 546.63 | 547.2 | (M + 1) | 1-{(trans,trans)-3,5-bis[(3-methoxyphenyl)carbonyl]-4-(3-fluoro-2-methylphenyl)piperidyl}-2-(dimethylamino)ethan-1-one |
| 518.58 | 519.1 | (M + 1) | 1-{(trans,trans)-3,5-bis[(3-hydroxyphenyl)carbonyl]-4-(3-fluoro-2-methylphenyl)piperidyl}-2-(dimethylamino)ethan-1-one |
| 633.75 | 634 | (M + 1) | 2-{(trans,trans)-3,5-bis[(3-methoxyphenyl)carbonyl]-4-(3-fluoro-2-methylphenyl)piperidyl}-N-[3-(dimethylamino)propyl]-3-hydroxypropanamide |
| 563.62 | 564 | (M + 1) | 2-{(trans,trans)-3,5-bis[(3-hydroxyphenyl)carbonyl]-4-(3-fluoro-2-methylphenyl)piperidyl}-N-(2-aminoethyl)-3-hydroxypropanamide |
| 516.56 | 517.1 | (M + 1) | (trans,trans)-1-(azetidin-3-ylcarbonyl)-4-(3-fluoro-2-methylphenyl)-5-[(3-hydroxyphenyl)carbonyl](3-piperidyl) 3-hydroxyphenyl ketone |
| 605.7 | 606 | (M + 1) | 2-{(trans,trans)-3,5-bis[(3-hydroxyphenyl)carbonyl]-4-(3-fluoro-2-methylphenyl)piperidyl}-N-[3-(dimethylamino)propyl]-3-hydroxypropanamide |
| 619.72 | 620 | (M + 1) | 2-{(trans,trans)-3,5-bis[(3-hydroxyphenyl)carbonyl]-4-(3-fluoro-2-methylphenyl)piperidyl}-N-[4-(dimethylamino)butyl]-3-hydroxypropanamide |
| 513.96 | 514.1 | (M + 1) | (trans,trans)-4-(3-fluoro-2-methylphenyl)-1-(2-hydroxyethyl)-5-[(3-hydroxyphenyl)carbonyl](3-piperidyl) 2-chloro-6-fluorophenyl ketone |
| 544.66 | 545.1 | (M + 1) | (trans,trans)-4-(3-fluoro-2-methylphenyl)-5-[(3-hydroxyphenyl)carbonyl]-1-(3-pyrrolidinylpropyl)(3-piperidyl) 3-hydroxyphenyl ketone |
| 504.59 | 505.2 | (M + 1) | (trans,trans)-1-[2-(dimethylamino)ethyl]-4-(3-fluoro-2-methylphenyl)-5-[(3-hydroxyphenyl)carbonyl](3-piperidyl) 3-hydroxyphenyl ketone |
| 560.7 | 561.2 | (M + 1) | (trans,trans)-4-(3-fluoro-2-methylphenyl)-5-[(3-methoxyphenyl)carbonyl]-1-[5-(methylamino)pentyl](3-piperidyl) 3-methoxyphenyl ketone |
| 504.59 | 505.2 | (M + 1) | (trans,trans)-4-(3-fluoro-2-methylphenyl)-5-[(3-hydroxyphenyl)carbonyl]-1-[3-(methylamino)propyl](3-piperidyl) 3-hydroxyphenyl ketone |
| 518.62 | 519.2 | (M + 1) | (trans,trans)-1-[3-(dimethylamino)propyl]-4-(3-fluoro-2-methylphenyl)-5-[(3-hydroxyphenyl)carbonyl](3-piperidyl) 3-hydroxyphenyl ketone |
| 533.63 | 534.2 | (M + 1) | (trans,trans)-4-(3-fluoro-2-methylphenyl)-1-(4-hydroxybutyl)-5-[(3-methoxyphenyl)carbonyl](3-piperidyl) 3-methoxyphenyl ketone |
| 530.63 | 531.3 | (M + 1) | (trans,trans)-4-(3-fluoro-2-methylphenyl)-5-[(3-hydroxyphenyl)carbonyl]-1-(1-methyl(4-piperidyl))(3-piperidyl) 3-hydroxyphenyl ketone |
| 551.63 | 552.2 | (M + 1) | 3-{(trans,trans)-3,5-bis[(3-hydroxyphenyl)carbonyl]-4-(3-fluoro-2-methylphenyl)piperidyl}thiolane-1,1-dione |
| 506.57 | 507.2 | (M + 1) | (trans,trans)-1-(2-amino-3-hydroxypropyl)-4-(3-fluoro-2-methylphenyl)-5-[(3-hydroxyphenyl)carbonyl](3-piperidyl) 3-hydroxyphenyl ketone |
| 560.7 | 561 | (M + 1) | (trans,trans)-1-{2-[bis(methylethyl)amino]ethyl}-4-(3-fluoro-2-methylphenyl)-5-[(3-hydroxyphenyl)carbonyl](3-piperidyl) 3-hydroxyphenyl ketone |
| 532.65 | 533 | (M + 1) | (trans,trans)-1-[2-(diethylamino)ethyl]-4-(3-fluoro-2-methylphenyl)-5-[(3-hydroxyphenyl)carbonyl](3-piperidyl) 3-hydroxyphenyl ketone |
| 532.65 | 533 | (M + 1) | (trans,trans)-1-[2-(dimethylamino)-2-methylpropyl]-4-(3-fluoro-2-methylphenyl)-5-[(3-hydroxyphenyl)carbonyl](3-piperidyl) 3-hydroxyphenyl ketone |
| 562.67 | 563 | (M + 1) | (trans,trans)-1-{1-[(dimethylamino)methyl]-2-hydroxyethyl}-4-(3-fluoro-2-methylphenyl)-5-[(3-methoxyphenyl)carbonyl](3-piperidyl) 3-methoxyphenyl ketone |
| 527 | 527.1 | (M + 1) | (trans,trans)-4-(3-fluoro-2-methylphenyl)-5-[(3-hydroxyphenyl)carbonyl]-1-[2-(methylamino)ethyl](3-piperidyl) 2-chloro-6-fluorophenyl ketone |
| 546.63 | 547 | (M + 1) | 1-{(trans,trans)-3,5-bis[(3-hydroxyphenyl)carbonyl]-4-(3-fluoro-2-methylphenyl)piperidyl}-4-(dimethylamino)butan-1-one |
| 558.64 | 559.1 | (M + 1) | 1-{(trans,trans)-3,5-bis[(3-hydroxyphenyl)carbonyl]-4-(3-fluoro-2-methylphenyl)piperidyl}-2-piperidylethan-1-one |
| 544.61 | 545.2 | (M + 1) | (trans,trans)-4-(3-fluoro-2-methylphenyl)-5-[(3-hydroxyphenyl)carbonyl]-1-(3-piperidylcarbonyl)(3-piperidyl) 3-hydroxyphenyl ketone |
| 559.63 | 560.2 | (M + 1) | 1-(2-{(trans,trans)-3,5-bis[(3-hydroxyphenyl)carbonyl]-4-(3-fluoro-2-methylphenyl)piperidyl}ethyl)-3-methylimidazolidin-2-one |
| 518.62 | 519.2 | (M + 1) | 1-[(2S)-2-(dimethylamino)propyl](trans,trans)-4-(3-fluoro-2-methylphenyl)-5-[(3-hydroxyphenyl)carbonyl](3-piperidyl) 3-hydroxyphenyl ketone |
| 534.62 | 535.2 | (M + 1) | 1-[(2R)-2-(dimethylamino)-3-hydroxypropyl](trans,trans)-4-(3-fluoro-2-methylphenyl)-5-[(3-hydroxyphenyl)carbonyl](3-piperidyl) 3-hydroxyphenyl ketone |

-continued

| Object MW | m/z Value | Ion | Chemical Name |
|---|---|---|---|
| 574.68 | 575.2 | (M + 1) | 1-((2R)-3-hydroxy-2-piperidylpropyl)(trans,trans)-4-(3-fluoro-2-methylphenyl)-5-[(3-hydroxyphenyl)carbonyl](3-piperidyl) 3-hydroxyphenyl ketone |
| 574.68 | 575.2 | (M + 1) | 1-[(2R)-2-(cyclopentylamino)-3-hydroxypropyl](trans,trans)-4-(3-fluoro-2-methylphenyl)-5-[(3-hydroxyphenyl)carbonyl](3-piperidyl) 3-hydroxyphenyl ketone |
| 534.62 | 535 | (M + 1) | (trans,trans)-1-{1-[(dimethylamino)methyl]-2-hydroxyethyl}-4-(3-fluoro-2-methylphenyl)-5-[(3-hydroxyphenyl)carbonyl](3-piperidyl) 3-hydroxyphenyl ketone |
| 545.6 | 546.1 | (M + 1) | (trans,trans)-4-(3-fluoro-2-methylphenyl)-5-[(3-hydroxyphenyl)carbonyl]-1-(piperazin-2-ylcarbonyl)(3-piperidyl) 3-hydroxyphenyl ketone |
| 531.61 | 532.2 | (M + 1) | 1-{(trans,trans)-3,5-bis[(3-hydroxyphenyl)carbonyl]-4-(3-fluoro-2-methylphenyl)piperidyl}1-3,3-dimethylbutan-1-one |
| 429.53 | 430.1 | (M + 1) | (trans,trans,trans,trans)-4-(3-fluoro-2-methylphenyl)-2,6-dimethyl-5-(phenylcarbonyl)(3-piperidyl) phenyl ketone |
| 514.63 | 515.2 | (M + 1) | 2-[(trans,trans,trans,trans)-3,5-bis(phenylcarbonyl)-4-(3-fluoro-2-methylphenyl)-2,6-dimethylpiperidyl]-N,N-dimethylacetamide |
| 487.6 | 488.2 | (M + 1) | (trans,trans,trans,trans)-4-(3-fluoro-2-methylphenyl)-1-(2-methoxyethyl)-2,6-dimethyl-5-(phenylcarbonyl)(3-piperidyl) phenyl ketone |
| 561.64 | 562.2 | (M + 1) | {(trans,trans)-3,5-bis[(3-hydroxyphenyl)carbonyl]-4-(3-fluoro-2-methylphenyl)piperidyl}-N-[3-(dimethylamino)propyl]carboxamide |
| 558.64 | 559.1 | (M + 1) | (trans,trans)-4-(3-fluoro-2-methylphenyl)-5-[(3-hydroxyphenyl)carbonyl]-1-[(1-methyl(4-piperidyl))carbonyl](3-piperidyl) 3-hydroxyphenyl ketone |
| 576.66 | 577.2 | (M + 1) | 4-(dimethylamino)butyl (trans,trans)-3,5-bis[(3-hydroxyphenyl)carbonyl]-4-(3-fluoro-2-methylphenyl)piperidinecarboxylate |
| 572.67 | 573.2 | (M + 1) | 1-{(trans,trans)-3,5-bis[(3-hydroxyphenyl)carbonyl]-4-(3-fluoro-2-methylphenyl)piperidyl}-3-piperidylpropan-1-one |
| 575.67 | 576.2 | (M + 1) | {(trans,trans)-3,5-bis[(3-hydroxyphenyl)carbonyl]-4-(3-fluoro-2-methylphenyl)piperidyl}-N-[3-(dimethylamino)propyl]-N-methylcarboxamide |
| 616.72 | 617.3 | (M + 1) | 1-(2-{(trans,trans)-3,5-bis[(3-hydroxyphenyl)carbonyl]-4-(3-fluoro-2-methylphenyl)piperidyl}ethyl)-3-[2-(dimethylamino)ethyl]imidazolidin-2-one |
| 548.62 | 549.2 | (M + 1) | 1-{(trans,trans)-4-(3-fluoro-2-methylphenyl)-5-[(2-fluorophenyl)carbonyl]-3-[(3-hydroxyphenyl)carbonyl]piperidyl}-4-(dimethylamino)butan-1-one |
| 546.63 | 547.2 | (M + 1) | 1-{(trans,trans)-3,5-bis[(3-hydroxyphenyl)carbonyl]-4-(3-fluoro-2-methylphenyl)piperidyl}-4-amino-2,2-dimethylbutan-1-one |
| 574.68 | 575.2 | (M + 1) | 1-{(trans,trans)-3,5-bis[(3-hydroxyphenyl)carbonyl]-4-(3-fluoro-2-methylphenyl)piperidyl}-4-(dimethylamino)-2,2-dimethylbutan-1-one |
| 561.64 | 562.2 | (M + 1) | {(trans,trans)-3,5-bis[(3-hydroxyphenyl)carbonyl]-4-(3-fluoro-2-methylphenyl)piperidyl}-N-[2-(dimethylamino)ethyl]-N-methylcarboxamide |
| 547.62 | 548.2 | (M + 1) | {(trans,trans)-3,5-bis[(3-hydroxyphenyl)carbonyl]-4-(3-fluoro-2-methylphenyl)piperidyl}-N-[2-(dimethylamino)ethyl]carboxamide |
| 548.6 | 549.2 | (M + 1) | 2-(dimethylamino)ethyl (trans,trans)-3,5-bis[(3-hydroxyphenyl)carbonyl]-4-(3-fluoro-2-methylphenyl)piperidinecarboxylate |
| 582.68 | 583.2 | (M + 1) | (trans,trans)-1-{[3-(dimethylamino)propyl]sulfonyl}-4-(3-fluoro-2-methylphenyl)-5-[(3-hydroxyphenyl)carbonyl](3-piperidyl) 3-hydroxyphenyl ketone |
| 574.06 | 575.1 | (M + 1) | (trans,trans)-1-[(3-chloropropyl)sulfonyl]-4-(3-fluoro-2-methylphenyl)-5-[(3-hydroxyphenyl)carbonyl](3-piperidyl) 3-hydroxyphenyl ketone |
| 534.62 | 535.2 | (M + 1) | 1-((2R)-2-amino-3-hydroxy-3-methylbutyl)(trans,trans)-4-(3-fluoro-2-methylphenyl)-5-[(3-hydroxyphenyl)carbonyl](3-piperidyl) 3-hydroxyphenyl ketone |
| 522.56 | 523.5 | (M + 1) | 2-{(trans,trans)-3,5-bis(phenylcarbonyl)-4-[4-(trifluoromethyl)phenyl]piperidyl}-N,N-dimethylacetamide |
| 523.45 | 523.8 | (M + 1) | 2-[(trans,trans)-4-(3,4-dichlorophenyl)-3,5-bis(phenylcarbonyl)piperidyl]-N,N-dimethylacetamide |
| 484.59 | 485 | (M + 1) | 2-[(trans,trans)-3,5-bis(phenylcarbonyl)-4-(3-methoxyphenyl)piperidyl]-N,N-dimethylacetamide |
| 523.45 | 523.7 | (M + 1) | 2-[(trans,trans)-4-(3,5-dichlorophenyl)-3,5-bis(phenylcarbonyl)piperidyl]-N,N-dimethylacetamide |
| 484.59 | 485 | (M + 1) | 2-[(trans,trans)-3,5-bis(phenylcarbonyl)-4-(4-methoxyphenyl)piperidyl]-N,N-dimethylacetamide |
| 523.45 | 523.8 | (M + 1) | 2-[(trans,trans)-4-(2,5-dichlorophenyl)-3,5-bis(phenylcarbonyl)piperidyl]-N,N-dimethylacetamide |
| 523.45 | 523.7 | (M + 1) | 2-[(trans,trans)-4-(2,4-dichlorophenyl)-3,5-bis(phenylcarbonyl)piperidyl]-N,N-dimethylacetamide |

-continued

| Object MW | m/z Value | Ion | Chemical Name |
|---|---|---|---|
| 484.59 | 485.4 | (M + 1) | 2-{(trans,trans)-3,5-bis(phenylcarbonyl)-4-[3-(hydroxymethyl)phenyl]piperidyl}-N,N-dimethylacetamide |
| 470.56 | 472.2 | (M + 1) | 2-[(trans,trans)-3,5-bis(phenylcarbonyl)-4-(2-hydroxyphenyl)piperidyl]-N,N-dimethylacetamide |
| 470.56 | 471.4 | (M + 1) | 2-[(trans,trans)-3,5-bis(phenylcarbonyl)-4-(3-hydroxyphenyl)piperidyl]-N,N-dimethylacetamide |
| 455.55 | 228.5 (100%) 456.3 (45%) | (M + 2)2 + (M + 1) | 2-[(trans,trans)-3,5-bis(phenylcarbonyl)-4-(3-pyridyl)piperidyl]-N,N-dimethylacetamide |
| 455.55 | 456.4 | (M + 1) | 2-[(trans,trans)-3,5-bis(phenylcarbonyl)-4-(2-pyridyl)piperidyl]-N,N-dimethylacetamide |
| 461.58 | 462.3 | (M + 1) | 2-[(trans,trans)-3,5-bis(phenylcarbonyl)-4-(1,3-thiazol-4-yl)piperidyl]-N,N-dimethylacetamide |
| 461.58 | 462.3 | (M + 1) | 2-[(trans,trans)-3,5-bis(phenylcarbonyl)-4-(1,3-thiazol-2-yl)piperidyl]-N,N-dimethylacetamide |
| 459.54 | 460.4 | (M + 1) | 2-[(trans,trans)-3,5-bis(phenylcarbonyl)-4-(5-methylisoxazol-3-yl)piperidyl]-N,N-dimethylacetamide |
| 475.6 | 576.5 | (M + 1) | 2-[(trans,trans)-3,5-bis(phenylcarbonyl)-4-(4-methyl(1,3-thiazol-2-yl))piperidyl]-N,N-dimethylacetamide |
| 490.57 | 491.4 | (M + 1) | (trans,trans)-1-(2-amino-isopropyl)-4-(3-fluoro-2-methylphenyl)-5-[(3-hydroxyphenyl)carbonyl](3-piperidyl) 3-hydroxyphenyl ketone |
| 504.59 | 505.6 | (M + 1) | (trans,trans)-1-(2-amino-tert-butyl)-4-(3-fluoro-2-methylphenyl)-5-[(3-hydroxyphenyl)carbonyl](3-piperidyl) 3-hydroxyphenyl ketone |
| 601.71 | 602.6 | (M + 1) | 2-{(trans,trans)-3,5-bis[(3-hydroxyphenyl)carbonyl]-4-(3-fluoro-2-methylphenyl)piperidyl}-2-methyl-1-(4-methylpiperazinyl)propan-1-one |
| 532.65 | 533.6 | (M + 1) | (trans,trans)-1-[2-(dimethylamino)-tert-butyl]-4-(3-fluoro-2-methylphenyl)-5-[(3-hydroxyphenyl)carbonyl](3-piperidyl) 3-hydroxyphenyl ketone |
| 575.67 | 576.7 | (M + 1) | 2-{(trans,trans)-3,5-bis[(3-hydroxyphenyl)carbonyl]-4-(3-fluoro-2-methylphenyl)piperidyl}-N-[2-(dimethylamino)ethyl]propanamide |
| 591.67 | 592.6 | (M + 1) | 2-{(trans,trans)-3,5-bis[(3-hydroxyphenyl)carbonyl]-4-(3-fluoro-2-methylphenyl)piperidyl}-N-[2-(dimethylamino)ethyl]-3-hydroxypropanamide |
| 519.56 | 520.5 | (M + 1) | (2R)-3-amino-2-{3,5-bis[(3-hydroxyphenyl)carbonyl]-4-(3-fluoro-2-methylphenyl)piperidyl}propanamide |
| 519.56 | 520.5 | (M + 1) | (2S)-2-{(trans,trans)-3,5-bis[(3-hydroxyphenyl)carbonyl]-4-(3-fluoro-2-methylphenyl)piperidyl}-3-aminopropanamide |
| 603.68 | 604.7 | (M + 1) | 2-{(trans,trans)-3,5-bis[(3-hydroxyphenyl)carbonyl]-4-(3-fluoro-2-methylphenyl)piperidyl}-3-hydroxy-1-(4-methylpiperazinyl)propan-1-one |
| 602.7 | 603.7 | (M + 1) | (2R)-2-{(trans,trans)-3,5-bis[(3-hydroxyphenyl)carbonyl]-4-(3-fluoro-2-methylphenyl)piperidyl}-3-amino-1-(4-methylpiperazinyl)propan-1-one |
| 602.7 | 603.7 | (M + 1) | (2S)-2-{(trans,trans)-3,5-bis[(3-hydroxyphenyl)carbonyl]-4-(3-fluoro-2-methylphenyl)piperidyl}-3-amino-1-(4-methylpiperazinyl)propan-1-one |
| 427.53 | 427 | (M + 1) | (trans,trans)-1-(2-hydroxyethyl)-4-(4-methylphenyl)-5-(phenylcarbonyl)(3-piperidyl)phenyl ketone |
| 580.46 | 581.5 | (M + 1) | 2-[(trans,trans)-3,5-bis(phenylcarbonyl)-4-(3-iodophenyl)piperidyl]-N,N-dimethylacetamide |
| 484.59 | 485 | (M + 1) | 2-[(trans,trans)-3,5-bis(phenylcarbonyl)-4-(2-methoxyphenyl)piperidyl]-N,N-dimethylacetamide |
| 522.56 | 523.5 | (M + 1) | 2-{(trans,trans)-3,5-bis(phenylcarbonyl)-4-[2-(trifluoromethyl)phenyl]piperidyl}-N,N-dimethylacetamide |
| 587.68 | 294.7 (100%) 588.5 (95%) | (M + 2)2 + (M + 1) | 2-{3,5-bis[(3-hydroxyphenyl)carbonyl]-4-(3-fluoro-2-methylphenyl)piperidyl}-1-(4-methylpiperazinyl)propan-1-one |
| 519.6 | | | 1-((2S)-2-methoxypropyl)(trans,trans)-4-(3-fluoro-2-methylphenyl)-5-[(3-methoxyphenyl)carbonyl](3-piperidyl) 3-methoxyphenyl ketone |
| 491.55 | | | 1-((1R)-2-hydroxy-isopropyl)(trans,trans)-4-(3-fluoro-2-methylphenyl)-5-[(3-hydroxyphenyl)carbonyl](3-piperidyl) 3-hydroxyphenyl ketone |
| 475.6 | | | 2-[(trans,trans)-3,5-bis(phenylcarbonyl)-4-(2-methyl(1,3-thiazol-4-yl))piperidyl]-N,N-dimethylacetamide |
| 561.64 | | | 2-{(trans,trans)-3,5-bis[(3-hydroxyphenyl)carbonyl]-4-(3-fluoro-2-methylphenyl)piperidyl}-N-[2-(dimethylamino)ethyl]acetamide |
| 518.62 | | | (trans,trans)-1-[2-(dimethylamino)-isopropyl]-4-(3-fluoro-2-methylphenyl)-5-[(3-hydroxyphenyl)carbonyl](3-piperidyl) 3-hydroxyphenyl ketone |
| 559.63 | | | 2-{(trans,trans)-3,5-bis[(3-hydroxyphenyl)carbonyl]-4-(3-fluoro-2-methylphenyl)piperidyl}-1-piperazinylethan-1-one |

-continued

| Object MW | m/z Value | Ion | Chemical Name |
|---|---|---|---|
| 630.75 | | | 2-{(trans,trans)-3,5-bis[(3-hydroxyphenyl)carbonyl]-4-(3-fluoro-2-methylphenyl)piperidyl}-3-(dimethylamino)-1-(4-methylpiperazinyl)propan-1-one |
| 630.75 | | | (2S)-2-{(trans,trans)-3,5-bis[(3-hydroxyphenyl)carbonyl]-4-(3-fluoro-2-methylphenyl)piperidyl}-3-(dimethylamino)-1-(4-methylpiperazinyl)propan-1-one |
| 668.78 | | | (2R)-2-{(trans,trans)-3,5-bis[(3-hydroxyphenyl)carbonyl]-4-(3-fluoro-2-methylphenyl)piperidyl}-N-[2-(dimethylammo)ethyl]-3-[(methylsulfonyl)amino]propanamide |
| 680.79 | | | (2R)-2-{(trans,trans)-3,5-bis[(3-hydroxyphenyl)carbonyl]-4-(3-fluoro-2-methylphenyl)piperidyl}-1-(4-methylpiperazinyl)-3-[(methylsulfonyl)amino]propan-1-one |
| 680.79 | | | (2S)-2-{(trans,trans)-3,5-bis[(3-hydroxyphenyl)carbonyl]-4-(3-fluoro-2-methylphenyl)piperidyl}-1-(4-methylpiperazinyl)-3-[(methylsulfonyl)amino]propan-1-one |
| 573.65 | | | 2-{(trans,trans)-3,5-bis[(3-hydroxyphenyl)carbonyl]-4-(3-fluoro-2-methylphenyl)piperidyl}-1-(4-methylpiperazinyl)ethan-1-one |

| Object MW | m/z Value | Ion | Chemical Name |
|---|---|---|---|
| 577.65 | 578.3 | (M + 1) | (2S)-2-(trifluoromethyl)pyrrolidinyl (trans,trans)-1-[4-(dimethylamino)butyl]-4-(3-fluoro-2-methylphenyl)-5-[(3-hydroxyphenyl)carbonyl](3-piperidyl) ketone |
| 613.66 | 614.2 | (M + 1) | (2R)-2-(trifluoromethyl)pyrrolidinyl (trans,trans)-4-(3-fluoro-2-methylphenyl)-5-[(3-hydroxyphenyl)carbonyl]-1-{2-[methyl(methylsulfonyl)amino]ethyl}(3-piperidyl) ketone |
| 613.66 | 614.1 | (M + 1) | (2S)-2-(trifluoromethyl)pyrrolidinyl (trans,trans)-4-(3-fluoro-2-methylphenyl)-5-[(3-hydroxyphenyl)carbonyl]-1-{2-[methyl(methylsulfonyl)amino]ethyl}(3-piperidyl) ketone |
| 619.69 | 620 | (M + 1) | 5-{[(2S)-2-(trifluoromethyl)pyrrolidinyl]carbonyl}(trans,trans)-4-(3-fluoro-2-methylphenyl)-1-[1-(2-methoxyethyl)(4-piperidyl)](3-piperidyl) 3-hydroxyphenyl ketone |
| 575.64 | 576 | (M + 1) | 5-{[(2S)-2-(trifluoromethyl)pyrrolidinyl]carbonyl}(trans,trans)-4-(3-fluoro-2-methylphenyl)-1-(1-methyl(4-piperidyl))(3-piperidyl) 3-hydroxyphenyl ketone |
| 613.66 | 614.2 | (M + 1) | (2S)-2-(trifluoromethyl)pyrrolidinyl (trans,trans)-4-(3-fluoro-2-methylphenyl)-5-[(3-hydroxyphenyl)carbonyl]-1-{2-[methyl(methylsulfonyl)amino]ethyl}(3-piperidyl) ketone |
| 607.68 | 608.3 | (M + 1) | (2R)-2-(trifluoromethyl)pyrrolidinyl (trans,trans)-4-(3-fluoro-2-methylphenyl)-1-{2-[(2-hydroxyethyl)(methylethyl)amino]ethyl}-5-[(3-hydroxyphenyl)carbonyl](3-piperidyl) ketone |
| 577.65 | 578.3 | (M + 1) | (2S)-2-(trifluoromethyl)pyrrolidinyl (trans,trans)-1-[2-(diethylamino)ethyl]-4-(3-fluoro-2-methylphenyl)-5-[(3-hydroxyphenyl)carbonyl](3-piperidyl) ketone |
| 593.71 | 594.3 | (M + 1) | (trans,trans)-4-(3-fluoro-2-methylphenyl)-5-[(3-hydroxyphenyl)carbonyl]-1-{2-[methyl(methylsulfonyl)amino]ethyl}(3-piperidyl) indolinyl ketone |
| 605.66 | 606 | (M + 1) | 5-{[(2S)-2-(trifluoromethyl)pyrrolidinyl]carbonyl}(trans,trans)-4-(3-fluoro-2-methylphenyl)-1-[1-(2-hydroxyethyl)(4-piperidyl)](3-piperidyl) 3-hydroxyphenyl ketone |
| 682.77 | 683.3 | (M + 1) | (2S)-2-(trifluoromethyl)pyrrolidinyl (trans,trans)-1-{2-[4-(ethylsulfonyl)piperazmyl]ethyl}-4-(3-fluoro-2-methylphenyl)-5-[(3-hydroxyphenyl)carbonyl](3-piperidyl) ketone |
| 561.61 | 562.3 | (M + 1) | (2S)-2-(trifluoromethyl)pyrrolidinyl (trans,trans)-1-(2-azetidinylethyl)-4-(3-fluoro-2-methylphenyl)-5-[(3-hydroxyphenyl)carbonyl](3-piperidyl) ketone |
| 549.6 | 550.2 | (M + 1) | (2S)-2-(trifluoromethyl)pyrrolidinyl (trans,trans)-1-[2-(dimethylamino)ethyl]-4-(3-fluoro-2-methylphenyl)-5-[(3-hydroxyphenyl)carbonyl](3-piperidyl) ketone |
| 549.6 | 550.2 | (M + 1) | (2S)-2-(trifluoromethyl)pyrrolidinyl (trans,trans)-1-[2-(dimethylamino)ethyl]-4-(3-fluoro-2-methylphenyl)-5-[(3-hydroxyphenyl)carbonyl](3-piperidyl) ketone |
| 549.6 | 550.2 | (M + 1) | (2R)-2-(trifluoromethyl)pyrrolidinyl (trans,trans)-1-[2-(dimethylamino)ethyl]-4-(3-fluoro-2-methylphenyl)-5-[(3-hydroxyphenyl)carbonyl](3-piperidyl) ketone |
| 557.68 | 558.1 | (M + 1) | (trans,trans)-4-(3-fluoro-2-methylphenyl)-5-[(3-hydroxyphenyl)carbonyl]-1-{2-[methyl(methylsulfonyl)amino]ethyl}(3-piperidyl) 1,2,5,6-tetrahydropyridyl ketone |

-continued

| Object MW | m/z Value | Ion | Chemical Name |
|---|---|---|---|
| 535.57 | 536.2 | (M + 1) | (2S)-2-(trifluoromethyl)pyrrolidinyl (trans,trans)-4-(3-fluoro-2-methylphenyl)-5-[(3-hydroxyphenyl)carbonyl]-1-[2-(methylamino)ethyl](3-piperidyl) ketone |
| 573.72 | 574.3 | (M + 1) | (trans,trans)-4-(3-fluoro-2-methylphenyl)-5-[(3-hydroxyphenyl)carbonyl]-1-{2-[methyl(methylsulfonyl)amino]ethyl}(3-piperidyl) 2-methylpiperidyl ketone |
| 478.48 | 479.2 | (M + 1) | (2S)-2-(trifluoromethyl)pyrrolidinyl (trans,trans)-4-(3-fluoro-2-methylphenyl)-5-[(3-hydroxyphenyl)carbonyl](3-piperidyl) ketone |
| 573.72 | 574.1 | (M + 1) | (trans,trans)-4-(3-fluoro-2-methylphenyl)-5-[(3-hydroxyphenyl)carbonyl]-1-{2-[methyl(methylsulfonyl)amino]ethyl}(3-piperidyl) 3-methylpiperidyl ketone |
| 482.59 | 483.2 | (M + 1) | (trans,trans)-4-(3-fluoro-2-methylphenyl)-1-(2-hydroxy-isopropyl)-5-[(3-hydroxyphenyl)carbonyl](3-piperidyl) piperidyl ketone |
| 559.69 | 560.3 | (M + 1) | (trans,trans)-4-(3-fluoro-2-methylphenyl)-5-[(3-hydroxyphenyl)carbonyl]-1-{2-[methyl(methylsulfonyl)amino]ethyl}(3-piperidyl) piperidyl ketone |
| 496.61 | 497.3 | (M + 1) | (trans,trans)-4-(3-fluoro-2-methylphenyl)-1-(2-hydroxy-2-methylpropyl)-5-[(3-hydroxyphenyl)carbonyl](3-piperidyl) piperidyl ketone |
| 510.64 | 511.3 | (M + 1) | (trans,trans)-4-(3-fluoro-2-methylphenyl)-1-(5-hydroxypentyl)-5-[(3-hydroxyphenyl)carbonyl](3-piperidyl) piperidyl ketone |
| 496.61 | 497.3 | (M + 1) | (trans,trans)-4-(3-fluoro-2-methylphenyl)-5-[(3-hydroxyphenyl)carbonyl]-1-(2-methoxyethyl)(3-piperidyl) azaperhydroepinyl ketone |
| 482.59 | 483.3 | (M + 1) | (trans,trans)-4-(3-fluoro-2-methylphenyl)-1-(2-hydroxyethyl)-5-[(3-hydroxyphenyl)carbonyl](3-piperidyl) azaperhydroepinyl ketone |
| 567.67 | 568.1 | (M + 1) | ((trans,trans)-4-(3-fluoro-2-methylphenyl)-5-[(3-hydroxyphenyl)carbonyl]-1-{2-[methyl(methylsulfonyl)amino]ethyl}(3-piperidyl))-N-benzamide |
| 587.75 | 588.2 | (M + 1) | (trans,trans)-4-(3-fluoro-2-methylphenyl)-5-[(3-hydroxyphenyl)carbonyl]-1-{2-[methyl(methylsulfonyl)amino]ethyl}(3-piperidyl) 3,3-dimethylpiperidyl ketone |
| 539.64 | 540.2 | (M + 1) | N-(2-{(trans,trans)-4-(3-fluoro-2-methylphenyl)-3-[(3-hydroxyphenyl)carbonyl]-5-(piperidylcarbonyl)piperidyl}ethyl)methoxy-N-methylcarboxamide |
| 482.59 | 483.3 | (M + 1) | (trans,trans)-4-(3-fluoro-2-methylphenyl)-5-[(3-hydroxyphenyl)carbonyl]-1-(2-methoxyethyl)(3-piperidyl) piperidyl ketone |
| 496.61 | 497.3 | (M + 1) | (trans,trans)-4-(3-fluoro-2-methylphenyl)-1-(3-hydroxybutyl)-5-[(3-hydroxyphenyl)carbonyl](3-piperidyl) piperidyl ketone |
| 573.72 | 574.3 | (M + 1) | (trans,trans)-4-(3-fluoro-2-methylphenyl)-5-[(3-hydroxyphenyl)carbonyl]-1-{2-[methyl(methylsulfonyl)amino]ethyl}(3-piperidyl) azaperhydroepinyl ketone |
| 625.71 | 626.2 | (M + 1) | methyl 2-[((trans,trans)-4-(3-fluoro-2-methylphenyl)-5-[(3-hydroxyphenyl)carbonyl]-1-{2-[methyl(methylsulfonyl)amino]ethyl}-3-piperidyl)carbonylamino]benzoate |
| 587.75 | 588.3 | (M + 1) | (trans,trans)-4-(3-fluoro-2-methylphenyl)-5-[(3-hydroxyphenyl)carbonyl]-1-{2-[methyl(methylsulfonyl)amino]ethyl}(3-piperidyl) azaperhydroocinyl ketone |
| 545.67 | 546.3 | (M + 1) | (trans,trans)-4-(3-fluoro-2-methylphenyl)-5-[(3-hydroxyphenyl)carbonyl]-1-{2-[(methylsulfonyl)amino]ethyl}(3-piperidyl) piperidyl ketone |
| 474.57 | 475.2 | (M + 1) | [(trans,trans)-4-(3-fluoro-2-methylphenyl)-1-(2-methoxyethyl)-5-(phenylcarbonyl)(3-piperidyl)]-N-benzamide |
| 595.67 | 596.3 | (M + 1) | (trans,trans)-4-(3-fluoro-2-methylphenyl)-5-[(3-hydroxyphenyl)carbonyl]-1-{2-[methyl(methylsulfonyl)amino]ethyl}(3-piperidyl) 3,3-difluoropiperidyl ketone |
| 466.59 | 467.3 | (M + 1) | (trans,trans)-4-(3-fluoro-2-methylphenyl)-1-(2-methoxyethyl)-5-(phenylcarbonyl)(3-piperidyl) piperidyl ketone |
| 617.73 | 618.2 | (M + 1) | methyl 1-[((trans,trans)-4-(3-fluoro-2-methylphenyl)-5-[(3-hydroxyphenyl)carbonyl]-1-{2-[methyl(methylsulfonyl)amino]ethyl}-3-piperidyl)carbonyl]piperidine-2-carboxylate |
| 468.56 | 469.3 | (M + 1) | (trans,trans)-4-(3-fluoro-2-methylphenyl)-1-(2-hydroxyethyl)-5-[(3-hydroxyphenyl)carbonyl](3-piperidyl) piperidyl ketone |

-continued

| Object MW | m/z Value | Ion | Chemical Name |
|---|---|---|---|
| 571.7 | 572.1 | (M + 1) | (trans,trans)-4-(3-fluoro-2-methylphenyl)-5-[(3-hydroxyphenyl)carbonyl]-1-{2-[methyl(methylsulfonyl)amino]ethyl}(3-piperidyl) 2-azabicyclo[2.2.1]hept-2-yl ketone |
| 595.67 | 596.2 | (M + 1) | (trans,trans)-4-(3-fluoro-2-methylphenyl)-5-[(3-hydroxyphenyl)carbonyl]-1-{2-[methyl(methylsulfonyl)amino]ethyl}(3-piperidyl) 4,4-difluoropiperidyl ketone |
| 534.59 | 535.3 | (M + 1) | (trans,trans)-4-(3-fluoro-2-methylphenyl)-5-[(3-hydroxyphenyl)carbonyl]-1-(4,4,4-trifluorobutyl)(3-piperidyl) piperidyl ketone |
| 577.68 | 578.1 | (M + 1) | (trans,trans)-4-(3-fluoro-2-methylphenyl)-5-[(3-hydroxyphenyl)carbonyl]-1-{2-[methyl(methylsulfonyl)amino]ethyl}(3-piperidyl) 3-fluoropiperidyl ketone |
| 573.72 | 574.2 | (M + 1) | (trans,trans)-4-(3-fluoro-2-methylphenyl)-5-[(3-hydroxyphenyl)carbonyl]-1-{2-[methyl(methylsulfonyl)amino]ethyl}(3-piperidyl) 4-methylpiperidyl ketone |
| 549.6 | 550.3 | (M + 1) | (2S)-2-(trifluoromethyl)pyrrolidinyl (trans,trans)-1-[2-(dimethylamino)ethyl]-4-(3-fluoro-2-methylphenyl)-5-[(3-hydroxyphenyl)carbonyl](3-piperidyl) ketone |
| 613.66 | 614.3 | (M + 1) | (2R)-2-(trifluoromethyl)pyrrolidinyl (trans,trans)-4-(3-fluoro-2-methylphenyl)-5-[(3-hydroxyphenyl)carbonyl]-1-{2-[methyl(methylsulfonyl)amino]ethyl}(3-piperidyl) ketone |
| 631.76 | 632.2 | (M + 1) | ethyl 1-[((trans,trans)-4-(3-fluoro-2-methylphenyl)-5-[(3-hydroxyphenyl)carbonyl]-1-{2-[methyl(methylsulfonyl)amino]ethyl}-3-piperidyl)carbonyl]piperidine-3-carboxylate |
| 543.65 | 544.1 | (M + 1) | (trans,trans)-4-(3-fluoro-2-methylphenyl)-5-[(3-hydroxyphenyl)carbonyl]-1-{2-[methyl(methylsulfonyl)amino]ethyl}(3-piperidyl) 3-pyrrolinyl ketone |
| 468.56 | 469.3 | (M + 1) | (trans,trans)-4-(3-fluoro-2-methylphenyl)-5-[(3-hydroxyphenyl)carbonyl]-1-(2-methoxyethyl)(3-piperidyl) pyrrolidinyl ketone |
| 559.69 | 560.3 | (M + 1) | (trans,trans)-4-(3-fluoro-2-methylphenyl)-5-[(3-hydroxyphenyl)carbonyl]-1-{2-[methyl(methylsulfonyl)amino]ethyl}(3-piperidyl) 2-methylpyrrolidinyl ketone |
| 589.72 | 590.2 | (M + 1) | (trans,trans)-4-(3-fluoro-2-methylphenyl)-5-[(3-hydroxyphenyl)carbonyl]-1-{2-[methyl(methylsulfonyl)amino]ethyl}(3-piperidyl) 2-(methoxymethyl)pyrrolidinyl ketone |
| 593.71 | 594.3 | (M + 1) | (trans,trans)-4-(3-fluoro-2-methylphenyl)-5-[(3-hydroxyphenyl)carbonyl]-1-{2-[methyl(methylsulfonyl)amino]ethyl}(3-piperidyl) isoindolin-2-yl ketone |
| 539.6 | 540.3 | (M + 1) | N-(2-{(trans,trans)-4-(3-fluoro-2-methylphenyl)-3-[(3-hydroxyphenyl)carbonyl]-5-(piperidylcarbonyl)piperidyl}-2-oxoethyl)methoxycarboxamide |
| 482.54 | 483.3 | (M + 1) | methyl (trans,trans)-4-(3-fluoro-2-methylphenyl)-3-[(3-hydroxyphenyl)carbonyl]-5-(piperidylcarbonyl)piperidinecarboxylate |
| 514.59 | 515.2 | (M + 1) | ethyl 2-({(trans,trans)-4-(3-fluoro-2-methylphenyl)-5-[(3-hydroxyphenyl)carbonyl]-1-(2-methoxyethyl)(3-piperidyl)}-N-methylcarbonylamino)acetate |
| 466.54 | 467.3 | (M + 1) | (trans,trans)-1-acetyl-4-(3-fluoro-2-methylphenyl)-3-[(3-hydroxyphenyl)carbonyl]-5-(piperidylcarbonyl)piperidine |
| 573.6 | 574.1 | (M + 1) | ((trans,trans)-4-(3-fluoro-2-methylphenyl)-5-[(3-hydroxyphenyl)carbonyl]-1-{2-[methyl(methylsulfonyl)amino]ethyl}(3-piperidyl))-N-(2,2,2-trifluoroethyl)carboxamide |
| 587.75 | 588.2 | (M + 1) | (trans,trans)-4-(3-fluoro-2-methylphenyl)-5-[(3-hydroxyphenyl)carbonyl]-1-{2-[methyl(methylsulfonyl)amino]ethyl}(3-piperidyl) 4,4-dimethylpiperidyl ketone |
| 452.56 | 453.3 | (M + 1) | (trans,trans)-4-(3-fluoro-2-methylphenyl)-1-(2-methoxyethyl)-5-(phenylcarbonyl)(3-piperidyl) pyrrolidinyl ketone |
| 549.6 | 550.2 | (M + 1) | (2R)-2-(trifluoromethyl)pyrrolidinyl (trans,trans)-1-[2-(dimethylamino)ethyl]-4-(3-fluoro-2-methylphenyl)-5-[(3-hydroxyphenyl)carbonyl](3-piperidyl) ketone |
| 454.53 | 455.3 | (M + 1) | (trans,trans)-4-(3-fluoro-2-methylphenyl)-1-(2-hydroxyethyl)-5-[(3-hydroxyphenyl)carbonyl](3-piperidyl) pyrrolidinyl ketone |
| 424.51 | 425.1 | (M + 1) | (trans,trans)-4-(3-fluoro-2-methylphenyl)-5-[(3-hydroxyphenyl)carbonyl](3-piperidyl) piperidyl ketone |

-continued

| Object MW | m/z Value | Ion | Chemical Name |
|---|---|---|---|
| 480.61 | 481.3 | (M + 1) | (trans,trans)-4-(3-fluoro-2-methylphenyl)-1-(2-methoxyethyl)-5-(phenylcarbonyl)(3-piperidyl) azaperhydroepinyl ketone |
| 482.59 | 483.3 | (M + 1) | (trans,trans)-4-(3-fluoro-2-methylphenyl)-1-(2-methoxyethyl)-5-(phenylcarbonyl)(3-piperidyl) 3-hydroxypiperidyl ketone |
| 557.68 | 558.3 | (M + 1) | ((trans,trans)-4-(3-fluoro-2-methylphenyl)-5-[(3-hydroxyphenyl)carbonyl]-1-{2-[methyl(methylsulfonyl)amino]ethyl}(3-piperidyl))-N-cyclopent-3-enylcarboxamide |
| 488.54 | 489.3 | (M + 1) | (trans,trans)-4-(3-fluoro-2-methylphenyl)-1-(2-methoxyethyl)-5-(phenylcarbonyl)(3-piperidyl) 3,3-difluoropyrrolidinyl ketone |
| 470.58 | 471.3 | (M + 1) | {(trans,trans)-4-(3-fluoro-2-methylphenyl)-5-[(3-hydroxyphenyl)carbonyl]-1-(2-methoxyethyl)(3-piperidyl)}-N-methyl-N-propylcarboxamide |
| 571.7 | 572.2 | (M + 1) | (trans,trans)-4-(3-fluoro-2-methylphenyl)-5-[(3-hydroxyphenyl)carbonyl]-1-{2-[methyl(methylsulfonyl)amino]ethyl}(3-piperidyl) 7-azabicyclo[2.2.1]hept-7-yl ketone |
| 498.59 | 499.3 | (M + 1) | (trans,trans)-4-(3-fluoro-2-methylphenyl)-5-[(3-hydroxyphenyl)carbonyl]-1-(2-methoxyethyl)(3-piperidyl) 3-hydroxypiperidyl ketone |
| 520.56 | 521.3 | (M + 1) | (trans,trans)-4-(3-fluoro-2-methylphenyl)-1-(2-methoxyethyl)-5-(phenylcarbonyl)(3-piperidyl) 3-(trifluoromethyl)pyrrolidinyl ketone |
| 480.61 | 481.3 | (M + 1) | [(trans,trans)-4-(3-fluoro-2-methylphenyl)-1-(2-methoxyethyl)-5-(phenylcarbonyl)(3-piperidyl)]-N-cyclohexylcarboxamide |
| 454.58 | 455.3 | (M + 1) | [(trans,trans)-4-(3-fluoro-2-methylphenyl)-1-(2-methoxyethyl)-5-(phenylcarbonyl)(3-piperidyl)]-N-methyl-N-propylcarboxamide |
| 635.79 | 636.2 | (M + 1) | (trans,trans)-4-(3-fluoro-2-methylphenyl)-5-[(3-hydroxyphenyl)carbonyl]-1-{2-[methyl(methylsulfonyl)amino]ethyl}(3-piperidyl) 2-phenylpiperidyl ketone |
| 496.61 | 497.3 | (M + 1) | (trans,trans)-4-(3-fluoro-2-methylphenyl)-1-(2-methoxyethyl)-5-(phenylcarbonyl)(3-piperidyl) 2-(hydroxymethyl)piperidyl ketone |
| 494.64 | 495.3 | (M + 1) | [(trans,trans)-4-(3-fluoro-2-methylphenyl)-1-(2-methoxyethyl)-5-(phenylcarbonyl)(3-piperidyl)]-N-cyclohexyl-N-methylcarboxamide |
| 581.7 | 582.2 | (M + 1) | ((trans,trans)-4-(3-fluoro-2-methylphenyl)-5-[(3-hydroxyphenyl)carbonyl]-1-{2-[methyl(methylsulfonyl)amino]ethyl}(3-piperidyl))-N-methyl-N-benzamide |
| 481.56 | 482.1 | (M + 1) | 1-{(trans,trans)-4-(3-fluoro-2-methylphenyl)-3-[(3-hydroxyphenyl)carbonyl]-5-(piperidylcarbonyl)piperidyl}-2-aminoethan-1-one |
| 534.59 | 535.3 | (M + 1) | (trans,trans)-4-(3-fluoro-2-methylphenyl)-1-(2-methoxyethyl)-5-(phenylcarbonyl)(3-piperidyl) 3-(trifluoromethyl)piperidyl ketone |
| 635.79 | 636.3 | (M + 1) | (trans,trans)-4-(3-fluoro-2-methylphenyl)-5-[(3-hydroxyphenyl)carbonyl]-1-{2-[methyl(methylsulfonyl)amino]ethyl}(3-piperidyl) 3-phenylpiperidyl ketone |
| 607.74 | 608.1 | (M + 1) | (trans,trans)-4-(3-fluoro-2-methylphenyl)-5-[(3-hydroxyphenyl)carbonyl]-1-{2-[methyl(methylsulfonyl)amino]ethyl}(3-piperidyl) 1,2,3,4-tetrahydroquinolyl ketone |
| 442.55 | 443 | (M + 1) | [(trans,trans)-4-phenyl-5-(phenylcarbonyl)-1-benzyl(3-piperidyl)]-N-methoxy-N-methylcarboxamide |
| 607.74 | 608.3 | (M + 1) | (trans,trans)-4-(3-fluoro-2-methylphenyl)-5-[(3-hydroxyphenyl)carbonyl]-1-{2-[methyl(methylsulfonyl)amino]ethyl}(3-piperidyl) 2-1,2,3,4-tetrahydroisoquinolyl ketone |
| 603.7 | 604.1 | (M + 1) | methyl 1-[((trans,trans)-4-(3-fluoro-2-methylphenyl)-5-[(3-hydroxyphenyl)carbonyl]-1-{2-[methyl(methylsulfonyl)amino]ethyl}-3-piperidyl)carbonyl]pyrrolidine-2-carboxylate |
| 496.61 | 497.3 | (M + 1) | (trans,trans)-4-(3-fluoro-2-methylphenyl)-1-(2-methoxyethyl)-5-(phenylcarbonyl)(3-piperidyl) 3,5-dimethylmorpholin-4-yl ketone |
| 468.56 | 469.3 | (M + 1) | (trans,trans)-4-(3-fluoro-2-methylphenyl)-1-(2-methoxyethyl)-5-(phenylcarbonyl)(3-piperidyl) morpholin-4-yl ketone |
| 438.53 | 439.3 | (M + 1) | (trans,trans)-4-(3-fluoro-2-methylphenyl)-1-(2-methoxyethyl)-5-(phenylcarbonyl)(3-piperidyl) azetidinyl ketone |
| 484.56 | 485.3 | (M + 1) | (trans,trans)-4-(3-fluoro-2-methylphenyl)-1-(2-hydroxyethyl)-5-[(3-hydroxyphenyl)carbonyl](3-piperidyl) 3-hydroxypiperidyl ketone |
| 534.59 | 535.3 | (M + 1) | (trans,trans)-4-(3-fluoro-2-methylphenyl)-1-(2-methoxyethyl)-5-(phenylcarbonyl)(3-piperidyl) 4-(trifluoromethyl)piperidyl ketone |
| 468.56 | 469.3 | (M + 1) | (trans,trans)-4-(3-fluoro-2-methylphenyl)-1-(2-methoxyethyl)-5-(phenylcarbonyl)(3-piperidyl) 3-hydroxypyrrolidinyl ketone |

-continued

| Object MW | m/z Value | Ion | Chemical Name |
|---|---|---|---|
| 470.58 | 471.3 | (M + 1) | [(trans,trans)-4-(3-fluoro-2-methylphenyl)-1-(2-methoxyethyl)-5-(phenylcarbonyl)(3-piperidyl)]-N-(2-methoxyethyl)-N-methylcarboxamide |
| 587.75 | 588.2 | (M + 1) | ((trans,trans)-4-(3-fluoro-2-methylphenyl)-5-[(3-hydroxyphenyl)carbonyl]-1-{2-[methyl(methylsulfonyl)amino]ethyl}(3-piperidyl))-N-(3-methylcyclohexyl)carboxamide |
| 456.55 | 457.3 | (M + 1) | [(trans,trans)-4-(3-fluoro-2-methylphenyl)-1-(2-methoxyethyl)-5-(phenylcarbonyl)(3-piperidyl)]-N-(2-hydroxyethyl)-N-methylcarboxamide |
| 454.58 | 455.3 | (M + 1) | [(trans,trans)-4-(3-fluoro-2-methylphenyl)-1-(2-methoxyethyl)-5-(phenylcarbonyl)(3-piperidyl)]-N-(tert-butyl)carboxamide |
| 472.55 | 473.3 | (M + 1) | {(trans,trans)-4-(3-fluoro-2-methylphenyl)-5-[(3-hydroxyphenyl)carbonyl]-1-(2-methoxyethyl)(3-piperidyl)}-N-(2-hydroxyethyl)-N-methylcarboxamide |
| 514.63 | 515.3 | (M + 1) | (trans,trans)-4-(3-fluoro-2-methylphenyl)-1-(2-methoxyethyl)-5-(phenylcarbonyl)(3-piperidyl) 2-1,2,3,4-tetrahydroisoquinolyl ketone |
| 602.72 | 603.1 | (M + 1) | {1-[((trans,trans)-4-(3-fluoro-2-methylphenyl)-5-[(3-hydroxyphenyl)carbonyl]-1-{2-[methyl(methylsulfonyl)amino]ethyl}(3-piperidyl))carbonyl]pyrrolidin-2-yl}-N-methylcarboxamide |
| 426.52 | 427.3 | (M + 1) | [(trans,trans)-4-(3-fluoro-2-methylphenyl)-1-(2-methoxyethyl)-5-(phenylcarbonyl)(3-piperidyl)]-N,N-dimethylcarboxamide |
| 429.48 | 444.2 | (M + 1) | ethyl (trans,trans)-4-(3-fluoro-2-methylphenyl)-5-[(3-hydroxyphenyl)carbonyl]-1-(2-methoxyethyl)piperidine-3-carboxylate |
| 427.51 | 428.2 | (M + 1) | ethyl (trans,trans)-4-(3-fluoro-2-methylphenyl)-1-(2-methoxyethyl)-5-(phenylcarbonyl)piperidine-3-carboxylate |
| 442.52 | 443.2 | (M + 1) | [(trans,trans)-4-(3-fluoro-2-methylphenyl)-1-(2-methoxyethyl)-5-(phenylcarbonyl)(3-piperidyl)]-N-(2-hydroxyethyl)carboxamide |

Example 13

Cellular IC50s

In vitro potency of small molecule inhibitors is determined by assaying human ovarian cancer cells (SKOV3) for viability following a 72-hour exposure to a 10-point dilution series of compound. Cell viability is determined by measuring the absorbance of formazon, a product formed by the bioreduction of MTS/PMS, a commercially available reagent. Each point on the dose-response curve is calculated as a percent of untreated control cells at 72 hours minus background absorption (complete growth inhibition).

Materials and Solutions:

Cells: SKOV3, Ovarian Cancer (human)

Media: RPMI medium+5% Fetal Bovine Serum+2 mM L-glutamine

Colorimetric Agent for Determining Cell Viability: Promega MTS tetrazolium compound.

Control Compound for max cell kill: Topotecan, 1 uM

Procedure:

Day 1—Cell Plating

1. Wash adherent SKOV3 cells in a T175 Flask with 10 mLs of PBS and add 2 mLs of 0.25% trypsin. Incubate for 5 minutes at 37° C. Rinse cells from flask using 8 mL of media (RPMI medium+5% FBS) and transfer to fresh 50 mL sterile conical. Determine cell concentration by adding 100 uL of cell suspension to 900 uL of ViaCount reagent (Guava Technology), an isotonic diluent in a micro-centrifuge tube. Place vial in Guava cell counter and set readout to acquire. Record cell count and calculate the appropriate volume of cells to achieve 300 cells/20 uL.
2. Add 20 ul of cell suspension (300 cells/well) to all wells of 384-well CoStar plates.
3. Incubate for 24 hours at 37° C., 100% humidity, and 5% $CO_2$, allowing the cells to adhere to the plates.

Day 2—Compound Addition

1. In a sterile 384-well CoStar assay plate, dispense 5 ul of compound at 250× highest desired concentration to wells B11-O11 (except for H11 control well) and B14-O14 (27 compounds per plate, edge wells are not used due to evaporation). 250× compound is used to ensure final uniform concentration of vehicle (DMSO) on cells is 0.4%. Dilute 14.3 ul of 10 mM Topotecan into 10 ml of 5.8% DMSO in RPMI medium giving a final concentration of 14.3 uM stock. Add 1.5 ul of this Topotecan stock to 20 ul of cell in column 13 (rows B-O) giving a final Topotecan concentration on cells of 1 uM. ODs from these wells will be used to subtract out for background absorbance of dead cells and vehicle. Add 80 ul of medium without DMSO to each compound well in column 11 and 14. Add 40 ul medium (containing 5.8% DMSO) to all remaining wells. Serially dilute compound 2-fold from column 11 to column 2 by transferring 40 ul from one column to the next taking care to mix thoroughly each time. Similarly serially dilute compound 2-fold from column 14 to column 23.

Final Plate Layout (27 compounds, 10×2 fold dilutions, duplicate plates)

2. For each compound plate, add 1.5 uL compound-containing medium in duplicate from the compound plate wells to the corresponding cell plates wells. Incubate plates for 72 hours at 37° C., 100% humidity, and 5% $CO_2$.

Day 5—MTS Addition and OD Reading
1. After 72 hours of incubation with drug, remove plates from incubator and add 4.5 ul MTS/PMS to each well. Incubate plates for 120 minutes at 37° C., 100% humidity, 5% $CO_2$. Read ODs at 490 nm after a 5 second shaking cycle in a 384-well spectrophotometer.

For Data analysis, calculate normalized % of control (absorbance-background), and use XLfit to generate a dose-response curve.

Example 14

Certain of the chemical entities described herein were evaluated for in vivo activity against SKOV-3 human ovarian carcinoma in a tumor growth delay (TGD) study. The study utilized eight groups (n=8) of athymic nude mice bearing established (63-144 mm3) SKOV-3 tumors on Day 1, and included a vehicle-treated tumor growth control group and a reference group treated with paclitaxel (30 mg/kg i.v. qod×5). A first chemical entity was evaluated at doses of 300 or 150 mg/kg administered intraperitoneally (i.p.) once daily and at 150 mg/kg administered i.p. twice daily. Doses were administered on study days 1 to 5 and 8 to 12. Tumors were measured twice weekly during the 60-day study. Each animal was euthanized when its tumor reached the endpoint volume of 1500 mm3 or on Day 60, whichever came first, and the time to endpoint (TTE) was calculated for each mouse. Treatment outcome was determined from percent tumor growth delay (% TGD), defined as the percent increase in median TTE of treated versus control mice, with differences in TTE values deemed significant at P □0.05 using logrank analysis. The results presented were calculated based on data acquired through day 33 of the study. The median TTE of the untreated control group was 20.8 days. The positive control treatment (30 mg/kg paclitaxel i.v. qod×5) produced the maximum median TTE possible in this study (12.2 days) corresponding to 58% TGD, which was statistically significant activity. The 250 and 500 mg/kg once daily treatments produced 15 and 58% TGD, respectively, which was statistically significant activity at 500 mg/kg. The 250 mg/kg twice daily treatment produced 57% TGD, which was statistically significant activity.

A second chemical entity was similarly evaluated at 500 mg/kg administered i.p. once daily. That chemical entity produced 35% TGD, which was statistically significant activity.

Many modifications and variations of this invention can be made without departing from its spirit and scope, as will be apparent to those skilled in the art. The specific embodiments described herein are for illustration only and are not intended to limit the invention in any way.

What is claimed is:

1. A compound of Formula I:

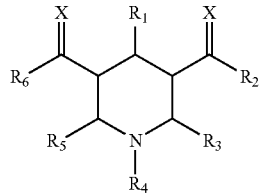

(Formula I)

or a pharmaceutically acceptable salt thereof, wherein

=X is chosen from =O and =N—$OR_7$, where $R_7$ is selected from hydrogen and alkyl, provided that at least one =X is =O $R_1$ is phenyl, which is optionally substituted with one, two, or three groups chosen from halo, lower alkyl, lower alkoxy, and hydroxy;

$R_2$ is phenyl, which is optionally substituted with one, two, or three groups chosen from halo, lower alkyl, lower alkoxy, and hydroxy;

$R_3$ is chosen from hydrogen and alkyl;

$R_4$ is chosen from hydrogen, optionally substituted alkyl, optionally substituted heterocycloalkyl, optionally substituted acyl, optionally substituted aryl, optionally substituted heteroaryl, aminocarbonyl, sulfonyl, optionally substituted alkoxycarbonyl, and optionally substituted cycloalkyl;

$R_5$ is chosen from hydrogen and alkyl; and $R_6$ is phenyl, which is optionally substituted with one, two, or three groups chosen from halo, lower alkyl, lower alkoxy, and hydroxy provided that:
the compound of Formula I is not (1-methyl-4-phenylpiperidine-3,5-diyl)bis(phenylmethanone); (1-benzyl-4-phenylpiperidine-3,5-diyl)bis(phenylmethanone); (1-(2-hydroxyethyl)-4-phenylpiperidine-3,5-diyl)bis(phenylmethanone); or (1-cyclohexyl-4-phenylpiperidine-3,5-diyl)bis(phenylmethanone).

2. The compound of claim 1, or a pharmaceutically acceptable salt thereof, wherein $R_1$ is phenyl optionally substituted with one, two, or three groups chosen from halo, methyl, ethyl, methoxy, ethoxy, and hydroxy.

3. The compound of claim 1, or a pharmaceutically acceptable salt thereof, wherein $R_1$ is phenyl optionally substituted with one, two, or three groups chosen halo, methyl, ethyl, methoxy, ethoxy, hydroxy, and isopropyl.

4. The compound of claim 1, or a pharmaceutically acceptable salt thereof, wherein $R_1$ is chosen from phenyl, 2,3-dimethylphenyl, 3-halo-2-methylphenyl, 2,3-dihalophenyl, 2-methylphenyl, 3-methylphenyl, 2-chloro-3-fluorophenyl, 2-halo-3-methylphenyl, 2-halo-phenyl, 3-halo-phenyl, 4-halo-phenyl, 2,6-dimethylphenyl, 4-methylphenyl, 3,4-dimethylphenyl, 2-methoxyphenyl, 3,4-dichlorophenyl, 3-methoxyphenyl, 3,5-dichlorophenyl, 4-methoxyphenyl, 2,5-dichlorophenyl, 2,4-dichlorophenyl, 2,3-dihalophenyl, 4-hydroxyphenyl, 2-hydroxyphenyl, 3-hydroxyphenyl, and 3-isopropylphenyl.

5. The compound of claim 1, or a pharmaceutically acceptable salt thereof, wherein $R_1$ is chosen from phenyl, 2,3-dimethylphenyl, 3-halo-2-methylphenyl, 2,3-dihalophenyl, and 2-methylphenyl.

6. The compound of claim 1, or a pharmaceutically acceptable salt thereof, wherein R2 is phenyl optionally substituted with one, two, or three groups chosen from halo, methyl, ethyl, methoxy, ethoxy, and hydroxy.

7. The compound of claim 1, or a pharmaceutically acceptable salt thereof, wherein $R_2$ is chosen from phenyl and hydroxyphenyl.

8. The compound of claim 1, or a pharmaceutically acceptable salt thereof, wherein $R_3$ is chosen from hydrogen and lower alkyl.

9. The compound of claim 8, or a pharmaceutically acceptable salt thereof, wherein $R_3$ is chosen from hydrogen and methyl.

10. The compound of claim 9, or a pharmaceutically acceptable salt thereof, wherein $R_3$ is hydrogen.

11. The compound of claim 1, or a pharmaceutically acceptable salt thereof, wherein $R_4$ is chosen from hydrogen, optionally substituted acyl, optionally substituted aminocarbonyl, optionally substituted sulfonyl, optionally substituted alkoxycarbonyl optionally substituted lower alkyl, and optionally substituted cycloalkyl.

12. The compound of claim 1, or a pharmaceutically acceptable salt thereof, wherein $R_4$ is chosen from hydrogen, allyl, acyl substituted with optionally substituted lower alkyl, aminocarbonyl substituted with optionally substituted lower alkyl, sulfonyl substituted with optionally substituted lower alkyl, alkoxycarbonyl substituted with optionally substituted lower alkyl, and lower alkyl optionally substituted with optionally substituted phenyl, hydroxy, lower alkoxy, alkoxycarbonyl, optionally substituted aminocarbonyl, heterocycloalkyl acyloxy, optionally substituted amino, and carboxy.

13. The compound of claim 1, or a pharmaceutically acceptable salt thereof, wherein $R_4$ is chosen from hydrogen, 2-hydroxyethyl, benzyl, 2-methoxyethyl, 2-hydroxycyclopentyl, 1,3-dihydroxypropan-2-yl, cyclopentyl, methyl, 2-morpholinoethyl, 2-methoxy-2-oxoethyl, 2-(methylamino)-2-oxoethyl, 2-acetoxyethyl, (R)-1-hydroxypropan-2-yl, (S)-1-hydroxypropan-2-yl, (R)-2-hydroxypropyl, (S)-2-hydroxypropyl, propyl, 2-(dim ethylamino)ethyl, 2-(piperazin-1-yl)ethyl, 2-amino-2-oxoethyl, carboxymethyl, 3-hydroxypropyl, ethyl, 3-ethoxy-3-oxopropyl, 1,3-dihydroxypropan-2-yl, (tetrahydrofuran-2-yl)methyl, 2-ethoxy-2-oxoethyl, 3,3-dimethyl-1-(methylamino)-1-oxobutan-2-yl, 2-oxoazepan-3-yl, 1-hydroxy-3-methylbutan-2-yl, 2-(piperazin-1-yl)ethyl, 2-(4-acetylpiperazin-1-yl)ethyl, 1-propionyl, 2-(dimethylamino)-2-oxoethyl, 2-(4-(tert-butoxycarbonyl)piperazin-1-yl)-2-oxoethyl, 2-oxo-2-(piperidin-1-yl)ethyl, 2-oxo-2-(piperazin-1-yl)ethyl, 2-(4-methylpiperazin-1-yl)-2-oxoethyl, 3-(dimethylamino)propylsulfonyl, 2-(dimethylamino)ethoxycarbonyl, 2-(dimethylamino)ethylaminocarbonyl, N-[2-(dimethylamino)ethyl]-N-methylaminocarbonyl 4-(dimethylamino)-2,2-dimethylbutan-1-one and 2-(2-(dimethylamino)ethylamino)-2-oxo ethyl.

14. The compound of claim 1, or a pharmaceutically acceptable salt thereof, wherein R5 is chosen from hydrogen and lower alkyl.

15. The compound of claim 14; or a pharmaceutically acceptable salt thereof, wherein $R_5$ is chosen from hydrogen and methyl.

16. The compound of claim 15, or a pharmaceutically acceptable salt thereof, wherein $R_5$ is hydrogen.

17. The compound of claim 1, or a pharmaceutically acceptable salt thereof, wherein $R_6$ is phenyl optionally substituted with one, two, or three groups chosen from halo, methyl, ethyl, methoxy, ethoxy, and hydroxy.

18. The compound of claim 1, or a pharmaceutically acceptable salt thereof, wherein $R_6$ is chosen from phenyl and hydroxyphenyl.

19. The compound of claim 1, or a pharmaceutically acceptable salt thereof, wherein $R_7$ is chosen from hydrogen and lower alkyl.

20. The compound of claim 19, or a pharmaceutically acceptable salt thereof, wherein $R_7$ is hydrogen.

21. The compound of claim 1, or a pharmaceutically acceptable salt thereof, wherein each occurrence of =X is chosen from =O and =N—OH.

22. The compound of claim 21, or a pharmaceutically acceptable salt thereof, wherein both =X are =O.

23. A compound chosen from:
(cis,trans)-1-cyclopentyl-4-phenyl-5-(phenylcarbonyl)(3-piperidyl)phenyl ketone
(cis,trans)-1-(3-hydroxypropyl)-4-phenyl-5-(phenylcarbonyl)(3-piperidyl)phenyl ketone
(cis,cis)-4-phenyl-5-(phenylcarbonyl)-1-propyl(3-piperidyl)phenyl ketone
(cis,trans)-1-((1S)-2-hydroxy-isopropyl)-4-phenyl-5-(phenylcarbonyl)(3-piperidyl)phenyl ketone
(cis,cis)-1-(2-methoxyethyl)-4-phenyl-5-(phenylcarbonyl)(3-piperidyl)phenyl ketone
(cis,trans)-1-(2-methoxyethyl)-4-phenyl-5-(phenylcarbonyl)(3-piperidyl)phenyl ketone
1-((1R)-2-hydroxy-isopropyl)(cis,trans)-4-phenyl-5-(phenylcarbonyl)(3-piperidyl)phenyl ketone
ethyl 3[(cis,cis)-3,5-bis(phenylcarbonyl)-4-phenylpiperidyl]propanoate
(cis,trans)-1-((2S)-2-hydroxypropyl)-4-phenyl-5-(phenylcarbonyl)(3-piperidyl)phenyl ketone
(cis,cis)-1-(oxolan-2-ylmethyl)-4-phenyl-5-(phenylcarbonyl)(3-piperidyl)phenyl ketone
(cis,trans)-1-(oxolan-2-ylmethyl)-4-phenyl-5-(phenylcarbonyl)(3-piperidyl)phenyl ketone
(cis,cis)-1-[2-hydroxy-1-(hydroxymethyl)ethyl]-4-phenyl-5-(phenylcarbonyl)(3-piperidyl)phenyl ketone
(cis,trans)-1-[2-hydroxy-1-(hydroxymethyl)ethyl]-4-phenyl-5-(phenylcarbonyl)(3-piperidyl)phenyl ketone
(cis,cis)-1-(2-morpholin-4-ylethyl)-4-phenyl-5-(phenylcarbonyl)(3-piperidyl)phenyl ketone
(cis,trans)-1-(2-morpholin-4-ylethyl)-4-phenyl-5-(phenylcarbonyl)(3-piperidyl)phenyl ketone
(cis,cis)-1-[2-(dimethylamino)ethyl]-4-phenyl-5-(phenylcarbonyl)(3-piperidyl)phenyl ketone
(cis,trans)-1-[2-(dimethylamino)ethyl]-4-phenyl-5-(phenylcarbonyl)(3-piperidyl)phenyl ketone
(cis,cis)-1-cyclopentyl-4-phenyl-5-(phenylcarbonyl)(3-piperidyl)phenyl ketone ethyl 3-((cis,trans)-3,5-bis(phenylcarbonyl)-4-phenylpiperidyl]propanoate
2-[(cis,trans)-3,5-bis(phenylcarbonyl)-4-phenylpiperidyl]-N-methylacetamide
1-((2S)-2-hydroxypropyl)(cis,cis)-4-phenyl-5-(phenylcarbonyl)(3-piperidyl)phenyl ketone
2-[3,5-bis(phenylcarbonyl)-4-phenylpiperidyl]-3,3-dimethyl-N-methylbutanamide
(cis,cis)-1-[2-hydroxy-1-(methylethyl)ethyl]-4-phenyl-5-(phenylcarbonyl)(3-piperidyl)phenyl ketone
(cis,trans)-4-(2,3-dimethylphenyl)-1-(2-hydroxyethyl)-5-(phenylcarbonyl)(3-piperidyl)phenyl ketone
(cis,trans)-4-(2,3-dimethylphenyl)-1-(3-hydroxypropyl)-5-(phenylcarbonyl)(3-piperidyl)phenyl ketone
(cis,trans)-4-(2,3-dimethylphenyl)-1-(2-morpholin-4-ylethyl)-5-(phenylcarbonyl)(3-piperidyl)phenyl ketone
(cis,trans)-4-(2,3-dimethylphenyl)-5-(phenylcarbonyl)-1-(2-piperazinylethyl)(3-piperidyl)phenyl ketone
4-{2-[(cis,trans)-4-(2,3-dimethylphenyl)-3,5-bis(phenylcarbonyl)piperidyl]ethyl}-1-acetylpiperazine
24(cis,trans)-4-(2,3-dimethylphenyl)-3,5-bis(phenylcarbonyl)piperidyl]-N-methylacetamide
(cis,trans)-4-(2,3-dimethylphenyl)-1-[2-hydroxy-1-(hydroxymethyl)ethyl)-5-(phenylcarbonyl)(3-piperidyl) phenyl ketone
1-[(cis,trans)-4-(2,3-dimethylphenyl)-3,5-bis(phenylcarbonyl)piperidyl]propan-1-one
2-[(trans,trans)-4-(2,3-dimethylphenyl)-3,5-bis(phenylcarbonyl)piperidyl]-N,N-dimethylacetamide
4-(2,3-dimethylphenyl)-5-(phenylcarbonyl)-1-prop-2-enyl(3-piperidyl)phenyl ketone
(cis,trans)-4-(2,3-dimethylphenyl)-5-[(3-fluorophenyl)carbonyl]-1-(2-morpholin-4-ylethyl)(3-piperidyl) 3-fluorophenyl ketone (cis,trans)-4-(2,3-dimethylphenyl)-5-[(3-fluorophenyl)carbonyl]-1-(2-hydroxyethyl)(3-piperidyl) 3-fluorophenyl ketone
(cis,trans)-1-[2-(dimethylamino)ethyl]-4-(2,3-dimethylphenyl)-5-[(3-fluorophenyl)carbonyl](3-piperidyl) 3-fluorophenyl ketone
(cis,trans)-4-(2,3-dimethylphenyl)-5-[(3-fluorophenyl)carbonyl]-1-(3-morpholin-4-ylpropyl)(3-piperidyl) 3-fluorophenyl ketone
(cis,trans)-4-(2,3-dimethylphenyl)-5-[(3-fluorophenyl)carbonyl]-1-[3-(4-methylpiperazinyl)propyl](3-piperidyl) 3-fluorophenyl ketone
(cis,trans)-4-(2,3-dimethylphenyl)-5-[(3-fluorophenyl)carbonyl]-1-(2-piperazinylethyl)(3-piperidyl) 3-fluorophenyl ketone
1-(3-{(cis,trans)-3,5-bis[(3-fluorophenyl)carbonyl]-4-(2,3-dimethylphenyl)piperidyl}propyl)pyrrolidin-2-one
1-(3-{(trans,trans)-3,5-bis[(3-fluorophenyl)carbonyl]-4-(2,3-dimethylphenyl)piperidyl}propyl)pyrrolidin-2-one
(cis,trans)-4-(2,3-dimethylphenyl)-1-(3-morpholin-4-ylpropyl)-5-(phenylcarbonyl)(3-piperidyl)phenyl ketone
(cis,trans)-4-(2,3-dimethylphenyl)-1-[3-(4-methylpiperazinyl)propyl]-5-(phenylcarbonyl)(3-piperidyl)phenyl ketone
(cis,trans)-1-[2-(dimethylamino)ethyl]-4-(2,3-dimethylphenyl)-5-(phenylcarbonyl)(3-piperidyl)phenyl ketone
1-{3-[(cis,trans)-4-(2,3-dimethylphenyl)-3,5-bis(phenylcarbonyl)piperidyl]propyl}pyrrolidin-2-one
(cis,trans)-4-(2,3-dimethylphenyl)-5-(phenylcarbonyl)-1-(2-(3-pyridyl)ethyl)(3-piperidyl)phenyl ketone
(cis,trans)-1-[3-(dimethylamino)propyl]-4-(2,3-dimethylphenyl)-5-(phenylcarbonyl)(3-piperidyl)phenyl ketone
(cis,trans)-4-(2,3-dimethylphenyl)-1-(3-imidazolylpropyl)-5-(phenylcarbonyl)(3-piperidyl)phenyl ketone
(cis,trans)-4-(2,3-dimethylphenyl)-1-(2-imidazolylethyl)-5-(phenylcarbonyl)(3-piperidyl)phenyl ketone
(cis,trans)-4-(2,3-dimethylphenyl)-5-(phenylcarbonyl)-1-(3-piperidylpropyl)(3-piperidyl)phenyl ketone
(cis,trans)-4-(2,3-dimethylphenyl)-1-(4-hydroxybutyl)-5-(phenylcarbonyl)(3-piperidyl)phenyl ketone
(cis,trans)-4-(2,3-dimethylphenyl)-5-(phenylcarbonyl)-1-(2-(2-piperidyl)ethyl)(3-piperidyl)phenyl ketone
(cis,trans)-1-(3-aminopropyl)-4-(2,3-dimethylphenyl)-5-(phenylcarbonyl)(3-piperidyl)phenyl ketone
(cis,trans)-1-(2-aminoethyl)-4-(2,3-dimethylphenyl)-5-(phenylcarbonyl)(3-piperidyl)phenyl ketone
(cis,trans)-1-(2-aminoethyl)-4-(2,3-dimethylphenyl)-5-[(3-fluorophenyl)carbonyl](3-piperidyl) 3-fluorophenyl ketone
2-[(cis,trans)-4-(2,3-dimethylphenyl)-3,5-bis(phenylcarbonyl)piperidyl]-N,N-dimethylacetamide
2-[(cis,trans)-3,5-bis(phenylcarbonyl)-4-phenylpiperidyl]-N,N-dimethylacetamide
(cis,trans)-4-(2,3-dimethylphenyl)-5-(phenylcarbonyl)(3-piperidyl)phenyl ketone
1-[4-(2,3-dimethylphenyl)-3,5-bis(phenylcarbonyl)piperidyl]-3-hydroxypropan-1-one
1-acetyl-4-(2,3-dimethylphenyl)-3,5-bis(phenylcarbonyl)piperidine
N-{2-[4-(2,3-dimethylphenyl)-3,5-bis(phenylcarbonyl)piperidyl]-2-oxoethyl}acetamide
2-(dimethylamino)-1-[4-(2,3-dimethylphenyl)-3,5-bis(phenylcarbonyl)piperidyl]ethan-1-one
1-[4-(2,3-dimethylphenyl)-35-bis(phenylcarbonyl)piperidyl]-2-hydroxyethan-1-one
2-[(cis,trans)-4-(2,3-dimethylphenyl)-3,5-bis(phenylcarbonyl)piperidyl]acetic acid
4-{2-[(cis,trans)-4-(2,3-dimethylphenyl)-3,5-bis(phenylcarbonyl)piperidyl]acetyl}-1-acetylpiperazine
2-[(cis,trans)-4-(2,3-dimethylphenyl)-3,5-bis(phenylcarbonyl)piperidyl]-N-[2-(dimethylamino)ethyl]-N-methylacetamide
2-[(trans,trans)-4-(2,3-dimethylphenyl)-3,5-bis(phenylcarbonyl)piperidyl]acetic acid
2-[(trans,trans)-4-(2,3-dimethylphenyl)-3,5-bis(phenylcarbonyl)piperidyl]-N-(2-hydroxyethyl)acetamide
(cis,cis)-4-(2,3-dimethylphenyl)-1-(2-morpholin-4-ylethyl)-5-(phenylcarbonyl)(3-piperidyl)phenyl ketone
(trans,trans)-4-(2,3-dimethylphenyl)-1-(2-morpholin-4-ylethyl)-5-(phenylcarbonyl)(3-piperidyl)phenyl ketone
2-{(trans,trans)-3,5-bis[(3-fluorophenyl)carbonyl]-4-(2,3-dimethylphenyl)piperidyl}-N,N-dimethylacetamide
2-[(trans,trans)-4-(2,3-dimethylphenyl)-3,5-bis(phenylcarbonyl)piperidyl]-N-(2-piperazinylethyl)acetamide
2-[(trans,trans)-4-(2,3-dimethylphenyl)-3,5-bis(phenylcarbonyl)piperidyl]-N-(2-morpholin-4-ylethyl)acetamide
2-[(trans,trans)-4-(2,3-dimethylphenyl)-3,5-bis(phenylcarbonyl)piperidyl]-1-piperazinylethan-1-one
4-{2-[(trans,trans)-4-(2,3-dimethylphenyl)-3,5-bis(phenylcarbonyl)piperidyl]acetyl}-1-acetylpiperazine
2-[(trans,trans)-4-(2,3-dimethylphenyl)-3,5-bis(phenylcarbonyl)piperidyl]-N-[2-(4-acetylpiperazinyl)ethyl]acetamide
2-[(trans,trans)-4-(2,3-dimethylphenyl)-3,5-bis(phenylcarbonyl)piperidyl]-N-[2-(dimethylamino)ethyl]-N-methylacetamide
2-[(trans,trans)-4-(2,3-dimethylphenyl)-3,5-bis(phenylcarbonyl)piperidyl]-N-methylacetamide
2-[(trans,trans)-4-(2,3-dimethylphenyl)-3,5-bis(phenylcarbonyl)piperidyl]-1-(4-methylpiperazinyl)ethan-1-one
2-[(trans,trans)-4-(2,3-dimethylphenyl)-3,5-bis(phenylcarbonyl)piperidyl)-1-morpholin-4-ylethan-1-one
2-{(trans,trans)-3,5-bis[(3-fluorophenyl)carbonyl]-4-(2,3-dimethylphenyl)piperidyl}-N-methylacetamide
2-[(trans,trans)-4-(2,3-dimethylphenyl)-3,5-bis(phenylcarbonyl)piperidyl]acetamide
(trans,trans)-4-(2,3-dimethylphenyl)-1-(2-hydroxyethyl)-5-(phenylcarbonyl)(3-piperidyl)phenyl ketone
(trans,trans)-4-(213-dimethylphenyl)-1-(3-hydroxypropyl)-5-(phenylcarbonyl)(3-piperidyl)phenyl ketone
N-{2-[(trans,trans)-4-(2,3-dimethylphenyl)-3,5-bis(phenylcarbonyl)piperidyl]ethyl}(tert-butoxy)carboxamide
(trans,trans)-1-[2-(dimethylamino)ethyl]-4-(2,3-dimethylphenyl)-5-(phenylcarbonyl)(3-piperidyl)phenyl ketone
3-[(trans,trans)-4-(2,3-dimethylphenyl)-3,5-bis(phenylcarbonyl)piperidyl]propanoic acid
(trans,trans)-4-(2,3-dimethylphenyl)-1-[3-(4-methylpiperazinyl)propyl]-5-(phenylcarbonyl)(3-piperidyl)phenyl ketone
(trans,trans)-1-(2-aminoethyl)-4-(2,3-dimethylphenyl)-5-(phenylcarbonyl)(3-piperidyl)phenyl ketone
2-[(trans,trans)-3,5-bis(phenylcarbonyl)-4-(3-fluoro-2-methylphenyl)piperidyl]-N,N-dimethylacetamide
(trans,trans)-4-(2,3-dimethylphenyl)-1-[2-hydroxy-1-(hydroxymethyl)ethyl]-5-(phenylcarbonyl)(3-piperidyl) phenyl ketone (trans,trans)-4-(2,3-dimethylphenyl)-5-(phenylcarbonyl)-1-(3-piperidylpropyl)(3-piperidyl)phenyl ketone
3-[(trans,trans)-4-(2,3-dimethylphenyl)-3,5-bis(phenylcarbonyl)piperidyl]-N,N-dimethylpropanamide
methyl (N-{2-[(trans,trans)-4-(2,3-dimethylphenyl)-3,5-bis(phenylcarbonyl)piperidyl]ethyl}methoxycarbonylamino)formate
N-{2-[(trans,trans)-4-(2,3-dimethylphenyl)-3,5-bis(phenylcarbonyl)piperidyl]ethyl}acetamide
2-[(trans,trans)-3,5-bis(2-pyridylcarbonyl)-4-(3-fluoro-2-methylphenyl)piperidyl]-N,N-dimethylacetamide
2-[(trans,trans)-3,5-bis(2-pyridylcarbonyl)-4-(3-fluoro-2-methylphenyl)piperidyl]acetamide
2-[(trans,trans)-3,5-bis(2-pyridylcarbonyl)-4-(3-fluoro-2-methylphenyl)piperidyl]-N-methylacetamide
N-{2-[(trans,trans)-4-(2,3-dimethylphenyl)-3,5-bis(phenylcarbonyl)piperidyl]ethyl}methoxycarboxamide
2-[(trans,trans)-3,5-bis(phenylcarbonyl)-4-(2-chlorophenyl)piperidyl]-N,N-dimethylacetamide
N-{2-[(trans,trans)-4-(2,3-dimethylphenyl)-3,5-bis(phenylcarbonyl)piperidyl]ethyl}-2-[2-(2-methoxyethoxy)ethoxy]acetamide
2-[(trans,trans)-3,5-bis(phenylcarbonyl)-4-(2-methylphenyl)piperidyl]-N,N-dimethylacetamide
2-[(trans,trans)-3,5-bis(phenylcarbonyl)-4-(3-chloro-2-methylphenyl)piperidyl]-N,N-dimethylacetamide
2-[(trans,trans)-3,5-bis(phenylcarbonyl)-4-phenylpiperidyl]acetamide
2-[(trans,trans)-3,5-bis(phenylcarbonyl)-4-phenylpiperidyl]-N,N-dimethylacetamide
tert-butyl 4-{2-[(trans,trans)-3,5-bis(phenylcarbonyl)-4-phenylpiperidyl]acetyl}piperazinecarboxylate
2-[(trans,trans)-3,5-bis(phenylcarbonyl)-4-(3-cyano-2-methylphenyl)piperidyl]-N,N-dimethylacetamide
2-{(trans,trans)-3,5-bis[(4-bromophenyl)carbonyl]-4-(3-fluoro-2-methylphenyl)piperidyl}-1-piperazinylethan-1-one
2-[(trans,trans)-4-(2,3-difluorophenyl)-35-bis(phenylcarbonyl)piperidyl]-N,N-dimethylacetamide
2-[(trans,trans)-3,5-bis(phenylcarbonyl)-4-(2-fluorophenyl)piperidyl]-N,N-dimethylacetamide
2-[(trans,trans)-3,5-bis(phenylcarbonyl)-4-phenylpiperidyl]-1-piperazinylethan-1-one
(trans,trans)-4-(2,3-dimethylphenyl)-1-methyl-5-(phenylcarbonyl)(3-piperidyl)phenyl ketone
(trans,trans)-1-methyl-4-(3-methylphenyl)-5-(phenylcarbonyl)(3-piperidyl)phenyl ketone
methyl 3-{(trans,trans)-1-[(N,N-dimethylcarbamoyl)methyl]-3,5-bis(phenylcarbonyl)(4-piperidyl)}-2-methylbenzoate
2-[(trans,trans)-3,5-bis(phenylcarbonyl)-4-(3-iodo-2-methylphenyl)piperidyl]-N,N-dimethylacetamide
2-[(trans,trans)-3,5-bis(phenylcarbonyl)-4-(3-chlorophenyl)piperidyl]-N,N-dimethylacetamide
(trans,trans)-4-(3-chloro-2-methylphenyl)-1-methyl-5-(phenylcarbonyl)(3-piperidyl)phenyl ketone
(trans,trans)-4-(2,3-dimethylphenyl)-1-ethyl-5-(phenylcarbonyl)(3-piperidyl)phenylketone
(trans,trans)-4-(2,3-dimethylphenyl)-5-(phenylcarbonyl)-1-propyl(3-piperidyl)phenyl ketone
2-[(trans,trans)-3,5-bis(phenylcarbonyl)-4-(3-methylphenyl)piperidyl]-N,N-dimethylacetamide
4-{2-[(trans,trans)-3,5-bis(phenylcarbonyl)-4-phenylpiperidyl]acetyl}piperazin-2-one
2-[(trans,trans)-3,5-bis(phenylcarbonyl)-4-(2-chloro-3-methylphenyl)piperidyl]-N,N-dimethylacetamide
2-[(trans,trans)-3,5-bis(phenylcarbonyl)-4-(2-chloro-3-fluorophenyl)piperidyl]-N,N-dimethylacetamide
2-{(trans,trans)-3,5-bis[(3-methoxyphenyl)carbonyl]-4-(3-fluoro-2-methylphenyl)piperidyl}-N,N-dimethylacetamide
2-{(trans,trans)-3,5-bis[(3-methoxyphenyl)carbonyl]-4-(3-fluoro-2-methylphenyl)piperidyl}-N-methylacetamide
2-{(trans,trans)-3,5-bis[(3-hydroxyphenyl)carbonyl]-4-(3-fluoro-2-methylphenyl)piperidyl}-N,N-dimethylacetamide
2-{(trans,trans)-3,5-bis[(3-hydroxyphenyl)carbonyl]-4-(3-fluoro-2-methylphenyl)piperidyl}-N-methylacetamide
2-{(trans,trans)-3,5-bis[(2-bromophenyl)carbonyl]-4-(3-fluoro-2-methylphenyl)piperidyl}-N,N-dimethylacetamide
(trans,trans)-5-[(2-bromophenyl)carbonyl-4-(3-fluoro-2-methylphenyl)-1-(2-hydroxyethyl)(3-piperidyl) 2-bromophenyl ketone
(trans,trans)-5-[(2-bromophenyl)carbonyl]-4-(3-fluoro-2-methylphenyl)-1-propyl(3-piperidyl) 2-bromophenyl ketone
2-{(trans,trans)-5-[(2-bromophenyl)carbonyl]-3-[(2-cyanophenyl)carbonyl]-4-(3-fluoro-2-methylphenyl)piperidyl}-N,N-dimethylacetamide
3-{(trans,trans)-1-[(N,N-dimethylcarbamoyl)methyl]-3,5-bis(phenylcarbonyl)(4-piperidyl)}-2-methylbenzoic acid
2-[(trans,trans)-3,5-bis(phenylcarbonyl)-4-(2-iodophenyl)piperidyl]-N,N-dimethylacetamide
2-[(trans,trans)-3,5-bis(phenylcarbonyl)-4-(4-chlorophenyl)piperidyl]-N,N-dimethylacetamide
2-[(trans,trans)-3,5-bis(phenylcarbonyl)-4-(4-fluorophenyl)piperidyl]-N,N-dimethylacetamide
2-[(trans,trans)-3,5-bis(phenylcarbonyl)-4-(3-fluorophenyl)piperidyl]-N,N-dimethylacetamide
(trans,trans)-4-(2,6-dimethylphenyl)-1-(2-hydroxyethyl)-5-(phenylcarbonyl)(3-piperidyl)phenyl ketone
2-{(trans,trans)-3,5-bis(phenylcarbonyl)-4-[3-(trifluoromethyl)phenyl]piperidyl}-N,N-dimethylacetamide
2-[(trans,trans)-3,5-bis(phenylcarbonyl)-4-(2-Cyanophenyl)piperidyl]-N,N-dimethylacetamide
(trans,trans)-4-(3-fluoro-2-methylphenyl)-1-(2-hydroxyethyl)-5-[(3-methoxyphenyl)carbonyl](3-piperidyl) 3-methoxyphenyl ketone
(trans,trans)-4-(3-fluoro-2-methylphenyl)-1-(2-hydroxyethyl)-5-[(3-hydroxyphenyl)carbonyl](3-piperidyl) 3-hydroxyphenyl ketone
(trans,trans)-4-(3-fluoro-2-methylphenyl)-1-(2-hydroxyethyl)-5-[(2-methoxyphenyl)carbonyl](3-piperidyl) 2-methoxyphenyl ketone
(trans,trans)-4-(2,3-dimethylphenyl)-5-(phenylcarbonyl)-1-benzyl(3-piperidyl)phenyl ketone
2-[(trans,trans)-3,5-bis(phenylcarbonyl)-4-(4-methylphenyl)piperidyl]-N,N-dimethylacetamide
2-[(cis,trans)-3,5-bis(phenylcarbonyl)-4-(4-methylphenyl)piperidyl]-N,N-dimethylacetamide
(trans,trans)-1-(2-hydroxyethyl)-4-(4-methylphenyl)-5-(phenylcarbonyl)(3-piperidyl)phenyl ketone
(cis,trans)-1-(2-aminoethyl)-4-(4-methylphenyl)-5-(phenylcarbonyl)(3-piperidyl)phenyl ketone
2-{(trans,trans)-3,5-bis[(2-methoxyphenyl)carbonyl]-4-(3-fluoro-2-methylphenyl)piperidyl}-N,N-dimethylacetamide 2-{(trans,trans)-3,5-bis[(2-hydroxyphenyl)carbonyl]-4-(3-fluoro-2-methylphenyl)piperidyl}-N,N-dimethylacetamide
(trans,trans)-4-(3-fluoro-2-methylphenyl)-1-(2-hydroxyethyl)-5-[(2-hydroxyphenyl)carbonyl](3-piperidyl) 2-hydroxyphenyl ketone
(trans,trans)-4-(3-fluoro-2-methylphenyl)-1-(2-hydroxyethyl)-5-[(4-methoxyphenyl)carbonyl](3-piperidyl) 4-methoxyphenyl ketone
2-{(trans,trans)-3,5-bis[(4-methoxyphenyl)carbonyl]-4-(3-fluoro-2-methylphenyl)piperidyl}-N,N-dimethylacetamide
(trans,trans)-4-(3-fluoro-2-methylphenyl)-1-(2-hydroxyethyl)-5-[(4-hydroxyphenyl)carbonyl](3-piperidyl) 4-hydroxyphenyl ketone
2-{(trans,trans)-3,5-bis[(4-hydroxyphenyl)carbonyl]-4-(3-fluoro-2-methylphenyl)piperidyl}-N,N-dimethylacetamide
methyl 3-({(trans,trans)-1-[(N,N-dimethylcarbamoyl)methyl]-5-[(3-carbamoylphenyl)carbonyl]-4-(3-fluoro-2-methylphenyl)-3-piperidyl}carbonyl)benzoate
(trans,trans)-4-(3,4-dimethylphenyl)-1-(2-hydroxyethyl)-5-(phenylcarbonyl)(3-piperidyl)phenyl ketone
2-[(trans,trans)-4-(3,4-dimethylphenyl)-3,5-bis(phenylcarbonyl)piperidyl]-N,N-dimethylacetamide
N-{2-[(trans,trans)-4-(2,3-dimethylphenyl)-3-((hydroxyimino)phenylmethyl)-5-(phenylcarbonyl)piperidyl]ethyl}(tert-butoxy)carboxamide
(trans,trans)-1-(2-aminoethyl)-4-(2,3-dimethylphenyl)-5-((hydroxyimino)phenylmethyl)(3-piperidyl)phenyl ketone
methyl 3-[((trans,trans)-1-[(N,N-dimethylcarbamoyl)methyl]-4-(3-fluoro-2-methylphenyl)-5-{[3-(methoxycarbonyl)phenyl]carbonyl)-3-piperidyl)carbonyl]benzoate
2-{(trans,trans)-3,5-bis(phenylcarbonyl)-4-[3-(hydroxymethyl)-2-methylphenyl]piperidyl}-N,N-dimethylacetamide
2-[(trans,trans)-35-bis(phenylcarbonyl)-4-(3-iodophenyl)piperidyl]-N,N-dimethylacetamide
2-[(trans,trans)-3,5-bis(phenylcarbonyl)-4-(2-methoxyphenyl)piperidyl]-N,N-dimethylacetamide
2-{(trans,trans)-3,5-bis(phenylcarbonyl)-4-[2-(trifluoromethyl)phenyl]piperidyl}-N,N-dimethylacetamide
2-[(trans,trans)-3,5-bis((hydroxyimino)phenylmethyl)-4-(2,3-dimethylphenyl)piperidyl]ethylamine
2-{(trans,trans)-3,5-bis(phenylcarbonyl)-4-[4-(trifluoromethyl)phenyl]piperidyl}-N,N-dimethylacetamide
2-[(trans,trans)-4-(3,4-dichlorophenyl)-3,5-bis(phenylcarbonyl)piperidyl]-N,N-dimethylacetamide
2-[(trans,trans)-3,5-bis(phenylcarbonyl)-4-(3-methoxyphenyl)piperidyl]-N,N-dimethylacetamide
2-[(trans,trans)-4-(3,5-dichlorophenyl)-3,5-bis(phenylcarbonyl)piperidyl]-N,N-dimethylacetamide
2-[(trans,trans)-3,5-bis(phenylcarbonyl)-4-(4-methoxyphenyl)piperidyl]-N,N-dimethylacetamide
(trans,trans)-4-(3-fluoro-2-methylphenyl)-5-{[3-(hydroxymethyl)phenyl]carbonyl}-1-(2-methoxyethyl)(3-piperidyl) 3-(hydroxymethyl)phenyl ketone
2-[(trans,trans)-4-(2,5-dichlorophenyl)-3,5-bis(phenylcarbonyl)piperidyl]-N,N-dimethylacetamide
2-[(trans,trans)-4-(2,4-dichlorophenyl)-3,5-bis(phenylcarbonyl)piperidyl]-N,N-dimethylacetamide
2-{(trans,trans)-3,5-bis(phenylcarbonyl)-4-[3-(hydroxymethyl)phenyl]piperidyl}-N,N-dimethylacetamide
(trans, trans)-1-(2-aminoethyl)-4-(3-fluoro-2-methylphenyl)-5-[(3-hydroxyphenyl)carbonyl](3-piperidyl) 3-hydroxyphenyl ketone
(trans, trans)-1-(2-aminoethyl)-4-(3-fluoro-2-methylphenyl)-5-[(3-methoxyphenyl)carbonyl](3-piperidyl) 3-methoxyphenyl ketone
2-[(trans,trans)-3,5-bis(phenylcarbonyl)-4-(2-hydroxyphenyl)piperidyl]-N,N-dimethylacetamide
2-[(trans,trans)-3,5-bis(phenylcarbonyl)-4-(3-hydroxyphenyl)piperidyl]-N,N-dimethylacetamide
N-{2-[(trans,trans)-4-(2,3-dimethylphenyl)-3,5-bis(phenylcarbonyl)piperidyl]ethyl}-2-[(3,5,6-trimethyl-1,7-dioxo(3-pyrazolino[1,2-a]3-pyrazolin-2-yl))methylthio]acetamide
N-{2-[(trans,trans)-4-(2,3-dimethylphenyl)-3,5-bis(phenylcarbonyl)piperidyl]ethyl}-6-[(7-nitrobenzo[2,3-c]1,2,5-oxadiazol-4-yl)amino]hexanamide
N-{2-[(trans,trans)-4-(2,3-dimethylphenyl)-3,5-bis(phenylcarbonyl)piperidyl]ethyl}-6-({[5-(dimethylamino)naphthyl]sulfonyl}amino)hexanamide
(trans,trans)-5-[(2-chlorophenyl)carbonyl]-4-(3-fluoro-2-methylphenyl)-1-(2-hydroxyethyl)(3-piperidyl) 2-chlorophenyl ketone
N-{2-[(trans,trans)-4-(2,3-dimethylphenyl)-3,5-bis(phenylcarbonyl)piperidyl]ethyl}(6,8-difluoro-7-hydroxy-2-oxochromen-3-yl)carboxamide
N-{2-[(trans,trans)-4-(2,3-dimethylphenyl)-3,5-bis(phenylcarbonyl)piperidyl]ethyl}-2-[7-(dimethylamino)-2-oxochromen-4-yl]acetamide
1-((2S)-2-methoxypropyl)(trans,trans)-4-(3-fluoro-2-methylphenyl)-5-[(3-methoxyphenyl)carbonyl](3-piperidyl) 3-methoxyphenyl ketone
1-((2S)-2-hydroxypropyl)(trans,trans)-4-(3-fluoro-2-methylphenyl)-5-[(3-hydroxyphenyl)carbonyl](3-piperidyl) 3-hydroxyphenyl ketone
1-((2R)-2-hydroxypropyl)(trans,trans)-4-(3-fluoro-2-methylphenyl)-5-[(3-methoxyphenyl)carbonyl](3-piperidyl) 3-methoxyphenyl ketone
1-((2R)-2-hydroxypropyl)(trans,trans)-4-(3-fluoro-2-methylphenyl)-5-[(3-hydroxyphenyl)carbonyl](3-piperidyl) 3-hydroxyphenyl ketone
(trans,trans)-1-(2,3-dihydroxypropyl)-4-(3-fluoro-2-methylphenyl)-5-[(3-methoxyphenyl)carbonyl](3-piperidyl) 3-methoxyphenyl ketone
(trans,trans)-1-(2,3-dihydroxypropyl)-4-(3-fluoro-2-methylphenyl)-5-[(3-hydroxyphenyl)carbonyl](3-piperidyl) 3-hydroxyphenyl ketone
(trans,trans)-1-(3-amino-2-hydroxypropyl)-4-(3-fluoro-2-methylphenyl)-5-[(3-methoxyphenyl)carbonyl](3-piperidyl) 3-methoxyphenyl ketone
(trans,trans)-1-(3-amino-2-hydroxypropyl)-4-(3-fluoro-2-methylphenyl)-5-[(3-hydroxyphenyl)carbonyl](3-piperidyl) 3-hydroxyphenyl ketone
N-(2-{(trans,trans)-3,5-bis[(3-hydroxyphenyl)carbonyl]-4-(3-fluoro-2-methylphenyl)piperidyl}ethyl)-N-methylacetamide
(trans,trans)-1-[2-(dimethylamino)ethyl-4-(3-fluoro-2-methylphenyl)-5-[(3-methoxyphenyl)carbonyl](3-piperidyl) 3-methoxyphenyl ketone
(trans,trans)-1-[2-(dimethylamino)ethyl]-4-(3-fluoro-2-methylphenyl)-5-[(3-hydroxyphenyl)carbonyl](3-piperidyl) 3-hydroxyphenyl ketone
(trans,trans)-4-(3-fluoro-2-methylphenyl)-5-[(3-methoxyphenyl)carbonyl]-1-(2-morpholin-4-ylethyl)(3-piperidyl) 3-methoxyphenyl ketone (trans,trans)-4-(3-fluoro-2-methylphenyl)-5-[(3-methoxyphenyl)carbonyl]-1-(pyrazol-5-ylmethyl)(3-piperidyl) 3-methoxyphenyl ketone
(trans,trans)-4-(3-fluoro-2-methylphenyl)-5-[(3-hydroxyphenyl)carbonyl]-1-(pyrazol-5-ylmethyl)(3-piperidyl) 3-hydroxyphenyl ketone
1-((1S)-2-hydroxy-isopropyl)(trans,trans)-4-(3-fluoro-2-methylphenyl)-5-[(3-methoxyphenyl)carbonyl](3-piperidyl) 3-methoxyphenyl ketone
1-((1S)-2-hydroxy-isopropyl)(trans,trans)-4-(3-fluoro-2-methylphenyl)-5-[(3-hydroxyphenyl)carbonyl](3-piperidyl) 3-hydroxyphenyl ketone
1-((1R)-2-hydroxy-isopropyl)(trans,trans)-4-(3-fluoro-2-methylphenyl)-5-[(3-methoxyphenyl)carbonyl](3-piperidyl) 3-methoxyphenyl ketone
1-((1R)-2-hydroxy-isopropyl)(trans,trans)-4-(3-fluoro-2-methylphenyl)-5-[(3-hydroxyphenyl)carbonyl](3-piperidyl) 3-hydroxyphenyl ketone
(trans,trans)-5-[(2-fluoro-5-methoxyphenyl)carbonyl]-4-(3-fluoro-2-methylphenyl)-1-(2-hydroxyethyl)(3-piperidyl) 2-fluoro-5-methoxyphenyl ketone
N-(2-{(trans,trans)-3,5-bis[(3-hydroxyphenyl)carbonyl]-4-(3-fluoro-2-methylphenyl)piperidyl}ethyl)acetamide
(trans,trans)-4-(3-fluoro-2-methylphenyl)-5-[(3-hydroxyphenyl)carbonyl]-1-(2-[(methylsulfonyl)amino]ethyl](3-piperidyl) 3-hydroxyphenyl ketone
N-(2-{(trans,trans)-3,5-bis[(3-hydroxyphenyl)carbonyl]-4-(3-fluoro-2-methylphenyl)piperidyl}ethyl)methoxycarboxamide
(trans,trans)-4-(3-fluoro-2-methylphenyl)-5-[(2-fluorophenyl)carbonyl]-1-(2-hydroxyethyl)(3-piperidyl) 2-fluorophenyl ketone
(trans,trans)-4-(3-fluoro-2-methylphenyl)-5-[(3-hydroxyphenyl)carbonyl]-1-[2-(methylamino)ethyl](3-piperidyl) 3-hydroxyphenyl ketone
(trans,trans)-4-(3-fluoro-2-methylphenyl)-5-[(3-hydroxyphenyl)carbonyl]-1-(2-[methyl(methylsulfonyl)amino]ethyl}(3-piperidyl) 3-hydroxyphenyl ketone
N-(2-{(trans,trans)-3,5-bis[(3-hydroxyphenyl)carbonyl]-4-(3-fluoro-2-methylphenyl)piperidyl}ethyl)methoxy-N-methylcarboxamide
2-[(trans,trans)-3,5-bis(phenylcarbonyl)-4-(3-ethylphenyl)piperidyl]-N,N-dimethylacetamide
(trans,trans)-4-(3-ethylphenyl)-1-(2-hydroxyethyl)-5-(phenylcarbonyl)(3-piperidyl)phenyl ketone
(trans,trans)-5-[(2-fluoro-3-hydroxyphenyl)carbonyl]-4-(3-fluoro-2-methylphenyl)-1-(2-hydroxyethyl)(3-piperidyl) 2-fluoro-3-hydroxyphenyl ketone
(trans,trans)-5-[(2-fluoro-3-hydroxyphenyl)carbonyl]-4-(3-fluoro-2-methylphenyl)-1-(2-hydroxyethyl)(3-piperidyl) 2-fluoro-3-methoxyphenyl ketone
(trans,trans)-4-(3-fluoro-2-methylphenyl)-1-(2-hydroxy-2-methylpropyl)-5-[(3-methoxyphenyl)carbonyl](3-piperidyl) 3-methoxyphenyl ketone
(trans,trans)-4-(3-fluoro-2-methylphenyl)-1-(2-hydroxy-2-methylpropyl)-5-[(3-hydroxyphenyl)carbonyl](3-piperidyl) 3-hydroxyphenyl ketone
(trans,trans)-4-(3-fluoro-2-methylphenyl)-1-(2-methoxyethyl)-5-(phenylcarbonyl)(3-piperidyl)phenyl ketone
(trans,trans)-4-(3-fluoro-2-methylphenyl)-5-[(3-hydroxyphenyl)carbonyl]-1-(2-methoxyethyl)(3-piperidyl) 3-hydroxyphenyl ketone
(trans,trans)-4-(3-fluoro-2-methylphenyl)-1-(2-hydroxyethyl)-5-[(3-methoxyphenyl)carbonyl](3-piperidyl) 3-hydroxyphenyl ketone
(trans,trans)-4-(3-fluoro-2-methylphenyl)-1-(2-methoxyethyl)-5-[(3-methoxyphenyl)carbonyl](3-piperidyl) 3-hydroxyphenyl ketone
(trans,trans)-4-(3-fluoro-2-methylphenyl)-1-(2-methoxyethyl)-5-[(3-methoxyphenyl)carbonyl](3-piperidyl) 2-fluorophenyl ketone
(trans,trans)-4-(3-fluoro-2-methylphenyl)-1-(2-hydroxyethyl)-5-[(3-hydroxyphenyl)carbonyl](3-piperidyl) 2-fluorophenyl ketone
(trans,trans)-1-(2,3-dihydroxypropyl)-4-(3-fluoro-2-methylphenyl)-5-[(3-hydroxyphenyl)carbonyl](3-piperidyl) 3-hydroxyphenyl ketone
1-((1R)-2-hydroxy-isopropyl)(trans,trans)-4-(3-fluoro-2-methylphenyl)-5-[(3-hydroxyphenyl)carbonyl](3-piperidyl) 3-hydroxyphenyl ketone
N-(2-{(trans,trans)-4-(3-fluoro-2-methylphenyl)-5-[(2-fluorophenyl)carbonyl]-3-[(3-methoxyphenyl)carbonyl]piperidyl}ethyl)methoxycarboxamide
(trans,trans)-4-(3-fluoro-2-methylphenyl)-5-[(3-methoxyphenyl)carbonyl]-1-{2-[(methylsulfonyl)amino]ethyl}(3-piperidyl) 2-fluorophenyl ketone
(trans,trans)-4-(3-fluoro-2-methylphenyl)-5-[(3-methoxyphenyl)carbonyl]-1-{2-[methyl(methylsulfonyl)amino]ethyl}(3-piperidyl) 2-fluorophenyl ketone
(trans,trans)-4-(3-fluoro-2-methylphenyl)-5-[(3-methoxyphenyl)carbonyl]-1-[2-(methylamino)ethyl](3-piperidyl) 2-fluorophenyl ketone
1-(2-{(trans,trans)-3,5-bis[(3-methoxyphenyl)carbonyl]-4-(3-fluoro-2-methylphenyl)piperidyl}ethyl)pyrrolidin-2-one
1-(2-{(trans,trans)-3,5-bis[(3-hydroxyphenyl)carbonyl]-4-(3-fluoro-2-methylphenyl)piperidyl}ethyl)pyrrolidin-2-one
N-{2-[(trans,trans)-4-(2,3-dimethylphenyl)-3,5-bis(phenylcarbonyl)piperidyl]ethyl}-3-(2-{2-[2-(2-aminoethoxy)ethoxy]ethoxy}ethoxy)propanamide
(trans,trans)-4-(2,3-dichlorophenyl)-5-[(3-methoxyphenyl)carbonyl]-1-[2-(methylamino)ethyl](3-piperidyl) 3-methoxyphenyl ketone
(trans,trans)-4-(3-chloro-2-fluorophenyl)-5-[(3-methoxyphenyl)carbonyl]-1-[2-(methylamino)ethyl](3-piperidyl) 3-methoxyphenyl ketone
(trans,trans)-4-(2,3-dichlorophenyl)-1-(2-hydroxyethyl)-5-[(3-hydroxyphenyl)carbonyl](3-piperidyl) 3-hydroxyphenyl ketone
(trans,trans)-4-(3-chloro-2-fluorophenyl)-1-(2-hydroxyethyl)-5-[(3-hydroxyphenyl)carbonyl](3-piperidyl) 3-hydroxyphenyl ketone
N-(2-{(trans,trans)-3,5-bis[(3-hydroxyphenyl)carbonyl]-4-(3-fluoro-2-methyl phenyl)piperidyl}-isopropyl)methoxycarboxamide
(trans,trans)-4-(3-fluoro-2-methylphenyl)-5-[(3-hydroxyphenyl)carbonyl]-1-{2-[(methylsulfonyl)amino]propyl}(3-piperidyl) 3-hydroxyphenyl ketone
N-((1S)-2-{(trans,trans)-3,5-bis[(3-hydroxyphenyl)carbonyl]-4-(3-fluoro-2-methylphenyl)piperidyl}-isopropyl)methoxycarboxamide
N-(2-{(trans,trans)-3,5-bis[(3-hydroxyphenyl)carbonyl]-4-(3-fluoro-2-methylphenyl)piperidyl}-tert-butyl)methoxycarboxamide
N-(2-{(trans,trans)-3,5-bis[(3-hydroxyphenyl)carbonyl]-4-(3-fluoro-2-methylphenyl)piperidyl}-isopropyl)methoxy-N-methylcarboxamide
(trans,trans)-4-(3-fluoro-2-methylphenyl)-5-[(3-hydroxyphenyl)carbonyl]-1-{2-[methyl(methylsulfonyl)amino]propyl}(3-piperidyl) 3-hydroxyphenyl ketone 1-{(2S)-2-[(methylsulfonyl)amino]propyl}(trans,trans)-4-(3-fluoro-2-methylphenyl)-5-[(3-hydroxyphenyl)carbonyl](3-piperidyl) 3-hydroxyphenyl ketone
1-(2-{(trans,trans)-4-(3-fluoro-2-methylphenyl)-5-[(2-fluorophenyl)carbonyl]-3-[(3-hydroxyphenyl)carbonyl]piperidyl}ethyl)pyrrolidin-2-one
(trans,trans)-4-(2,3-dichlorophenyl)-5-[(3-hydroxyphenyl)carbonyl]-1-(2-[methyl(methylsulfonyl)amino]ethyl}(3-piperidyl) 3-hydroxyphenyl ketone
(trans,trans)-4-(3-chloro-2-fluorophenyl)-5-[(3-hydroxyphenyl)carbonyl]-1-{2-[methyl(methylsulfonyl)amino]ethyl}(3-piperidyl) 3-hydroxyphenyl ketone
N-(2-{(trans,trans)-4-(2,3-dichlorophenyl)-3,5-bis[(3-hydroxyphenyl)carbonyl]piperidyl}ethyl)methoxy-N-methylcarboxamide
N-(2-{(trans,trans)-3,5-bis[(3-hydroxyphenyl)carbonyl]-4-(3-chloro-2-fluorophenyl)piperidyl}ethyl)methoxy-N-methylcarboxamide
(trans,trans)-4-(2-fluoro-3-methylphenyl)-5-[(3-hydroxyphenyl)carbonyl]-1-{2-[methyl(methylsulfonyl)amino]ethyl}(3-piperidyl) 3-hydroxyphenyl ketone
N-(2-{(trans,trans)-3,5-bis[(3-hydroxyphenyl)carbonyl]-4-(2-fluoro-3-methylphenyl)piperidyl}ethyl)methoxy-N-methylcarboxamide
(trans,trans)-4-(2-fluoro-3-methylphenyl)-1-(2-hydroxyethyl)-5-[(3-hydroxyphenyl)carbonyl](3-piperidyl) 3-hydroxyphenyl ketone
N-(2-{(trans,trans)-3,5-bis[(3-hydroxyphenyl)carbonyl]-4-(3-fluoro-2-methylphenyl)piperidyl}ethyl)-N-methyl(methylamino)carboxamide
2-{(trans,trans)-35-bis[(3-hydroxyphenyl)carbonyl]-4-(3-fluoro-2-methylphenyl)piperidyl}acetamide
2-{(trans,trans)-3,5-bis[(3-hydroxyphenyl)carbonyl]-4-(3-fluoro-2-methylphenyl)piperidyl}-4-methylpentanamide
(trans,trans)-1-(benzimidazol-2-ylmethyl)-4-(3-fluoro-2-methylphenyl)-5-[3-hydroxyphenyl)carbonyl](3-piperidyl) 3-hydroxyphenyl ketone
(trans,trans)-4-(2,6-difluoro-3-methylphenyl)-1-(2-hydroxyethyl)-5-[(3-hydroxyphenyl)carbonyl](3-piperidyl) 3-hydroxyphenyl ketone
N-(2-{(trans,trans)-3,5-bis[(3-hydroxyphenyl)carbonyl]-4-(3-fluoro-2-methylphenyl)piperidyl}ethyl)amino-N-methylamide
(trans,trans)-1-(2-aminoethyl)-4-(3-fluoro-2-methylphenyl)-5-[(3-methoxyphenyl)carbonyl](3-piperidyl) 3-methoxyphenyl ketone
(trans,trans)-4-(3-fluoro-2-methylphenyl)-5-[(3-hydroxyphenyl)carbonyl]-1-(4-piperidyl)(3-piperidyl) 3-hydroxyphenyl ketone
(trans,trans)-4-(3-fluoro-2-methylphenyl)-5-[(3-hydroxyphenyl)carbonyl]-1-[1-(methylsulfonyl)(4-piperidyl)](3-piperidyl) 3-hydroxyphenyl ketone
(trans,trans)-4-(2,6-difluoro-3-methylphenyl)-5-[(3-hydroxyphenyl)carbonyl]-1-{2-[methyl(methylsulfonyl)amino]ethyl}(3-piperidyl) 3-hydroxyphenyl ketone
N-(2-{(trans,trans)-4-(2,6-difluoro-3-methylphenyl)-3,5-bis[(3-hydroxyphenyl)carbonyl]piperidyl}ethyl)methoxy-N-methylcarboxamide
(trans,trans)-5-[(2-fluoro-3-methoxyphenyl)carbonyl]-4-(3-fluoro-2-methylphenyl)-1-{2-[methyl(methylsulfonyl)amino]ethyl}(3-piperidyl) 2-fluoro-3-methoxyphenyl ketone
(trans,trans)-5-[(2-fluoro-3-hydroxyphenyl)carbonyl]-4-(3-fluoro-2-methylphenyl)-1-{2-[(methylsulfonyl)amino]ethyl}(3-piperidyl) 2-fluoro-3-hydroxyphenyl ketone
N-(2-{(trans,trans)-3,5-bis[(3-hydroxyphenyl)carbonyl]-4-(3-fluoro-2-methylphenyl)piperidyl}ethyl)aminoamide
(trans,trans)-1-(2-{[(dimethylamino)sulfonyl]amino}ethyl)-4-(3-fluoro-2-methylphenyl)-5-[(3-hydroxyphenyl)carbonyl](3-piperidyl) 3-hydroxyphenyl ketone
(trans,trans)-1-(2-{[(dimethylamino)sulfonyl]methylamino}ethyl)-4-(3-fluoro-2-methylphenyl)-5-[(3-hydroxyphenyl)carbonyl](3-piperidyl) 3-hydroxyphenyl ketone
(trans,trans)-4-(3-fluoro-2-methylphenyl)-5-[(3-hydroxyphenyl)carbonyl]-1-(2,2,6,6-tetramethyl(4-piperidyl))(3-piperidyl) 3-hydroxyphenyl ketone
(trans,trans)-4-(3-fluoro-2-methylphenyl)-1-(2-methoxyethyl)-5-[(3-methoxyphenyl)carbonyl](3-piperidyl) 2,3-difluorophenyl ketone
(trans,trans)-5-[(2-fluoro-3-hydroxyphenyl)carbonyl]-4-(3-fluoro-2-methylphenyl)-1-[2-(methylamino)ethyl](3-piperidyl) 2-fluoro-3-hydroxyphenyl ketone
(trans,trans)-1-(2-aminoethyl)-5-[(6-fluoro-3-hydroxyphenyl)carbonyl]-4-(3-fluoro-2-methylphenyl)(3-piperidyl) 6-fluoro-3-hydroxyphenyl ketone
(trans,trans)-4-(3-fluoro-2-methylphenyl)-1-(2-hydroxyethyl)-5-[(3-hydroxyphenyl)Carbonyl](3-piperidyl) 2,3-difluorophenyl ketone
(trans,trans)-4-(3-fluoro-2-methylphenyl)-5-[(3-methoxyphenyl)carbonyl]-1-(3,3,3-trifluoro-2-hydroxypropyl)(3-piperidyl) 3-methoxyphenyl ketone
(trans,trans)-4-(3-fluoro-2-methylphenyl)-5-[(3-hydroxyphenyl)carbonyl]-1-(3,3,3-trifluoro-2-hydroxypropyl)(3-piperidyl) 3-hydroxyphenyl ketone
1-(2-{(trans,trans)-3,5-bis[(3-methoxyphenyl)carbonyl]-4-(3-fluoro-2-methylphenyl)piperidyl}ethyl)imidazolidin-2-one
1-(2-{(trans,trans)-3,5-bis[(3-hydroxyphenyl)carbonyl]-4-(3-fluoro-2-methylphenyl)piperidyl}ethyl)imidazolidin-2-one
1-((2R)-2-aminocyclohexyl)(trans,trans)-4-(3-fluoro-2-methylphenyl)-5-[(3-hydroxyphenyl)carbonyl](3-piperidyl) 3-hydroxyphenyl ketone
(trans,trans)-1-(2-aminocyclohexyl)-4-(3-fluoro-2-methylphenyl)-5-[(3-hydroxyphenyl)carbonyl](3-piperidyl) 3-hydroxyphenyl ketone
(trans,trans)-4-(3-fluoro-2-methylphenyl)-5-[(3-hydroxyphenyl)carbonyl]-1-(2-[(methylsulfonyl)amino]cyclohexyl}(3-piperidyl) 3-hydroxyphenyl ketone
(trans,trans)-5-[(2-fluoro-3-hydroxyphenyl)carbonyl]-4-(3-fluoro-2-methylphenyl)-1-{2-[methyl(methylsulfonyl)amino]ethyl}(3-piperidyl) 2-fluoro-3-hydroxyphenyl ketone
(trans,trans)-4-(3-fluoro-2-methylphenyl)-5-[(3-hydroxyphenyl)carbonyl]-1-benzyl(3-piperidyl) 3-hydroxyphenyl ketone
(trans,trans)-4-(3-fluoro-2-methylphenyl)-5-[(3-hydroxyphenyl)carbonyl]-1-pyrrolidin-3-yl(3-piperidyl) 3-hydroxyphenyl ketone
(trans,trans)-4-(3-fluoro-2-methylphenyl)-5-[(3-hydroxyphenyl)carbonyl]-1-[1-(methylsulfonyl)pyrrolidin-3-yl](3-piperidyl) 3-hydroxyphenyl ketone
methyl 3-{(trans,trans)-3,5-bis[(3-hydroxyphenyl)carbonyl]-4-(3-fluoro-2-methylphenyl)piperidyl}pyrrolidinecarboxylate
3-{(trans,trans)-3,5-bis[(3-hydroxyphenyl)carbonyl]-4-(3-fluoro-2-methylphenyl)piperidyl}-1-acetylpyrrolidine 3-{(trans,trans)-3,5-bis[(3-hydroxyphenyl)carbonyl]-4-(3-fluoro-2-methylphenyl)piperidyl}pyrrolidinecarboxamide (3-((trans,trans)-3,5-bis[(3-hydroxyphenyl)carbonyl]-4-(3-fluoro-2-methylphenyl)piperidyl}pyrrolidinyl)-N-methylcarboxamide (trans,trans)-1-(1-[(dimethylamino)sulfonyl]pyrrolidin-3-yl]-4-(3-fluoro-2-methylphenyl)-5-[(3-hydroxyphenyl)carbonyl](3-piperidyl) 3-hydroxyphenyl ketone (trans,trans)-4-(3-fluoro-2-methylphenyl)-5-[(3-methoxyphenyl)carbonyl]-1-[2-(methylamino)ethyl](3-piperidyl) 2-fluoro-3-methoxyphenyl ketone (trans,trans)-4-(3-fluoro-2-methylphenyl)-1-(2-hydroxyethyl)-5-[(3-hydroxyphenyl)carbonyl](3-piperidyl) 2-fluoro-3-hydroxyphenyl ketone (trans,trans)-4-(3-fluoro-2-methylphenyl)-5-[(3-hydroxyphenyl)carbonyl]-1-[2-(methylamino)ethyl](3-piperidyl) 2-fluoro-3-hydroxyphenyl ketone 4-((trans,trans)-3,5-bis[(3-hydroxyphenyl)carbonyl]-4-(3-fluoro-2-methylphenyl)piperidyl]-3-hydroxythiolane-1,1-dione (2-{(trans,trans)-3,5-bis[(3-hydroxyphenyl)carbonyl]-4-(3-fluoro-2-methylphenyl)piperidyl}ethyl)aminomethylsulfonamide (trans,trans)-4-(3-fluoro-2-methylphenyl)-5-[(3-hydroxyphenyl)carbonyl]-1-(3-piperidylmethyl)(3-piperidyl) 3-hydroxyphenyl ketone (trans,trans)-4-(3-fluoro-2-methylphenyl)-5-[(3-hydroxyphenyl)carbonyl]-1-(3-piperidyl)(3-piperidyl) 3-hydroxyphenyl ketone (trans,trans)-4-(3-fluoro-2-methylphenyl)-5-[(3-hydroxyphenyl)carbonyl]-1-[2-(methylamino)ethyl](3-piperidyl) 2-fluoro-3-(trifluoromethyl)phenyl ketone (trans,trans)-4-(3-fluoro-2-methylphenyl)-5-[(3-hydroxyphenyl)carbonyl]-1-[2-(methylamino)ethyl](3-piperidyl) 2-fluoro-3-methylphenyl ketone (trans,trans)-4-(3-fluoro-2-methylphenyl)-1-(2-hydroxyethyl)-5-[(3-hydroxyphenyl)carbonyl](3-piperidyl) 2-fluoro-3-methylphenyl ketone (trans,trans)-4-(3-fluoro-2-methylphenyl)-5-[(3-hydroxyphenyl)carbonyl]-1-thian-4-yl(3-piperidyl) 3-hydroxyphenyl ketone (trans,trans)-4-(3-fluoro-2-methylphenyl)-1-(4-hydroxycyclohexyl)-5-[(3-hydroxyphenyl)carbonyl](3-piperidyl) 3-hydroxyphenyl ketone (trans,trans)-4-(3-fluoro-2-methylphenyl)-5-[(3-hydroxyphenyl)carbonyl]-1-(pyrrolidin-2-ylmethyl)(3-piperidyl) 3-hydroxyphenyl ketone (trans,trans)-1-(4-aminobutyl)-4-(3-fluoro-2-methylphenyl)-5-[(3-methoxyphenyl)carbonyl](3-piperidyl) 3-methoxyphenyl ketone (trans,trans)-1-(4-aminobutyl)-4-(3-fluoro-2-methylphenyl)-5-[(3-hydroxyphenyl)carbonyl](3-piperidyl) 3-hydroxyphenyl ketone 2-{(trans,trans)-3,5-bis[(3-hydroxyphenyl)carbonyl]-4-(3-fluoro-2-methylphenyl)piperidyl}-3-(dimethylamino)propanoic acid (trans,trans)-1-acetyl-3,5-bis[(3-methoxyphenyl)Carbonyl]-4-(3-fluoro-2-methylphenyl)piperidine (trans,trans)-4-(3-fluoro-2-methylphenyl)-1-(2-methoxyethyl)-5-[(3-methoxyphenyl)carbonyl](3-piperidyl) 3-chloro-2-[(2-methoxyethyl)amino]phenyl ketone (trans,trans)-4-(3-fluoro-2-methylphenyl)-5-[(3-methoxyphenyl)carbonyl]-1-[2-(methylamino)ethyl](3-piperidyl) 3-chloro-2-{[2-(methylamino)ethyl]aminophenyl ketone 2-{(trans,trans)-3,5-bis[(3-hydroxyphenyl)carbonyl]-4-(3-fluoro-2-methylphenyl)piperidyl}-3-(dimethylamino)propanamide 2-{(trans,trans)-3,5-bis[(3-hydroxyphenyl)carbonyl]-4-(3-fluoro-2-methylphenyl)piperidyl}-3-(dimethylamino)-N,N-dimethylpropanamide (trans,trans)-1-[4-(dimethylamino)butyl]-4-(3-fluoro-2-methylphenyl)-5-[(3-hydroxyphenyl)carbonyl](3-piperidyl) 3-hydroxyphenyl ketone (trans,trans)-4-(3-fluoro-2-methylphenyl)-5-[(3-hydroxyphenyl)carbonyl]-1-[4-(methylamino)butyl](3-piperidyl) 3-hydroxyphenyl ketone 2-{(trans,trans)-3,5-bis[(3-hydroxyphenyl)carbonyl]-4-(3-fluoro-2-methylphenyl)piperidyl}-N-[2-(methylamino)ethyl]acetamide 2-{(trans,trans)-3,5-bis[(3-hydroxyphenyl)carbonyl]-4-(3-fluoro-2-methylphenyl)piperidyl}-N-(2-aminoethyl)acetamide 1-{(trans,trans)-3,5-bis[(3-hydroxyphenyl)carbonyl]-4-(3-fluoro-2-methylphenyl)piperidyl}-3-(methylamino)propan-1-one (trans,trans)-4-(3-fluoro-2-methylphenyl)-5-[(3-hydroxyphenyl)carbonyl]-1-[2-(methylamino)ethyl](3-piperidyl) 3-chloro-2-{[2-(methylamino)ethyl]amino}phenyl ketone (trans,trans)-1-acetyl-3,5-bis[(3-hydroxyphenyl)carbonyl]-4-(3-fluoro-2-methylphenyl)piperidine (trans,trans)-4-(3-fluoro-2-methylphenyl)-1-(2-hydroxyethyl)-5-[(3-hydroxyphenyl)carbonyl](3-piperidyl) 3-chloro-2-fluorophenyl ketone N-(2-{(trans,trans)-3,5-bis[(3-methoxyphenyl)carbonyl]-4-(3-fluoro-2-methylphenyl)piperidyl}-2-oxoethyl)(tert-butoxy)-N-methylcarboxamide (trans,trans)-1-(5-aminopentyl)-4-(3-fluoro-2-methylphenyl)-5-[(3-methoxyphenyl)carbonyl](3-piperidyl) 3-methoxyphenyl ketone (trans,trans)-1-(5-aminopentyl)-4-(3-fluoro-2-methylphenyl)-5-[(3-hydroxyphenyl)carbonyl](3-piperidyl) 3-hydroxyphenyl ketone (trans,trans)-1-[5-(dimethylamino)pentyl]-4-(3-fluoro-2-methylphenyl)-5-[(3-hydroxyphenyl)carbonyl](3-piperidyl) 3-hydroxyphenyl ketone 1-{(trans,trans)-3,5-bis[(3-hydroxyphenyl)carbonyl]-4-(3-fluoro-2-methylphenyl)piperidyl}-2-aminoethan-1-one 2-{(trans,trans)-3,5-bis[(3-hydroxyphenyl)carbonyl]-4-(3-fluoro-2-methylphenyl)piperidyl}-3-(dimethylamino)-N-methylpropanamide (trans,trans)-4-(3-fluoro-2-methylphenyl)-5-[(3-hydroxyphenyl)carbonyl]-1-(1,2,2,6,6-pentamethyl(4-piperidyl))(3-piperidyl) 3-hydroxyphenyl ketone (trans,trans)-1-(2-amino-isopropyl)-4-(3-fluoro-2-methylphenyl)-5-[(3-hydroxyphenyl)carbonyl](3-piperidyl) 3-hydroxyphenyl ketone 1-{(trans,trans)-3,5-bis[(3-hydroxyphenyl)carbonyl]-4-(3-fluoro-2-methylphenyl)piperidyl}-2-(methylamino)ethan-1-one 1-{(trans,trans)-3,5-bis[(3-methoxyphenyl)carbonyl]-4-(3-fluoro-2-methylphenyl)piperidyl}-2-(dimethylamino)ethan-1-one 1-{(trans,trans)-3,5-bis[(3-hydroxyphenyl)carbonyl]-4-(3-fluoro-2-methylphenyl)piperidyl}-2-(dimethylamino)ethan-1-one 2-{(trans,trans)-3,5-bis[(3-methoxyphenyl)carbonyl]-4-(3-fluoro-2-methylphenyl)piperidyl}-N-[3-(dimethylamino)propyl]-3-hydroxypropanamide 2-{(trans,trans)-35-bis[(3-hydroxyphenyl)carbonyl]-4-(3-fluoro-2-methylphenyl)piperidyl}-N-(2-aminoethyl)-3-hydroxypropanamide (trans,trans)-1-(azetidin-3-ylcarbonyl)-4-(3-fluoro-2-methylphenyl)-5-[(3-hydroxyphenyl)carbonyl](3-piperidyl) 3-hydroxyphenyl ketone 2-{(trans,trans)-3,5-bis[(3-hydroxyphenyl)carbonyl]-4-(3-fluoro-2-methylphenyl)piperidyl}-N-[3(dimethylamino)propyl]-3-hydroxypropanamide 2-{(trans,trans)-3,5-bis[(3-hydroxyphenyl)carbonyl]-4-(3-fluoro-2-methylphenyl)piperidyl}N-4-(dimethylamino)butyl]3-hydroxypropanamide (trans,trans)-4-(3-fluoro-2-methylphenyl)-1-(2-hydroxyethyl)-5-[(3-hydroxyphenyl)carbonyl](3-piperidyl) 2-chloro-6-fluorophenyl ketone (trans,trans)-4-(3-fluoro-2-methylphenyl)-5-[(3-hydroxyphenyl)carbonyl]-1-(3-pyrrolidinylpropyl)(3-piperidyl) 3-hydroxyphenyl ketone (trans,trans)-1-[2-(dimethylamino)ethyl]-4-(3-fluoro-2-methylphenyl)-5-[(3-hydroxyphenyl)carbonyl](3-piperidyl) 3-hydroxyphenyl ketone (trans,trans)-4-(3-fluoro-2-methylphenyl)-5-[(3-methoxyphenyl)carbonyl]-1-[5-(methylamino)pentyl](3-piperidyl) 3-methoxyphenyl ketone (trans,trans)-4-(3-fluoro-2-methylphenyl)-5-[(3-hydroxyphenyl)carbonyl]-1-[3-(methylamino)propyl](3-piperidyl) 3-hydroxyphenyl ketone (trans,trans)-1-[3-(dimethylamino)propyl]-4-(3-fluoro-2-methylphenyl)-5-[(3-hydroxyphenyl)carbonyl](3-piperidyl) 3-hydroxyphenyl ketone (trans,trans)-4-(3-fluoro-2-methylphenyl)-1-(4-hydroxybutyl)-5-[(3-methoxyphenyl)carbonyl](3-piperidyl) 3-methoxyphenyl ketone (trans,trans)-4-(3-fluoro-2-methylphenyl)-5-[(3-hydroxyphenyl)carbonyl]-1-(1-methyl(4-piperidyl))(3-piperidyl) 3-hydroxyphenyl ketone 3-{(trans,trans)-3,5-bis[(3-hydroxyphenyl)carbonyl]-4-(3-fluoro-2-methylphenyl)piperidyl}thiolane-1,1-dione (trans,trans)-1-(2-amino-3-hydroxypropyl)-4-(3-fluoro-2-methylphenyl)-5-[(3-hydroxyphenyl)carbonyl](3-piperidyl) 3-hydroxyphenyl ketone (trans,trans)-1-{2-[bis(methylethyl)amino]ethyl}-4-(3-fluoro-2-methylphenyl)-5-[(3-hydroxyphenyl)carbonyl](3-piperidyl) 3-hydroxyphenyl ketone (trans,trans)-1-[2-(dimethylamino)ethyl]-4-(3-fluoro-2-methylphenyl)-5-[(3-hydroxyphenyl)carbonyl](3-piperidyl) 3-hydroxyphenyl ketone (trans,trans)-1-[2-(dimethylamino)-2-methylpropyl]-4-(3-fluoro-2-methylphenyl)-5-[(3-hydroxyphenyl)carbonyl](3-piperidyl) 3-hydroxyphenyl ketone (trans,trans)-1-{1-[(dimethylamino)methyl]-2-hydroxyethyl}-4-(3-fluoro-2-methylphenyl)-5-[(3-methoxyphenyl)carbonyl](3-piperidyl) 3-methoxyphenyl ketone 2-{(trans,trans)-3,5-bis[(3-hydroxyphenyl)carbonyl]-4-(3-fluoro-2-methylphenyl)piperidyl}-N-[2-(dimethylamino)ethyl]acetamide (trans,trans)-1-(2-amino-tert-butyl)-4-(3-fluoro-2-methylphenyl)-5-[(3-hydroxyphenyl)carbonyl](3-piperidyl) 3-hydroxyphenyl ketone (trans,trans)-4-(3-fluoro-2-methylphenyl)-5-[(3-hydroxyphenyl)carbonyl]-1-[2-(methylamino)ethyl](3-piperidyl) 2-chloro-6-fluorophenyl ketone 1-{(trans,trans)-3,5-bis[(3-hydroxyphenyl)carbonyl]-4-(3-fluoro-2-methylphenyl)piperidyl}-4-(dimethylamino)butan-1-one 1-{(trans,trans)-3,5-bis[(3-hydroxyphenyl)carbonyl]-4-(3-fluoro-2-methylphenyl)piperidyl}-2-piperidylethan-1-one (trans,trans)-4-(3-fluoro-2-methylphenyl)-5-[(3-hydroxyphenyl)carbonyl]-1-(3-piperidylcarbonyl)(3-piperidyl) 3-hydroxyphenyl ketone 1-(2-((trans,trans)-3,5-bis[(3-hydroxyphenyl)carbonyl]-4-(3-fluoro-2-methylphenyl)piperidyl]ethyl)-3-methylimidazolidin-2-one 1-[(2S)-2-(dimethylamino)propyl](trans,trans)-4-(3-fluoro-2-methylphenyl)-5-[(3-hydroxyphenyl)carbonyl](3-piperidyl) 3-hydroxyphenyl ketone 1-[(2R)-2-(dimethylamino)-3-hydroxypropyl](trans,trans)-4-(3-fluoro-2-methylphenyl)-5-[(3-hydroxyphenyl)carbonyl](3-piperidyl) 3-hydroxyphenyl ketone 1-((2R)-3-hydroxy-2-piperidylpropyl)(trans,trans)-4-(3-fluoro-2-methylphenyl)-5-[(3-hydroxyphenyl)carbonyl](3-piperidyl) 3-hydroxyphenyl ketone 1-[(2R)-2-(cyclopentylamino)-3-hydroxypropyl](trans,trans)-4-(3-fluoro-2-methylphenyl)-5-[(3-hydroxyphenyl)carbonyl](3-piperidyl) 3-hydroxyphenyl ketone (trans,trans)-1-[2-(dimethylamino)-isopropyl]-4-(3-fluoro-2-methylphenyl)-5-[(3-hydroxyphenyl)carbonyl](3-piperidyl) 3-hydroxyphenyl ketone 2-{(trans,trans)-3,5-bis[(3-hydroxyphenyl)carbonyl]-4-(3-fluoro-2-methylphenyl)piperidyl}-2-methyl-1-(4-methylpiperazinyl)propan-1-one (trans,trans)-1-[2-(dimethylamino)-tert-butyl]-4-(3-fluoro-2-methylphenyl)-5-[(3-hydroxyphenyl)carbonyl](3-piperidyl) 3-hydroxyphenyl ketone 2-{(trans,trans)-3,5-bis[(3-hydroxyphenyl)carbonyl]-4-(3-fluoro-2-methylphenyl)piperidyl}-N-[2-(dimethylamino)ethyl]propanamide 2-{(trans,trans)-3,5-bis[(3-hydroxyphenyl)carbonyl]-4-(3-fluoro-2-methylphenyl)piperidyl}-N-[2-(dimethylamino)ethyl]-3-hydroxypropanamide 2-{(trans,trans)-3,5-bis[(3-hydroxyphenyl)carbonyl]-4-(3-fluoro-2-methylphenyl)piperidyl}-1-piperazinylethan-1-one (2R)-3-amino-2-{3,5-bis[(3-hydroxyphenyl)carbonyl]-4-(3-fluoro-2-methylphenyl)piperidyl}propanamide (2S)-2-{(trans,trans)-3,5-bis[(3-hydroxyphenyl)carbonyl]-4-(3-fluoro-2-methylphenyl)piperidyl}-3-aminopropanamide 2-{3,5-bis[(3-hydroxyphenyl)carbonyl]-4-(3-fluoro-2-methylphenyl)piperidyl)-1-(4-methylpiperazinyl)propan-1-one (trans,trans)-1-{1-[(dimethylamino)methyl]-2-hydroxyethyl}-4-(3-fluoro-2-methylphenyl)-5-[(3-hydroxyphenyl)carbonyl](3-piperidyl) 3-hydroxyphenyl ketone (trans,trans)-4-(3-fluoro-2-methylphenyl)-5-[(3-hydroxyphenyl)carbonyl]-1-(piperazin-2-ylcarbonyl)(3-piperidyl) 3-hydroxyphenyl ketone 1-{(trans,trans)-3,5-bis[(3-hydroxyphenyl)carbonyl]-4-(3-fluoro-2-methylphenyl)piperidyl}-3,3-dimethylbutan-1-one (trans,trans,trans)-4-(3-fluoro-2-methylphenyl)-2,6-dimethyl-5-(phenylcarbonyl)(3-piperidyl)phenyl ketone 2-[(trans,trans,trans,trans)-3,5-bis(phenylcarbonyl)-4-(3-fluoro-2-methylphenyl)-2,6-dimethylpiperidyl]-N,N-dimethylacetamide (trans,trans,trans,trans)-4-(3-fluoro-2-methylphenyl)-1-(2-methoxyethyl)-2,6-dimethyl-5-(phenylcarbonyl)(3-piperidyl)phenyl ketone {(trans,trans)-3,5-bis[(3-hydroxyphenyl)carbonyl]-4-(3-fluoro-2-methylphenyl)piperidyl)-N-[3-(dimethylamino)propyl]carboxamide (trans,trans)-4-(3-fluoro-2-methylphenyl)-5-[(3-hydroxyphenyl)carbonyl]-1-[(1-methyl(4-piperidyl))carbonyl](3-piperidyl) 3-hydroxyphenyl ketone 4-(dimethylamino)butyl (trans,trans)-3,5-bis[(3-hydroxyphenyl)carbonyl]-4-(3-fluoro-2-methylphenyl)piperidinecarboxylate 1-{(trans,trans)-3,5-bis[(3-hydroxyphenyl)carbonyl]-4-(3-fluoro-2-methylphenyl)piperidyl}-3-piperidylpropan-1-one {(trans,trans)-3,5-bis[(3-hydroxyphenyl)carbonyl]-4-(3-fluoro-2-methylphenyl)piperidyl}-N-[3-(dimethylamino)propyl]-N-methylcarboxamide 1-(2-{(trans,trans)-3,5-bis[(3-hydroxyphenyl)carbonyl]-4-(3-fluoro-2-methylphenyl)piperidyl}ethyl)-3-[2-(dimethylamino)ethyl]imidazolidin-2-one 1-{(trans,trans)-4-(3-fluoro-2-methylphenyl)-5-((2-fluorophenyl)carbonyl]-3-[(3-hydroxyphenyl)carbonyl]piperidyl}-4-(dimethylamino)butan-1-one 2-{(trans,trans)-3,5-bis[(3-hydroxyphenyl)carbonyl]-4-(3-fluoro-2-methylphenyl)piperidyl}-3-hydroxy-1-(4-methylpiperazinyl)propan-1-one (2R)-2-{(trans,trans)-3,5-bis[(3-hydroxyphenyl)carbonyl]-4-(3-fluoro-2-methylphenyl)piperidyl}-3-amino-1-(4-methylpiperazinyl)propan-1-one (2S)-2-{(trans,trans)-3,5-bis[(3-hydroxyphenyl)carbonyl]-4-(3-fluoro-2-methylphenyl)piperidyl}-3-amino-1-(4-methylpiperazinyl)propan-1-one 1-{(trans,trans)-3,5-bis[(3-hydroxyphenyl)carbonyl]-4-(3-fluoro-2-methylphenyl)piperidyl}-4-amino-2,2-dimethylbutan-1-one 1-{(trans,trans)-3,5-bis[(3-hydroxyphenyl)carbonyl]-4-(3-fluoro-2-methylphenyl)piperidyl}-4-(dimethylamino)-2,2-dimethylbutan-1-one {(trans,trans)-3,5-bis[(3-hydroxyphenyl)carbonyl]-4-(3-fluoro-2-methylphenyl)piperidyl}-N-[2-(dimethylamino)ethyl]-N-methylcarboxamide {(trans,trans)-3,5-bis[3-hydroxyphenyl)carbonyl]-4-(3-fluoro-2-methylphenyl)piperidyl}-N-[2-(dimethylamino)ethyl]carboxamide 2-(dimethylamino)ethyl (trans,trans)-3,5-bis[(3-hydroxyphenyl)carbonyl]-4-(3-fluoro-2-methylphenyl)piperidinecarboxylate (trans,trans)-1-{[3-(dimethylamino)propyl]sulfonyl}-4-(3-fluoro-2-methylphenyl)-5-[(3-hydroxyphenyl)carbonyl](3-piperidyl) 3-hydroxyphenyl ketone (trans,trans)-1-[(3-chloropropyl)sulfonyl]-4-(3-fluoro-2-methylphenyl)-5-[(3-hydroxyphenyl)carbonyl](3-piperidyl) 3-hydroxyphenyl ketone 1-((2R)-2-amino-3-hydroxy-3-methylbutyl)(trans,trans)-4-(3-fluoro-2-methylphenyl)-5-[(3-hydroxyphenyl)carbonyl](3-piperidyl) 3-hydroxyphenyl ketone 2-{(trans,trans)-3,5-bis[(3-hydroxyphenyl)carbonyl]-4-(3-fluoro-2-methylphenyl)piperidyl}-3-(dimethylamino)-1-(4-methylpiperazinyl)propan-1-one (2S)-2-{(trans,trans)-3,5-bis[(3-hydroxyphenyl)carbonyl]-4-(3-fluoro-2-methylphenyl)piperidyl}-3-(dimethylamino)-1-(4-methylpiperazinyl)propan-1-one (2R)-2-{(trans,trans)-3,5-bis[(3-hydroxyphenyl)carbonyl]-4-(3-fluoro-2-methylphenyl)piperidyl}-N-[2-(dimethylamino)ethyl]-3-[(methylsulfonyl)amino]propanamide (2R)-2-{(trans,trans)-3,5-bis[(3-hydroxyphenyl)carbonyl]-4-(3-fluoro-2-methylphenyl)piperidyl}-1-(4-methylpiperazinyl)-3-[(methylsulfonyl)amino]propan-1-one (2S)-2-{(trans,trans)-3,5-bis[(3-hydroxyphenyl)carbonyl]-4-(3-fluoro-2-methylphenyl)piperidyl}-1-(4-methylpiperazinyl)-3-[(methylsulfonyl)amino]propan-1-one 2-{(trans,trans)-3,5-bis[(3-hydroxyphenyl)carbonyl]-4-(3-fluoro-2-methylphenyl)piperidyl}-1-(4-methylpiperazinyl)ethan-1-one and (trans, trans)-1-(3-(dimethylamino)propylsulfonyl)-4-(3-fluoro-2-methylphenyl)piperidine-3,5-diyl)bis((3-hydroxyphenyl)methanone) and pharmaceutically acceptable salts thereof.

24. A pharmaceutical composition comprising a therapeutically effective amount of a compound of claim 1, or a pharmaceutically acceptable salt thereof together with at least one pharmaceutically acceptable vehicle chosen from carriers, adjuvants, and excipients.

25. A pharmaceutical composition of claim 24 wherein the composition is formulated in a form chosen from injectable fluids, aerosols, creams, gels, tablets, pills, capsules, syrups, ophthalmic solutions, and transdermal patches.

* * * * *